US012661399B2

(12) United States Patent
Berglund et al.

(10) Patent No.: US 12,661,399 B2
(45) Date of Patent: Jun. 23, 2026

(54) METHOD OF TREATING AN IMMUNE-RELATED DISORDER OR DISEASE ASSOCIATED WITH AN ORGAN OR TISSUE TRANSPLANT WITH A COMBINATION OF AN ANTI-CD2 ANTIBODY AND A CTLA-4 CO-STIMULATION BLOCKADE

(71) Applicant: Zelarion Malta Limited, Birkirkara (MT)

(72) Inventors: David Berglund, New York, NY (US); Erik Berglund, New York, NY (US); Felix Sellberg, Uppsala (SE); Christian Binder, Stockholm (SE)

(73) Assignee: Zelarion Malta Limited, Birkirkara (MT)

( * ) Notice: Subject to any disclaimer, the term of this patent is extended or adjusted under 35 U.S.C. 154(b) by 524 days.

(21) Appl. No.: 18/012,089

(22) PCT Filed: Jun. 22, 2021

(86) PCT No.: PCT/EP2021/066989
§ 371 (c)(1),
(2) Date: Dec. 21, 2022

(87) PCT Pub. No.: WO2021/259927
PCT Pub. Date: Dec. 30, 2021

(65) Prior Publication Data
US 2023/0365687 A1 Nov. 16, 2023

Related U.S. Application Data

(60) Provisional application No. 63/182,095, filed on Apr. 30, 2021, provisional application No. 63/135,381, filed on Jan. 8, 2021, provisional application No. 63/042,844, filed on Jun. 23, 2020.

(51) Int. Cl.
| | |
|---|---|
| *A61K 47/48* | (2006.01) |
| *A61K 38/17* | (2006.01) |
| *A61K 39/395* | (2006.01) |
| *A61K 47/68* | (2017.01) |
| *A61P 37/06* | (2006.01) |
| *C07K 14/705* | (2006.01) |
| *C07K 16/28* | (2006.01) |

(52) U.S. Cl.
CPC ...... *A61K 39/3955* (2013.01); *A61K 38/1774* (2013.01); *A61K 47/68* (2017.08); *A61P 37/06* (2018.01); *C07K 14/70521* (2013.01); *C07K 16/2806* (2013.01); *C07K 2317/41* (2013.01); *C07K 2317/52* (2013.01); *C07K 2317/732* (2013.01); *C07K 2317/734* (2013.01); *C07K 2317/76* (2013.01); *C07K 2317/92* (2013.01); *C07K 2319/30* (2013.01)

(58) Field of Classification Search
CPC ............ A61K 39/3955; A61K 38/1774; A61K 47/68; A61P 37/06; C07K 14/70521; C07K 16/2806
See application file for complete search history.

(56) References Cited

U.S. PATENT DOCUMENTS

| | | |
|---|---|---|
| 6,692,743 B1 | 2/2004 | Bazin et al. |
| 2002/0159999 A1 | 10/2002 | Sykes |
| 2003/0068320 A1 | 4/2003 | Dingivan |
| 2013/0183322 A1 | 7/2013 | Reisner |
| 2022/0226329 A1 | 7/2022 | Kawai |
| 2024/0270845 A1 | 8/2024 | Berglund et al. |
| 2024/0285756 A1 | 8/2024 | Berglund et al. |

FOREIGN PATENT DOCUMENTS

| | | |
|---|---|---|
| WO | WO 1998/007444 | 2/1998 |
| WO | WO 2002/069904 | 9/2002 |
| WO | WO 2002/098370 | 12/2002 |
| WO | WO 2004/022097 | 3/2004 |
| WO | WO 2012/032525 | 3/2012 |
| WO | WO 2014/133729 | 9/2014 |
| WO | WO 2019/108860 | 6/2019 |
| WO | WO 2020/227647 | 11/2020 |
| WO | WO 2020/247872 | 12/2020 |
| WO | WO 2021/259927 | 12/2021 |
| WO | WO 2023/036745 | 3/2023 |

OTHER PUBLICATIONS

Adams et al., 2016, "Costimulation Blockade in Autoimmunity and Transplantation: The CD28 Pathway," Journal of Immunology, 197(6):2045-2050.
Andreola et al., 2011, "Mechanisms of donor-specific tolerance in recipients of haploidentical combined bone marrow/kidney transplantation," American Journal of Transplantation, 11(6):1236-1247.
Arduin et al., 2015, "Highly reduced binding to high and low affinity mouse Fc gamma receptors by L234A/L235A and N297A Fc mutations engineered into mouse IgG2a," Molecular Immunology, 63(2):456-463.
Arulanandam et al., 1993, "The CD58 (LFA-3) binding site is a localized and highly charged surface area on the AGFCC'C" face of the human CD2 adhesion domain," Proceedings of the National Academy of Sciences (PNAS), 90(24):11613-11617.
Benvenuto et al., 2018, "New frontiers in immunosuppression," Journal of Thoracic Disease, 10(5):3141-3155.
Bierer and Burakoff, 1989, "T-lymphocyte activation: the biology and function of CD2 and CD4," Immunological Reviews, 111:267-294.

(Continued)

*Primary Examiner* — Zachary C Howard
(74) *Attorney, Agent, or Firm* — Jones Day

(57) ABSTRACT
Provided herein are improved anti-CD2 antibodies and methods for their use in the treatment and/or prevention of chronic or acute disorders of the immune system. Also provided herein are methods for treating or preventing an immune related disorder or disease in a subject by administering an anti-CD2 antibody or an antigen-binding fragment thereof and a CTLA-4 co-stimulation blockade. Compositions for use with these methods and kits are also disclosed.

19 Claims, 35 Drawing Sheets
Specification includes a Sequence Listing.

(56)        References Cited

OTHER PUBLICATIONS

Binder et al., 2020, "CD2 Immunobiology," Frontiers in Immunology, 11:1090 (14 pages).

Binder et al., 2020, "Siplizumab, an Anti-CD2 Monoclonal Antiody, Induces a Unique Set of Immune Modulatory Effects Compared to Alemtuzumab and Rabbit Anti-Thymocyte Globulin In Vitro," Frontiers in Immunology, 11:592553 (17 pages).

Bockenstedt et al., 1988, "The CD2 ligand LFA-3 activates T cells but depends on the expression and function of the antigen receptor," Journal of Immunology, 141(6):1904-1911.

Branco et al., 1999, "Selective deletion of antigen-specific, activated T cells by a humanized MAB to CD2 (MEDI-507) is mediated by NK cells," Transplantation, 68(10):1588-1596.

Chung and Dilling, 2020, "Immunosuppressive strategies in lung transplantation," Annals of Translational Medicine, 8(6):409 (13 pages).

Clark et al., 1988, "Activation of rat T lymphocytes by anti-CD2 monoclonal antibodies," Journal of Experimental Medicine, 167(6):1861-1872.

ClinicalTrials.gov Identifier: NCT04311632, "A Dose Escalation Study in de Novo Renal Transplantation," 2020 (9 pages).

Damschroder et al., 2004, "Analysis of human and primate CD2 molecules by protein sequence and epitope mapping with anti-human CD2 antibodies," Molecular Immunology, 41(10):985-1000.

Davies and Sutton, 2015, "Human IgG4: a structural perspective," Immunological Reviews, 268(1):139-159.

Demetris et al., 2016, "2016 Comprehensive Update of the Banff Working Group on Liver Allograft Pathology: Introduction of Antibody-Mediated Rejection," American Journal of Transplantation, 16(10):2816-2835.

Einarsdottir et al., 2014, "On the perplexingly low rate of transport of IgG2 across the human placenta," PLoS One, 9(9):e108319 (9 pages).

European Association for the Study of the Liver, 2016, "EASL Clinical Practive Guidelines: Liver transplantation," Journal of Hepatology, 64(2):433-485.

GenBank Accession No. NM_001328609.1, "*Homo sapiens* CD2 molecule (CD2), transcript variant 1, mRNA," retrieved from the Internet on Jul. 14, 2023 from: https://www.ncbi.nlm.nih.gov/nuccore/NM_001328609.1/ (4 pages).

GenBank Accession No. NM_001767.5, "*Homo sapiens* CD2 molecule (CD2), transcript variant 2, mRNA," retrieved from the Internet on Jul. 14, 2023 from: https://www.ncbi.nlm.nih.gov/nuccore/NM_001767.5/ (5 pages).

Golay et al., 2003, "Rituximab-mediated antibody-dependent cellular cytotoxicity against neoplastic B cells is stimulated strongly by interleukin-2," Haematologica, 88(9):1002-1012.

Grier et al., 2012, "Human immunodeficiency-causing mutation defines CD16 in spontaneous NK cell cytotoxicity," Journal of Clinical Investigation, 122(10):3769-3780.

Hawthorne et al., 2017, ">12 Month function of genetically modified porcine neonatal islet xenografts in baboons," XP002805102, Database Em Base, Elsevier Science Publishers, Amsterdam, NL, Database accession No. EM B-618839635 (2 pages).

International Search Report and Written Opinion dated Jan. 10, 2022 for PCT/EP2021/066989 (21 pages).

Kellner et al., 2017, "Modulating Cytotoxic Effector Functions by Fc Engineering to Improve Cancer Therapy," Transfusion Medicine and Hemotherapy, 44(5):327-336.

Kinnear et al., 2013, "Costimulation blockade: current perspectives and implications for therapy," Transplantation, 95(4):527-535.

Krummel and Allison, 1995, "CD28 and CTLA-4 have opposing effects on the response of T cells to stimulation," Journal of Experimental Medicine, 182(2):459-465.

Lo et al., 2011, "Selective targeting of human alloresponsive CD8+ effector memory T cells based on CD2 expression," American Journal of Transplantation, 11(1):22-33.

Lo et al., 2011, "Selective targeting of human alloresponsive CD8<+> effector memory T cells based on CD2 expression,"

XP002805103, Database Em Base, Elsevier Science Publishers, Amsterdam, NL, Database accession No. EM B-2011013403 (1 page).

Massart et al., 2017, "Operational tolerance in kidney transplantation and associated biomarkers," Clinical & Experimental Immunology, 189(2):138-157.

Newell and Turka, 2015, "Tolerance signatures in transplant recipients," Current Opinion in Organ Transplantation, 20(4):400-405.

Ng et al., 2001, "Human CD4(+)CD25(+) cells: a naturally occurring population of regulatory T cells," Blood, 98(9):2736-2744.

Nizet et al., 1999, "Apoptosis of human naive NK cells mediated by a rat IgG2b anti CD2 mAb through a fractricidal ADCC reaction," Immunology Letters, 68(2-3):229-235.

O'Mahony et al., 2007, "EBV-Related Lymphoproliferative Disease Complicating Therapy with Siplizumab, a Novel Anti-CD2 Mediated T- and NK-Cell Depleting Agent, in Patients with T-Cell Malignancies," Blood, 110(11):3565 (2 pages).

Orange et al., 2003, "The mature activating natural killer cell immunologic synapse is formed in distinct stages," Proceedings of the National Academy of Sciences (PNAS), 100(24):14151-14156.

Paul and Lal, 2017, "The Molecular Mechanism of Natural Killer Cells Function and Its Importance in Cancer Immunotherapy," Frontiers in Immunology, 8:1124 (15 pages).

Peterson and Seed, 1987, "Monoclonal antibody and ligand binding sites of the T cell erythrocyte receptor (CD2)," Nature, 329(6142):842-846.

Podestà et al., 2019, "Siplizumab selectively depletes effector memory T cells and promotes a relative expansion of alloreactive regulatory T cells in vitro," American Journal of Transplantation, 20(1):88-100.

Sambucci et al. 2018, "FoxP3 isoforms and PD-1 expression by T regulatory cells in multiple sclerosis," Scientific Reports, 8(1):3674 (9 pages).

Schlothauer et al., 2016, "Novel human IgG1 and IgG4 Fc-engineered antibodies with completely abolished immune effector functions," Protein Engineering, Design and Selection, 29(10):457-466.

Sellberg et al., 2020, "Pharmacokinetic and pharmacodynamic study of a clinically effective anti-CD2 monoclonal antibody," Scandinavian Journal of Immunology, 91(1):e12839 (11 pages).

Shaffer et al., 2007, "Regulatory T-cell recovery in recipients of haploidentical nonmyeloablative hematopoietic cell transplantation with a humanized anti-CD2 mAb, MEDI-507, with or without fludarabine," Experimental Hematology, 35(7):1140-1152.

Silva et al., 2015, "The S228P mutation prevents in vivo and in vitro IgG4 Fab-arm exchange as demonstrasted using a combination of novel quantitative immunoassays and physiological matrix preparation," Journal of Biological Chemistry, 290(9):5462-5469.

Sjögren et al., 2013, "EndoS2 is a unique and conserved enzyme of serotype M49 group A *Streptococcus* that hydrolyses N-linked glycans on IgG and α1-acid glycoprotein," Biochemical Journal, 455(1):107-118.

Sjögren et al., 2015, "EndoS and EndoS2 hydrolyze Fc-glycans on therapeutic antibodies with different glycoform selectivity and can be used for rapid quantification of high-mannose glycans," Glycobiology, 25(10):1053-1063.

Thum et al., 2004, "An increase in the absolute count of CD56dimCD16+CD69+ NK cells in the peripheral blood is associated with a poorer IVF treatment and pregnancy outcome," Human Reproduction, 19(10):2395-2400.

Tradtrantip et al., 2013, "Enzymatic deglycosylation converts pathogenic neuromyelitis optica anti-aquaporin-4 immunoglobulin G into therapeutic antibody," Annals of Neurology, 73(1):77-85.

Valenzuela and Schaub, 2018, "The Biology of IgG Subclasses and Their Clinical Relevance to Transplantation," Transplantation, 102(Suppl. 1):S7-S13.

Van der Mark et al., 2020, "Developments in lung transplantation over the past decade," European Respiratory Review, 29(157):190132 (16 pages).

Van der Merwer et al., 1994, "Human cell-adhesion molecule CD2 binds CD58 (LFA-3) with a very low affinity and an extremely fast dissociation rate but does not bind CD48 or CD59," Biochemistry, 33(33):10149-10160.

(56) References Cited

OTHER PUBLICATIONS

Vidarsson et al., 2014, "IgG subclasses and allotypes: from structure to effector functions," Frontiers in Immunology, 5:520 (17 pages).

Walunas et al., 1994, "CTLA-4 can function as a negative regulator of T cell activation," Immunity, 1(5):405-413.

Wang et al.,, 2018, "IgG Fc engineering to modulate antibody effector functions," Protein Cell, 9(1):63-73.

Watzl, C, 2014, "How to trigger a killer: modulation of natural killer cell reactivity on many levels," Advances in Immunology, 124:137-170.

Zhang and Vignali, 2016, "Co-stimulatory and Co-inhibitory Pathways in Autoimmunity," Immunity, 44(5):1034-1051.

International Search Reprot and Written Opinion dated Nov. 30, 2022 for PCT/EP2022/074646 (13 pages).

Benjamini et al., 1991, "Immunology: A Short Course," 2nd edition, p. 40, Wiley-Liss.

Bhattacharya et al., 2017, "Impact of genetic variation on three dimensional structure and function of proteins," PLoS ONE 12(3):e0171355.

Brudno et al., 2016, "Toxicities of chimeric antigen receptor T cells: recognition and management," Blood, 127(26):3321-3330.

Chauhan, et al., 2019, "Rituximab in kidney disease and transplant," Animal Model Exp Med, 2:76-82.

ClinicalTrials.gov Identifier: NCT00801632, "Combined Kidney and Bone Marrow Transplantation to Prevent Kidney Transplant Rejection," 2015 (17 pages).

ClinicalTrials.gov Identifier: NCT02108600, "Tocilizumab for Renal Graft Inflammation," 2021 (14 pages).

Dey et al., 2005, "Anti-tumour response despite loss of donor chimaerism in patients treated with non-myeloablative conditioning and allogeneic stem cell transplantation," British Journal of Haematology, 2005, 128, 351-359, doi:10.1111/j.1365-2141.2004.05328.x.

Ferrara et al., 2015, "Recombinant renewable polyclonal antibodies," mAbs, 7(1):32-42.

Hay, K., 2018, "Cytokine release syndrome and neurotoxicity after CD19chimeric antigen receptor-modified (CAR-) T cell therapy," British Journal of Haematology, 183:364-374.

Kawai et al, 2014, "Long-Term Results in Recipients of Combined HLA-Mismatched Kidney and Bone Marrow Transplantation Without Maintenance Immunosuppression: Kidney Transplant Without Immunosuppression," Amerian Journal of Transplantation, 14(7):1599-1611.

Latinne, et al., 1996, "An anti-CD2 mAb induces immunosuppression and hyporesponsiveness of CD2+ human T cells in vitro," International Immunology, 8(7): 1113-1119.

Le et al, 2018, "FDA Approval Summary: Tocilizumab for Treatment of Chimeric Antigen Receptor T Cell-Induced Severe or Life-Threatening Cytokine Release Syndrome," The Oncologist, 23:943-947.

Lee et al, 2020, "Inducing Transient Mixed Chimerism for Allograft Survival Without Maintenance Immunosuppression With Combined Kidney and Bone Marrow Transplantation: Protocol Optimization," 104(7):1472-1482.

LoCasico et al., 2010, "Mixed Chimerism, Lymphocyte Recovery, and Evidence for Early Donor-Specific Unresponsiveness in Patients Receiving Combined Kidney and Bone Marrow Transplantation to Induce Tolerance," Transplantation, 90(1):1607-1615.

Lowsky et al., 2022, "Establishment of Chimerisn and Organ Transplant Tolerance in Laboratory Animals: Safety and Efficacy of Adaptation to Humans," Frontiers in Immunology, vol. 13.

Nizet et al., 2000, "The Experimental (In Vitro) and Clinical (In Vivo) Immunosuppressive Effects of a Rat IgG2b Anti-Human CD2 mAb, LO-CD2a/BTI-322," Transplantation, 69(7):1420-1429.

Podestà et al., 2022, "Chimerism-Based Tolerance to Kidney Allografts in Humans: Novel Insights and Future Perspectives," Frontiers in Immunology, vol. 12.

Sasaki et al, 2018, "Preclinical and clinical studies for transplant tolerance via the mixed chimerism approach," Human Immunology, 79(5):258-265.

Savage et al. 2018, "Early expansion of donor-specific Tregs in tolerant kidney transplant recipients," JCI Insight., 3(22): e124086. doi: 10.1172/jci.insight.124086.

Schinnerling et al, 2017, "The role of interleukin-6 signalling and its therapeutic blockage in skewing the T cell balance in rheumatoid arthritis," Clinical and Experimental Immunology, 189(1):12-20.

Sprangers et al., 2017, "Origin of Enriched regulatory t cells in patients receiving combined kidney/bone marrow transplantation to induce transplantation tolerance," Am J Transplant. 17(8): 2020-2032. doi: 10.1111/ajt.14251.

Tada et al., 2016, "The balance between Foxp3 and Ror-γt expression in peripheral blood is altered by tocilizumab and abatacept in patients with rheumatoid arthritis," BMC Musculoskeletal Disorders, 17:290.

Tokuriki et al., 2009, "Stability effects of mutations and protein evolvability," Current Opinion in Structural Biology, 19:596-604.

Xu et al., 2004, "The anti-CD2 monoclonal antibody BTI-322 generates unresponsiveness by activation-associated T cell depletion," Clinical and Experimental Immunology, 138(3):476-483.

8A                8B                8C

Molecule 5A (IgG2)    Molecule 6A (IgG2)    Molecule 7A (IgG2)
Molecule 5B (IgG4)    Molecule 6B (IgG4)    Molecule 7B (IgG4)

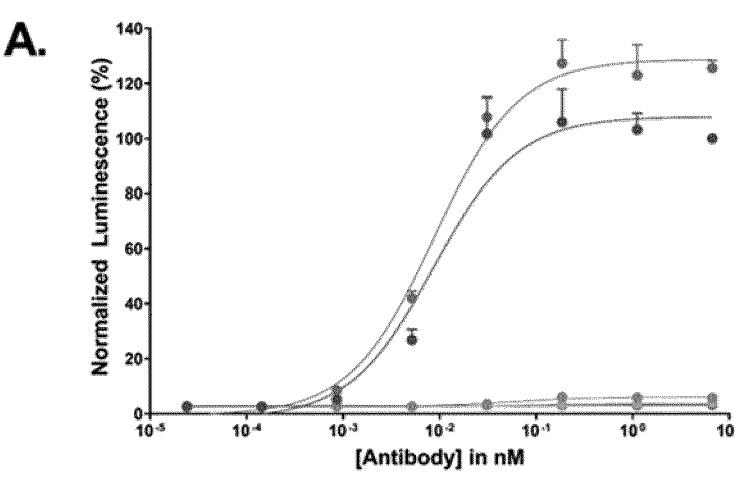
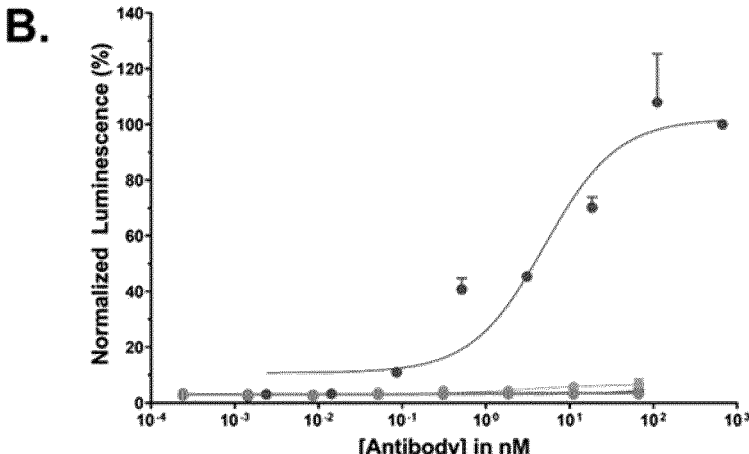
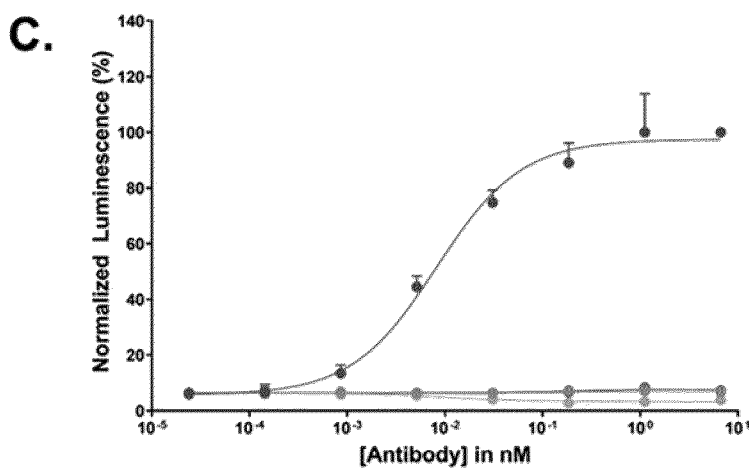
FIG. 9

FIG.
18A
FIG.
18B
FIG.
18C
FIG.
18D
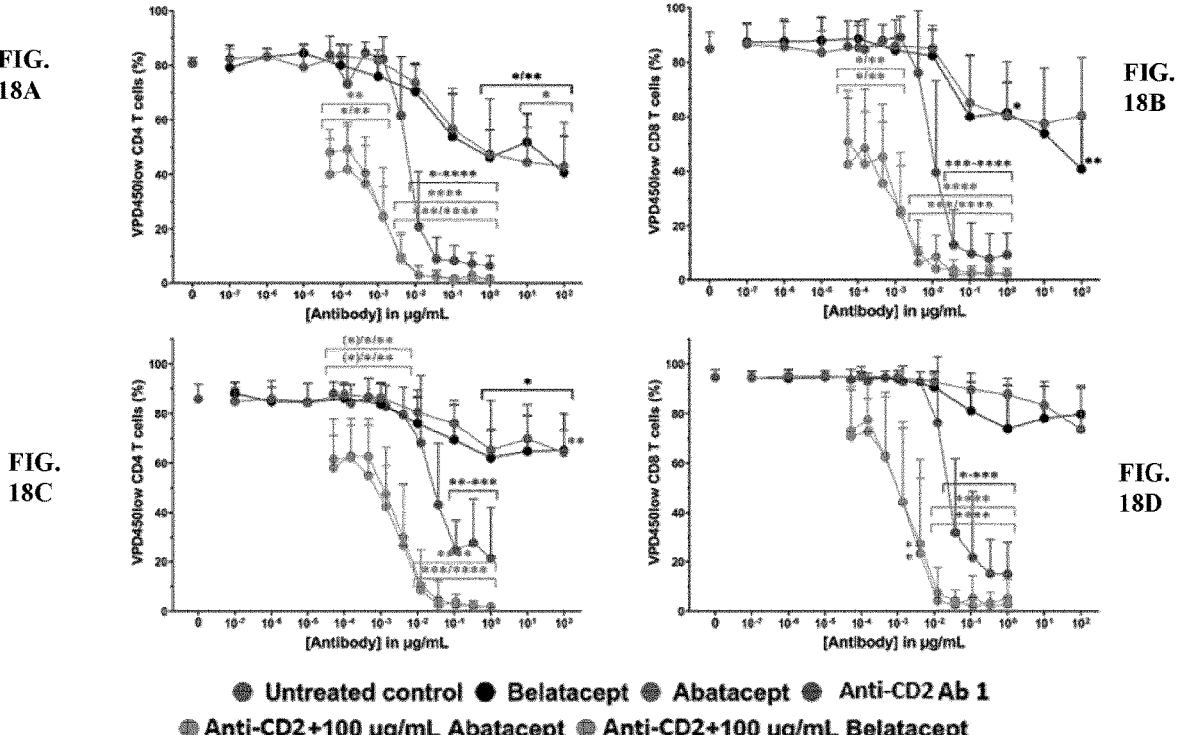
● Untreated control ● Belatacept ● Abatacept ● Anti-CD2 Ab 1
● Anti-CD2+100 µg/mL Abatacept ● Anti-CD2+100 µg/mL Belatacept
    Ab 1                                    Ab 1

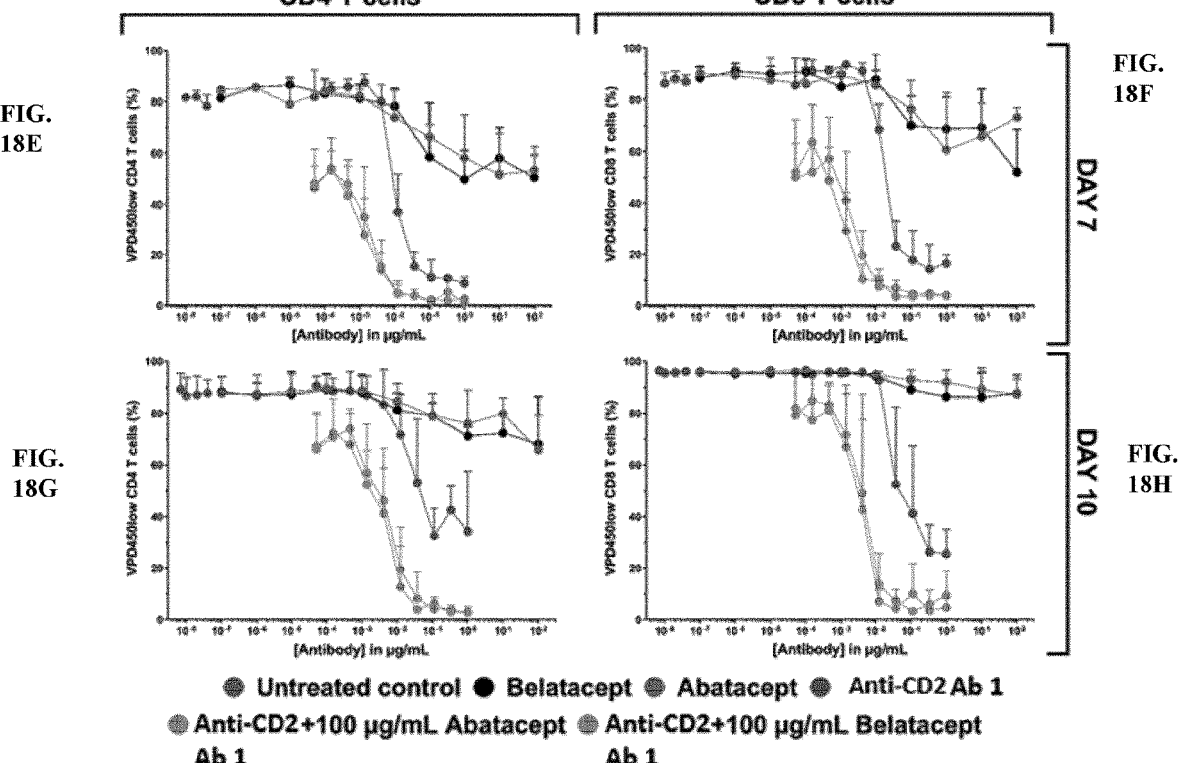
FIG.
18E
FIG.
18F
FIG.
18G
FIG.
18H

FIG.
19A
FIG.
19B
FIG.
19C
FIG.
19D
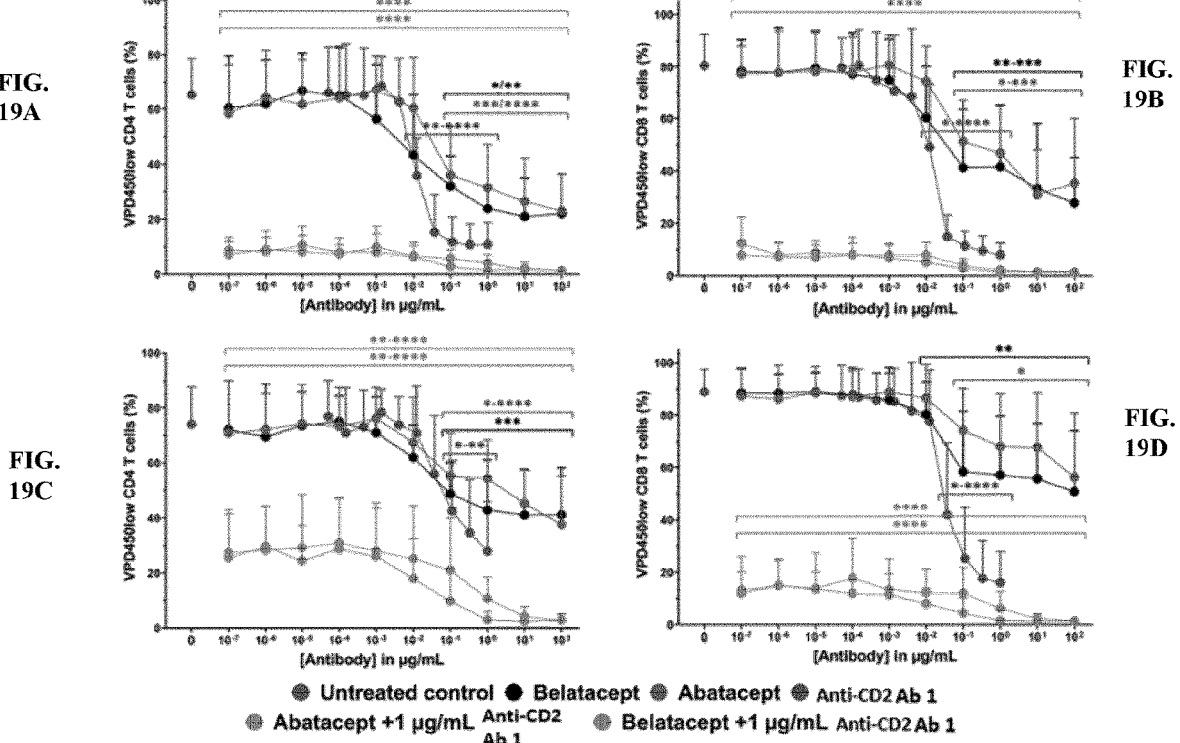

FIG.
23A
FIG.
23B
FIG.
23C
FIG.
23D
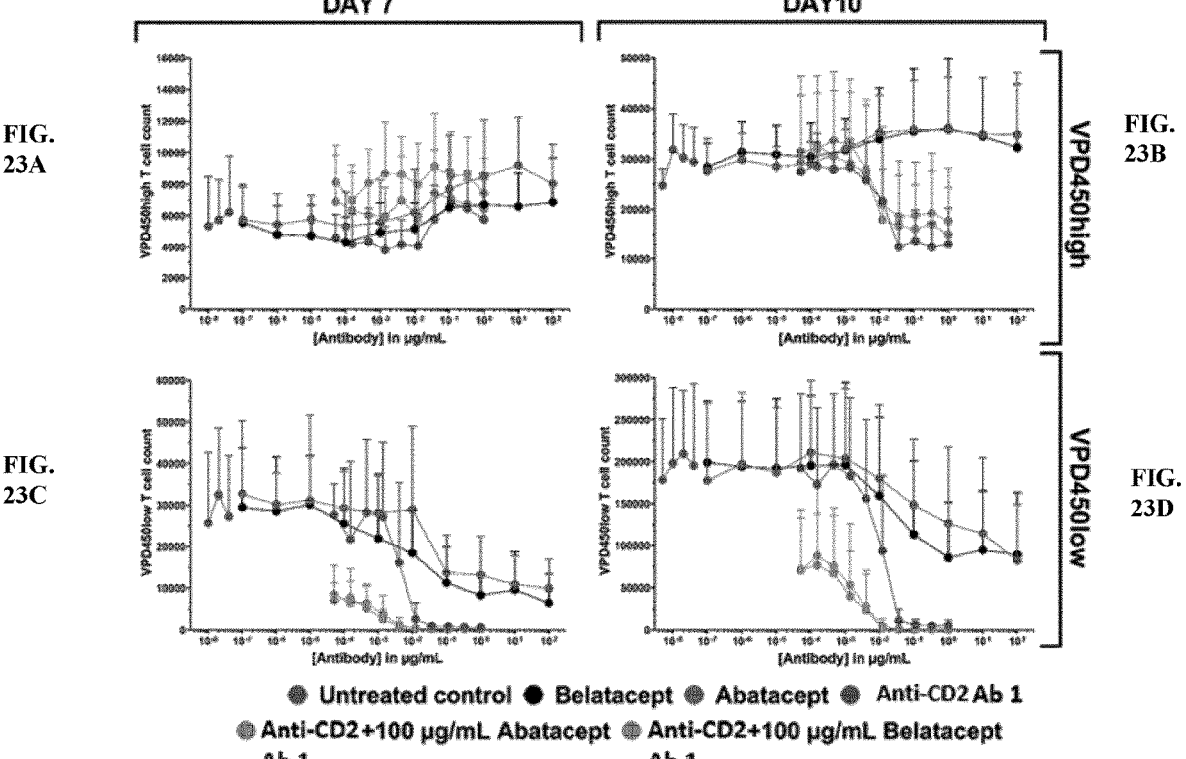

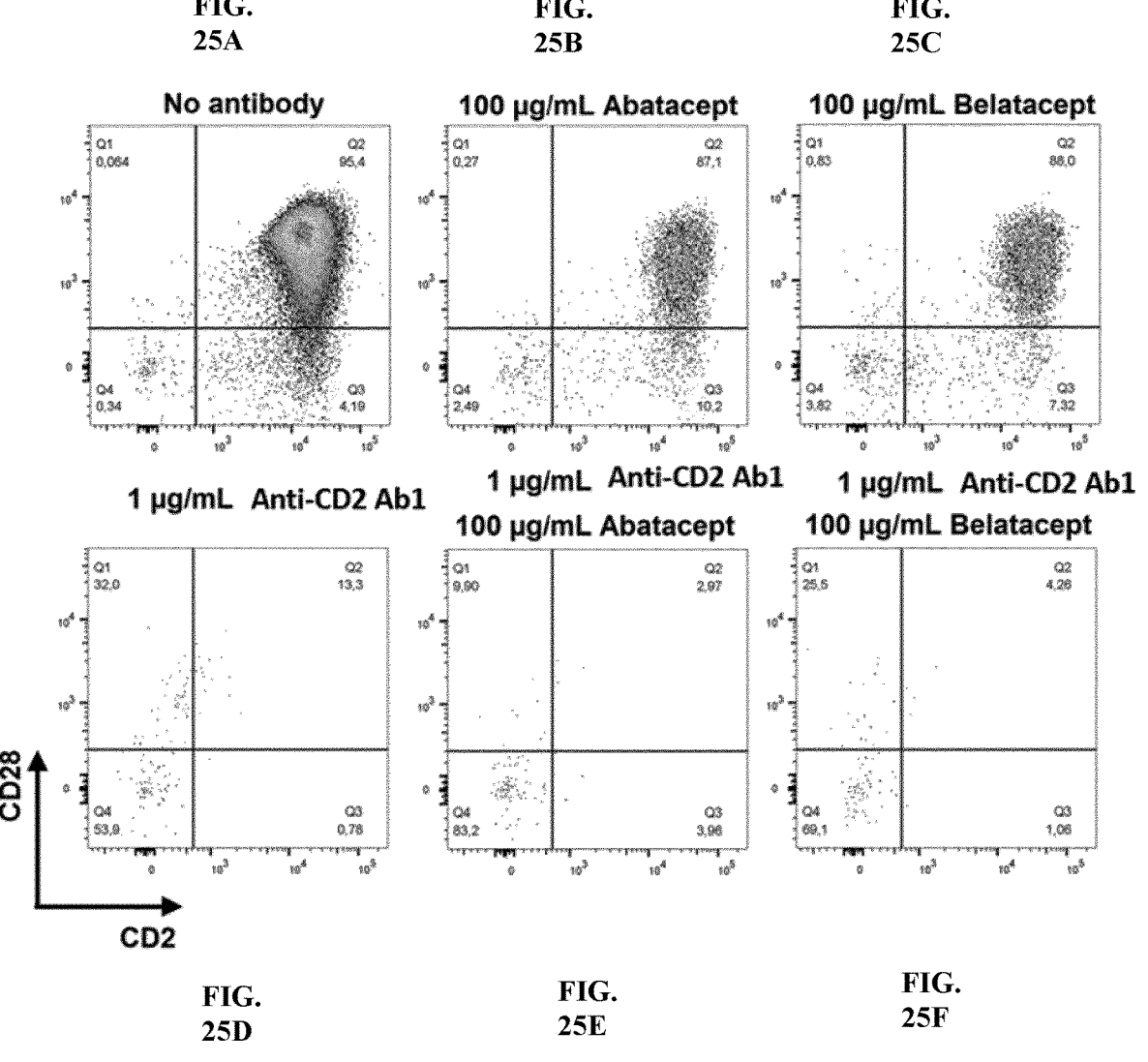
FIG.
25A
FIG.
25B
FIG.
25C
FIG.
25D
FIG.
25E
FIG.
25F

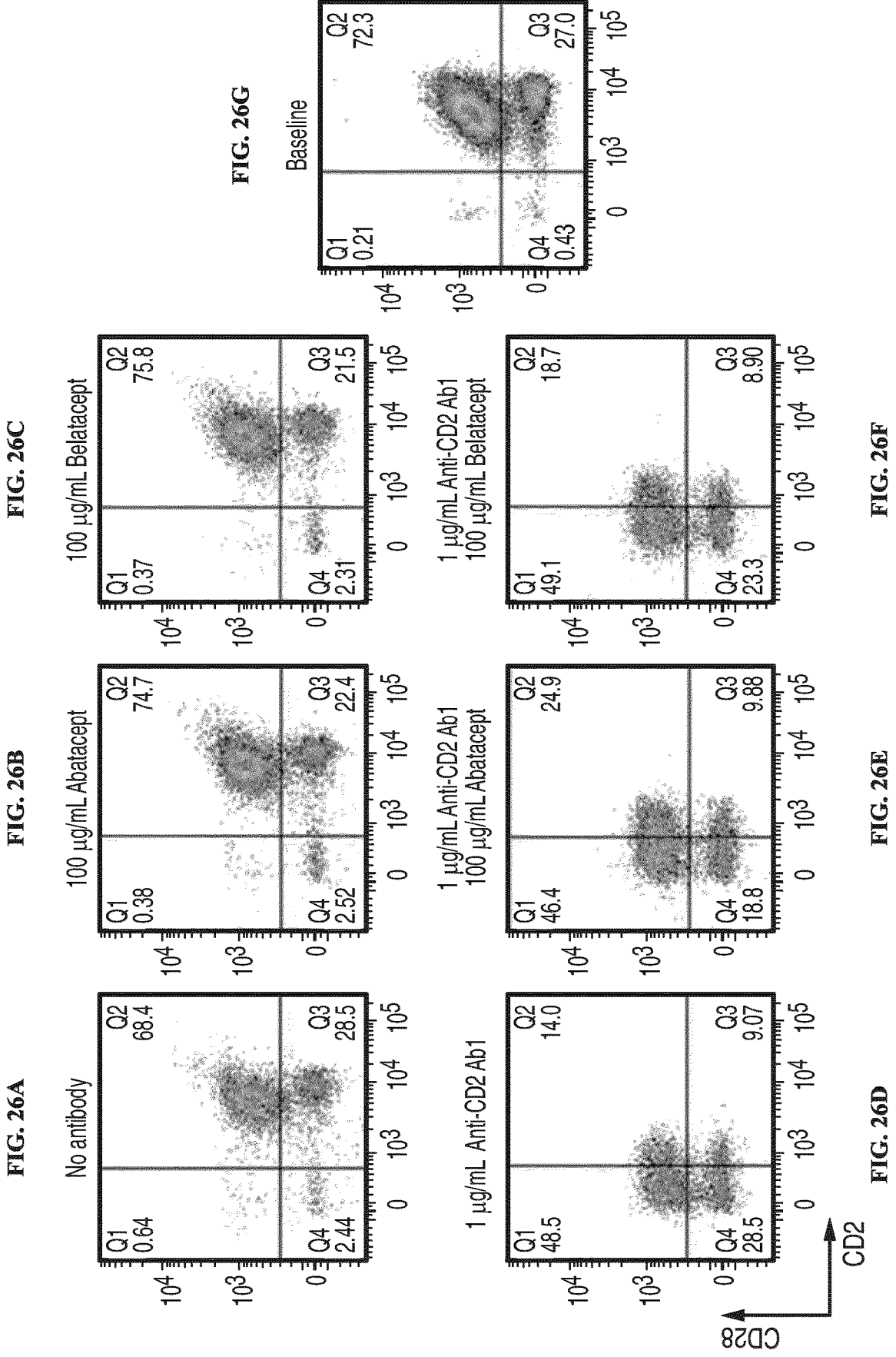

FIG. 27A                                              FIG. 27B

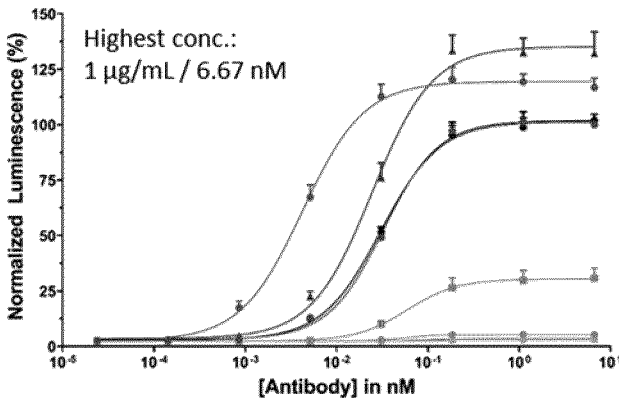
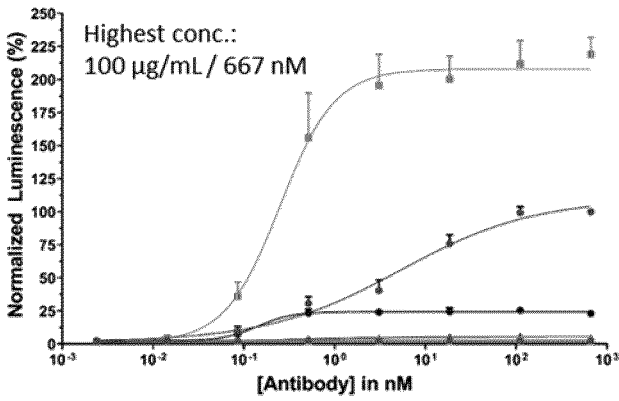
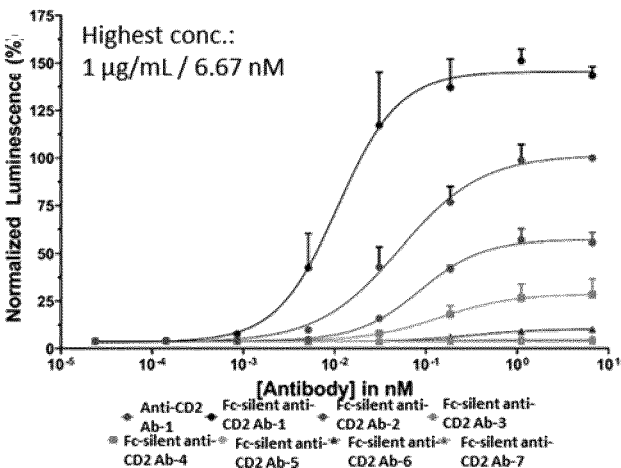
FIG. 28

METHOD OF TREATING AN IMMUNE-RELATED DISORDER OR DISEASE ASSOCIATED WITH AN ORGAN OR TISSUE TRANSPLANT WITH A COMBINATION OF AN ANTI-CD2 ANTIBODY AND A CTLA-4 CO-STIMULATION BLOCKADE

CROSS-REFERENCE TO RELATED APPLICATIONS

This application is a U.S. National Stage Application of International Patent Application No. PCT/EP2021/066989, filed Jun. 22, 2021, which claims the benefit of U.S. Provisional Application No. 63/182,095, filed Apr. 30, 2021, U.S. Provisional Application No. 63/135,381, filed Jan. 8, 2021, and U.S. Provisional Application No. 63/042,844, filed Jun. 23, 2020, the content of each of which is incorporated herein by reference in its entirety.

REFERENCE TO SEQUENCE LISTING SUBMITTED ELECTRONICALLY

This application incorporates by reference a Sequence Listing submitted with this application in ASCII format via EFS-Web entitled "14526-005-999_Sequence_Listing.txt" created on Dec. 20, 2022 and having a size of 33,907 bytes.

1. FIELD

The present application relates to improved anti-CD2 antibodies and their use in the treatment and/or prevention of chronic or acute disorders of the immune system. Uses of these antibodies in the induction and maintenance of immune tolerance is also disclosed. Also, provided herein are methods for treating or preventing an immune related disorder or disease in a subject by administering an anti-CD2 antibody or an antigen-binding fragment thereof and a CTLA-4 co-stimulation blockade. Compositions for use with these methods and kits are also disclosed

2. BACKGROUND

Patients with disorders of the immune system (e.g., chronic inflammatory disorders of the immune system) must undertake long-term treatment to manage their condition. Therefore, potential treatment regimens must prioritize minimizing the use of immunosuppressants that cause organ damage and other adverse effects, while treating the symptoms of the disease and maintaining quality of life of the patient. Thus, there exists an outstanding need for therapies that minimize adverse side effects of standard immunosuppressant therapies. Further, there is a need for improved methods and compositions for the treatment of immune associated disorders, such as autoimmune disease and immune disorders associated with organ transplantation as long-term results of organ transplantation remain unsatisfactory. Chronic rejection of the donor graft and health issues associated with long-term immunosuppressant use continue to be serious complications of the procedure. There exists an outstanding need for therapies that can be chronically administered to patients over the course of months or years without the adverse side effects of standard immunosuppressant therapies. There is also a need for methods and compositions that can treat acute symptoms of an immune associated disease, e.g., by alleviating the signs and symptoms of the disorder, reducing the likelihood of recurrence of the disorder, preventing an organ or tissue transplant rejection, and/or preventing an immune disorder from occurring in a subject who is likely to develop an immune disorder.

Siplizumab is a humanized IgG1κ monoclonal antibody directed against the human CD2 glycoprotein, a receptor expressed on virtually all mature human T cells and on the vast majority of thymocytes (Bierer B E, Burakoff S J., *Immunol Rev.* 1989; 111:267-294). CD2 promotes the adhesion of T cells to antigen-presenting cells through its interaction with the ligand LFA-3 (CD58) (van der Merwe P A, Barclay A N, Mason D W, et al. *Biochemistry.* 1994; 33(33):10149-10160). Binding of CD2 to LFA-3 also leads to a cascade of intracellular signals necessary for T cell activation, conferring an important costimulatory function to this molecule (Bockenstedt L K. et al., *J Immunol.* 1988; 141(6):1904-1911).

Siplizumab has been used in conditioning regimens for hematopoietic cell transplantation and tolerance induction with combined kidney-bone marrow transplantation (CKBMT). Siplizumab depletes T cells globally while enriching regulatory T cells (Tregs) early following transplantation. In recipients of hematopoietic cell transplantation to treat malignancies (Shaffer J. et al., *Exp Hematol.* 2007; 35(7): 1140-1152) and CKBMT recipients (Andreola G. et al., *Am J Transplant.* 2011; 11(6):1236-1247), a marked early enrichment in regulatory T cells (Tregs) was observed during the T cell reconstitution phase.

As monoclonal antibodies have become integral in the treatment of various types of diseases, engineering of these therapeutic antibodies have become more sophisticated in order to design and produce antibodies that are optimized for a specific purpose (Kellner et al., *Transfus Med Hemother.* 2017 September; 44(5): 327-336). Modification of the Fc is an example of such engineering. Fc-mediated effector functions, such as antibody-dependent cell-mediated cytotoxicity (ADCC), is an important component of some therapeutic regimens while being a hindrance in others. Modifications that silence Fc signaling can benefit patients for whom ADCC would cause further complications. For patients in need of long-term immunosuppression, an antibody engineered to provide immune modulatory activity while lacking ADCC activity would be beneficial.

The present disclosure also describes the combination therapy of an anti-CD2 antibody or antigen fragment thereof and a CTLA-4 co-stimulation blockade for the treatment or prevention of an immune associated disease or disorder in a subject. CTLA-4 inhibits the immune response in two principal ways—it competes with CD28 for the B7 ligands and thus blocks costimulation, and it also negatively signals to inhibit T cell activation (Krummel and Allison, 1995, J Exp Med 182:459-465; Walunas et al., 1994, Immunity 1:405-413). Abatacept which is a fusion protein composed of the Fc region of the immunoglobulin IgG1 fused to the extracellular domain of CTLA-4 binds to the CD80 and CD86 molecule, and prevents a T cell from being activated. Belatacept is a fusion protein composed of the Fc fragment of a human IgG1 immunoglobulin linked to the extracellular domain of CTLA-4 and differs from abatacept by two amino acids. Similarly to abatacept, belatacept has specificity for CD80 antigen and CD86 antigen and acts as a negative regulator of peripheral T cell function. The present disclosure provides that the combination therapy (of an anti-CD2 antibody or antigen fragment thereof and a CTLA-4 co-stimulation blockade) shows synergistic effect in comparison to when only one of, but not both, the anti-CD2 antibody or antigen fragment thereof or the CTLA-4 co-stimulation blockade is administered to a subject.

3. SUMMARY

Wherever the specification discusses "an anti-CD2 antibody," the same disclosure can also pertain to a "CD2-binding molecule" and vice versa. Provided herein is a recombinant anti-CD2 antibody, wherein the antibody is an IgG antibody wherein the ability of the antibody to mediate antibody-dependent cellular cytotoxicity is reduced or eliminated while the immune regulatory activity of the antibody is maintained relative to siplizumab. Also provided herein is a recombinant anti-CD2 antibody, wherein the antibody is an IgG antibody and at least one consensus N-glycosylation site of the constant region of the heavy chain is not glycosylated. In certain embodiments, at least one consensus sequence of the antibody has been mutated such that it is no longer glycosylated. Also provided herein is a recombinant anti-CD2 antibody, wherein the Fc region is mutated such that the antibody lacks the ability to bind to Fc receptors and C1q.

The "anti-CD2 antibody," or "CD2-binding molecule" disclosed herein can also comprise enlarged anti-CD2 variants wherein additional components are added to the Fc region. These components can include, but are not limited to, an scFv, a CH2 domain, and a CH3 domain.

Provided herein is a recombinant anti-CD2 antibody, wherein the antibody is an IgG antibody and at least one consensus N-linked glycosylation site of the constant region of the heavy chain carries one of the oligosaccharides shown in FIG. 33A.

Also provided herein is a recombinant anti-CD2 antibody, wherein the antibody is an IgG antibody that has been expressed in a mammalian cell and wherein the antibody has been treated with an endoglycosidase. In certain embodiments, the mammalian cell is an NS0 murine myeloma cell, a PER.C6® human cell, or a Chinese Hamster Ovary (CHO) cell. In certain embodiments, the endoglycosidase is EndoS2. In certain embodiments, the amino acid residues of N18, K55, and T59 of human CD2 determine the affinity of said antibody to human CD2.

In certain embodiments, the ability of the antibody to mediate antibody-dependent cellular cytotoxicity is reduced or eliminated while the immune regulatory activity of the antibody is maintained. In a further embodiment, said immune regulatory activity can include induction of CD4+/CD25+ T cells. In a further embodiment, said immune regulatory activity can include increased FoxP3 expression. In a further embodiment, said immune regulatory activity can include suppression of CD69+ NK cells. In certain embodiments, the antibody is an IgG1, an IgG2, or an IgG4. In a further embodiment, the antibody is humanized. In an even further embodiment, the antibody is fully human.

In certain embodiments, the antibody can comprise a heavy chain variable region CDR 1 of SEQ ID NO:3, a heavy chain variable region CDR 2 of SEQ ID NO:4, a heavy chain variable region CDR 3 of SEQ ID NO:5, a light chain variable region CDR 1 of SEQ ID NO:6, a light chain variable region CDR 2 of SEQ ID NO:7, and a light chain variable region CDR 3 of ID NO:8. In a further embodiment, the antibody Fc region has a point mutation resulting in Fc silencing. In a further embodiment, the antibody is an IgG1. In a further embodiment, the antibody is an IgG2. In a further embodiment, the antibody is an IgG4. In yet a further embodiment, the antibody has a different native constant region than siplizumab. In yet a further embodiment, the antibody has a different native constant region than siplizumab and a point mutation in the Fc region resulting in Fc silencing.

In a certain embodiment, the heavy chain variable region of the antibody comprises the amino acid sequence of SEQ ID NO:1 or an amino acid sequence that is at least 80%, 85%, 90%, 95%, 98%, or 99% identical to the amino acid sequence of SEQ ID NO:1; and wherein the light chain variable region comprises the amino acid sequence of SEQ ID NO:2 or an amino acid sequence that is at least 80%, 85%, 90%, 95%, 98%, or 99% identical to the amino acid sequence of SEQ ID NO:2.

In certain embodiments, the sequence of the heavy chain constant region of the CD2-binding molecule (or anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 09, 10, 11, 12, or 13. In certain embodiments, the sequence of the light chain constant region of the CD2-binding molecule (or anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 14 or 15.

In still a further embodiment, the heavy chain of the antibody comprises the DNA sequence of SEQ ID NO:16 or a DNA sequence that is at least 80%, 85%, 90%, 95%, 98%, or 99% identical to the DNA sequence of SEQ ID NO:16; and wherein the light chain comprises the DNA sequence of SEQ ID NO:17 or a DNA sequence that is at least 80%, 85%, 90%, 95%, 98%, or 99% identical to the DNA sequence of SEQ ID NO:17.

Provided herein is a pharmaceutical formulation comprising the antibody of any one of the preceding claims. In a certain embodiment, said pharmaceutical formulation is suitable for chronic administration. Also provided herein are methods of treating a chronic disorder of the immune system in a patient, wherein the method comprises administering to the patient the antibody described herein. In certain embodiments, the patient is being treated for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, or at least 20 years.

Provided herein are methods of maintaining immune tolerance to a transplant in a transplant recipient, wherein the method comprises administering to the transplant recipient the antibody described herein. In certain embodiments, the antibody is administered to the transplant recipient for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, or at least 20 years. In further embodiments, the acute or chronic disorder of the immune system can include, but is not limited to, graft-versus-host disease (GVHD), rheumatoid arthritis, ankylosing spondylitis, type-1 diabetes mellitus, psoriasis, ulcerative colitis, inflammatory bowel disease (Crohn's disease), celiac disease, Sjögren's disease, lupus, multiple sclerosis, focal segmental glomerulosclerosis, atopic dermatitis, amyotrophic lateral sclerosis, primary biliary cirrhosis, and primary sclerosing cholangitis, and severe asthma.

Provided herein is a method of treating or preventing an immune related disorder or disease in a subject by (a) administering an anti-CD2 antibody or an antigen-binding fragment thereof to the subject; and (b) administering a CTLA-4 co-stimulation blockade to the subject. In some embodiments, the anti-CD2 antibody or an antigen-binding fragment thereof is administered prior to, concurrently with, or after the CTLA-4 co-stimulation blockade is administered to the subject. In some embodiments, the subject is resistant to a treatment of the immune-related disorder or disease. In some embodiments, the subject is a treatment-naïve subject.

In some embodiments, a dose of the anti-CD2 antibody or antigen-binding fragment thereof is not therapeutically effective when the CTLA-4 co-stimulation blockade is not administered to the subject. In some embodiments, a dose of the CTLA-4 co-stimulation blockade is not therapeutically effective when the anti-CD2 antibody or antigen-binding fragment thereof is not administered to the subject.

In some embodiments, administration of the anti-CD2 antibody or antigen-binding fragment thereof and the CTLA-4 co-stimulation blockade to the subject is synergistic in comparison to the administration of one of, but not both, the anti-CD2 antibody or antigen-binding fragment thereof or the CTLA-4 co-stimulation blockade to the subject. In some embodiments, the number of cells in a biological sample obtained from the subject after both the anti-CD2 antibody or antigen-binding fragment thereof and the CTLA-4 co-stimulation blockade are administered to the subject is about or at least about 10% lower as compared to the number of cells in a biological sample obtained from the subject after the anti-CD2 antibody or antigen-binding fragment thereof or after the CTLA-4 co-stimulation blockade, but not both, is administered to the subject.

In some embodiments, a method provided herein results in a greater decrease in the number of cells in a biological sample obtained from the subject after both the anti-CD2 antibody or antigen-binding fragment thereof and the CTLA-4 co-stimulation blockade are administered to the subject as compared to a decrease in the number of cells in a biological sample obtained from the subject prior to at least one of the anti-CD2 antibody or antigen-binding fragment thereof and/or the CTLA-4 co-stimulation blockade is administered to the subject. In some embodiments, the number of cells in the biological sample obtained from the subject is lower by about or at least about 10%, 15%, 20%, 25%, 30%, 35%, 40%, 45%, 50%, 55%, 60%, 65%, 70%, 75%, 80%, 85%, 90%, 100%, or more than 100%.

In some embodiments, a method provided herein results in a greater decrease in the level of CD2 in a biological sample obtained from the subject after both the anti-CD2 antibody or antigen-binding fragment thereof and the CTLA-4 co-stimulation blockade are administered to the subject as compared to a decrease in the level of CD2 in a biological sample obtained from the subject prior to at least one of the anti-CD2 antibody or antigen-binding fragment thereof and/or the CTLA-4 co-stimulation blockade is administered to the subject. In some embodiments, a method provided herein results in a greater decrease in the level of CD2 in a biological sample obtained from the subject after both the anti-CD2 antibody or antigen-binding fragment thereof and the CTLA-4 co-stimulation blockade are administered to the subject as compared to a decrease in the level of CD2 in a biological sample obtained from the subject after the anti-CD2 antibody or antigen-binding fragment thereof or after the CTLA-4 co-stimulation blockade, but not both, is administered to the subject. In some embodiments, the decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%.

In some embodiments, administration of the anti-CD2 antibody or antigen-binding fragment thereof and the CTLA-4 co-stimulation blockade results in a greater decrease in alloimmune response in the subject in comparison to a decrease in alloimmune response after the administration of one of, but not both, the anti-CD2 antibody or to the administration of the CTLA-4 co-stimulation blockade to the subject. In some embodiments, the greater decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%. In some embodiments, the alloimmune response is determined using an in vitro human T cell proliferation assay or a mixed lymphocyte reaction (MLR) assay.

In some embodiments, the anti-CD2 antibody or an antigen-binding fragment thereof comprises is an Fc-silent anti-CD2 antibody, BTI-322, CB.219, LO-CD2b, siplizumab, and/or an antigen-binding fragment thereof. In some embodiments, the anti-CD2 antibody or an antigen-binding fragment thereof comprises (a) a heavy chain variable region CDR 1 of SEQ ID NO: 3; (b) a heavy chain variable region CDR 2 of SEQ ID NO: 4; (c) a heavy chain variable region CDR 3 of SEQ ID NO: 5; (d) a light chain variable region CDR 1 of SEQ ID NO: 6; (e) a light chain variable region CDR 2 of SEQ ID NO: 7; and (d) a light chain variable region CDR 3 of SEQ ID NO: 8. In some embodiments, the antibody is a humanized antibody. In some embodiments, the antibody is siplizumab.

In some embodiments, the CTLA-4 co-stimulation blockade is a fusion protein comprising the Fc fragment of a human IgG1 immunoglobulin and the extracellular domain of CTLA-4. In some embodiments, the CTLA-4 co-stimulation blockade comprises a sequence that is about or at least about 80%, 85%, 90%, 95%, 98%, 99%, or 100% identical to SEQ ID NO:22. In some embodiments, the CTLA-4 co-stimulation blockade comprises a sequence that is identical to SEQ ID NO:22. In some embodiments, the CTLA-4 co-stimulation blockade comprises a sequence that is about or at least about 80%, 85%, 90%, 95%, 98%, 99%, or 100% identical to SEQ ID NO:23. In some embodiments, the CTLA-4 co-stimulation blockade comprises a sequence that is identical to SEQ ID NO:23. In some embodiments, the CTLA-4 co-stimulation blockade is abatacept. In some embodiments, the CTLA-4 co-stimulation blockade is belatacept.

In some embodiments, the immune related disorder or disease is systemic lupus erythematosis, rheumatoid arthritis, psoriatic arthritis, polyarticular juvenile idiopathic arthritis (JIA), osteoarthritis, juvenile chronic arthritis, a spondyloarthropathy, systemic sclerosis, an idiopathic inflammatory myopathy, Sjögren's syndrome, systemic vasculitis, sarcoidosis, autoimmune hemolytic anemia, pernicious anemia, autoimmune thrombocytopenia, thyroiditis, diabetes mellitus, immune-mediated renal disease, a demyelinating disease of the central or peripheral nervous system, idiopathic demyelinating polyneuropathy, Guillain-Barre syndrome, lyme disease, a chronic inflammatory demyelinating polyneuropathy, a hepatobiliary disease, infectious or autoimmune chronic active hepatitis, primary biliary cirrhosis, Goodpasture syndrome, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, contact dermatitis, psoriasis, an allergic disease, asthma, allergic rhinitis, atopic dermatitis, food hypersensitivity, urticaria, multiple sclerosis, uveitis, an immunologic disease of the lung, eosinophilic pneumonia, idiopathic pulmonary fibrosis, hypersensitivity pneumonitis, a disease associated with an organ transplant, disease associated with a tissue transplant, graft rejection, graft-versus-host-disease, Devic's disease, acute disseminated encephalomyelitis, acute demyelinating optic neuritis, demyelinative transverse myelitis, Miller-Fisher syndrome, encephalomyelradiculoneuropathy, acute demyelinative polyneuropathy, tumefactive multiple sclerosis, Balo's concentric sclerosis, alopecia areata, ankylosing spondylitis, meniere's disease, antiphospholipid syndrome, mixed connective tissue disease, autoimmune addison's disease, myasthenia gravis, autoimmune hepatitis, pemphigus vulgaris, behcet's disease, bullous pemphigoid, polyarthritis nodosa, cardiomyopathy, polychondritis, celiac sprue-dermatitis, polyglandular syndromes, chronic fatigue syndrome (cfids), polymyalgia rheumatica, chronic inflammatory demyelinating, polymyositis and dermatomyositis, primary agammaglobulinemia, churg-strauss syndrome, cicatricial pemphigoid, crest syndrome, raynaud's phenomenon, cold agglutinin disease, reiter's syndrome, crohn's disease, rheumatic fever, discoid lupus, essential mixed cryoglobulinemia, fibromyalgia, scleroderma, grave's disease, sjogren's syndrome, stiff-man syndrome, hashimoto's thyroiditis, takayasu arteritis, temporal arteritis/giant cell arteritis, idiopathic thrombocytopenia purpura (ITP), ulcerative colitis, IgA nephropathy, insulin dependent diabetes (type I), lichen planus, vitiligo, or any combination thereof. In some embodiments, the immune related disorder or disease is rheumatoid arthritis, polyarticular juvenile idiopathic arthritis (JIA), psoriatic arthritis, or a combination thereof.

In some embodiments, the immune related disorder or disease is a disease associated with an organ transplant, a disease associated with a tissue transplant, or a combination thereof. In some embodiments, the anti-CD2 antibody or antigen-binding fragment thereof is administered to the subject at least once within two weeks after the organ and/or tissue transplant. In some embodiments, the anti-CD2 antibody or antigen-binding fragment thereof is administered to the subject on the day of the organ and/or tissue transplant, on day 1 after the organ and/or tissue transplant and/or on day 4 after the organ and/or tissue transplant. the anti-CD2 antibody or antigen-binding fragment thereof is administered intravenously or subcutaneously to the subject.

In some embodiments, a method of treatment provided herein further comprises administering an additional agent to the subject. In some embodiments, the additional agent is an immunosuppressant agent. In some embodiments, the additional agent is one or more of a steroid, a calcineurin inhibitor, a cyclosporine, a cyclophosphamide, an antimetabolite therapy, NSAID, an agent used for treating rheumatoid arthritis, and/or an mTOR inhibitor. In some embodiments, the additional agent is basiliximab induction, mycophenolate mofetil, corticosteroids, or a combination thereof.

4. BRIEF DESCRIPTION OF THE FIGURES

The foregoing and other objects, features, and advantages will be apparent from the following description of particular embodiments of the invention, as illustrated in the accompanying drawings. The drawings are not necessarily to scale, emphasis instead being placed upon illustrating the principles of various embodiments of the invention.

FIG. 1 shows the lack Fc γ receptor (FcγR) IIIA signaling induced by CD2-binding molecule 1 (a deglycosylated CD2-binding molecule) as compared to the Fc-RIIIA signaling of anti-CD2 Ab1 (e.g., siplizumab (MEDI-507)). In vivo, cells expressing FcγRIIIA are the main mediators of antibody-dependent cellular cytotoxicity (ADCC). Without Fc-RIIIA-binding and signaling, CD2-expressing cells bound by CD2-binding molecule 1 will not be depleted via ADCC.

Figure 5:
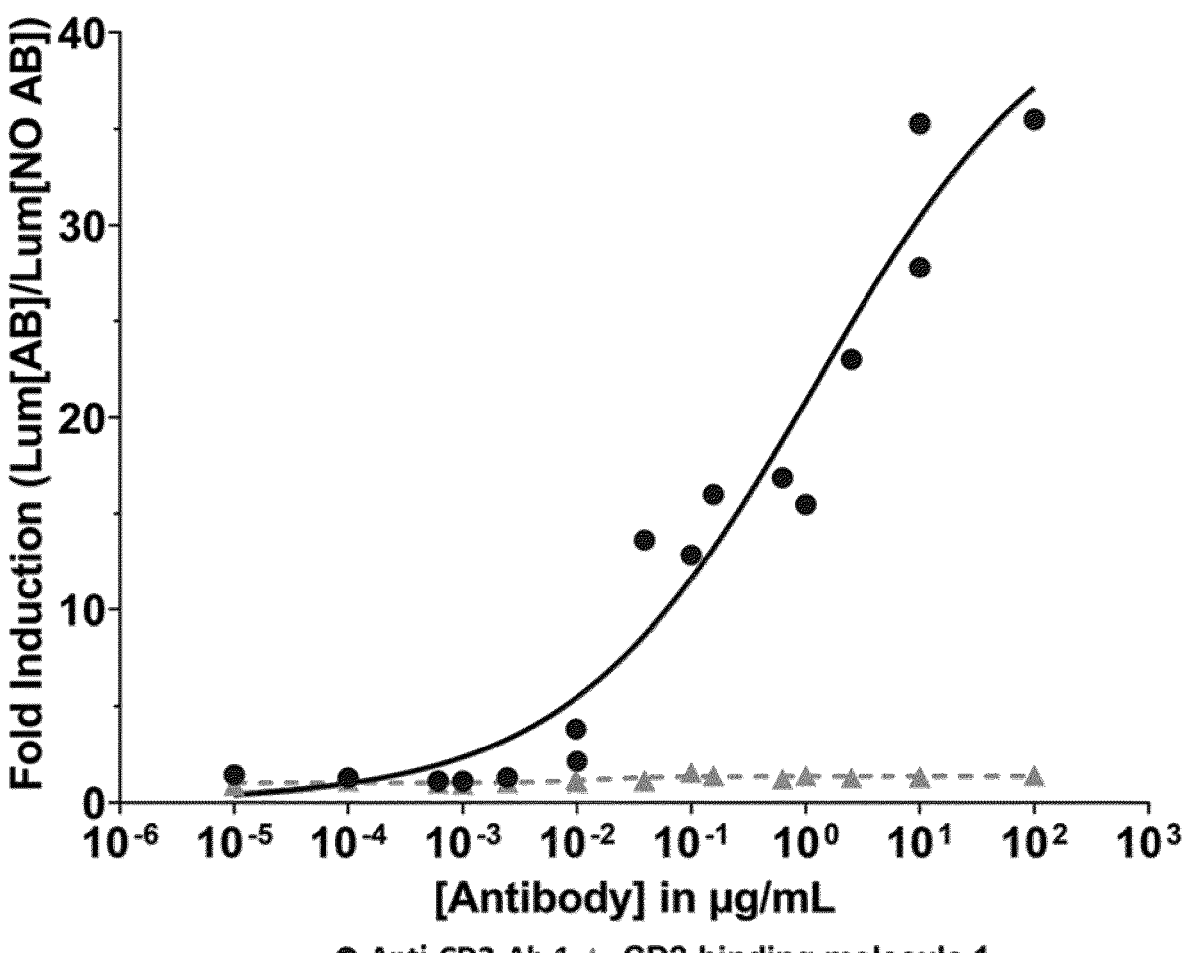

FIG. 5 shows the lack of Fc γ receptor (FcγR) HA signaling induced by CD2-binding molecule 1 (a deglycosylated CD2-binding molecule) as compared to the FcγRIIA signaling of anti-CD2 Ab1 (e.g., siplizumab (MEDI-507)). In vivo, cells expressing FcγRIIA are the main mediators of antibody-dependent cell phagocytosis (ADCP). Without FcγRIIA-binding and signaling, CD2-expressing cells bound by CD2-binding molecule 1 will likely not be depleted via ADCP.

Figure 6:
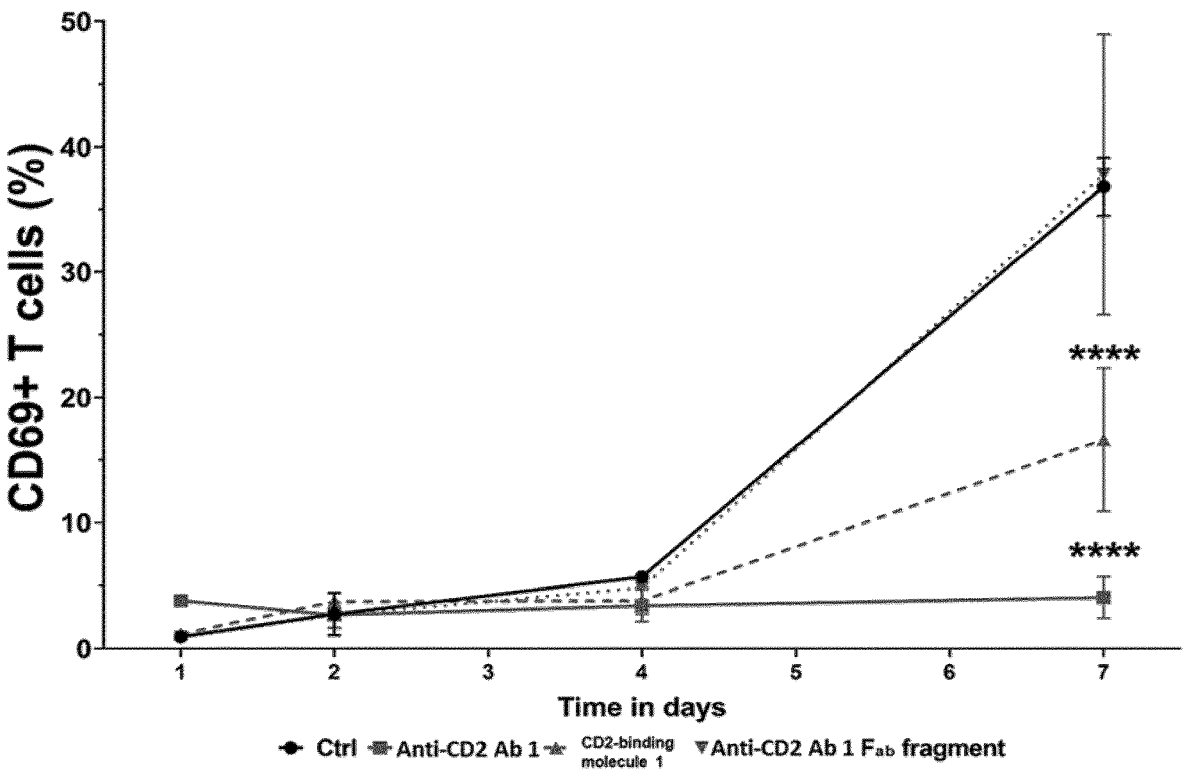

FIG. 6 shows the immunomodulatory activity of the antibodies and fragments as measured by their ability to inhibit the activation of CD69+ T cells. The anti-CD2 Ab1 (e.g., siplizumab) Fab fragment did not inhibit activation of CD69+ T cells compared to control while both the anti-CD2 Ab1 (e.g., siplizumab) and CD2-binding molecule 1 (a deglycosylated CD2-binding molecule) inhibited activation. The immune regulatory activity of CD2-binding molecule 1 is maintained while the ADCC activity is eliminated.

Figure 7:
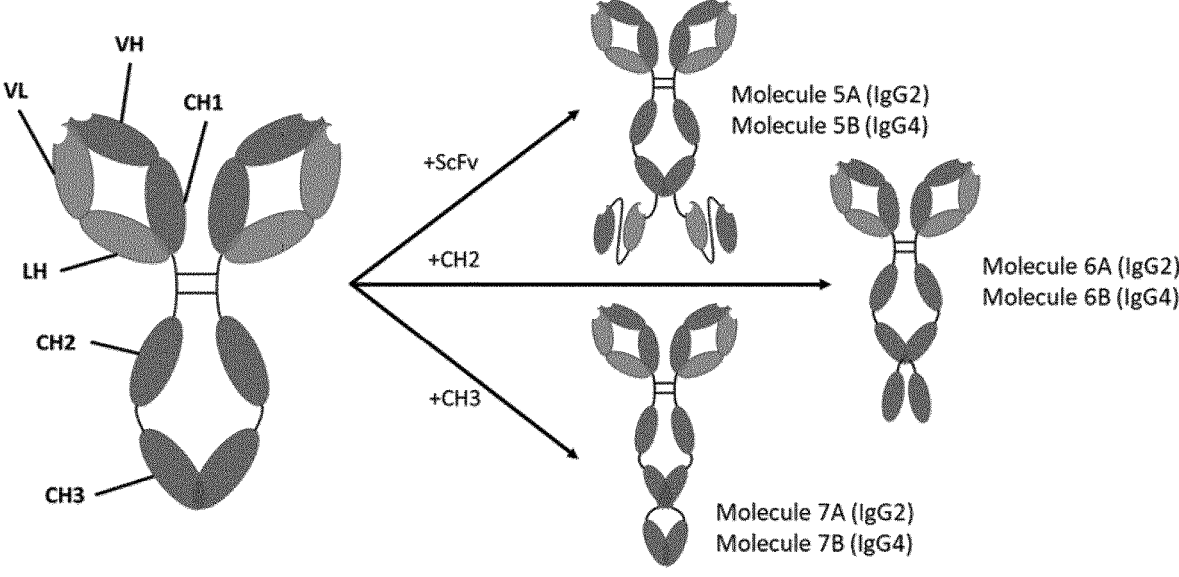

FIG. 7 shows the construction of enlarged anti-CD2 variants by adding either scFv, CH2-, or CH3-regions to the Fc portion of genetically engineered IgG2 or IgG4 versions of Siplizumab (IgG1).

Figure 8:
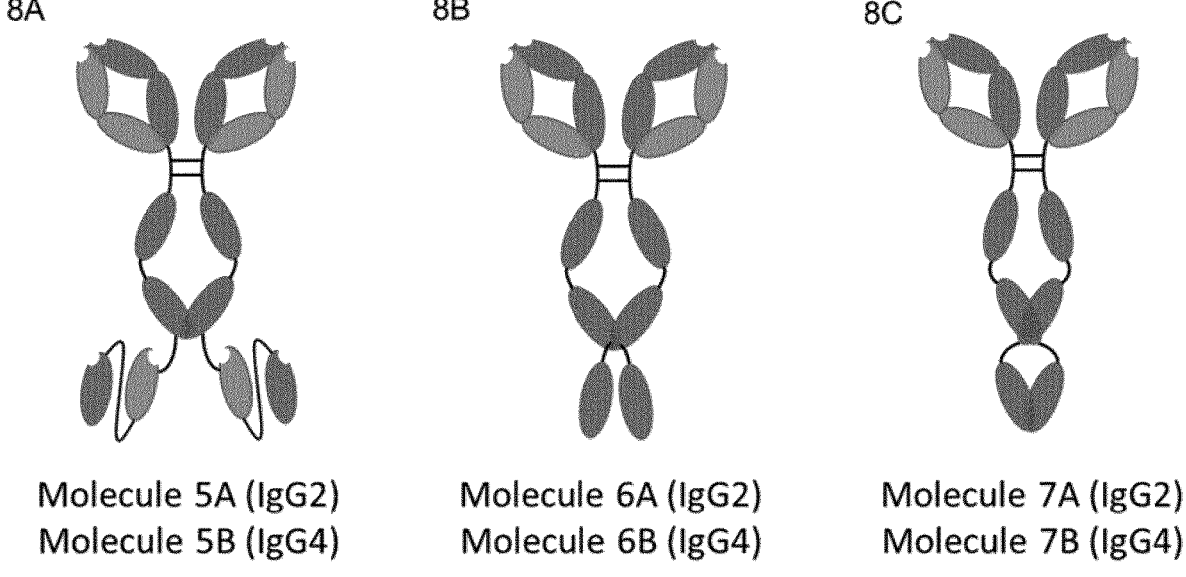

FIG. 8A-8C is an illustration of the enlarged anti-CD2 variants. FIG. 8A illustrates Molecule 5A (IgG2) and Molecule 5B (IgG4). FIG. 8B illustrates Molecule 6A (IgG2) and Molecule 6B (IgG4). FIG. 8C illustrates Molecule 7A (IgG2) and Molecule 7B (IgG4).

FIGS. 9A-9C show Jurkat reporter cells (Promega) stably expressing Fc γ receptor (FcγR) I (FIG. 9A), FcγRIIA (FIG. 9B), or FcγRIIIA (FIG. 9C), respectively, were incubated with increasing concentrations of anti-CD2 antibody. Data normalized to luminescence induced by the highest concentration of anti-CD2 Ab1 (e.g., siplizumab) (mean±SD; n=3). Reporter cells bind the Fc-fragment of a target-bound IgG antibody with their FcγR which induces expression of a luciferase reporter gene resulting in a luminescence signal upon addition of assay substrate (Promega). Cells were incubated with increasing doses of anti-CD2 Ab1 (e.g., siplizumab), CD2-binding molecule 1 (a deglycosylated CD2-binding molecule), CD2-binding molecule 2 (Fc-silent (FcS) anti-CD2 IgG1), CD2-binding molecule 3 (FcS anti-CD2 IgG2) and CD2-binding molecule 4 (FcS anti-CD2 IgG4), respectively.

FIGS. 10A-10B show CD2 expression on different lymphocyte (sub-)populations. Data displayed as average median fluorescence intensity±SEM (n=5; *p<0.05, p<0.01). FIG. 10A shows CD2 expression on different T and NK cell subpopulations. CD56$^{bright}$ NK cells express CD2 at levels comparable to that of T cells. In contrast, CD56$^{dim}$ and CD56$^{neg}$ NK cells express significantly lower levels of CD2 (p=0.0074 and p=0.0111, respectively, repeated-measure one-way ANOVA followed by Dunnett's multiple comparison test). FIG. 10B** shows CD2 expression on resting and activated lymphocyte populations. CD2 expression was markedly upregulated after activation on T cells (p=0.0034), CD56$^{dim}$ NK cells (p=0.0024), CD56$^{bright}$ NK cells (p=0.017) and CD56$^{neg}$ CD16+ NK cells (0.0029). No difference was observed on B Cells (two-tailed paired t-test).

FIGS. 11A-11B show expression of Fc gamma receptor (FcγR) II (CD32) and FcγRIII (CD16) on NK cells. On average 91.0% of NK cells express FcγRIII while 19.2% express FcγRII (n=9). Mean shown as horizontal line (FIG. 11A). Representative plot of FcγRII and FcγRIII expression on NK cells (CD3– CD56+ and/or CD16+ lymphocytes). Upper shows representative plots of NK cells from donor with relatively low CD32 expression and lower shows representative plots of NK cells from donor with relatively high CD32 expression. (FIG. 11B).

FIGS. 12A-12B show CD69 expression on NK cells in mixed lymphocyte reaction (MLR) and autologous lymphocyte culture (ALC) over time. CD69 Expression without addition of antibody (No antibody) and with added antibody was assessed at baseline (day 0) and after one, two, four and seven days by flow cytometry. Significance testing was conducted via two-way ANOVA with untreated controls (no antibody) serving as the comparison data set (*p<0.05, p<0.01, *p<0.001, **p<0.0001). Anti-CD2 Ab1 (e.g., siplizumab) and CD2-binding molecule 1 (a deglycosylated CD2-binding molecule) were used at 10 μg/mL, a dose which has previously determined to saturate target antigen over seven days. Data displayed as mean±SD (n=12). FIG. 12A shows the percentage of CD69+ NK cells in MLR over time. FIG. 12B** shows percentage of CD69+ NK cells in ALC over time.

Figure 13:
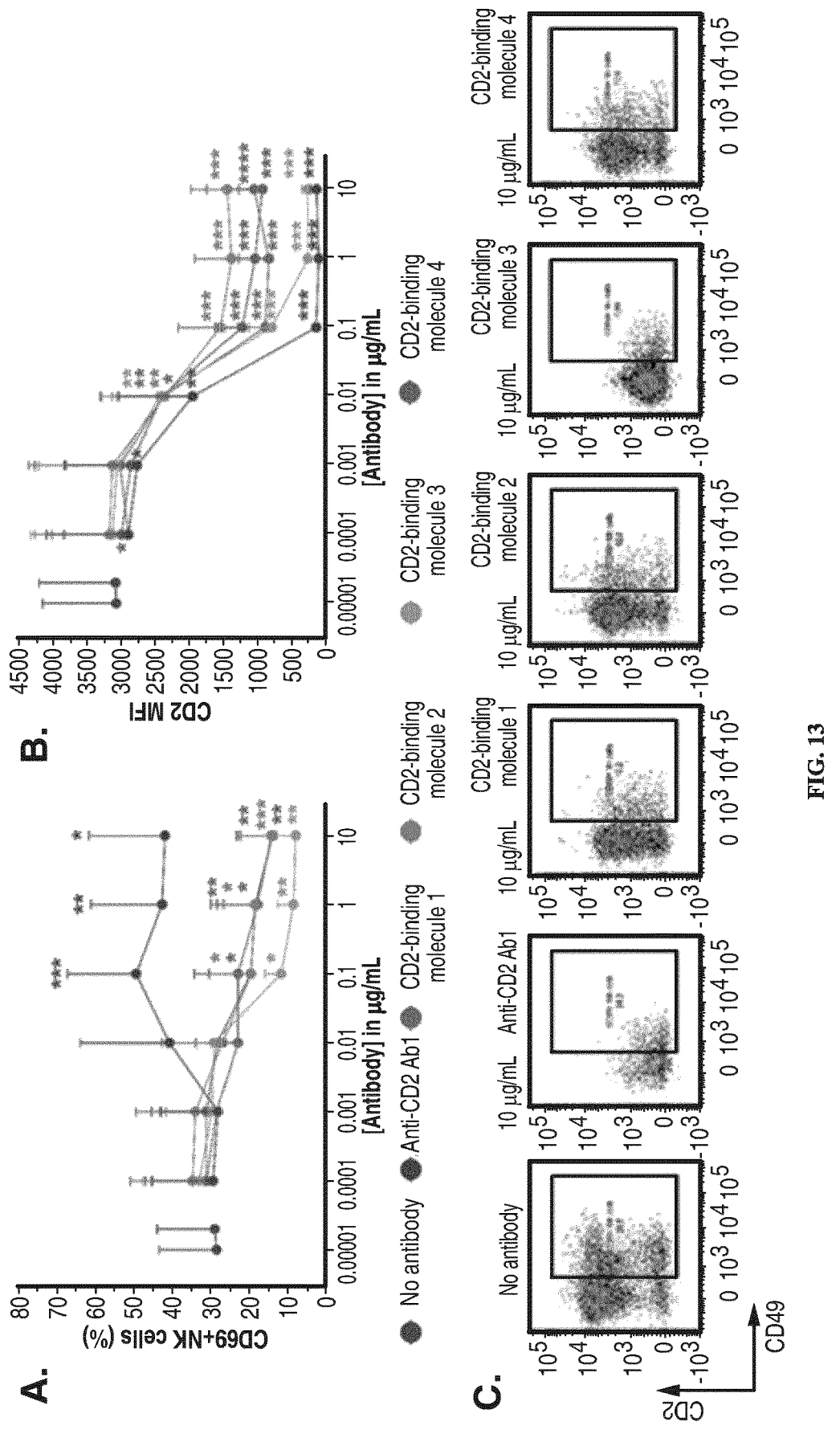

FIGS. 13A-13C show CD69 and CD2 expression on NK cells after seven days of mixed lymphocyte reaction (MLR). Significance testing was conducted via one-way ANOVA with untreated controls (no antibody) serving as the comparison data set (*p<0.05, p<0.01, *p<0.001, **p<0.0001). Anti-CD2 Ab1 (e.g., siplizumab), CD2-binding molecule 1 (a deglycosylated CD2-binding molecule), CD2-binding molecule 2 (Fc-silent (FcS) anti-CD2 IgG1), CD2-binding molecule 3 (FcS anti-CD2 IgG2) and CD2-binding molecule 4 (FcS anti-CD2 IgG4) were used at 0.0001-10 μg/mL. Data displayed as mean percentage of CD69+ NK cells f SD (FIG. 13A) or average median CD2 fluorescence intensity+SD (CD2 MFI; n=9) (FIG. 13B). Representative dot plots of CD2 and CD69 expression on NK cells in untreated controls (no antibody) or 10 μg/mL anti-CD2 (FIG. 13C**).

FIGS. 14A-14D show NK cell fratricide. Purified NK cells were incubated with no antibody, 0.001-10 μg/mL anti-CD2 Ab1 (e.g., siplizumab) or 0.001-10 μg/mL CD2-binding molecule 2, 3, or 4 (FcS anti-CD2 IgG antibodies) overnight. Significance testing was conducted via one-way ANOVA with untreated controls (no antibody) serving as the comparison data set (N=6; *p<0.05, p<0.01, *p<0.001, **p<0.0001). FIG. 14A shows NK cell lysis; mean percentage of 7-AAD+ NK cells+SD. FIG. 14B shows NK cell count; mean normalized NK cell count+SD. FIG. 14C shows CD56$^{dim}$ NK cell count; mean normalized CD56$^{dim}$ NK cell count+SD. FIG. 14D** shows CD56$^{bright}$ NK cell count; mean normalized CD56$^{bright}$ NK cell count+SD.

FIGS. 15A-15C show NK cell degranulation and ADCC in purified NK cell culture. Purified NK cells were incubated with no antibody, 0.001-10 μg/mL anti-CD2 Ab1 (e.g., siplizumab), or 0.001-10 μg/mL of CD2-binding molecule 2, 3, or 4 (FcS anti-CD2 IgG antibodies). Significance testing was conducted via one-way ANOVA with untreated controls (no antibody) serving as the comparison data set (N=6; *p<0.05, p<0.01, *p<0.001). FIG. 15A shows NK cell degranulation; mean percentage of CD107a+ NK cells+SD. FIG. 15B shows CD16 expression on NK cells; average median CD16 fluorescence intensity+SD on NK cells. FIG. 15A shows representative heatmap dot plots illustrating CD16 downregulation and NK cell degranulation with increasing doses of anti-CD2 Ab1 (e.g., siplizumab) in purified NK cell culture.

FIGS. 16A-16C shows natural NK cell cytotoxicity. Purified NK cells were pre-incubated no antibody, 0.001-10 μg/mL anti-CD2 Ab1 (e.g., siplizumab) or 0.001-10 μg/mL of CD2-binding molecule 2, 3, or 4 (Fc-silent (FcS) anti-CD2 IgG antibodies) for 30 minutes (FIG. 16A) or two days (FIG. 16B) followed by addition of HLA class I-target cells (SPI-801). Significance testing was conducted via one-way ANOVA with untreated controls (no antibody) serving as the comparison data set (N=6; *p<0.05, p<0.01, *p<0.001). FIG. 16C shows representative histograms of NK cell degranulation in response to HLA class I-target cells without addition of antibody (NK+SPI-801), without addition of antibody and HLA class I-target cells (NK) or in the presence of anti-CD2 Ab1 (e.g., siplizumab)/CD2-binding molecule 2 (FcS anti-CD2 IgG1).

Figure 17:
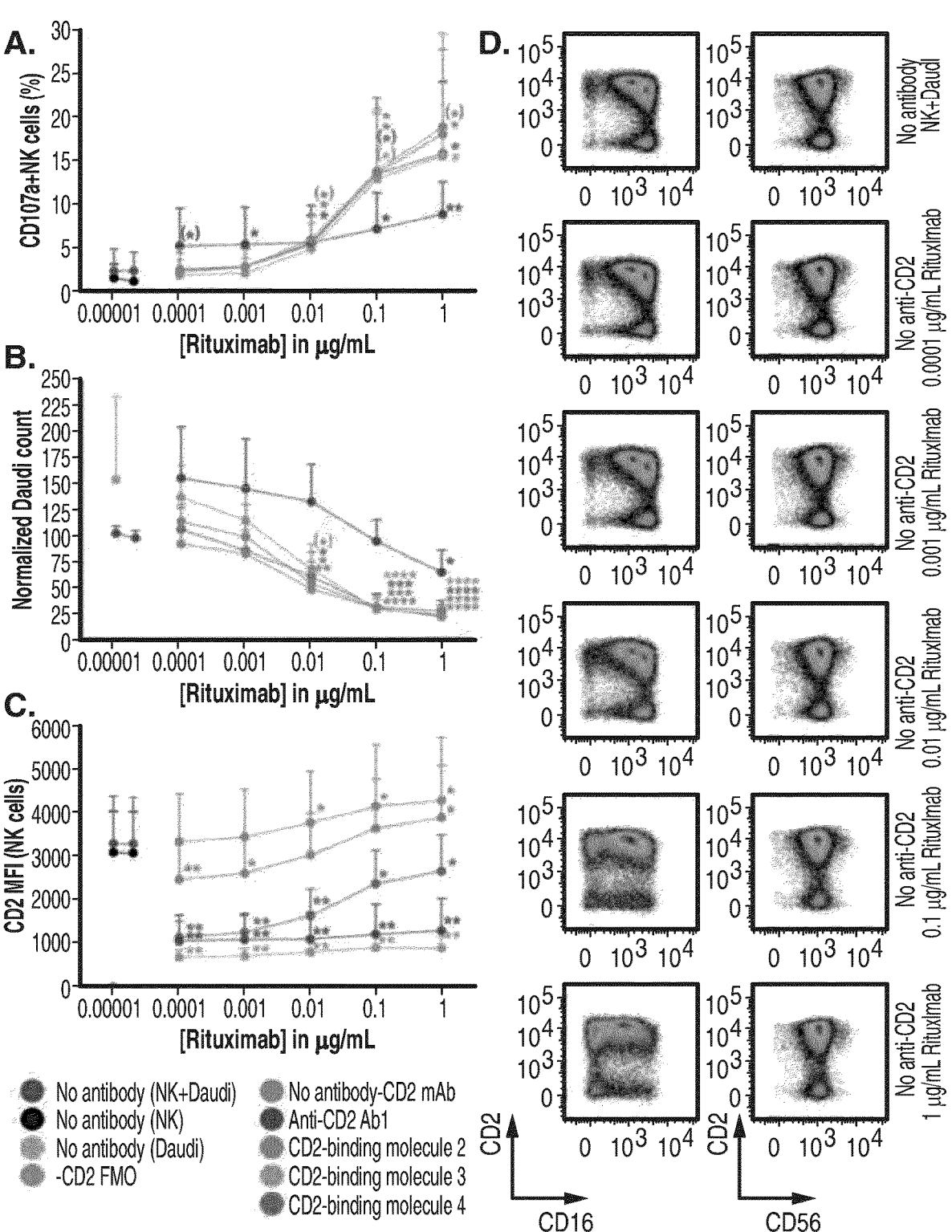

FIGS. 17A-17D show antibody-dependent cytotoxicity. Purified NK cells were pre-incubated no antibody or saturating doses of anti-CD2 Ab1 (e.g., siplizumab)/CD2-binding molecule 2, 3, or 4 (FcS anti-CD2 antibodies) before addition of titrated doses of anti-CD2 Ab1 (e.g., siplizumab) and CD20+ target cells (Daudi). Significance testing was conducted via one-way ANOVA with untreated controls (no antibody) serving as the comparison data set (N=6; (*) p<0.1, *p<0.05, p<0.01, *p<0.001, **p<0.0001). FIG. 17A shows NK cell degranulation; mean percentage of CD107a+ NK cells+SD. FIG. 17B shows target cell depletion; mean normalized target cell count+SD. FIG. 17C shows CD2 expression; average median CD2 fluorescence intensity+SD on NK cells. FIG. 17D** shows representative dot plots illustrating increased CD2 expression on NK cells resulting ADCC induction.

FIGS. 18A-18H show mean T cell (CD4 and CD8) proliferation after cells were incubated for 7 days or 10 days with a control, anti-CD2 antibody 1, belatacept, abatacept, a combination of anti-CD2 antibody 1 and belatacept, or a combination of anti-CD2 antibody 1 and abatacept. The graphs in FIGS. 18A-18H show mean percentage of proliferated T cells in mixed lymphocyte reaction (MLR)+ standard deviation (SD) (n=6). FIGS. 18A and 18E show the mean CD4 T cell proliferation after seven days of mixed lymphocyte reaction (MLR); FIGS. 18B and 18F show the mean CD8 T cell proliferation after seven days of MLR; FIGS. 18C and 18G show the mean CD4 T cell proliferation after 10 days of MLR; and FIGS. 18D and 18H show the mean CD8 T cell proliferation after 10 days of MLR. MLRs were supplemented with increasing concentrations of abatacept ($1×10^{-7}$ to 100 μg/mL), belatacept ($1×10^{-7}$ to 100 μg/mL), and anti-CD2 antibody 1 ($5.08×10^{-5}$ to 1 μg/mL). Titration series of anti-CD2 antibody 1 ($5.08×10^{-5}$ to 1 μg/mL) were supplemented with 100 μg/mL abatacept or 100 μg/mL belatacept. Statistical analysis was conducted via one-way ANOVA followed by Dunnett's multiple comparison test with untreated controls (no antibody) as the comparison data set (*p<0.05, p<0.01, *p<0.001, ****p<0.0001). Treatment with a combination of anti-CD2 antibody 1 and belatacept or a combination of anti-CD2 antibody 1 and abatacept resulted in a lower percentage of live cells as compared to treatment with belatacept or abatacept alone.

Figures 19E, 19F, 19G, 19H:
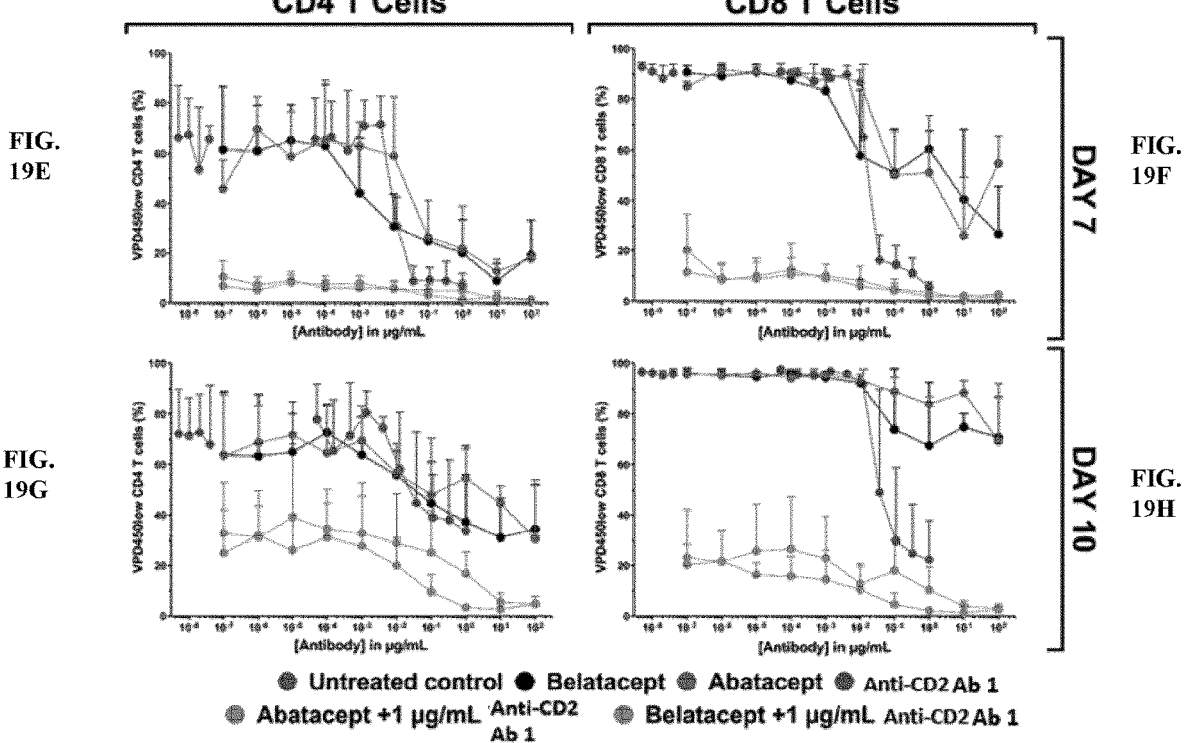

FIGS. 19A-19H show mean T cell (CD4 and CD8) proliferation after cells were incubated for 7 days or 10 days with a control, anti-CD2 antibody 1, belatacept, abatacept, a combination of anti-CD2 antibody 1 and belatacept, or a combination of anti-CD2 antibody 1 and abatacept. The graphs in FIGS. 19A-19D show mean percentage of proliferated T cells in MLR+SD (n=9). FIGS. 19A and 19E show the mean CD4 T cell proliferation after seven days of mixed lymphocyte reaction (MLR); FIGS. 19B and 19F show the mean CD8 T cell proliferation after seven days of MLR; FIGS. 19C and 19G show the mean CD4 T cell proliferation after 10 days of MLR; and FIGS. 19D and 19H show the mean CD8 T cell proliferation after 10 days of MLR. MLRs were supplemented with increasing concentrations of abatacept ($1\times10^{-7}$ to 100 µg/mL), belatacept ($1\times10^{-7}$ to 100 µg/mL), and anti-CD2 antibody 1 ($5.08\times10^{-5}$ to 1 µg/mL). Titration series of abatacept or belatacept ($1\times10^{-7}$ to 100 µg/mL) were supplemented with 1 µg/mL anti-CD2 antibody 1 throughout the entire titration series. Statistical analysis was conducted via one-way ANOVA followed by Dunnett's multiple comparison test with untreated controls (no antibody) as the comparison data set ($^{*}p<0.05$, $^{}p<0.01$, $^{*}p<0.001$, $^{****}p<0.0001$).

Figure 20:
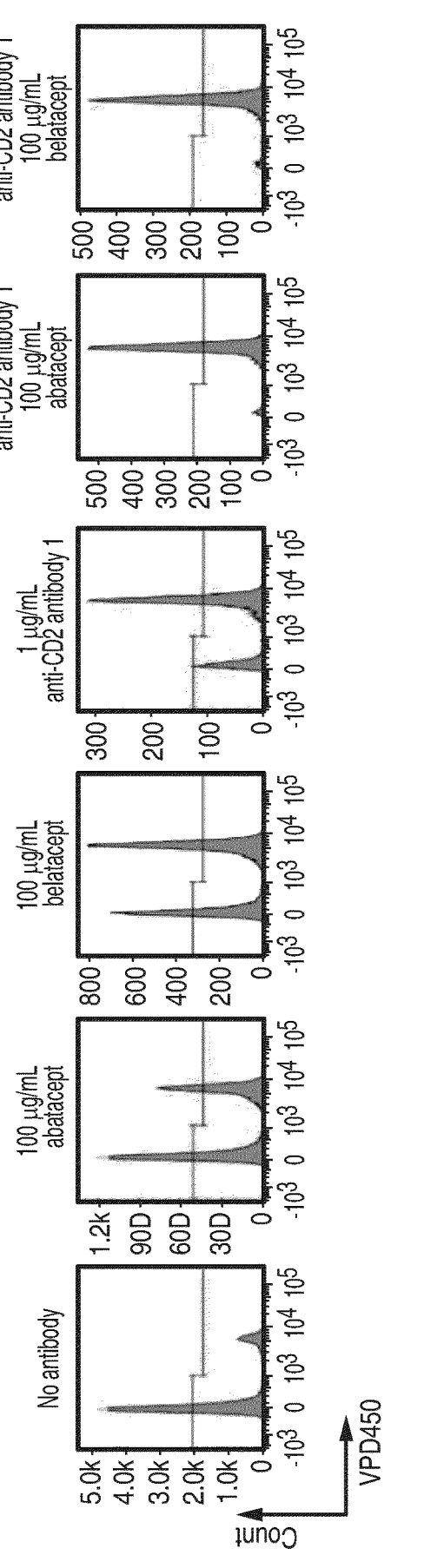

FIG. 20 shows representative histograms showing inhibition of CD4 T cell proliferation after 10 days of MLR in different treatment groups.

Figure 21:
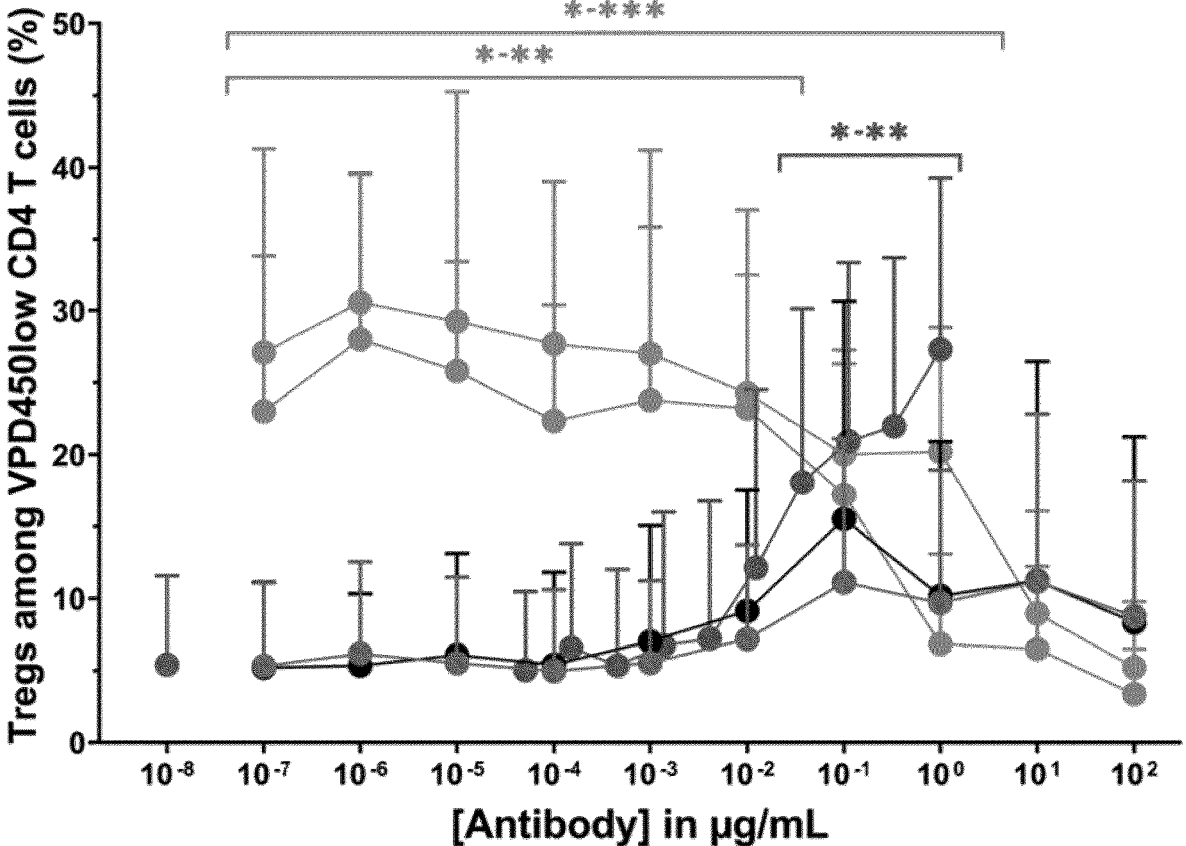

FIG. 21 shows a graph representing regulatory T cell (Treg) enrichment. MLRs were supplemented with increasing concentrations of abatacept ($1\times10^{-7}$ to 100 µg/mL), belatacept ($1\times10^{-7}$ to 100 µg/mL) and anti-CD2 antibody 1 ($5.08\times10^{-7}$ to 1 µg/mL). Titration series of abatacept or belatacept ($1\times10^{-7}$ to 100 µg/mL) were supplemented with 1 µg/mL anti-CD2 antibody 1 throughout the entire titration series. Statistical analysis was conducted via one-way ANOVA followed by Dunnett's multiple comparison test with untreated controls (no antibody) as the comparison data set ($^{*}p<0.05$, $^{}p<0.01$, $^{*}p<0.001$).

Figures 22A, 22B:
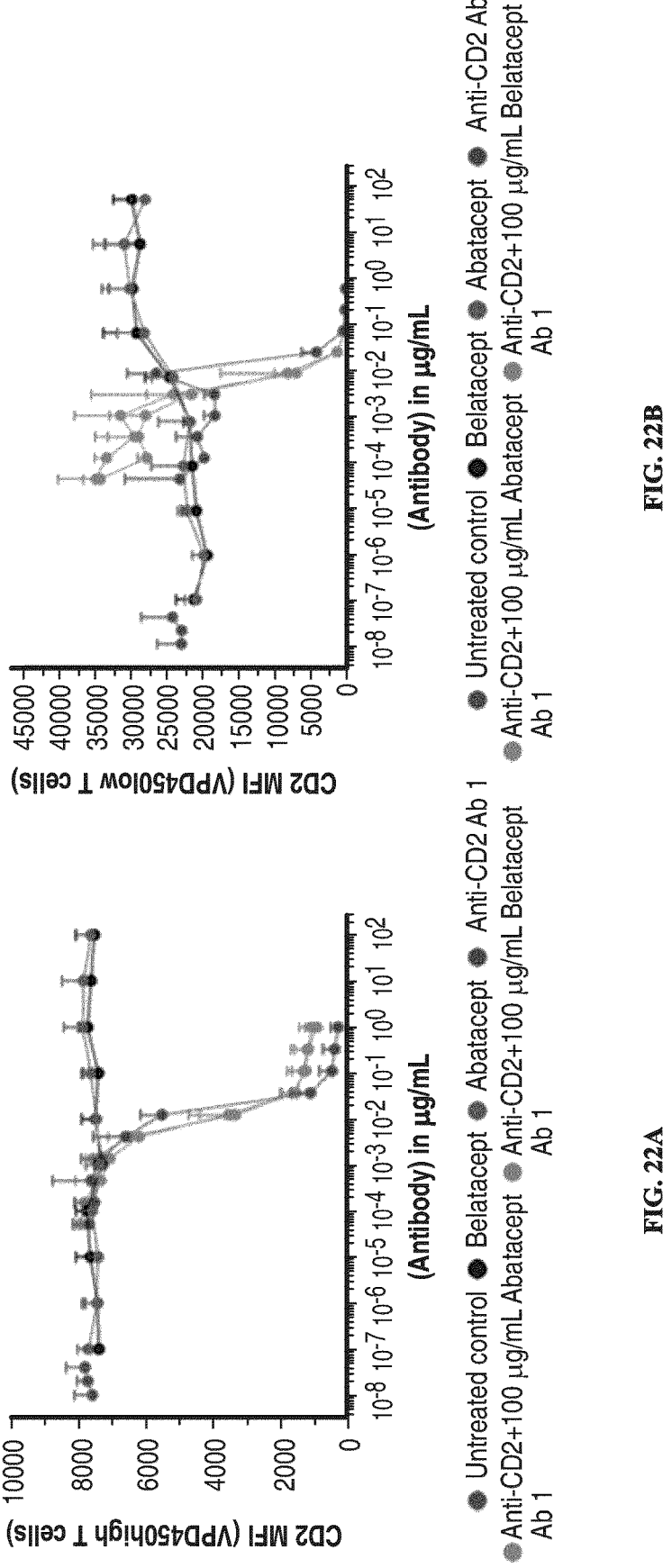
Figures 24A, 24B, 24C, 24D:
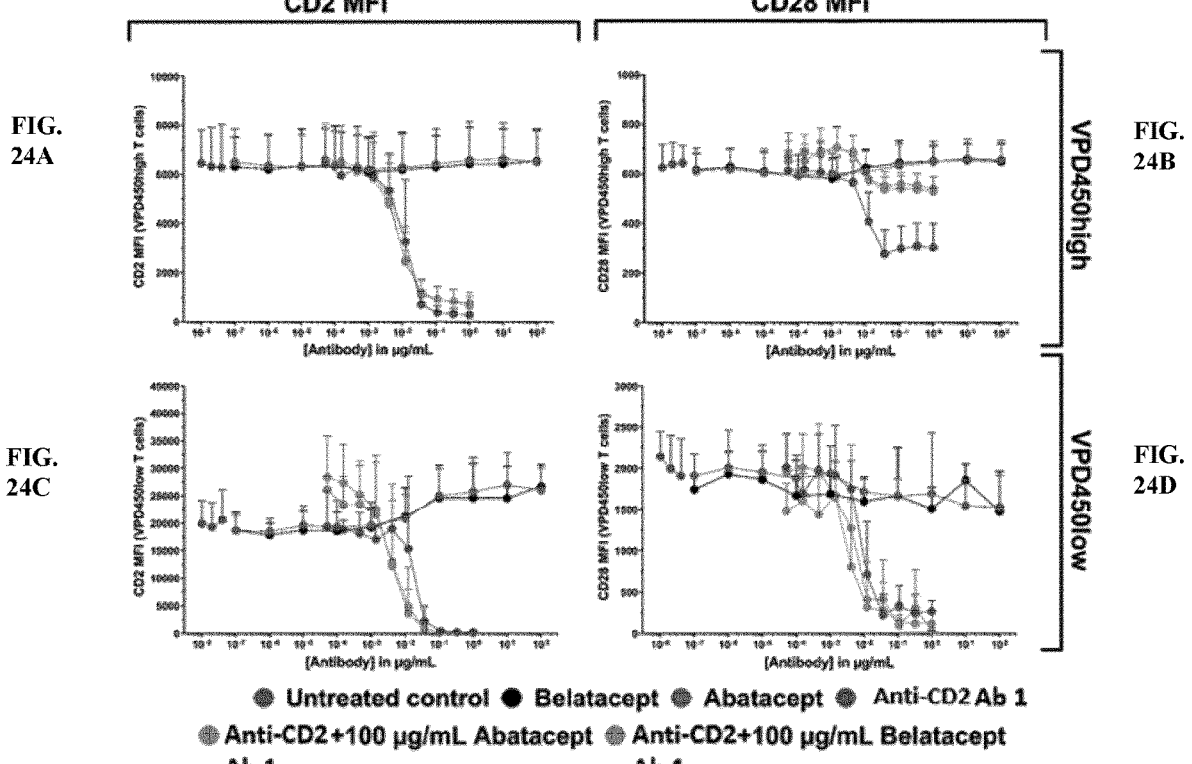
Figures 27C, 27D:
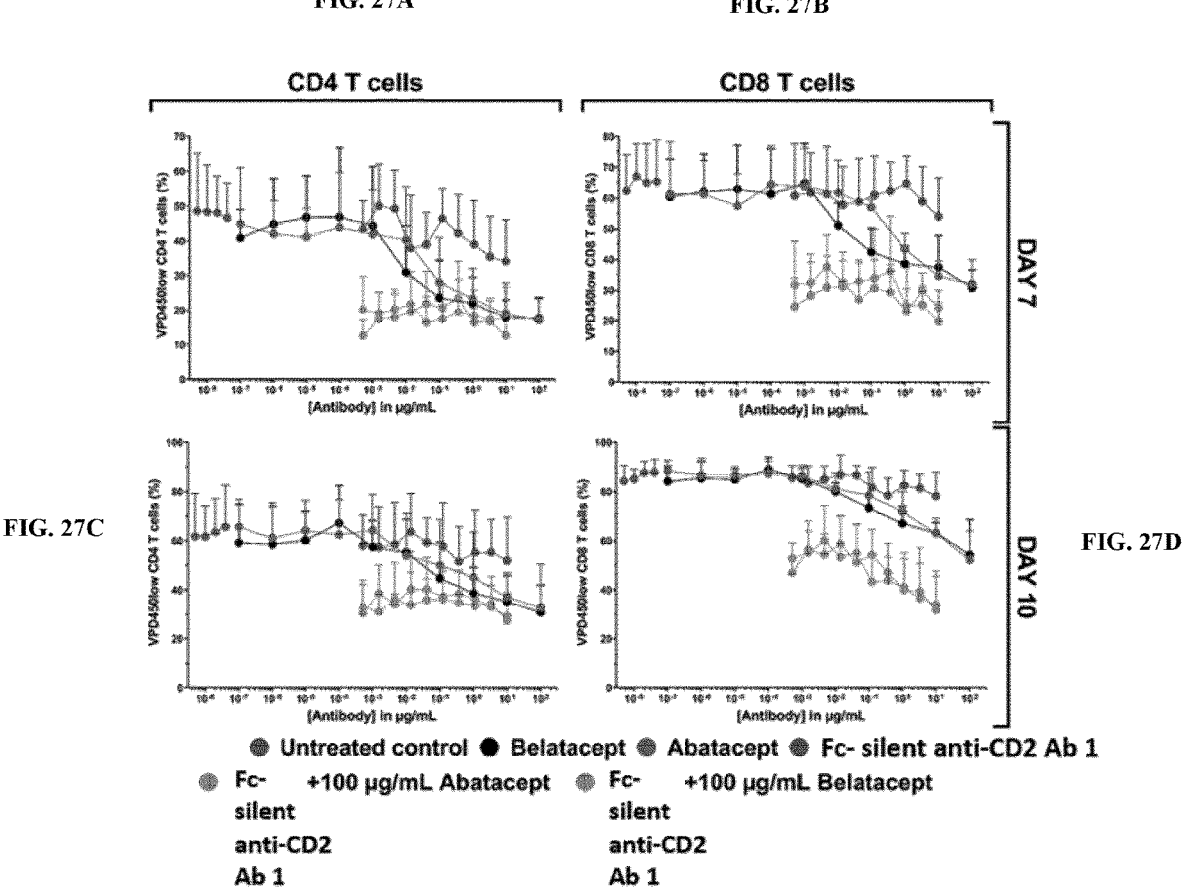

FIGS. 22A-22B show the average level CD2 after cells were incubated for 7 days or 10 days with a control, anti-CD2 antibody 1, belatacept, abatacept, a combination of anti-CD2 antibody 1 and belatacept, or a combination of anti-CD2 antibody 1 and abatacept. Treatment with a combination of anti-CD2 antibody 1 and belatacept or a combination of anti-CD2 antibody 1 and abatacept resulted in lower levels of CD2 as compared to treatment with belatacept or abatacept alone.

FIGS. 23A-23D show the number of T cells after cells were incubated for 7 days or 10 days with a control, anti-CD2 antibody 1, belatacept, abatacept, a combination of anti-CD2 antibody 1 and belatacept, or a combination of anti-CD2 antibody 1 and abatacept. Treatment with a combination of anti-CD2 antibody 1 and belatacept or a combination of anti-CD2 antibody 1 and abatacept resulted in a lower number of cells as compared to treatment with belatacept or abatacept alone.

FIGS. 24A-24D show the average level of CD2 or CD28 after cells were incubated with a control, anti-CD2 antibody 1, belatacept, abatacept, a combination of anti-CD2 antibody 1 and belatacept, or a combination of anti-CD2 antibody 1 and abatacept. Treatment with a combination of anti-CD2 antibody 1 and belatacept or a combination of anti-CD2 antibody 1 and abatacept resulted in lower levels of CD2 and CD28 as compared to treatment with belatacept or abatacept alone.

FIGS. 25A-25F show flow cytometry graphs using Violet Proliferation Dye 450 (VPD450) low T cells after cells were incubated with a control, anti-CD2 antibody 1, belatacept, abatacept, a combination of anti-CD2 antibody 1 and belatacept, or a combination of anti-CD2 antibody 1 and abatacept.

FIGS. 26A-26G show flow cytometry graphs using Violet Proliferation Dye 450 (VPD450) high T cells after cells were incubated with a control, anti-CD2 antibody 1, belatacept, abatacept, a combination of anti-CD2 antibody 1 and belatacept, or a combination of anti-CD2 antibody 1 and abatacept.

FIGS. 27A-27D show mean T cell (CD4 and CD8) proliferation after cells were incubated for 7 days or 10 days with a control, Fc-silent anti-CD2 (IgG4), belatacept, abatacept, a combination of Fc-silent anti-CD2 antibody 1 (IgG4) and belatacept, or a combination of Fc-silent anti-CD2 antibody 1 (IgG4) and abatacept. Treatment with a combination of Fc-silent anti-CD2 antibody 1 and belatacept or a combination of Fc-silent anti-CD2 antibody 1 and abatacept resulted in a lower percentage of cells as compared to treatment with belatacept or abatacept alone.

FIG. 28 shows a cell-based FcγR binding assay. Different concentrations of antibodies such as anti-CD2 antibody (or siplizumab), Fc silent anti-CD2 Ab-1, Fc silent anti-CD2 Ab-2, Fc silent anti-CD2 Ab-3, Fc silent anti-CD2 Ab-4, Fc silent anti-CD2 Ab-5, Fc silent anti-CD2 Ab-6, or Fc silent anti-CD2 Ab-7) were tested for FcγRI, FcγRIIA, and FcγRIIIA binding assays.

Figure 29A:
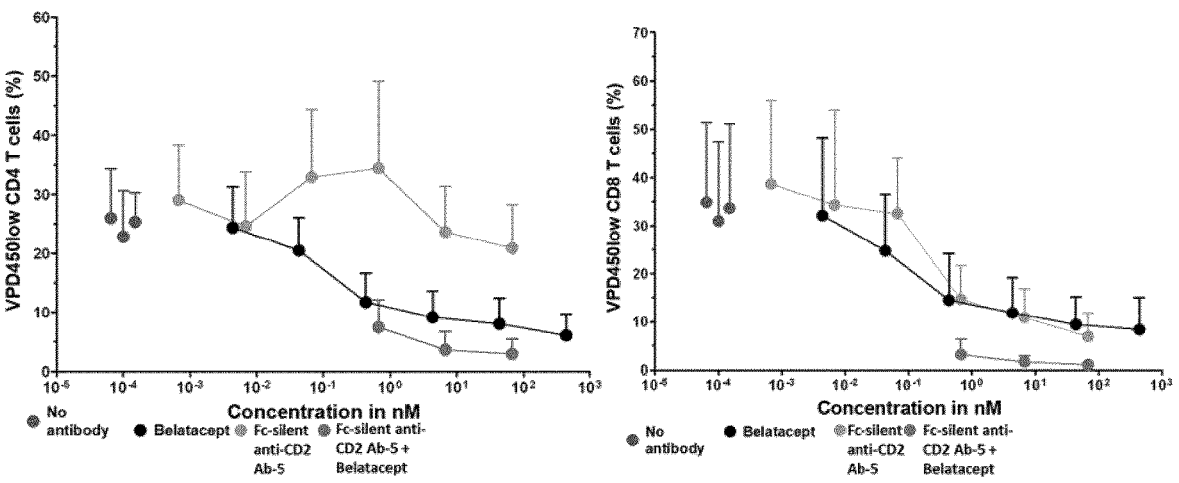
Figure 29B:
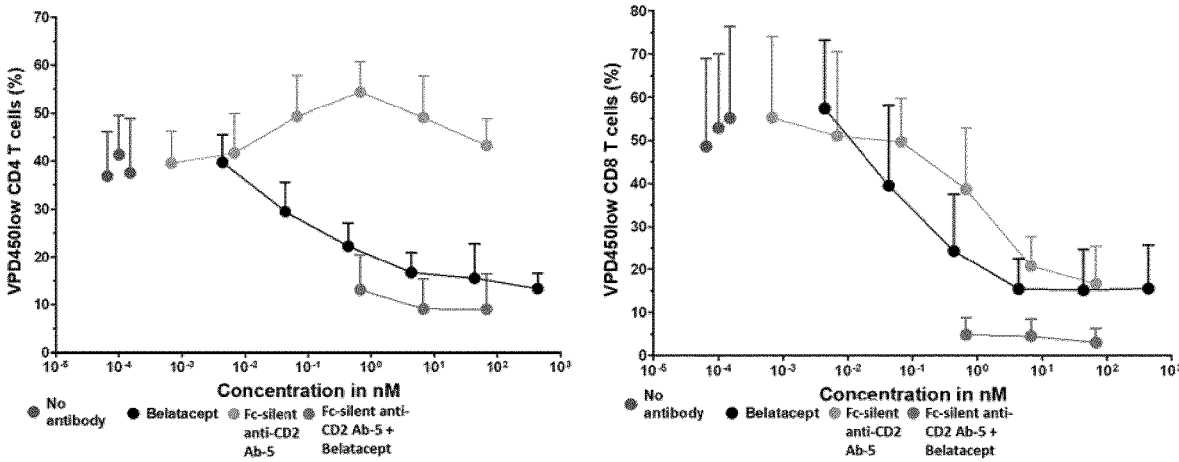

FIGS. 29A-29B show mean T cell (CD4 and CD8) proliferation after cells were incubated for 7 days (FIG. 29A) or 10 days (FIG. 29B) with a control, Fc silent anti-CD2 Ab-5, belatacept, or a combination of Fc silent anti-CD2 Ab-5 and belatacept (n=6; three independent MLRs).

Figure 30A:
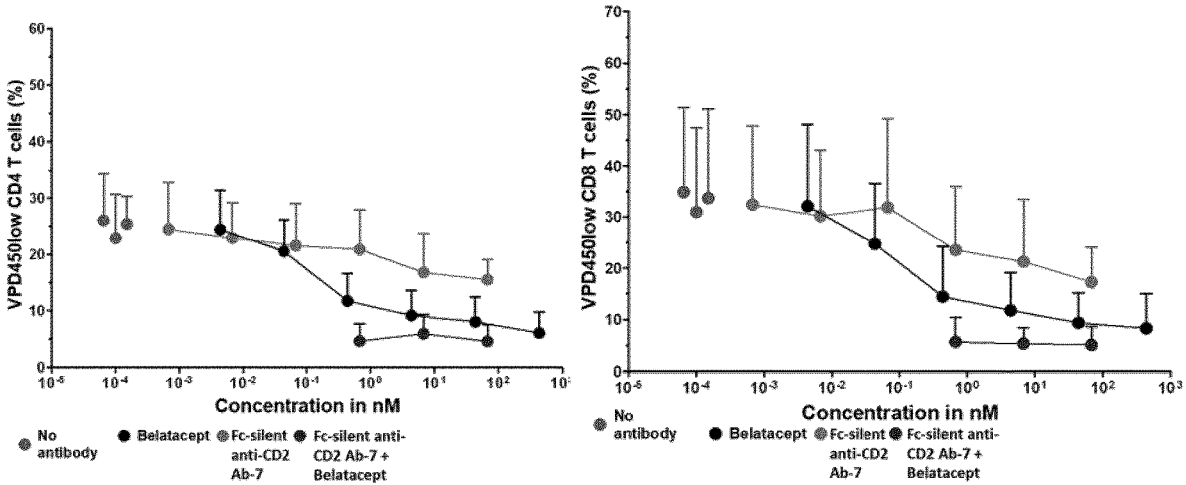
Figure 30B:
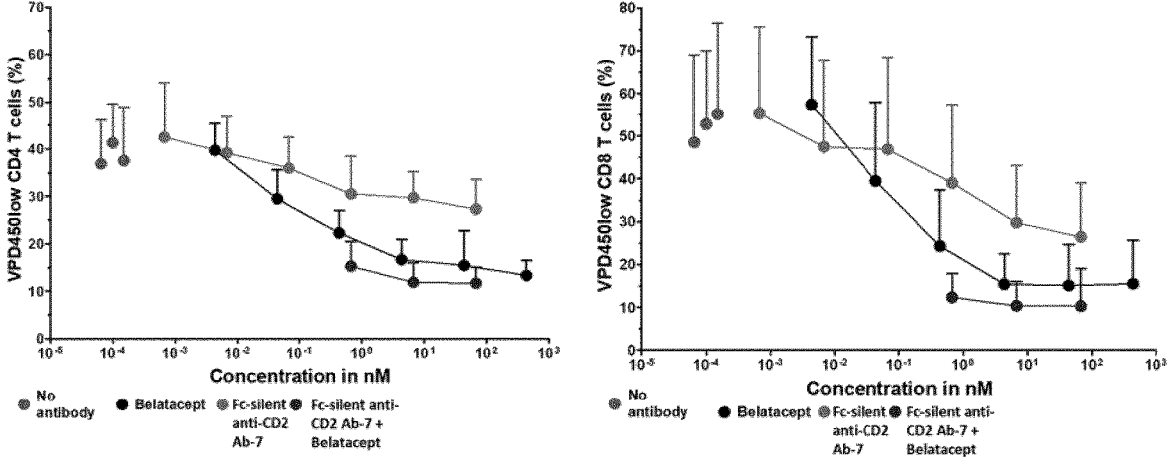

FIGS. 30A-30B show mean T cell (CD4 and CD8) proliferation after cells were incubated for 7 days (FIG. 30A) or 10 days (FIG. 30B) with a control, Fc silent anti-CD2 Ab-7, belatacept, or a combination of Fc silent anti-CD2 Ab-7 and belatacept (n=6; three independent MLRs).

Figure 31A:
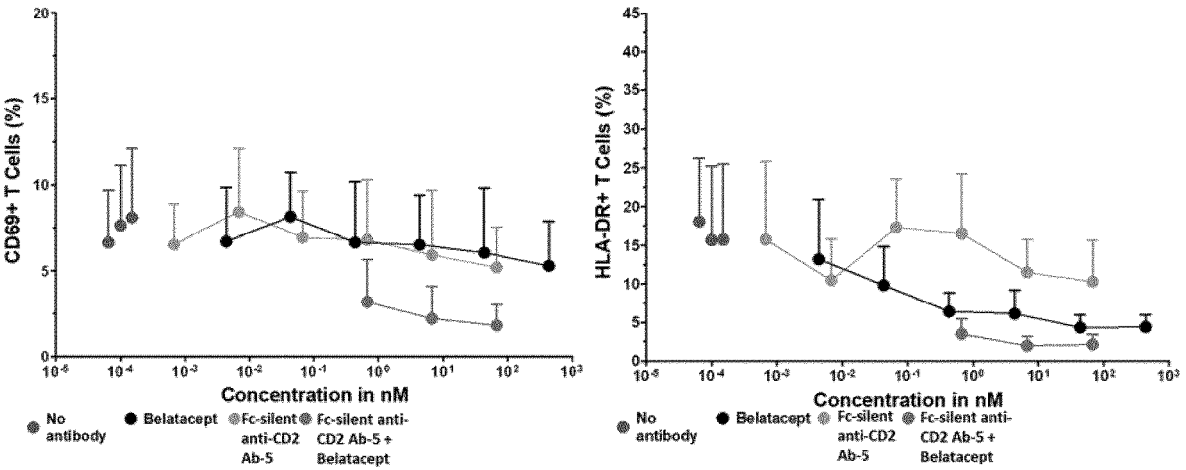
Figure 31B:
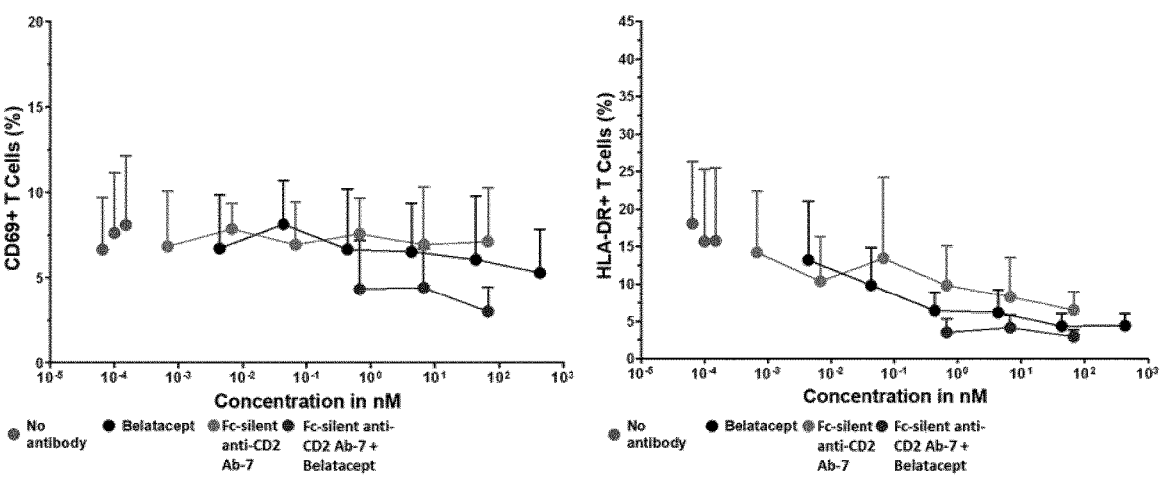

FIGS. 31A-31B show mean T cell activation (CD69+ and HLA-DR+) after cells were incubated with a control, Fc silent anti-CD2 Ab-5, belatacept, or a combination of Fc silent anti-CD2 Ab-5 and belatacept (n=6; three independent MLRs) (FIG. 31A); or with a control, Fc silent anti-CD2 Ab-7, belatacept, or a combination of Fc silent anti-CD2 Ab-7 and belatacept (n=6; three independent MLRs) (FIG. 31B).

Figure 32A:
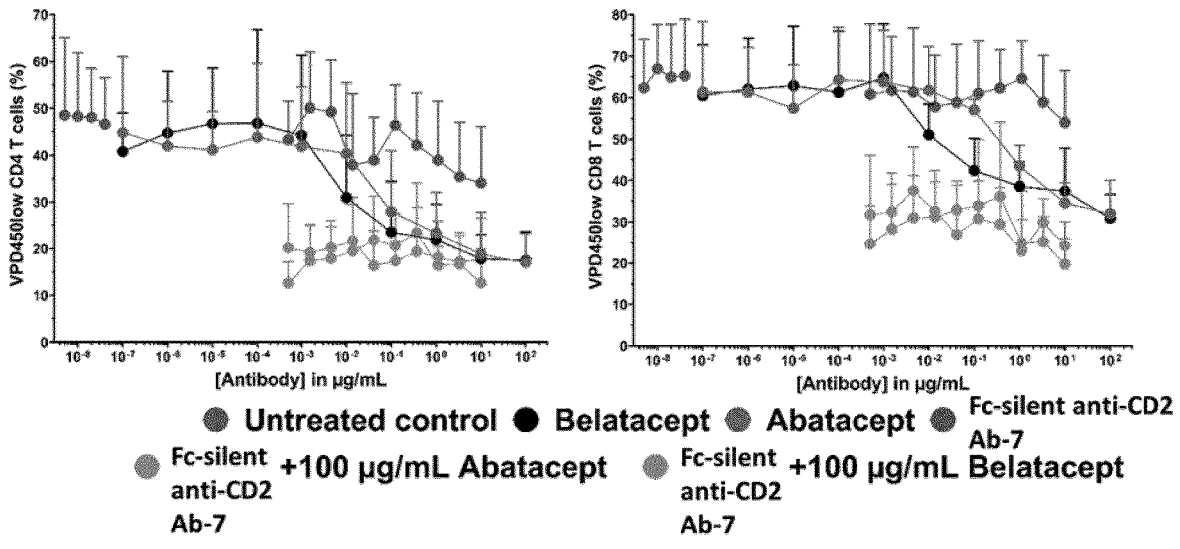
Figure 32B:
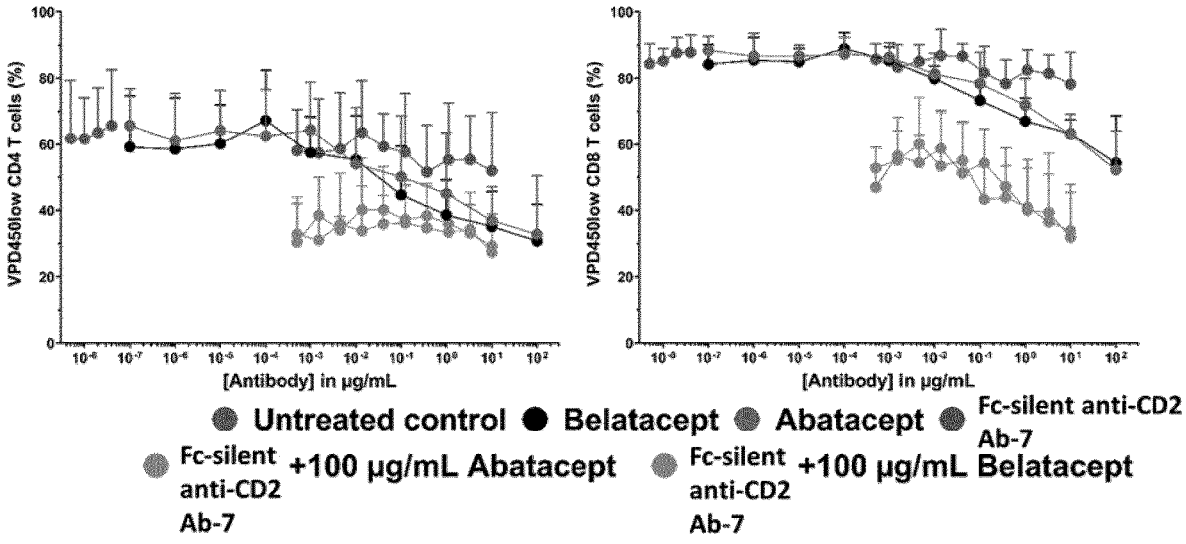

FIGS. 32A-32B show mean T cell (CD4 and CD8) proliferation after cells were incubated for 7 days (FIG. 32A) or 10 days (FIG. 32B) with a control, Fc silent anti-CD2 Ab7, belatacept, abatacept, a combination of Fc silent anti-CD2 Ab7 and belatacept, or a combination of Fc silent anti-CD2 Ab7 and abatacept. Treatment with a combination of Fc silent anti-CD2 Ab7 and belatacept or a combination of Fc silent anti-CD2 Ab7 and abatacept resulted in a lower percentage of cells as compared to treatment with belatacept alone, abatacept alone, or Fc silent anti-CD2 Ab7 alone (n=6; two independent MLRs).

Figure 33A:
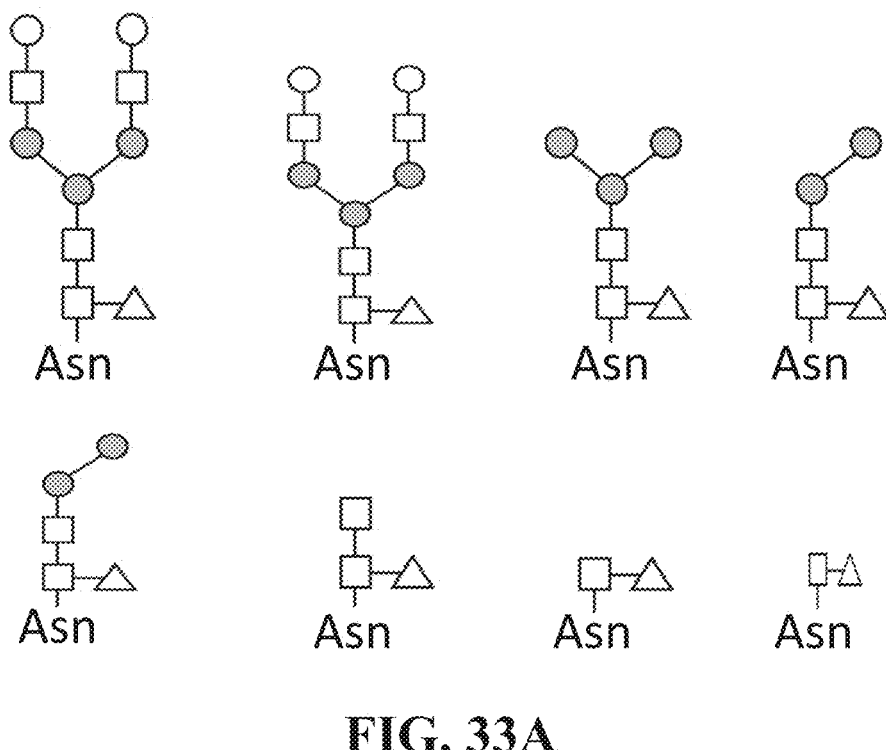
Figure 33B:
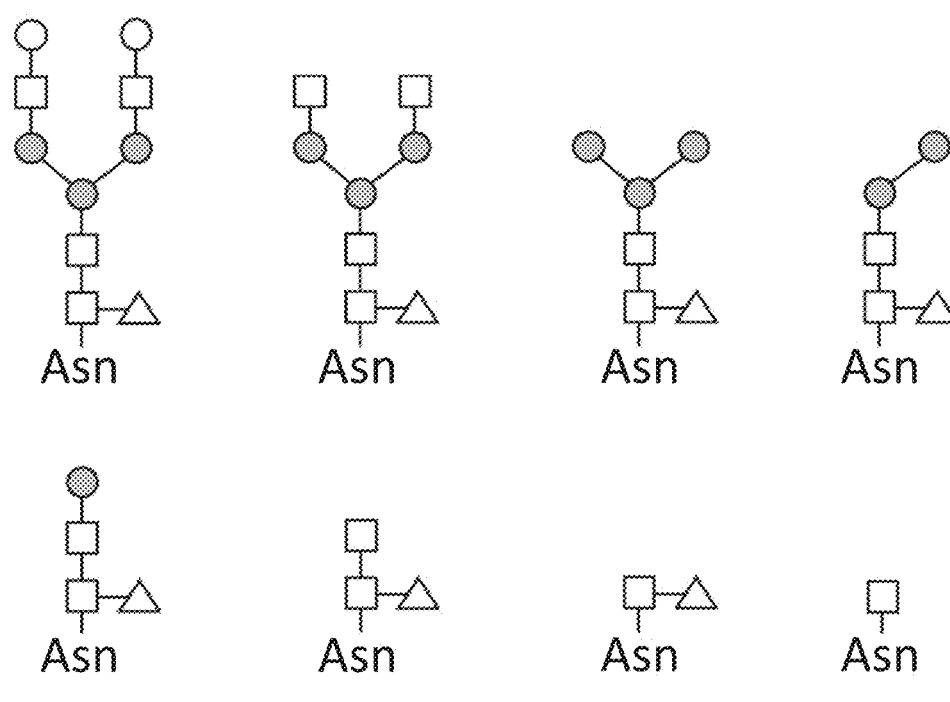

FIGS. 33A-33B depict oligosaccharides provided herein. An empty triangle represents fucose; an empty square represents N-acetylglucosamine. a grey circle represents mannose; and an empty circle represents galactose.

5. DETAILED DESCRIPTION OF THE INVENTION

Described herein is a CD2-binding molecule (or an anti-CD2 antibody or antigen binding fragment thereof) wherein the ability of the molecule to mediate antibody-dependent cellular cytotoxicity is reduced or eliminated while the immune regulatory activity of the molecule is maintained. The CD2-binding molecule (or an anti-CD2 antibody or antigen binding fragment thereof) described herein can be administered to patients long-term to treat chronic disease of the immune system or to transplant patients.

The CD2-binding molecule (or an anti-CD2 antibody or antigen binding fragment thereof) is described in Section 5.1. Specifically, the binding specificity of the CD2-binding molecule (or an anti-CD2 antibody or antigen binding fragment thereof) is described in Section 5.1.1; the immunomodulatory activity of the CD2-binding molecule (or an anti-CD2 antibody or antigen binding fragment thereof) is described in Section 5.1.3; and functional modifications of the CD2-binding molecule (or an anti-CD2 antibody or antigen binding fragment thereof) are described in Section 5.1.4. Methods for generating the CD2-binding molecule (or anti-CD2 antibody or antigen-binding fragment thereof) are described in Section 5.2. The therapeutic uses and methods of said CD2-binding molecule (or anti-CD2 antibody or antigen-binding fragment thereof) are described in Section 5.3. Pharmaceutical compositions of said CD2-binding molecule (or anti-CD2 antibody or antigen-binding fragment thereof) are described in Section 5.4. Kits are described in Section 5.5. Methods to assess clinical outcomes of the methods described herein are described in Section 5.6. Examples of the methods provided herein are described in Section 6.

5.1 CD2-Binding Molecule (or an Anti-CD2 Antibody or Antigen Binding Fragment Thereof)

The CD2-binding molecule (or an anti-CD2 antibody or antigen binding fragment thereof) described herein binds to CD2 as detailed in Section 5.1.1. As described herein, the CD2-binding molecule (or an anti-CD2 antibody or antigen binding fragment thereof) can be an antibody. As described herein, the CD2-binding molecule (or an anti-CD2 antibody or antigen binding fragment thereof) can be an antigen-binding fragment. As defined herein, an antibody refers to an immunoglobulin including IgG, IgM, IgE, IgA, and IgD. The antibody described herein can be a monoclonal antibody or a polyclonal antibody. In some embodiments the antibody can be a chimeric antibody. In some embodiments, the antibody can be a humanized antibody. In a specific embodiment, the antibody is a recombinant antibody. In a specific embodiment, the antibody is a fully human antibody. In a specific embodiment, the CD2-binding molecule (or an anti-CD2 antibody or antigen binding fragment thereof) described herein is an IgG. In a certain embodiment, the IgG can be an IgG$_1$, IgG$_2$, IgG$_3$, or an IgG$_4$. In specific embodiments, the CD2-binding molecule (or an anti-CD2 antibody or antigen binding fragment thereof) described herein is an IgG$_1$, IgG$_2$, or an IgG$_4$. As described herein, the CD2-binding molecule (or an anti-CD2 antibody or antigen binding fragment thereof) described herein can be an antigen-binding fragment. In certain embodiments, an antigen-binding fragment is, or can comprise, Fab, F(ab')$_2$, scFv (VH fused to a VL), or sdAb.

In some embodiments, the term "anti-CD2 antibody or an antigen binding fragment thereof" is used interchangeably with the term "CD2-binding molecule". In some embodiments, a CD2-binding molecule (or an anti-CD2 antibody or antigen binding fragment thereof) for use with the present methods and compositions has the CDR sequences of rat anti-CD2 monoclonal antibody BTI-322. In some embodiments, a CD2-binding molecule (or an anti-CD2 antibody or antigen binding fragment thereof) can be a humanized IgG1 version of BTI-322 (siplizumab; MEDI-507). In some embodiments, a CD2-binding molecule (or an anti-CD2 antibody or antigen binding fragment thereof) is an Fc-silent anti-CD2 antibody or an antigen-binding fragment thereof. In some embodiments, a CD2-binding molecule (or an anti-CD2 antibody or antigen binding fragment thereof) is BTI-322 or an antigen-binding fragment thereof. In some embodiments, a CD2-binding molecule (or an anti-CD2 antibody or antigen binding fragment thereof) is CB.219 or an antigen-binding fragment thereof. In some embodiments, a CD2-binding molecule (or an anti-CD2 antibody or antigen binding fragment thereof) is LO-CD2b or an antigen-binding fragment thereof. In some embodiments, a CD2-binding molecule (or an anti-CD2 antibody or antigen binding fragment thereof) is siplizumab or an antigen-binding fragment thereof. In some embodiments, a CD2-binding molecule (or an anti-CD2 antibody or antigen binding fragment thereof) is anti-CD2 antibody 1 or an antigen-binding fragment thereof. In some embodiments, the anti-CD2 antibody 1 of the disclosure is siplizumab or an antigen-binding fragment thereof. In some embodiments, the methods described herein include administering at least one, at least two, at least three, or more than at least three CD2-binding molecule (or an anti-CD2 antibody or antigen binding fragment thereof). In some embodiments, the methods described herein include administering one or more than one CD2-binding molecule (or an anti-CD2 antibody or antigen binding fragment thereof). In certain embodiments, the methods described herein include administering a CD2-binding molecule (or an anti-CD2 antibody or antigen binding fragment thereof) in combination with a CTLA-4 co-stimulation blockade to a subject.

An antibody as described herein can be comprised of two heavy and two light chains connected by a disulfide bond. Each heavy chain can comprise a variable region (VH) and a constant region. Each light chain can comprise a variable region (VL) and a constant region. The variable region of both the heavy and the light chain dictates the binding of the antibody to the antigen. The complementarity determining regions (CDRs) are variable loops on the variable regions of the heavy and light chain. There are three CDRs on each heavy chain and three CDRs on each light chain. In certain embodiments, the antibody as described herein binds to CD2. See Section 5.1.1.

In certain embodiments, administration of the CD2-binding molecule (or an anti-CD2 antibody or antigen binding fragment thereof) described herein does not result in target cell depletion; see Section 5.1.2. In certain embodiments, the CD2-binding molecule (or an anti-CD2 antibody or antigen binding fragment thereof) described herein exhibits immunomodulatory activity; see Section 5.1.3. In a specific embodiment, the ability of the CD2-binding molecule (or an anti-CD2 antibody or antigen binding fragment thereof) described herein to refrain from target cell depletion while retaining immunomodulatory activity is accomplished by eliminating glycosylation of Fc region; see Section 5.1.4.

5.1.1 Binding Specificity of CD2-Binding Molecule (or Anti-CD2 Antibody or Antigen-Binding Fragment Thereof)

The CD2-binding molecule (or anti-CD2 antibody or antigen-binding fragment thereof) as described herein binds specifically to CD2 (also called T11, SRBC (sheep red blood cell receptor), and LFA-2). In a specific embodiment, the CD2-binding molecule (or anti-CD2 antibody or antigen-binding fragment thereof) described herein binds to human CD2 (GenBank Accession No. NM_001328609.1 (isoform 1); NM_001767.5 (isoform 2)). In certain embodiments, a CD2-binding molecule (or anti-CD2 antibody or antigen-binding fragment thereof) provided herein can bind competitively with siplizumab (MedImmune Inc.; International Publication No. WO 02/098370). Siplizumab (MEDI-507) is a humanized version of the CD2-specific rat antibody BTI-322 (MedImmune Inc.; International Publication No. WO 02/098370). Siplizumab is an IgG1 kappa class monoclonal antibody and binds to the CD2 found on human T cells and human NK cells. Siplizumab is composed of two heavy chains (~50 kDa) and two light chains (~25 kDa).

As defined herein, an epitope is the region of the antigen to which the antibody or the antigen-binding fragment binds. In some embodiments, the epitope can be linear. In other embodiments, the epitope can be conformational. In some embodiments, the epitope can be formed by contiguous amino acids. In other embodiments, the epitope can be formed by noncontiguous amino acids. In certain embodiments, the CD2-binding molecule (or anti-CD2 antibody or antigen-binding fragment thereof) described herein binds to an epitope on CD2. In certain embodiments, the CD2-binding molecule (or anti-CD2 antibody or antigen-binding fragment thereof) described herein binds to the same epitope of CD2 as siplizumab. In certain embodiments, a CD2-binding molecule (or anti-CD2 antibody or antigen-binding fragment thereof) provided herein can bind competitively with siplizumab in an appropriate in vitro competitive binding assay such as the one detailed by Clark et al., *J Exp Med.* 1988 Jun. 1; 167(6):1861-72. In certain embodiments, the CD2-binding molecule (or anti-CD2 antibody or antigen-binding fragment thereof) provided herein has the same $IC_{50}$ value as siplizumab, approximately 1 nM (Branco et al., *Transplantation.* 1999 Nov. 27; 68(10):1588-96). In certain embodiments, the CD2-binding molecule (or anti-CD2 antibody or antigen-binding fragment thereof) provided herein has a lower $IC_{50}$ value than siplizumab. In certain embodiments, the CD2-binding molecule (or anti-CD2 antibody or antigen-binding fragment thereof) provided herein has a higher $IC_{50}$ value than siplizumab. In certain embodiments, the CD2-binding molecule (or anti-CD2 antibody or antigen-binding fragment thereof) provided herein has an $IC_{50}$ value of 0.5 nM, 0.6 nM, 0.7 nM, 0.8 nM, 0.9 nM, 1.0 nM, 1.1 nM, 1.2 nM, 1.3 nM, 1.4 nM, 1.5 nM, between 0.5 nM and 0.8 nM, between 0.6 nM and 0.9 nM, between 0.7 nM and 1.0 nM, between 0.8 nM and 1.1 nM, between 0.9 nM and 1.2 nM, between 1.0 nM and 1.3 nM, between 1.1 nM and 1.4 nM, or between 1.2 nM and 1.5 nM.

In certain embodiments, the sequence of the VH region of the CD2-binding molecule (or an anti-CD2 antibody or antigen binding fragment thereof) described herein is 80%, 85%, 90%, 91%, 92%, 93%, 94%, 95%, 96%, 97%, 98%, 99%, or 100% identical to SEQ ID NO: 01. In certain embodiments, the sequence of the VL region of the CD2-binding molecule (or an anti-CD2 antibody or antigen binding fragment thereof) described herein is 80%, 85%, 90%, 91%, 92%, 93%, 94%, 95%, 96%, 97%, 98%, 99%, or 100% identical to SEQ ID NO: 02. In certain embodiments, the sequence of the VH CDR1 of the CD2-binding molecule (or an anti-CD2 antibody or antigen binding fragment thereof) described herein can be SEQ ID NO: 03. In certain embodiments, the sequence of the VH CDR2 of the CD2-binding molecule (or an anti-CD2 antibody or antigen binding fragment thereof) described herein can be SEQ ID NO: 04. In certain embodiments, the sequence of the VH CDR3 of the CD2-binding molecule (or an anti-CD2 antibody or antigen binding fragment thereof) described herein can be SEQ ID NO: 05. In certain embodiments, the sequence of the VL CDR1 of the CD2-binding molecule (or an anti-CD2 antibody or antigen binding fragment thereof) described herein can be SEQ ID NO: 06. In certain embodiments, the sequence of the VL CDR2 of the CD2-binding molecule (or an anti-CD2 antibody or antigen binding fragment thereof) described herein can be SEQ ID NO: 07. In certain embodiments, the sequence of the VL CDR3 of the CD2-binding molecule (or an anti-CD2 antibody or antigen binding fragment thereof) described herein can be SEQ ID NO: 08. These sequences are shown in Table 1.

In certain embodiments, the CD2-binding molecule (or an anti-CD2 antibody or antigen binding fragment thereof) for use with the methods provided herein has a heavy chain variable region comprising VH CDRs of SEQ ID NOS: 3-5, respectively, and a VL of SEQ ID NO: 2. In certain embodiments, the CD2-binding molecule (or an anti-CD2 antibody or antigen binding fragment thereof) for use with the methods provided herein has a heavy chain variable region comprising VL CDRs of SEQ ID NOS: 6-8, respectively, and a VH of SEQ ID NO: 1.

In certain embodiments, the CD2-binding molecule (or an anti-CD2 antibody or antigen binding fragment thereof) for use with the methods provided herein has a heavy chain variable region CDR 1 of SEQ ID NO: 3; a heavy chain variable region CDR 2 of SEQ ID NO: 4; a heavy chain variable region CDR 3 of SEQ ID NO: 5; a light chain variable region CDR 1 of SEQ ID NO: 6; a light chain variable region CDR 2 of SEQ ID NO: 7; and a light chain variable region CDR 3 of SEQ ID NO: 8. In certain embodiments, the CD2-binding molecule (or an anti-CD2 antibody or antigen binding fragment thereof) for use with the methods provided herein has a heavy chain variable region CDR 1 comprising a sequence that is at least about or about 75%, 80%, 85%, 90%, 95%, 96%, 97%, 98%, 99%, or 100% identical to SEQ ID NO: 3; a heavy chain variable region CDR 2 comprising a sequence that is at least about or about 75%, 80%, 85%, 90%, 95%, 96%, 97%, 98%, 99%, or 100% identical to SEQ ID NO: 4; a heavy chain variable region CDR 3 comprising a sequence that is at least about or about 75%, 80%, 85%, 90%, 95%, 96%, 97%, 98%, 99%, or 100% identical to SEQ ID NO: 5; a light chain variable region CDR 1 comprising a sequence that is at least about or about 75%, 80%, 85%, 90%, 95%, 96%, 97%, 98%, 99%, or 100% identical to SEQ ID NO: 6; a light chain variable region CDR 2 comprising a sequence that is at least about or about 75%, 80%, 85%, 90%, 95%, 96%, 97%, 98%, 99%, or 100% identical to SEQ ID NO: 7; and/or a light chain variable region CDR 3 comprising a sequence that is at least about or about 75%, 80%, 85%, 90%, 95%, 96%, 97%, 98%, 99%, or 100% identical to SEQ ID NO: 8.

In certain embodiments, the CD2-binding molecule (or an anti-CD2 antibody or antigen binding fragment thereof) for use with the methods provided herein has a heavy chain variable region CDR 1 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 3; a heavy chain variable region CDR 2 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 4; a heavy chain variable region CDR 3 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 5; a light chain variable region CDR 1 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 6; a light chain variable region CDR 2 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 7; and/or a light chain variable region CDR 3 comprising a sequence that has about or at least about 1 amino acid substitution, about or at least about 2 amino acid substitutions, about or at least about 3 amino acid substitutions, about or at least about 4 amino acid substitutions, or more than at least about 4 amino acid substitutions relative to SEQ ID NO: 8.

In some embodiments, an amino acid substitution is a conservative substitution. Illustrative examples for conserved amino acid exchanges are amino acid substitutions that maintain structural and/or functional properties of the amino acids' side-chains, e.g., an aromatic amino acid is substituted for another aromatic amino acid, an acidic amino acid is substituted for another acidic amino acid, a basic amino acid is substituted for another basic amino acid, and an aliphatic amino acid is substituted for another aliphatic amino acid. In some embodiments, a conservative amino acid substitution is one in which the amino acid residue is replaced with an amino acid residue having a side chain with a similar charge. Families of amino acid residues having side chains with similar charges have been defined in the art.

These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In contrast, examples of non-conserved amino acid exchanges are amino acid substitutions that do not maintain structural and/or functional properties of the amino acids' side-chains, e.g., an aromatic amino acid is substituted for a basic, acidic, or aliphatic amino acid, an acidic amino acid is substituted for an aromatic, basic, or aliphatic amino acid, a basic amino acid is substituted for an acidic, aromatic or aliphatic amino acid, and an aliphatic amino acid is substituted for an aromatic, acidic or basic amino acid.

In certain embodiments, a CD2-binding molecule (or an anti-CD2 antibody or antigen binding fragment thereof) for use with the present methods and compositions comprises 1, 2, or 3 of the heavy chain CDRs of BTI-322 or of siplizumab. In certain embodiments, a CD2-binding molecule (or an anti-CD2 antibody or antigen binding fragment thereof) for use with the present methods and compositions comprises 1, 2, or 3 of the light chain CDRs of BTI-322 or of siplizumab. In certain embodiments, a CD2-binding molecule (or an anti-CD2 antibody or antigen binding fragment thereof) for use with the present methods and compositions comprises 1, 2, 3, 4, 5, or all 6 of the CDRs of BTI-322 or of siplizumab. In certain embodiments, the CD2-binding molecule (or an anti-CD2 antibody or antigen binding fragment thereof) for use with the methods described herein comprises 1, 2, 3, 4, 5, or all 6 of the CDRs described herein. In certain embodiments, 1, 2, 3, 4, 5, and/or all 6 of the CDRs of BTI-322 or of siplizumab have 1, 2, 3, 4, 5, 6, 7, 8, 9, or 10 amino acid substitutions. In a more specific embodiment, such an amino acid substitution is a conservative amino acid substitution.

TABLE 1

| Sequences of CD2-binding molecule (or an anti-CD2 antibody or an antigen binding fragment thereof) | |
| --- | --- |
| Description | Sequence |
| VH region (SEQ ID NO: 01) | QVQLVQSGAEVQRPGASVKVSCKASGYIFTEYYMYWVRQAPG QGLELVGRIDPEDGSIDYVEKFKKKVTLTADTSSSTAYMELSSLT SDDTAVYYCARGKFNYRFAYWGQGTLVTVSS |
| VL region (SEQ ID NO: 02) | DVVMTQSPPSLLVTLGQPASISCRSSQSLLHSSGNTYLNWLLQRP GQSPQPLIYLVSKLESGVPDRFSGSGSGTDFTLKISGVEAEDVGV YYCMQFTHYPYTFGQGTKLEIK |
| VH CDR 1 (SEQ ID NO: 03) | EYYMY |
| VH CDR 2 (SEQ ID NO: 04) | RIDPEDGSIDYVEKFKK |
| VH CDR 3 (SEQ ID NO: 05) | GKFNYRFAY |
| VL CDR 1 (SEQ ID NO: 06) | RSSQSLLHSSGNTYLN |

TABLE 1-continued

Sequences of CD2-binding molecule (or an anti-CD2 antibody or an antigen binding fragment thereof)

| Description | Sequence |
|---|---|
| VL CDR 2 (SEQ ID NO: 07) | LVSKLES |
| VL CDR 3 (SEQ ID NO: 08) | MQFTHYPYT |

In a certain embodiment, the CD2-binding molecule (or anti-CD2 antibody or antigen-binding fragment thereof) described herein has the same six CDR sequences as siplizumab. In a certain embodiment, the CD2-binding molecule (or anti-CD2 antibody or antigen-binding fragment thereof) described herein can share five of the six CDR sequences of siplizumab. In certain embodiments, one of the CDRs of the CD2-binding molecule (or anti-CD2 antibody or antigen-binding fragment thereof) described herein is different from the counterpart CDR of siplizumab and that the CDR sequence is different by one amino acid. In certain embodiments, the difference between said CDR sequence of the CD2-binding molecule (or anti-CD2 antibody or antigen-binding fragment thereof) described herein and the counterpart CDR of siplizumab is a conservative amino acid substitution. For example, a CD2-binding molecule (or anti-CD2 antibody or antigen-binding fragment thereof) can have one, two, three, four, five, or six conservative amino acid substitutions relative to the set of six CDRs of siplizumab, or relative to the set of three CDRs in the heavy chain of siplizumab, or relative to the set of three CDRs in the light chain of siplizumab.

In certain embodiments, the VL CDR1, VL CDR2, or VL CDR3 of the CD2-binding molecule (or anti-CD2 antibody or antigen-binding fragment thereof) described herein is the CDR that differs from its siplizumab counterpart. In other embodiments, the VH CDR1, VH CDR2, or VH CDR3 of the CD2-binding molecule (or anti-CD2 antibody or antigen-binding fragment thereof) described herein is the CDR that differs from its siplizumab counterpart. In certain embodiments, the different CDR of the CD2-binding molecule (or anti-CD2 antibody or antigen-binding fragment thereof) described herein is longer than the sequence of its siplizumab counterpart. In other embodiments, the different CDR of the CD2-binding molecule (or anti-CD2 antibody or antigen-binding fragment thereof) described herein is shorter than the sequence of its siplizumab counterpart.

In certain embodiments, the sequence of the heavy chain constant region (CH) of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 09. In certain embodiments, the sequence of the heavy chain constant region of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 10. In certain embodiments, the sequence of the heavy chain constant region of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 11. In certain embodiments, the sequence of the heavy chain constant region of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 12. In certain embodiments, the sequence of the heavy chain constant region of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 13. In certain embodiments, the sequence of the light chain constant region (CL) of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 14. In certain embodiments, the sequence of the light chain constant region of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 15.

In certain embodiments, the CD2-binding molecule (or anti-CD2 antibody or antigen-binding fragment thereof) described herein can be directed to three regions of human CD2 known in the art as $T11_1$, $T11_2$, and $T11_3$ (Peterson, A., Seed, B., 1987. Nature 329, 842-846; Branco et al., 1999. Transplantation 68, 1588-1596; Arulanandam, A. R., et al., 1993. Proc. Natl. Acad. Sci. U.S.A. 90, 11613-11617; Damschroder et al., 2004. Molecular Immunology 41, 985-1000). Three residues in the adhesion domain of human CD2 that are critical for its binding to siplizumab are N18, K55, and T5 (Damschroder et al., 2004. Molecular Immunology 41, 985-1000). In certain embodiments, the residues N18, K55, and T59 in the extracellular CD2 domain are critical residues in the binding affinity of the CD2-binding molecule (or anti-CD2 antibody or antigen-binding fragment thereof) described herein to human CD2. In certain embodiments, the CD2-binding molecule (or anti-CD2 antibody or antigen-binding fragment thereof) described herein binds the same epitope as siplizumab. In certain embodiments, the CD2-binding molecule (or anti-CD2 antibody or antigen-binding fragment thereof) described herein binds competitively with siplizumab to human CD2.

In certain embodiments, the DNA sequence of the CD2-binding molecule (or anti-CD2 antibody or antigen-binding fragment thereof) can be modified to optimize the product yield during manufacture. The sequence optimization will increase product yield while not impacting product quality secretion of the molecule during production since the amino acid sequence generated will be the same as described in Table 1. The optimized DNA sequence for the CD2-binding molecule (or anti-CD2 antibody or antigen-binding fragment thereof) heavy chain and light chain are presented in Table 2.

TABLE 2

Optimized sequences of CD2-binding molecule (or an anti-CD2 antibody or antigen-binding fragment thereof)

| Description | Sequence |
|---|---|
| Optimized Heavy chain sequence (SEQ ID NO: 16) | CAAGTGCAGCTGGTGCAGAGCGGAGCTGAGGTGCAGAGACC CGGCGCCAGCGTCAAGGTGAGCTGTAAGGCCAGCGGCTACA TCTTCACAGAATACTACATGTACTGGGTGAGGCAAGCCCCCG GCCAAGGACTGGAGCTGGTGGGCAGAATCGATCCAGAGGAT GGCAGCATCGACTACGTGGAGAAGTTCAAGAAGAAGGTGAC TCTGACAGCCGACACAAGCAGCAGCACTGCTTACATGGAGCT GAGCTCTCTGACTAGCGATGACACTGCCGTGTACTACTGTGC TAGGGGCAAGTTCAACTATAGGTTCGCCTACTGGGGCCAAGG CACTCTGGTGACAGTCAGCAGCGCTAGCACCAAGGGCCCATC GGTCTTCCCCCTGGCACCCTCCTCCAAGAGCACCTCTGGGGG CACAGCGGCCCTGGGCTGCCTGGTCAAGGACTACTTCCCCGA ACCGGTGACGGTGTCGTGGAACTCAGGCGCCCTGACCAGCGG CGTGCACACCTTCCCGGCCGTCCTACAGTCCTCAGGACTCTA CTCCCTCAGCAGCGTGGTGACCGTGCCCTCCAGCAGCTTGGG CACCCAGACCTACATCTGCAACGTGAATCACAAGCCCAGCAA CACCAAGGTGGACAAGAAGGTTGAGCCCAAATCTTGTGACA AAACTCACACATGCCCACCGTGCCCAGCACCTGAACTCCTGG GGGGACCGTCAGTCTTCCTCTTCCCCCCAAAACCCAAGGACA CCCTCATGATCTCCCGGACCCCTGAGGTCACATGCGTGGTGG TGGACGTGAGCCACGAAGACCCTGAGGTCAAGTTCAACTGGT ACGTGGACGGCGTGGAGGTGCATAATGCCAAGACAAAGCCG CGGGAGGAGCAGTACAACAGCACGTACCGTGTGGTCAGCGT CCTCACCGTCCTGCACCAGGACTGGCTGAATGGCAAGGAGTA CAAGTGCAAGGTCTCCAACAAAGCCCTCCCAGCCCCCATCGA GAAAACCATCTCCAAAGCCAAAGGGCAGCCCCGAGAACCAC AGGTGTACACCCTGCCCCCATCCCGGGACGAGCTGACCAAGA ACCAGGTCAGCCTGACCTGCCTGGTCAAAGGCTTCTATCCCA GCGACATCGCCGTGGAGTGGGAGAGCAATGGGCAGCCGGAG AACAACTACAAGACCACGCCTCCCGTGCTGGACTCCGACGGC TCCTTCTTCCTCTACAGCAAGCTCACCGTGGACAAGAGCAGG TGGCAGCAGGGGAACGTCTTCTCATGCTCCGTGATGCATGAG GCTCTGCACAACCACTACACGCAGAAGAGCCTCTCCCTGTCT CCGGGTAAATGATGA |
| Optimized Light (SEQ ID NO: 17) chain sequence | GACGTGGTGATGACTCAGAGCCCTCCTTCTCTGCTGGTGACT CTGGGCCAGCCAGCCAGCATCAGCTGTAGGAGCAGCCAGTCT CTGCTGCACTCCAGCGGCAACACTTATCTGAACTGGCTGCTG CAGAGACCCGGCCAGAGCCCTCAGCCTCTGATCTACCTCGTG AGCAAGCTGGAGAGCGGCGTGCCAGATAGGTTTAGCGGCAG CGGAAGCGGCACTGACTTCACTCTGAAGATCAGCGGCGTGGA AGCTGAGGATGTGGGCGTCTACTACTGCATGCAGTTCACACA CTACCCATACACTTTCGGCCAAGGCACAAAGCTGGAAATCAA GCGTACGGTGGCTGCACCATCTGTCTTCATCTTCCCGCCATCT GATGAGCAGTTGAAATCTGGAACTGCCTCTGTTGTGTGCCTG CTGAATAACTTCTATCCCAGAGAGGCCAAAGTACAGTGGAAG GTGGATAACGCCCTCCAATCGGGTAACTCCCAGGAGAGTGTC ACAGAGCAGGACAGCAAGGACAGCACCTACAGCCTCAGCAG CACCCTGACGCTGAGCAAAGCAGACTACGAGAAACACAAAG TCTACGCCTGCGAAGTCACCCATCAGGGCCTGAGCTCGCCCG TCACAAAGAGCTTCAACAGGGGAGAGTGTTGATGA |

In certain embodiments, the sequence of the heavy chain of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 16. In certain embodiments, the sequence of the light chain of the CD2-binding molecule (or an anti-CD2 antibody or antigen-binding fragment thereof) described herein is 80%, 85%, 90%, 91%, 92%, 93%, 94%, 95%, 96%, 97%, 98%, 99%, or 100% identical to SEQ ID NO: 17.

In certain embodiments, the CD2-binding molecule (or anti-CD2 antibody or antigen-binding fragment thereof) interferes with the CD58/CD2 signaling cascade. In certain embodiments, the CD2-binding molecule (or anti-CD2 antibody or antigen-binding fragment thereof) blocks CD58. An example of a compound that inhibits the CD58/CD2 pathway is alefacept.

In certain embodiments, the depleting version of splizumab may be used for the treatment of autoimmune diseases.

5.1.2 Reduced or Absent ADCC Activity

In certain embodiments, a CD2-binding molecule (or an anti-CD2 antibody or an antigen binding fragment thereof) described herein has no or has reduced antibody-dependent cellular cytotoxicity ("ADCC"). Said CD2-binding molecule (or an anti-CD2 antibody or an antigen binding fragment thereof) can be generated as to exhibit reduced or absent ADCC using methods including, but not limited to, Fc silencing, subclass switching, deglycosylation, and other mutations or modifications of the Fc region. These methods are described, for example, in U.S. Provisional Application No. 63/135,381, which is incorporated herein by reference in its entirety for non-limiting examples of a CD2-binding molecule (or an anti-CD2 antibody or an antigen binding fragment thereof) that may be used in the methods described herein. These methods are also described further in sections 5.1.4, 5.2.2, and 5.2.3, and in the examples.

ADCC activity can be determined by any commercially available kit (see, e.g. Promega ADCC Reporter Bioassay, Core Kit (Cat. #G7010, G7018), or any appropriate assay. Such assays can include, but are not limited to, a flow cytometry-based assay, a fluorometric assay, or a bioluminescent reporter assay.

In certain embodiments, the CD2-binding molecule (or an anti-CD2 antibody or an antigen binding fragment thereof) described herein exhibits at most 90% of the ADCC activity of siplizumab in an in vitro assay. An example of such an assay is described in the methods of Golay et al., *Haematologica.* January 2003; 88:1002-1012. Specifically, the CD2-binding molecule (or an anti-CD2 antibody or an antigen binding fragment thereof) provided herein exhibits at most 0%, 5%, 10%, 20%, 30%, 40%, 50%, 60%, 70%, 80%, or at most 90% of the ADCC activity as compared to siplizumab.

In certain embodiments, in vivo administration of the CD2-binding molecule (or an anti-CD2 antibody or an antigen binding fragment thereof) provided herein exhibits at most 90% of the ADCC activity as compared to in vivo administration of siplizumab in a humanized mouse model or a human subject in a clinical setting. Specifically, in vivo administration of the CD2-binding molecule (or an anti-CD2 antibody or an antigen binding fragment thereof) provided herein exhibits at most 0%, 5%, 10%, 20%, 30%, 40%, 50%, 60%, 70%, 80%, or at most 90% of the ADCC activity as in vivo administration of siplizumab in a humanized mouse model or a human subject in a clinical setting.

5.1.3 Preservation of Immunomodulatory Activity

In certain embodiments, a CD2-binding molecule (or anti-CD2 antibody or antigen-binding fragment thereof) provided herein exhibits immunomodulatory activity despite absent or reduced ADCC. Said CD2-binding molecule (or anti-CD2 antibody or antigen-binding fragment thereof) can be generated as to exhibit reduced or absent ADCC using methods including, but not limited to, Fc silencing, subclass switching, deglycosylation, and other mutations or modifications of the Fc region. These methods are described further in sections 5.1.4, 5.2.2, and 5.2.3, and in the examples.

Immunomodulatory activities exhibited by the CD2-binding molecule (or anti-CD2 antibody or antigen-binding fragment thereof) described herein can include, but are not limited to, the inhibition of the activation and proliferation of CD4+/CD25+ T cells, increasing percentage of FOXP3+ regulatory T cells, and the suppression of CD69+ NK cells. In certain embodiments, the CD2-binding molecule (or anti-CD2 antibody or antigen-binding fragment thereof) described herein exhibits the same immunomodulatory activity (e.g., the same type and at the same level) as siplizumab. The determination of immunomodulatory activity can be achieved by any appropriate method known in the art. These methods can include, but are not limited to, cell proliferation assays, T cell activation functional assays, ELISPOT assays, intracellular staining, cytokine capture, tetramer staining, spectra-typing assays, and biosensor assays. As an example, T cell activation can be determined by any commercially available assay kit (see, e.g. Promega T Cell Activation Bioassay (NFAT or IL-2) (Cat. #J1621 or J1651)), or any appropriate assay, wherein briefly an assay plate is coated with anti-CD3 antibodies, human PBMCs or mouse peripheral target cells are added, anti-CD28 is added to the cells, and proliferation is quantified.

In certain embodiments, the CD2-binding molecule (or anti-CD2 antibody or antigen-binding fragment thereof) described herein can inhibit the activation and proliferation of CD4+/CD25+ T cells to a level that is at least 50% of the level achieved by siplizumab in an in vitro assay. An example of such an assay is described in the methods of Ng et al., *Blood.* 2001; 98:2736-2744. Specifically, the CD2-binding molecule (or anti-CD2 antibody or antigen-binding fragment thereof) described herein can inhibit the activation and proliferation of CD4+/CD25+ T cells in vitro to a level at least 50%, 55%, 60%, 65%, 70%, 75%, 80%, 85%, 90%, 95%, or 100% of the level achieved by siplizumab.

In certain embodiments, in vivo administration of the CD2-binding molecule (or anti-CD2 antibody or antigen-binding fragment thereof) provided herein exhibits at least 50% of the level of CD4+/CD25+ T cell activation/proliferation as compared to in vivo administration of siplizumab in a humanized mouse model or a human subject in a clinical setting. Specifically, in vivo administration of the CD2-binding molecule (or anti-CD2 antibody or antigen-binding fragment thereof) provided herein exhibits at least 50%, 55%, 60%, 65%, 70%, 75%, 80%, 85%, 90%, 95%, or 100% of the level of CD4+/CD25+ T cell activation/proliferation as compared to in vivo administration of siplizumab in a humanized mouse model or a human subject in a clinical setting.

In certain embodiments, the CD2-binding molecule (or anti-CD2 antibody or antigen-binding fragment thereof) described herein can increase the amount of FOXP3+ regulatory T cells as compared to siplizumab. In certain embodiments, the CD2-binding molecule (or anti-CD2 antibody or antigen-binding fragment thereof) described herein can increase the amount of FOXP3+ regulatory T cells to a level of at least 50% of the amount achieved by siplizumab in an in vitro assay. An example of such an assay is described in the methods of Sambucci et al., *Scientific Reports.* 8: 3674 (2018). Specifically, the CD2-binding molecule (or anti-CD2 antibody or antigen-binding fragment thereof) described herein can increase the amount of FOXP3+ regulatory T cells in vitro to a level at least 50%, 55%, 60%, 65%, 70%, 75%, 80%, 85%, 90%, 95%, or 100% of the amount of FOXP3+ regulatory T cells achieved by siplizumab.

In certain embodiments, in vivo administration of the CD2-binding molecule (or anti-CD2 antibody or antigen-binding fragment thereof) described herein exhibits at least 50% of the level of FOXP3+ regulatory T cells as compared to in vivo administration of siplizumab in a humanized mouse model or a human subject in a clinical setting. Specifically, in vivo administration of the CD2-binding molecule (or anti-CD2 antibody or antigen-binding fragment thereof) described herein exhibits at least 50%, 55%, 60%, 65%, 70%, 75%, 80%, 85%, 90%, 95%, or 100% of the level of FOXP3+ regulatory T cells as compared to in vivo administration of siplizumab in a humanized mouse model or a human subject in a clinical setting.

In certain embodiments, the CD2-binding molecule (or anti-CD2 antibody or antigen-binding fragment thereof) described herein can inhibit the expression of CD69+ NK cells as compared to siplizumab. In certain embodiments, the CD2-binding molecule (or anti-CD2 antibody or antigen-binding fragment thereof) provided herein exhibits at most 50% of the expression of CD69+ NK cells as compared to siplizumab in an in vitro assay. An example of such an assay is described in the methods of Thum et el., *Human*

*Reproduction.* 19:10, pp. 2395-2400, 2004. Specifically, the CD2-binding molecule (or anti-CD2 antibody or antigen-binding fragment thereof) described herein exhibits at most 10%, 20%, 30%, 40%, 50%, 60%, 70%, 80%, or at most 90% of the expression of CD69+ NK cells in vitro as compared to siplizumab.

In certain embodiments, in vivo administration of the CD2-binding molecule (or anti-CD2 antibody or antigen-binding fragment thereof) provided herein exhibits at most 50% of the expression of CD69+ NK cells as compared to in vivo administration of siplizumab in a humanized mouse model or a human subject in a clinical setting. Specifically, in vivo administration of the CD2-binding molecule (or anti-CD2 antibody or antigen-binding fragment thereof) provided herein exhibits at most 10%, 20%, 30%, 40%, 50%, 60%, 70%, 80%, or at most 90% of the expression of CD69+ NK cells as compared to in vivo administration of siplizumab in a humanized mouse model or a human subject in a clinical setting.

In a specific embodiment, the CD2-binding molecule (or anti-CD2 antibody or antigen-binding fragment thereof) described herein can perform one of these immune regulatory activities. In a specific embodiment, the CD2-binding molecule (or anti-CD2 antibody or antigen-binding fragment thereof) described herein can perform more than one of these immune regulatory activities. In a specific embodiment, the CD2-binding molecule (or anti-CD2 antibody or antigen-binding fragment thereof) described herein can perform all of these immune regulatory activities. In a specific embodiment, administration of the CD2-binding molecule (or anti-CD2 antibody or antigen-binding fragment thereof) described herein completely abrogates ADCC activity in a recipient while retaining immunomodulatory activity.

5.1.4 Modifications of Fc Region

In certain embodiments, a CD2-binding molecule (or an anti-CD2 antibody or antigen binding fragment thereof) described herein is an IgG1 antibody and has a modification in the Fc region. In certain embodiments, a CD2-binding molecule (or an anti-CD2 antibody or antigen binding fragment thereof) described herein is an IgG2 antibody and has a modification in the Fc region. In certain embodiments, a CD2-binding molecule (or an anti-CD2 antibody or antigen binding fragment thereof) described herein is an IgG3 antibody and has a modification in the Fc region. In certain embodiments, a CD2-binding molecule (or an anti-CD2 antibody or antigen binding fragment thereof) described herein is an IgG4 antibody and has a modification in the Fc region. In certain embodiments, a CD2-binding molecule (or an anti-CD2 antibody or antigen binding fragment thereof) described herein comprises at least one mutation (e.g., about or at least one, about or at least two, about or at least three, about or at least four, about or at least five, about or at least six, about or at least seven, about or at least eight, about or at least nine, about or at least ten, or more than about ten mutations) in comparison to siplizumab. In certain embodiments, a CD2-binding molecule (or an anti-CD2 antibody or antigen binding fragment thereof) described herein comprises about one mutation, about two mutations, about three mutations, about four mutations, about five mutations, about six mutations, about seven mutations, about eight mutations, about nine mutations, about ten mutations, or more than about ten mutations in relation to siplizumab (e.g., mutation in the Fc region of siplizumab). In certain embodiments, a CD2-binding molecule (or an anti-CD2 antibody or antigen binding fragment thereof) described herein comprises siplizumab CDRs in IgG1 heavy chain and at least one mutation (e.g., about or at least one, about or at least two, about or at least three, about or at least four, about or at least five, about or at least least six, about or at least seven, about or at least eight, about or at least nine, about or at least ten, or more than about ten mutations). In certain embodiments, a CD2-binding molecule (or an anti-CD2 antibody or antigen binding fragment thereof) described herein comprises siplizumab CDRs in IgG2 heavy chain and at least one mutation (e.g., about or at least one, about or at least two, about or at least three, about or at least four, about or at least five, about or at least six, about or at least seven, about or at least eight, about or at least nine, about or at least ten, or more than about ten mutations). In certain embodiments, a CD2-binding molecule (or an anti-CD2 antibody or antigen binding fragment thereof) described herein comprises siplizumab CDRs in IgG3 heavy chain and at least one mutation (e.g., about or at least one, about or at least two, about or at least three, about or at least least four, about or at least five, about or at least six, about or at least seven, about or at least eight, about or at least nine, about or at least ten, or more than about ten mutations). In certain embodiments, a CD2-binding molecule (or an anti-CD2 antibody or antigen binding fragment thereof) described herein comprises siplizumab CDRs in IgG4 heavy chain and at least one mutation (e.g., about or at least one, about or at least two, about or at least three, about or at least four, about or at least five, about or at least least six, about or at least seven, about or at least eight, about or at least nine, about or at least ten, or more than about ten mutations). The mutation can comprise of at least one alteration in the amino acid sequence of a CD2-binding molecule (or an anti-CD2 antibody or antigen binding fragment thereof) as compared to the wild-type counterpart wherein the alteration results in the reduction or elimination of the binding of the Fc region to its cognate receptor. In some embodiments, a mutation is one or more mutation and includes a mutation in amino acid position L234, L235, P329, V234, G237, P238, H268, V309, A330, P331, and/or S228 (e.g., based on Edelman (EU) numbering). In some embodiments, a mutation is one or more mutation and includes a mutation in amino acid position L234 and/or L235. In some embodiments, a mutation is one or more mutation and includes a mutation in amino acid position L234, L235, and/or P329. In some embodiments, a mutation is one or more mutation and includes a mutation in amino acid position V234, G237, P238, H268, V309, A330, and/or P331. In some embodiments, a mutation is one or more mutation and includes a mutation in amino acid position S228. In some embodiments, a mutation is one or more mutation and includes a mutation in amino acid position S228, P329, and/or L235. In some embodiments, a mutation is one or more mutation and includes L234A (or another conservative amino acid mutation). In some embodiments, a mutation is one or more mutation and includes L235A (or another conservative amino acid mutation). In some embodiments, a mutation is one or more mutation and includes P329G (or another conservative amino acid mutation). In some embodiments, a mutation is one or more mutation and includes V234A (or another conservative amino acid mutation). In some embodiments, a mutation is one or more mutation and includes G237A (or another conservative amino acid mutation). In some embodiments, a mutation is one or more mutation and includes P238S (or another conservative amino acid mutation). In some embodiments, a mutation is one or more mutation and includes H268A (or another conservative amino acid mutation). In some embodiments, a mutation is one or more mutation and includes V309L (or another conservative amino acid mutation). In some embodiments, a mutation is one or more mutation and includes A330S (or another conservative amino acid mutation). In some embodiments, a mutation is one or more mutation and includes P331S (or another conservative amino acid mutation). In some embodiments, a mutation is one or more mutation and includes S228P (or another conservative amino acid mutation). In some embodiments, a mutation is one or more mutation and includes L235E (or another conservative amino acid mutation). In some embodiments, the mutation includes L234A and L235A (or other conservative amino acid mutations). In some embodiments, the mutation includes P329G, L234A and L235A (or other conservative amino acid mutations). In some embodiments, the mutation includes V234A, G237A, P238S, H268A, V309L, A330S, and P331S (or other conservative amino acid mutations) (e.g., for IgG2). In some embodiments, a mutation is one or more mutation and includes S228P (or another conservative amino acid mutation) (e.g., for IgG4). In some embodiments, a mutation is one or more mutation and includes P329G, S228P, and L235E (or another conservative amino acid mutations) (e.g., for IgG4). In some embodiments, the amino acid position is a position based on any antibody numbering scheme (e.g., Edelman (EU) numbering). In some embodiments, the amino acid position is a position based on Edelman (EU) numbering. In some embodiments, the amino acid position is a position based on Kabat numbering scheme. In some embodiments, the amino acid position is a position based on Clothia numbering scheme. In some embodiments, the amino acid position is a position based on IMGT numbering scheme. The modification can comprise of at least one alteration in the amino acid sequence of the CD2-binding molecule (or anti-CD2 antibody or antigen-binding fragment thereof) Fc region as compared to the wild-type Fc region wherein the alteration results in the reduction or elimination of the binding of the Fc region to its cognate receptor. The Fc receptor is located on immune effectors cells including B cells, NK cells, macrophages, and neutrophils. Without being bound by theory, in wild type IgG, the Fc interaction with the Fc receptor (FcR) leads to downstream effector cell functions including stimulating the phagocytic or cytotoxic activities of the immune cell. Reduction or elimination of Fc/FcR interaction results in elimination of effector functions.

In certain embodiments, the CD2-binding molecule (or an anti-CD2 antibody or antigen binding fragment thereof) exhibits reduced binding to the FcγRIIIA receptor as compared to siplizumab. In certain embodiments, the CD2-binding molecule (or an anti-CD2 antibody or antigen binding fragment thereof) exhibits reduced binding to the FcγRIIA receptor as compared to siplizumab. In certain embodiments, the CD2-binding molecule (or an anti-CD2 antibody or antigen binding fragment thereof) exhibits reduced binding to the FcγRI receptor as compared to siplizumab. In certain embodiments, the CD2-binding molecule (or an anti-CD2 antibody or antigen binding fragment thereof) exhibits increased binding to the FcγRIIIA receptor as compared to siplizumab. In certain embodiments, the CD2-binding molecule (or an anti-CD2 antibody or antigen binding fragment thereof) exhibits increased binding to the FcγRIIA receptor as compared to siplizumab. In certain embodiments, the CD2-binding molecule (or an anti-CD2 antibody or antigen binding fragment thereof) exhibits increased binding to the FcγRI receptor as compared to siplizumab. In certain embodiments, the CD2-binding molecule (or an anti-CD2 antibody or antigen binding fragment thereof) as described herein binds at 0%, 5%, 10%, 15%, 20%, 25%, 30%, 35%, 40%, 45%, 50%, 55%, 60%, 65%, 70%, 75%, 80%, 85%, 90%, or 95% of the binding ability exhibited by siplizumab. In certain embodiments, the CD2-binding molecule (or an anti-CD2 antibody or antigen binding fragment thereof) as described herein has about or at least about 5%, 10%, 15%, 20%, 25%, 30%, 35%, 40%, 45%, 50%, 55%, 60%, 65%, 70%, 75%, 80%, 85%, 90%, or 95% higher binding ability (e.g., to FcγRIIA, FcγRIIIA, and/or FcγRI) as compared to the binding ability exhibited by siplizumab (e.g., to FcγRIIA, FcγRIIIA, and/or FcγRI). In certain embodiments, the CD2-binding molecule (or an anti-CD2 antibody or antigen binding fragment thereof) as described herein has about or at least about 5%, 10%, 15%, 20%, 25%, 30%, 35%, 40%, 45%, 50%, 55%, 60%, 65%, 70%, 75%, 80%, 85%, 90%, or 95% lower binding ability (e.g., to FcγRIIA, FcγRIIIA, and/or FcγRI) as compared to the binding ability exhibited by siplizumab (e.g., to FcγRIIA, FcγRIIIA, and/or FcγRI). Assays to detect binding events can include, but are not limited to, Enzyme-Linked Immunosorbent Assays (ELISAs) and/or surface plasmon resonance (SPR) methods such as the Biacore system.

In certain embodiments, the Fc region can be modified by any appropriate method known in the art. In certain embodiments, a modification can result in Fc silencing. In certain embodiments, the modification can include the mutation of the amino acid sequence of the IgG Fc. In certain embodiments, the modification can include the mutation of the glycosylation site (N297) or of the consensus sequence comprising N297. In certain embodiments, modifications can include mutations that inhibit FcγR and C1q binding. In certain embodiments, these mutations can include any or all of the mutations K322A, L234A and L235A. In certain embodiments, the CD2-binding molecule (or an anti-CD2 antibody or antigen binding fragment thereof) described herein can be a Fab, wherein no Fc is present. In certain embodiments, the CD2-binding molecule (or an anti-CD2 antibody or antigen binding fragment thereof) described herein is an IgG4 antibody. Without being bound by theory, the IgG4 subclass is desirable for therapeutic purposes due to the lack of effector functions including ADCC (Davies and Sutton, *Immunol Rev.* 2015 November; 268(1): 139-15). In certain embodiments, the CD2-binding molecule (or an anti-CD2 antibody or antigen binding fragment thereof) as described herein is an IgG2 antibody. Without being bound by theory, therapeutically beneficial characteristics of the IgG2 subclass include that IgG2 does not cross placenta (Einarsdottir et al., *PLoS One.* 2014 Sep. 24; 9(9):e108319) and that IgG2 has very low/no Fc receptor binding capacity (Vidarsson et al., *Front Immunol.* 2014; 5: 520).

In certain embodiments, the CD2-binding molecule (or anti-CD2 antibody or antigen-binding fragment thereof) described herein can have an antigen binding variable region and a Fc region. In certain embodiments, the Fc region of the CD2-binding molecule (or anti-CD2 antibody or antigen-binding fragment thereof) described herein contains a glycosylation consensus sequence in each of the heavy chains of the antibody. In certain embodiments, the glycosylation consensus sequence is Asn-X-Ser. In certain embodiments, the glycosylation consensus sequence is Asn-X-Thr. In certain embodiments, the CD2-binding molecule (or anti-CD2 antibody or antigen-binding fragment thereof) described herein is glycosylated at Asn297. In certain embodiments, the CD2-binding molecule (or anti-CD2 antibody or antigen-binding fragment thereof) described herein has been deglycosylated. In certain embodiments, the glycan attached to the asparagine residue can be an N-linked glycan. In certain embodiments, the glycan attached to the asparagine residue can be an O-linked glycan. In a specific embodiment, the CD2-binding molecule (or anti-CD2 antibody or antigen-binding fragment thereof) described herein can contain a single N-linked glycosylation site on Asn297 of the heavy chain.

In certain embodiments, the CD2-binding molecule (or anti-CD2 antibody or antigen-binding fragment thereof) described herein can be glycosylated at the Fc glycosylation consensus sequence. In certain embodiments, the CD2-binding molecule (or anti-CD2 antibody or antigen-binding fragment thereof) described herein is deglycosylated. In a certain embodiment, the deglycosylation of the CD2-binding molecule (or anti-CD2 antibody or antigen-binding fragment thereof) described herein is achieved by modifying the Fc region, specifically by introducing a point mutation of position N297. In a certain embodiment, the mutation introduced at position 297 (N297) can be, but is not limited to, N297G, N297Q, or N297A. Without being bound by theory, the N297 point mutation will result in the lack of glycosylation and silencing of Fc signaling. In a certain embodiment, the deglycosylation of the CD2-binding molecule (or anti-CD2 antibody or antigen-binding fragment thereof) described herein is achieved by chemical or enzymatic degradation of the CD2-binding molecule (or anti-CD2 antibody or antigen-binding fragment thereof) glycan structures; see Section 5.2.3. In a specific embodiment, the chemical or enzymatic methods of glycan degradation preserves the Fc amino acid sequence.

In certain embodiments, the constant region of the CD2-binding molecule (or anti-CD2 antibody or antigen-binding fragment thereof) described herein can be switched with the constant region of an antibody of a different subclass. Without being bound by theory, while the variable region does not change, a subclass-switched antibody retains its specific affinity while interacting with different effector molecules (Valenzuela and Schaub, *Transplantation*. 2018 January; 102(1S Suppl 1):S7-S13). In a certain embodiment, the constant region of the CD2-binding molecule (or anti-CD2 antibody or antigen-binding fragment thereof) described herein can be switched with a constant region of a different antibody. In a certain embodiment, this switch will result in the CD2-binding molecule (or anti-CD2 antibody or antigen-binding fragment thereof) becoming a different subclass of antibody than it was originally. In certain embodiments, the constant region of the CD2-binding molecule (or anti-CD2 antibody or antigen-binding fragment thereof) can be switched with a different antibody while preserving the specific binding of the variable regions. In certain embodiments, the constant region of the CD2-binding molecule (or anti-CD2 antibody or antigen-binding fragment thereof) can be switched with a different antibody and the specific variable region in preserved, wherein the VH region of the CD2-binding molecule (or anti-CD2 antibody or antigen-binding fragment thereof) is 80%, 85%, 90%, 91%, 92%, 93%, 94%, 95%, 96%, 97%, 98%, 99%, or 100% identical to SEQ ID NO: 01, and the sequence of the VL region of the CD2-binding molecule (or anti-CD2 antibody or antigen-binding fragment thereof) is 80%, 85%, 90%, 91%, 92%, 93%, 94%, 95%, 96%, 97%, 98%, 99%, or 100% identical to SEQ ID NO: 02.

In certain embodiments, the CD2-binding molecule (or anti-CD2 antibody or antigen binding fragment thereof) binds specifically to the same epitope in human CD2 as siplizumab. In certain embodiments, the CD2-binding molecule (or anti-CD2 antibody or antigen binding fragment thereof) can be an animal-specific antibody, a human-specific antibody, a chimeric antibody, a humanized antibody, a full length antibody, an antibody fragment, a single chain variable fragment (scFv), a naturally occurring antibody, a synthetic antibody, an engineered antibody, enlarged anti-CD2 variants wherein additional components are added to the Fc region (e.g., a component can include an scFv, a CH2 domain, and/or a CH3 domain), or a combination thereof. In certain embodiments, the antibody Fc region has a point mutation (e.g., in N297) resulting in Fc silencing. In certain embodiments, the antibody is an IgG1. In certain embodiments, the antibody is an IgG2. In certain embodiments, the antibody is an IgG4. In certain embodiments, the antibody has a different native constant region than siplizumab. In certain embodiments, the antibody has a different native constant region than siplizumab and a point mutation in the Fc region resulting in Fc silencing. In some embodiments, the CD2-binding molecule (or anti-CD2 antibody or antigen binding fragment thereof) is a humanized anti-CD2 monoclonal antibody. In a specific embodiment, the CD2-binding molecule (or anti-CD2 antibody or antigen binding fragment thereof) is siplizumab. In certain embodiments, the anti-CD2-binding molecule (or anti-CD2 antibody or antigen binding fragment thereof) as described herein can have a modified Fc region wherein the modification can include, but is not limited to, a point mutation resulting in Fc silencing, a switched native constant region, or an Fc silenced switched new native constant region. These combinations of different antibody subclasses and modifications produce different versions of the CD2-binding molecule (or anti-CD2 antibody or antigen binding fragment thereof) which are outlined in Table 3. In certain embodiments, the CD2-binding molecule (or anti-CD2 antibody or antigen binding fragment thereof) as described herein can be an IgG1, an IgG2, or an IgG4 subclass of antibody. In certain embodiments, the CD2-binding molecule (or anti-CD2 antibody or antigen binding fragment thereof) as described herein can have a modified Fc region wherein the modification can include, but is not limited to, a point mutation resulting in Fc silencing, a switched native constant region, or an Fc silenced switched new native constant region. These combinations of different antibody subclasses and modifications produce different versions of the CD2-binding molecule (or anti-CD2 antibody or antigen binding fragment thereof) which are outlined in Table 3.

TABLE 3

| Examples of versions of CD2-binding molecule (or anti-CD2 antibody or antigen-binding fragment thereof) | |
| --- | --- |
| IgG subclass | Modification of CD2-binding molecule (or anti-CD2 antibody or antigen-binding fragment thereof) |
| IgG1 | A point mutation resulting in silenced Fc |
| IgG1 | same variable region but combined with a different native constant region |
| IgG1 | same variable region but combined with a Fc-silenced new native constant region |
| IgG2 | same variable region but combined with a different native constant region |
| IgG2 | same variable region but combined with a Fc-silenced new native constant region |
| IgG4 | same variable region but combined with a different native constant region |
| IgG4 | same variable region but combined with a Fc-silenced new native constant region |

Comparisons of CD2-binding molecules (or anti-CD2 antibody or antigen binding fragment thereof) are outlined in Table 4.

TABLE 4

| | | | | | IgG |
| Molecule | VH region: | VL region: | Deglycosylated | Fc modification | subclass |
| --- | --- | --- | --- | --- | --- |
| CD2-binding molecule 1 | SEQ ID NO: 01 | SEQ ID NO: 02 | Yes | None | IgG1 |
| CD2-binding molecule 2 | SEQ ID NO: 01 | SEQ ID NO: 02 | No | LALA-PG mutations | IgG1 |
| CD2-binding molecule 3 | SEQ ID NO: 01 | SEQ ID NO: 02 | No | V234A, G237A, P238S, H268A, V309L, A330S, P331S | IgG2 |
| CD2-binding molecule 4 | SEQ ID NO: 01 | SEQ ID NO: 02 | No | S228P, L235E, P329G | IgG4 |

Comparisons of CD2-binding molecules (or anti-CD2 antibody or antigen-binding fragment thereof)s In certain embodiments, the CD2-binding molecule (or an anti-CD2 antibody or antigen binding fragment thereof) described herein, including examples presented above, have little to no ADCC activity compared to siplizumab, yet retain the immunomodulatory effects exhibited by siplizumab.

In certain embodiments, the CD2-binding molecule (or anti-CD2 antibody or antigen-binding fragment thereof) provided herein can have a molecular weight that is higher than the molecular weight of an unmodified IgG1 antibody. In certain embodiments, this increase of molecular weight can be accomplished by the addition of duplicate regions of the molecule. In certain embodiments, the regions can be attached to the CD2-binding molecule (or anti-CD2 antibody or antigen-binding fragment thereof) through such means known in the art such as, but not limited to, chemical conjugation, recombinant fusion, and covalent attachment.

In certain embodiments, the additional regions to be attached to the CD2-binding molecule (or anti-CD2 antibody or antigen-binding fragment thereof), can include, but are not limited to, duplicate regions of the molecule such as an additional variable heavy chain (VH), an additional variable light chain (VL), a scFv comprising the fusion of an additional VH and an additional VL, an additional CH2 domain, or an additional CH3 domain. In certain embodiments, the additional regions can be attached to the Fc region of the CD2-binding molecule (or anti-CD2 antibody or antigen-binding fragment thereof).

In certain embodiments, an scFv can be attached to the Fc region of the CD2-binding molecule (or an anti-CD2 antibody or antigen binding fragment thereof). In certain embodiments the scFv can comprise a fusion of the VH and the VL of siplizumab. In certain embodiments, the scFv can comprise a fusion of a VH, wherein the VH can comprise an amino acid sequence of SEQ ID NO: 1, and a VL, wherein the VL is can comprise an amino acid sequence of SEQ ID NO: 2. In a specific embodiment, the scFv binds to CD2. In a certain embodiment, the CDRs of the scFv are the same as the CDRs of siplizumab. In certain embodiments, the scFv attached to the Fc region of the CD2-binding molecule (or anti-CD2 antibody or antigen-binding fragment thereof) described herein binds to an epitope on CD2. In certain embodiments, the scFv attached to the Fc region of the CD2-binding molecule (or an anti-CD2 antibody or antigen binding fragment thereof) described herein binds to the same epitope of CD2 as siplizumab. In certain embodiments, the scFv can be generated from an IgG2 antibody or an IgG4 antibody.

In certain embodiments, an additional CH2 domain can be attached to the Fc. In certain embodiments, the CH2 domain can comprises an amino acid sequence that is at least 80%, 85%, 90%, 95%, 98%, or 99% identical to the amino acid sequence of SEQ ID NO:18 or 19. In certain embodiments, the additional CH2 domain can be generated from an IgG2 antibody or an IgG4 antibody. In certain embodiments, an additional CH3 domain can be attached to the Fc. In certain embodiments, the CH3 domain can comprise an amino acid sequence that is at least 80%, 85%, 90%, 95%, 98%, or 99% identical to the amino acid sequence of SEQ ID NO:20 or 21. In certain embodiments, the additional CH3 domain can be generated from an IgG2 antibody or an IgG4 antibody. In a certain embodiment, the additional domains can be attached to the C-terminal end of the Fc. In certain embodiments, the domains can be attached to the CD2-binding molecule (or anti-CD2 antibody or antigen-binding fragment thereof) through such means known in the art such as, but not limited to, chemical conjugation, recombinant fusion, and covalent attachment. In certain embodiments, the domains can be attached to the CD2-binding molecule (or anti-CD2 antibody or antigen-binding fragment thereof) through such means known in the art such as, but not limited to, chemical conjugation, recombinant fusion, and covalent attachment. Examples of CD2 antibody or antigen-binding fragment thereof that can be used in disclosure and production thereof are described, for example, in U.S. Provisional Application No. 63/042,844, which is incorporated herein by reference in its entirety.

5.2 Production of CD2 Binding Molecule

Provided herein are methods for producing the CD2-binding molecule (or anti-CD2 antibody or antigen-binding fragment thereof) described herein, wherein the ability of the molecule to mediate antibody-dependent cellular cytotoxicity is reduced or eliminated while the immune regulatory activity of the molecule is maintained relative to siplizumab. Methods for producing the CD2-binding molecule (or anti-CD2 antibody or antigen-binding fragment thereof) described herein include recombinant expression techniques, selection methods, transformation into host cells, and purification of the CD2-binding molecule (or anti-CD2 antibody or antigen-binding fragment thereof); see Section 5.2.1. Also provided herein are methods for producing fragments of the CD2-binding molecule (or anti-CD2 antibody or antigen-binding fragment thereof); see Section 5.2.2, deglycosylated CD2-binding molecule (or anti-CD2 antibody or antigen-binding fragment thereof); see Section 5.2.3, and cells comprising vectors for recombinantly expressing the CD2-binding molecule (or anti-CD2 antibody or antigen-binding fragment thereof) described herein; see Section 5.2.4.

In certain embodiments, the CD2-binding molecule (or anti-CD2 antibody or antigen-binding fragment thereof) described herein can comprise a VH of SEQ ID NO: 01, a VL of SEQ ID NO: 02, a CH of SEQ ID NO: 09, and a CL of SEQ ID NO: 14; a VH of SEQ ID NO: 01, a VL of SEQ ID NO: 02, a CH of SEQ ID NO: 10, and a CL of SEQ ID NO: 14; a VH of SEQ ID NO: 01, a VL of SEQ ID NO: 02, a CH of SEQ ID NO: 11, and a CL of SEQ ID NO: 14; a VH of SEQ ID NO: 01, a VL of SEQ ID NO: 02, a CH of SEQ ID NO: 12, and a CL of SEQ ID NO: 14; or a VH of SEQ ID NO: 01, a VL of SEQ ID NO: 02, a CH of SEQ ID NO: 13, and a CL of SEQ ID NO: 14. In certain embodiments, the CD2-binding molecule (or anti-CD2 antibody or antigen-binding fragment thereof) described herein can comprise a VH of SEQ ID NO: 01, a VL of SEQ ID NO: 02, a CH of SEQ ID NO: 09, and a CL of SEQ ID NO: 15; a VH of SEQ ID NO: 01, a VL of SEQ ID NO: 02, a CH of SEQ ID NO: 10, and a CL of SEQ ID NO: 15; a VH of SEQ ID NO: 01, a VL of SEQ ID NO: 02, a CH of SEQ ID NO: 11, and a CL of SEQ ID NO: 15; a VH of SEQ ID NO: 01, a VL of SEQ ID NO: 02, a CH of SEQ ID NO: 12, and a CL of SEQ ID NO: 15; or a VH of SEQ ID NO: 01, a VL of SEQ ID NO: 02, a CH of SEQ ID NO: 13, and a CL of SEQ ID NO: 15.

In certain embodiments, the CD2-binding molecule (or anti-CD2 antibody or antigen-binding fragment thereof) described herein can comprise a heavy chain of SEQ ID NO: 16; a VL of SEQ ID NO: 02, and a CL of SEQ ID NO: 14; a heavy chain of SEQ ID NO: 16; a VL of SEQ ID NO: 02, and a CL of SEQ ID NO: 15; a VH of SEQ ID NO: 01; a CH of SEQ ID NO: 09; and a light chain of SEQ ID NO: 17; a VH of SEQ ID NO: 01; a CH of SEQ ID NO: 10; and a light chain of SEQ ID NO: 17; a VH of SEQ ID NO: 01; a CH of SEQ ID NO: 11; and a light chain of SEQ ID NO: 17; a VH of SEQ ID NO: 01; a CH of SEQ ID NO: 12; and a light chain of SEQ ID NO: 17; a VH of SEQ ID NO: 01; a CH of SEQ ID NO: 13; and a light chain of SEQ ID NO: 17; or a heavy chain of SEQ ID NO: 16 and a light chain of SEQ ID NO: 17.

In certain embodiments, the CD2-binding molecule (or anti-CD2 antibody or antigen-binding fragment thereof) may comprise enlarged variants. In certain embodiments, the Fc of the CD2-binding molecule (or anti-CD2 antibody or antigen-binding fragment thereof) described herein comprises an additional region such that the molecular weight of the CD2-binding molecule (or anti-CD2 antibody or antigen-binding fragment thereof) is increased by 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, 51 kDa, 52 kDa, 53 kDa, 54 kDa, 55 kDa, 56 kDa, 57 kDa, 58 kDa, 59 kDa, or 60 kDa. In certain embodiments, the Fc of the CD2-binding molecule (or anti-CD2 antibody or antigen-binding fragment thereof) described herein comprises an additional region such that the molecular weight of the CD2-binding molecule (or anti-CD2 antibody or antigen-binding fragment thereof) is increased by a range of 10 kDa to 15 kDa, 11 kDa to 16 kDa, 12 kDa to 17 kDa, 13 kDa to 18 kDa, 14 kDa to 19 kDa, 15 kDa to 20 kDa, 16 kDa to 21 kDa, 17 kDa to 22 kDa, 18 kDa to 23 kDa, 19 kDa to 24 kDa, 20 kDa to 25 kDa, 21 kDa to 26 kDa, 22 kDa to 27 kDa, 23 kDa to 28 kDa, 24 kDa to 29 kDa, 25 kDa to 30 kDa, 26 kDa to 31 kDa, 27 kDa to 32 kDa, 28 kDa to 33 kDa, 29 kDa to 34 kDa, 30 kDa to 35 kDa, 31 kDa to 36 kDa, 32 kDa to 37 kDa, 33 kDa to 38 kDa, 34 kDa to 39 kDa, 35 kDa to 40 kDa, 36 kDa to 41 kDa, 37 kDa to 42 kDa, 38 kDa to 43 kDa, 39 kDa to 44 kDa, 40 kDa to 45 kDa, 41 kDa to 46 kDa, 42 kDa to 47 kDa, 43 kDa to 48 kDa, 44 kDa to 49 kDa, 45 kDa to 50 kDa, 46 kDa to 51 kDa, 47 kDa to 52 kDa, 48 kDa to 53 kDa, 49 kDa to 54 kDa, 50 kDa to 55 kDa, 51 kDa to 56 kDa, 52 kDa to 57 kDa, 53 kDa to 58 kDa, 54 kDa to 59 kDa, or 55 kDa to 60 kDa.

In certain embodiments, duplicate regions of the CD2-binding molecule (or anti-CD2 antibody or antigen-binding fragment thereof) may be attached to the molecule to produce enlarged variants. In certain embodiments, these regions can be attached to the Fc region of the CD2-binding molecule (or anti-CD2 antibody or antigen-binding fragment thereof) through such means known in the art such as, but not limited to, chemical conjugation, recombinant fusion, and covalent attachment.

In certain embodiments, the enlarged variants of the CD2-binding molecules (or anti-CD2 antibody or antigen-binding fragment thereof)s can be derived from an IgG1, IgG 2, or IgG4. In certain embodiments, an additional scFv can be attached to the Fc of the CD2-binding molecule (or anti-CD2 antibody or antigen-binding fragment thereof) to produce an enlarged variant (FIG. 7, FIG. 8A). In certain embodiments, the scFv can comprise a VH and VL wherein the VH can comprise an amino acid sequence that is at least 80%, 85%, 90%, 95%, 98%, or 99% identical to the amino acid sequence of SEQ ID NO:1, and wherein the VL can comprise an amino acid sequence that is at least 80%, 85%, 90%, 95%, 98%, or 99% identical to the amino acid sequence of SEQ ID NO:2.

In certain embodiments, an additional CH2 domain can be attached to the Fc of the CD2-binding molecule (or anti-CD2 antibody or antigen-binding fragment thereof) to produce an enlarged variant (FIG. 7, FIG. 8B). In certain embodiments, the additional CH2 domain can comprise an amino acid sequence that is at least 80%, 85%, 90%, 95%, 98%, or 99% identical to the amino acid sequence of SEQ ID NO:18 or 19. In certain embodiments, an additional CH3 domain can be attached to the Fc of the CD2-binding molecule (or anti-CD2 antibody or antigen-binding fragment thereof) to produce an enlarged variant (FIG. 7, FIG. 8C). In certain embodiments, the additional CH3 domain can comprise an amino acid sequence that is at least 80%, 85%, 90%, 95%, 98%, or 99% identical to the amino acid sequence of SEQ ID NO:20 or 21. In a preferred embodiment, the additional fragment or domains can be attached to the C-terminal end of the Fc. In certain embodiments, the enlarged anti-CD2 variant can be an IgG2 antibody. In certain embodiments, the enlarged anti-CD2 variant can be an IgG4 antibody. The details of enlarged anti-CD2 variants are shown in Table 5.

In certain embodiments, the additional region attached to the CD2-binding molecule (or anti-CD2 antibody or antigen-binding fragment thereof) can comprise an unrelated or artificial amino acid sequence. In certain embodiments, the additional region attached to the CD2-binding molecule (or anti-CD2 antibody or antigen-binding fragment thereof) can comprise a fragment, such as a structural domain, from another human protein. In certain embodiments, the additional region attached to the CD2-binding molecule (or anti-CD2 antibody or antigen-binding fragment thereof) can comprise a fragment of a domain from another human protein. In certain embodiments, the addition of such an additional region does not interfere with the binding activity of the parent CD2-binding molecule (or anti-CD2 antibody or antigen-binding fragment thereof) and/or does not increase the immunogenicity of the resulting anti-CD2 binder relative to the parent CD2-binding molecule (or anti-CD2 antibody or antigen-binding fragment thereof) in humans.

TABLE 5

Enlarged anti-CD2 variants

| Description | IgG subclass | Additional antibody component | Theoretical protein weight |
|---|---|---|---|
| Molecule 5A | IgG2 | scFv | 199.4 kDa |
| Molecule 5B | IgG4 | scFv | 199.6 kDa |
| Molecule 6A | IgG2 | CH2 domain | 170.1 kDa |
| Molecule 6B | IgG4 | CH2 domain | 170.3 kDa |
| Molecule 7A | IgG2 | CH3 domain | 171.2 kDa |
| Molecule 7B | IgG4 | CH3 domain | 171.4 kDa |

5.2.1 Recombinant Expression Systems

Described herein are methods for producing the CD2-binding molecule (or anti-CD2 antibody or antigen-binding fragment thereof). The CD2-binding molecule (or anti-CD2 antibody or antigen-binding fragment thereof) described herein can be produced by any appropriate expression method known in the art. These methods of producing antibodies can include, but are not limited to, the use of hybridoma cells, bacteria, yeast cells, insect cells, transgenic animals, transgenic plants, phage display, ribosome display, and recombinant expression in mammalian cell lines. In certain embodiments, the method to produce the recombinant antibody that binds CD2 at the same epitope as siplizumab can include isolation, amplifying, and cloning of the VH and VL genes of the antibody; the joining together of the heavy and light fragments; and then cloning the chains into special phage vectors. Upon integration, antibodies are displayed on the cell surface and the antibody with desired binding specificity can be selected for by using any appropriate selection method known in the art. These methods can include, but are not limited to, panning, use of paramagnetic beads, fluorescence-activated cell sorting (FACS), Enzyme-Linked Immunosorbent Assays (ELISAs), and/or surface plasmon resonance (SPR) methods such as the Biacore system.

After selection, the genes for the antibody can be transferred into an expression vector. In certain embodiments, a strong promoter is also inserted into the expression vector. The promoter can be a viral promoter, such as CMV or SV40; or a non-viral promoter such as elongation factor (EF)-1 promotor, UBC, PGK, or CAG promoter. The expression vector is transformed into a host cell line and integrated into the host cell genome. In certain embodiments, the host cell line can include bacteria, yeast, or mammalian cell lines. In a specific embodiment, the mammalian cell lines that can be used as a host cell line for recombinant antibody production includes, but are not limited to, Chinese hamster ovary (CHO) cell line, NS0 cell line, Sp2/0 cell line, PER.C6 cell line, and human embryonic kidney (HEK) cell line.

In certain embodiments, the CD2-binding molecule (or anti-CD2 antibody or antigen-binding fragment thereof) described herein can be recovered from the host cell cultures and purified by any appropriate method known in the art. Standard antibody purification methods include, but are not limited to, protein-A affinity chromatography, Q-sepharose anion exchange chromatography, sulfopropyl-sepharose cation exchange chromatography, high performance liquid chromatography (HPLC), protein G purification, ammonium sulfate or ethanol precipitation, acid extraction, phosphocellulose chromatography, hydrophobic interaction chromatography, affinity chromatography, hydroxylapatite chromatography and lectin chromatography.

5.2.2 Production of CD2-Binding Fragments

In addition to the procedural steps described above, modifications or additional steps can be taken to produce CD2-binding fragments. These CD2-binding molecule fragments (or anti-CD2 antibody or antigen-binding fragment thereof) can include, but are not limited to, Fabs, F(ab')2, scFv, and sdAb. In specific embodiments, the fragment produced binds to the same epitope as siplizumab. In certain embodiments, the procedure to produce a CD2-binding scFv includes isolation, amplifying, and cloning of the VH and VL genes of the antibody in addition to a linker. A flexible peptide linker is needed to join the VH and VL fragments. In certain embodiments, the procedure to produce CD2-binding sdAb includes isolation, amplifying, and cloning of camelid or shark VH region, that results in a sole VH region lacking a paired VL region, attached to a constant region.

In certain embodiments, the CD2-binding molecule (or anti-CD2 antibody or antigen-binding fragment thereof) described herein can be treated with papain to produce Fab binding fragments. In certain embodiments, the CD2-binding molecule (or anti-CD2 antibody or antigen-binding fragment thereof) described herein can be treated with pepsin to produce F(ab')$_2$. In a specific embodiment, the sequence of the VH region of the Fab, F(ab')$_2$, scFv, or sdAb described herein is 80%, 85%, 90%, 91%, 92%, 93%, 94%, 95%, 96%, 97%, 98%, 99%, or 100% identical to SEQ ID NO: 01. In a specific embodiment, the sequence of the VL region of the Fab, F(ab')$_2$, scFv, or sdAb described herein is 80%, 85%, 90%, 91%, 92%, 93%, 94%, 95%, 96%, 97%, 98%, 99%, or 100% identical to SEQ ID NO: 02.

5.2.3 Deglycosylation of CD2-Binding Antibody

Described herein are methods for the production of a deglycosylated CD2-binding molecule (or anti-CD2 antibody or antigen-binding fragment thereof) described in Section 5.1.4. In some embodiments, the glycans of the CD2-binding molecule (or anti-CD2 antibody or antigen-binding fragment thereof) can be modified using chemical methods, such as treatment with trifluoromethanesulfonic (TFMS) acid. In another embodiment, the glycans of the CD2-binding molecule (or anti-CD2 antibody or antigen-binding fragment thereof) can be modified using enzymatic methods. In a specific embodiment, the chemical or enzymatic methods of glycan degradation preserves the Fc amino acid sequence of the CD2-binding molecule (or anti-CD2 antibody or antigen-binding fragment thereof) described herein.

Enzymes that can be used to modify the glycans of the CD2-binding molecule (or anti-CD2 antibody or antigen-binding fragment thereof) described herein can include, but are not limited to Peptide-N-Glycosidase F (PNGase F), Peptide-N-Glycosidase A (PNGase A), endoglycosidase H, endoglycosidase F, endo-β-N-acetylglucosaminidase (EndoS), endo-α-N-acetylgalactosaminidase, sialidase A, β1-4 galactosidase S, β-N-acetylhexosaminidase, and EndoS2. In a certain embodiment, the CD2-binding molecule (or anti-CD2 antibody or antigen-binding fragment thereof) described herein is treated with an endoglycosidase. In a specific embodiment, the endoglycosidase used to degrade the glycan structures of the CD2-binding molecule (or anti-CD2 antibody or antigen-binding fragment thereof) described herein is EndoS (Sjogren et al., *Glycobiology*, 2015, vol. 25, no. 10, 1053-1063). In a specific embodiment, the endoglycosidase used to degrade the glycan structures of the CD2-binding molecule (or anti-CD2 antibody or antigen-binding fragment thereof) described herein is EndoS2 (Sjogren et al., *Biochem. J.* (2013) 455, 107-118).

EndoS and EndoS2, secreted from *Streptococcus pyogenes*, specifically remove N-linked glycans from the chitobiose core of the heavy chain of human IgG. Incubation with endoglycosidase EndoS2 from *Streptococcus pyogenes* results in cleavage between the two GlcNAc residues in the chitobiose core of N-glycans, while leaving the core GlcNAc intact. In certain embodiments, the CD2 binding molecule described herein is treated with EndoS or EndoS2. Both EndoS and EndoS2 remove complex glycans while EndoS2 removes high-mannose glycans.

In a certain embodiment, the CD2-binding molecule (or anti-CD2 antibody or antigen-binding fragment thereof) described herein is an IgG antibody. In certain embodiments, said CD2-binding molecule (or anti-CD2 antibody or antigen-binding fragment thereof) described herein has at least one consensus N-linked glycosylation site of the constant region of the heavy chain. In certain embodiments, said CD2-binding molecule (or anti-CD2 antibody or antigen-binding fragment thereof) described herein carries at least one of the oligosaccharides illustrated in FIG. 33B. In a specific embodiment, the CD2-binding molecule (or anti-CD2 antibody or antigen-binding fragment thereof) described herein is treated with EndoS. In a specific embodiment, the CD2-binding molecule (or anti-CD2 antibody or antigen-binding fragment thereof) described herein is treated with EndoS2. In a specific embodiment, the CD2-binding molecule (or anti-CD2 antibody or antigen-binding fragment thereof) described herein is deglycosylated. In a specific embodiment, the CD2-binding molecule (or anti-CD2 antibody or antigen-binding fragment thereof) described herein is an IgG antibody, wherein the ability of the antibody to mediate antibody-dependent cellular cytotoxicity is reduced or eliminated while the immune regulatory activity of the antibody is maintained relative to siplizumab.

In certain embodiments, the deglycosylation of the CD2 binding molecule described herein can be determined by any appropriate method known in the art. Standard methods to determine deglycosylation include, but are not limited to, size-exclusion chromatography analysis, tertiary structure analysis, thermal stability evaluation, guanidine HCl induced denaturation, resistance to papain digestion, and reduced mass data of heavy chains measured by liquid chromatography-mass spectroscopy (LC-MS).

5.2.4 Cells and Vectors

Provided herein are cells expressing the CD2-binding molecule (or anti-CD2 antibody or antigen-binding fragment thereof) as described herein. Provided herein are ex vivo cells recombinantly expressing the CD2-binding molecule (or anti-CD2 antibody or antigen-binding fragment thereof) and described herein. Also provided herein are expression vectors comprising nucleotide sequences that encode the CD2-binding molecule (or anti-CD2 antibody or antigen-binding fragment thereof) as described herein. In a specific embodiment, the cell is an ex vivo cell.

In certain embodiments, the gene expression can be placed under the control of a promoter. The promoter can be a viral promoter, such as CMV or SV40; or a non-viral promoter such as elongation factor (EF)-1 promotor, UBC, PGK, or CAG promoter. In certain embodiments, a nucleotide sequence that encodes the CD2-binding molecule (or anti-CD2 antibody or antigen-binding fragment thereof) described herein is cloned into an appropriate vector. In certain embodiments, the vector can be a mammalian vector. In certain embodiments, the vector can be a viral vector. In certain embodiments, the expression vector is transformed into a cell (e.g. an ex vivo cell). In certain embodiments, the cell expresses the vector such that the nucleotide sequence is transcribed and translated by the host cell. In certain embodiments, the host cell line can include bacteria, yeast, or mammalian cell lines. In a specific embodiment, the host cells line is a mammalian cell. In a certain embodiment, the mammalian cell lines that can be used as a host cell line for recombinant antibody production includes, but are not limited to, Chinese hamster ovary (CHO) cell line, NS0 cell line, Sp2/0 cell line, PER.C6 cell line, and human embryonic kidney (HEK) cell line.

In certain embodiments, the host cell line can be genetically modified. In certain embodiments, the modification can be made with the goal of improved productivity of the expression of the recombinant protein. In certain embodiments, the modification can be made to act upon the recombinant protein the host cell expresses. In a specific embodiment, the host cell line has been genetically modified to express a desired glycosyltransferases. In a specific embodiment, the host cell line has been genetically modified to express EndoS or EndoS2.

5.3 Therapeutic Uses and Methods

Provided herein are methods for using the CD2-binding molecule (or anti-CD2 antibody or antigen-binding fragment thereof) as described herein, wherein the ability of said molecule to mediate antibody-dependent cellular cytotoxicity is reduced or eliminated while the immune regulatory activity of said molecule is maintained relative to siplizumab. Provided herein are methods for treating a human subject who has a chronic or acute inflammatory disorder of the immune system. Also provided herein are methods for preventing a human subject from developing chronic or acute inflammatory disorder of the immune system. In further embodiments, the acute or chronic disorder of the immune system can be, but is not limited to, graft-versus-host disease (GVHD), rheumatoid arthritis, ankylosing spondylitis, type-1 diabetes mellitus, psoriasis, ulcerative colitis, inflammatory bowel disease (Crohn's disease), celiac disease, Sjögren's disease, lupus, multiple sclerosis, focal segmental glomerulosclerosis, atopic dermatitis, amyotrophic lateral sclerosis, primary biliary cirrhosis, and primary sclerosing cholangitis, and severe asthma. In certain embodiments, the method comprises administering to the human subject who has a chronic or acute inflammatory disorder of the immune system the CD2-binding molecule (or anti-CD2 antibody or antigen-binding fragment thereof) described herein or the pharmaceutical composition comprising the CD2-binding molecule (or anti-CD2 antibody or antigen-binding fragment thereof) described herein. In certain embodiments, the CD2-binding molecule (or anti-CD2 antibody or antigen-binding fragment thereof) described herein or the pharmaceutical composition comprising the CD2-binding described herein is administered to the patient for a long period of time.

Also provided herein are methods for treating a human subject undergoing an organ or bone marrow transplantation procedure. In certain embodiments, the method comprises administering the CD2-binding molecule (or anti-CD2 antibody or antigen-binding fragment thereof) described herein to the organ to be transplanted. In certain embodiments, the method comprises administering to the human subject the CD2-binding molecule (or anti-CD2 antibody or antigen-binding fragment thereof) described herein or the pharmaceutical composition comprising the CD2-binding molecule (or anti-CD2 antibody or antigen-binding fragment thereof) described herein.

The methods provided herein can include administration of an anti-CD2 antibody or an antigen-binding fragment thereof and a CTLA-4 co-stimulation blockade to a subject. In some embodiments, an anti-CD2 antibody or an antigen-binding fragment thereof and a CTLA-4 co-stimulation blockade is administered to a subject to prevent or treat an immune related disorder or disease in a subject. In some embodiments, the methods provided herein include administration of an anti-CD2 antibody or an antigen-binding fragment thereof, a CTLA-4 co-stimulation blockade, and another active agent to the subject. In some embodiments, the subject has been diagnosed with at least one immune related disorder or disease. In some embodiments, the subject has at least one symptom associated with an immune related disorder or disease. In some embodiments, the methods provided herein are used to prevent an immune related disorder or disease from occurring in a subject. The methods provided herein can also include maintaining immune tolerance to a transplant subject by administering an anti-CD2 antibody or an antigen-binding fragment thereof and a CTLA-4 co-stimulation blockade to the subject. In some embodiments, the subject is predisposed or likely to develop an immune related disorder or disease. In some embodiments, the subject has been diagnosed with, is likely to develop, or has symptoms associated with at least one immune related disorder or disease, at least two, at least three, at least four, or more than at least four immune related disorders or diseases. In some embodiments, the immune related disorder or disease is an acute or chronic disorder of the immune system.

In some embodiments, an anti-CD2 antibody or an antigen-binding fragment thereof is administered to a subject prior to, concurrently with, or after a CTLA-4 co-stimulation blockade is administered to the subject. In some embodiments, a first dose of an anti-CD2 antibody or an antigen-binding fragment thereof is administered to a subject prior to, concurrently with, or after a first dose of a CTLA-4 co-stimulation blockade is administered to the subject. Dosage of a therapeutic agent (e.g., an anti-CD2 antibody or an antigen-binding fragment thereof and a CTLA-4 co-stimulation blockade) is dependent upon many factors including, but not limited to, the type of tissue affected, the type of autoimmune disease being treated, the severity of the disease, and a subject's health and response to the treatment with the agents. Accordingly, dosages of the agents can vary depending on each subject and the mode of administration. In some embodiments, a dose of the anti-CD2 antibody or antigen-binding fragment thereof is not therapeutically effective when the CTLA-4 co-stimulation blockade is not administered to the subject. In some embodiments, a dose of the CTLA-4 co-stimulation blockade is not therapeutically effective when the anti-CD2 antibody or antigen-binding fragment thereof is not administered to the subject. In some embodiments, a lower dose of the anti-CD2 antibody or antigen-binding fragment thereof is administered to the subject when the CTLA-4 co-stimulation blockade is also administered to the subject. In some embodiments, a lower dose of the CTLA-4 co-stimulation blockade is administered to the subject when the anti-CD2 antibody or antigen-binding fragment thereof is also administered to the subject. In some embodiments, the dose is lower by about or at least about 2%, 5%, 7%, 10%, 15%, 20%, 25%, 30%, 35%, 40%, 45%, 50%, 55%, 60%, 65%, 70%, or more than 70% lower. In some embodiments, the dose is lower by about or at least about 2-fold, 5-fold, 7-fold, 10-fold, 15-fold, 20-fold, 25-fold, 30-fold, 35-fold, 40-fold, 45-fold, 50-fold, 55-fold, 60-fold, 65-fold, 70-fold, 80-fold, or more than 80-fold lower. In some embodiments, the dose is lower by about or at least about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 15 mg/kg, 17 mg/kg, 20 mg/kg, or more than 20 mg/kg lower. In some embodiments, the dose is lower by about or at least about 5 mg, 10 mg, 20 mg, 30 mg, 40 mg, 50 mg, 75 mg, 100 mg, 150 mg, 175 mg, 200 mg, 250 mg, 300 mg, 350 mg, 400 mg, 450 mg, 500 mg, or more than 500 mg lower.

Examples of an immune related disorder or disease that can be treated with a method described herein include, but are not limited to, systemic lupus erythematosis, rheumatoid arthritis, psoriatic arthritis, polyarticular juvenile idiopathic arthritis (JIA), osteoarthritis, juvenile chronic arthritis, a spondyloarthropathy, systemic sclerosis, an idiopathic inflammatory myopathy, Sjögren's syndrome, systemic vasculitis, sarcoidosis, autoimmune hemolytic anemia, pernicious anemia, autoimmune thrombocytopenia, thyroiditis, diabetes mellitus, immune-mediated renal disease, a demyelinating disease of the central or peripheral nervous system, idiopathic demyelinating polyneuropathy, Guillain-Barre syndrome, lyme disease, a chronic inflammatory demyelinating polyneuropathy, a hepatobiliary disease, infectious or autoimmune chronic active hepatitis, primary biliary cirrhosis, Goodpasture syndrome, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, contact dermatitis, psoriasis, an allergic disease, asthma, allergic rhinitis, atopic dermatitis, food hypersensitivity, urticaria, multiple sclerosis, uveitis, an immunologic disease of the lung, eosinophilic pneumonia, idiopathic pulmonary fibrosis, hypersensitivity pneumonitis, a disease associated with an organ transplant, disease associated with a tissue transplant, graft rejection, graft-versus-host-disease (GVHD), Devic's disease, acute disseminated encephalomyelitis, acute demyelinating optic neuritis, demyelinative transverse myelitis, Miller-Fisher syndrome, encephalomyelradiculoneuropathy, acute demyelinative polyneuropathy, tumefactive multiple sclerosis, Balo's concentric sclerosis, alopecia areata, ankylosing spondylitis, meniere's disease, antiphospholipid syndrome, mixed connective tissue disease, autoimmune addison's disease, myasthenia gravis, autoimmune hepatitis, pemphigus vulgaris, behcet's disease, bullous pemphigoid, polyarthritis nodosa, cardiomyopathy, polychondritis, celiac sprue-dermatitis, polyglandular syndromes, chronic fatigue syndrome (cfids), polymyalgia rheumatica, chronic inflammatory demyelinating, polymyositis and dermatomyositis, primary agammaglobulinemia, churg-strauss syndrome, cicatricial pemphigoid, crest syndrome, raynaud's phenomenon, cold agglutinin disease, reiter's syndrome, crohn's disease, rheumatic fever, discoid lupus, essential mixed cryoglobulinemia, fibromyalgia, scleroderma, grave's disease, sjogren's syndrome, stiff-man syndrome, hashimoto's thyroiditis, takayasu arteritis, temporal arteritis/giant cell arteritis, idiopathic thrombocytopenia purpura (ITP), ulcerative colitis, focal segmental glomerulosclerosis, IgA nephropathy, insulin dependent diabetes (type I), lichen planus, and vitiligo.

In some embodiments, an immune related disorder or disease is rheumatoid arthritis, polyarticular juvenile idiopathic arthritis (JIA), and/or psoriatic arthritis. In some embodiments, an immune related disorder or disease is rheumatoid arthritis. In some embodiments, an immune related disorder or disease is a disorder or a disease associated with an organ transplant and/or a disorder or a disease associated with a tissue transplant. In some embodiments, an immune related disorder or disease is a disorder or a disease associated with any organ and/or tissue transplant in a human body. In some embodiments, an immune related disorder or disease is a disorder or a disease associated with lung, kidney, pancreas, heart, liver, skin, stomach, intestine, gastrointestinal tract transplant and/or a tissue transplant therefrom. In some embodiments, an immune related disorder or disease is a disorder or a disease associated with a liver transplant and/or a liver tissue transplant.

In some embodiments, the methods provided herein include administration of an anti-CD2 antibody or an antigen-binding fragment thereof and a CTLA-4 co-stimulation blockade to a subject who has received an organ and/or tissue transplant from a donor. As used herein, a donor is an individual from which the organ (e.g., liver or kidney) to be transplanted is taken. The donor can be of the same species as the recipient and the donor can be alive or deceased. The donor can be related to the recipient or not related to the recipient. As used herein, a recipient is a subject who will receive the transplanted organ (e.g., liver or kidney) and/or tissue. The recipient can be related or not related to the donor. The recipient can be HLA-matched or HLA-mismatched with the donor.

In some embodiments, the transplanted organ (e.g., liver or kidney) may be a whole organ, a part of an organ, tissue or cells derived from an organ. In some embodiments, a whole organ (e.g., liver or kidney) is transplanted. In some embodiments, a partial organ (e.g., liver or kidney) is transplanted.

In some embodiments, the methods described herein include administration of an anti-CD2 antibody or an antigen-binding fragment thereof and a CTLA-4 co-stimulation blockade to a subject who has undergone a splenectomy (e.g., to a subject who underwent splenectomy before receiving an organ transplant).

The procedure for obtaining and implanting the organ (e.g., liver or kidney) is well-known to the skilled artisan. Any procedure for the surgical removal from the donor and the surgical implantation in the recipient can be used with the methods provided herein. In certain embodiments, the organ (e.g., liver or kidney) can be treated between removal and implantation.

In certain embodiments, the patient is treated for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, 20 years, or more than 20 years.

In some embodiments, the methods described herein results in a decrease in cell proliferation. In some embodiments, the methods described herein results in a decrease in a number of cells in a biological sample obtained from the subject after both the anti-CD2 antibody or antigen-binding fragment thereof and the CTLA-4 co-stimulation blockade are administered to the subject. In some embodiments, the decrease in the number of cells after both the anti-CD2 antibody or antigen-binding fragment thereof and the CTLA-4 co-stimulation blockade are administered to the subject is greater as compared to a decrease in the number of cells in a biological sample obtained from the subject prior to the administration of the anti-CD2 antibody or antigen-binding fragment thereof to the subject, prior to the administration of the CTLA-4 co-stimulation blockade to the subject, or prior to both. In some embodiments, the decrease in the number of cells after both the anti-CD2 antibody or antigen-binding fragment thereof and the CTLA-4 co-stimulation blockade are administered to the subject is higher as compared to the decrease in the number of cells in a comparable method used to treat the immune associated disorder in a comparable subject, which comparable method does not include administration of both the anti-CD2 antibody or antigen-binding fragment thereof and the CTLA-4 co-stimulation blockade. In some embodiments, the comparable subject has been diagnosed with or suspected of having the same immune associated disorder as the subject. In some embodiments, the comparable subject has at least one symptom in common as the subject. In some embodiments, the decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%. In some embodiments, the number of cells in a biological sample obtained from the subject after both the anti-CD2 antibody or antigen-binding fragment thereof and the CTLA-4 co-stimulation blockade are administered to the subject is about or at least about 5%, 10%, 15%, 20%, 25%, 30%, 35%, 40%, 45%, 50%, 55%, 60%, 65%, 70%, 75%, 80%, 85%, 90%, 95%, 100%, or more than 100% lower as compared to the number of cells in a biological sample obtained from the subject before both the anti-CD2 antibody or antigen-binding fragment thereof and the CTLA-4 co-stimulation blockade are administered to the subject, or after one of the anti-CD2 antibody or antigen-binding fragment thereof or the CTLA-4 co-stimulation blockade, but not both, is administered to the subject.

In some embodiments, the methods described herein results in a decrease in the level of CD2. In some embodiments, the methods described herein results in a decrease in the level of CD2 in a biological sample obtained from the subject after both the anti-CD2 antibody or antigen-binding fragment thereof and the CTLA-4 co-stimulation blockade are administered to the subject. In some embodiments, the decrease in the level of CD2 after both the anti-CD2 antibody or antigen-binding fragment thereof and the CTLA-4 co-stimulation blockade are administered to the subject is greater as compared to a decrease in the level of CD2 in a biological sample obtained from the subject prior to the administration of the anti-CD2 antibody or antigen-binding fragment thereof to the subject, prior to the administration of the CTLA-4 co-stimulation blockade to the subject, or prior to both. In some embodiments, the decrease in the level of CD2 after both the anti-CD2 antibody or antigen-binding fragment thereof and the CTLA-4 co-stimulation blockade are administered to the subject is higher as compared to the decrease in the level of CD2 in a comparable method used to treat the immune associated disorder in a comparable subject, which comparable method does not include administration of both the anti-CD2 antibody or antigen-binding fragment thereof and the CTLA-4 co-stimulation blockade. In some embodiments, the comparable subject has been diagnosed with or suspected of having the same immune associated disorder as the subject. In some embodiments, the comparable subject has at least one symptom in common as the subject. In some embodiments, the decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%. In some embodiments, the level of CD2 in a biological sample obtained from the subject after both the anti-CD2 antibody or antigen-binding fragment thereof and the CTLA-4 co-stimulation blockade are administered to the subject is about or at least about 5%, 10%, 15%, 20%, 25%, 30%, 35%, 40%, 45%, 50%, 55%, 60%, 65%, 70%, 75%, 80%, 85%, 90%, 95%, 100%, or more than 100% lower as compared to the level of CD2 in a biological sample obtained from the subject before both the anti-CD2 antibody or antigen-binding fragment thereof and the CTLA-4 co-stimulation blockade are administered to the subject, or after one of the anti-CD2 antibody or antigen-binding fragment thereof or the CTLA-4 co-stimulation blockade, but not both, is administered to the subject.

In some embodiments, the methods described herein results in a synergistic effect. In some embodiments, the methods described herein results in a synergistic effect in a subject after both the anti-CD2 antibody or antigen-binding fragment thereof and the CTLA-4 co-stimulation blockade are administered to the subject. In some embodiments, administration of the anti-CD2 antibody or antigen-binding fragment thereof and the CTLA-4 co-stimulation blockade to the subject is synergistic in comparison to the administration of one of, but not both, the anti-CD2 antibody or antigen-binding fragment thereof or the CTLA-4 co-stimulation blockade to the subject. In some embodiments, the methods described herein results in a reduced alloimmune response. In some embodiments, the methods described herein results in a reduced alloimmune response in a subject after both the anti-CD2 antibody or antigen-binding fragment thereof and the CTLA-4 co-stimulation blockade are administered to the subject. In some embodiments, the decrease in alloimmune response after both the anti-CD2 antibody or antigen-binding fragment thereof and the CTLA-4 co-stimulation blockade are administered to the subject is greater as compared to a decrease in alloimmune response in the subject prior to the administration of the anti-CD2 antibody or antigen-binding fragment thereof to the subject, prior to the administration of the CTLA-4 co-stimulation blockade to the subject, or prior to both. In some embodiments, the decrease in alloimmune response after both the anti-CD2 antibody or antigen-binding fragment thereof and the CTLA-4 co-stimulation blockade are administered to the subject is greater as compared to the decrease in the alloimmune response in a comparable method used to treat the immune associated disorder in a comparable subject, which comparable method does not include administration of both the anti-CD2 antibody or antigen-binding fragment thereof and the CTLA-4 co-stimulation blockade to the subject. In some embodiments, the comparable subject has been diagnosed with or suspected of having the same immune associated disorder as the subject. In some embodiments, the comparable subject has at least one symptom in common as the subject. In some embodiments, the decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%. In some embodiments, the alloimmune response in a subject after both the anti-CD2 antibody or antigen-binding fragment thereof and the CTLA-4 co-stimulation blockade are administered to the subject is about or at least about 5%, 10%, 15%, 20%, 25%, 30%, 35%, 40%, 45%, 50%, 55%, 60%, 65%, 70%, 75%, 80%, 85%, 90%, 95%, 100%, or more than 100% lower as compared to the alloimmune response in the subject before both the anti-CD2 antibody or antigen-binding fragment thereof and the CTLA-4 co-stimulation blockade are administered to the subject, or after one of the anti-CD2 antibody or antigen-binding fragment thereof or the CTLA-4 co-stimulation blockade, but not both, is administered to the subject.

5.3.1 Treatment of Patients with Inflammatory Immune Disorders and Subjects Suitable for Treatment Described herein are methods for treating a human subject with a chronic or acute inflammatory disorder of the immune system. Described herein are methods for treating a human subject with an immune related disorder or disease. Described herein are methods for preventing an immune related disorder or disease in a subject. Individuals who have an inflammatory immune disorder may follow the methods described herein with the goal of treating the symptoms of the disorder. In certain embodiments, the acute or chronic disorder of the immune system can be, but is not limited to, graft-versus-host disease (GVHD), rheumatoid arthritis, ankylosing spondylitis, type-1 diabetes mellitus, psoriasis, ulcerative colitis, inflammatory bowel disease (Crohn's disease), celiac disease, Sjögren's disease, lupus, multiple sclerosis, focal segmental glomerulosclerosis, atopic dermatitis, amyotrophic lateral sclerosis, primary biliary cirrhosis, and primary sclerosing cholangitis, and severe asthma. In certain embodiments, the depleting version of siplizumab can be used for the treatment of autoimmune diseases. In some embodiments, a depleting CD2 binding molecule (or an anti-CD2 antibody or antigen binding fragment thereof) is used in combination with a CTLA-4 co-stimulation blockade and/or in combination with another agent as described herein (e.g., for treating a subject with a chronic condition such as a chronic or acute inflammatory disorder of the immune system; or for treating a subject with a CD8+ T-cell driven condition). In some embodiments, a non-depleting CD2 binding molecule (or an anti-CD2 antibody or antigen binding fragment thereof) is used in combination with a CTLA-4 co-stimulation blockade and/or in combination with another agent as described herein (e.g., for treating a subject with a chronic condition such as a chronic or acute inflammatory disorder of the immune system; or for treating a subject with a CD8+ T-cell driven condition).

The terms "subject," "recipient," and "patient" are used interchangeably herein. In some embodiments, the subject is a mammal. In some embodiments, a subject or a subject in need is a subject who has or is predicted of having or developing an immune related disorder or disease. In some embodiments, a subject or a subject in need is a subject who has or will undergo transplant surgery. In some embodiments, a subject or a subject in need is a subject who has chronic or acute inflammatory disorder of the immune system. In some embodiments, the subject is a primate. In certain embodiments, the subject is a human. In some embodiments, the subject is an adult human. In some embodiments, the subject is a child. In some embodiments, the subject is a pediatric patient. In some embodiments, the subject is a juvenile human. In some embodiments, the subject is at least 5 years old, 10 years old, 15 years old, 18 years old, 21 years old, 50 years old, 60 years old, 65 years old, 70 years old, or more than 70 years old. In some embodiments, the subject is at most 5 years old, 10 years old, 15 years old, 18 years old, or 21 years old. In some embodiments, the subject has not received prior treatment for an immune associated disorder or disease. In some embodiments, the subject has not received prior treatment for an immune associated disorder or disease in the past 1 month, 2 months, 3 months, 4, months, 5 months, 6 months, 9 months, 1 year, 2 years, or more than 2 years prior to administration of the anti-CD2 antibody or an antigen-binding fragment thereof and/or the CTLA-4 co-stimulation blockade to the subject. In some embodiments, the subject is a treatment naïve subject. In some embodiments, the subject is treatment naïve to a treatment for an immune associated disorder or disease. In some embodiments, the subject is naïve to methotrexate. In some embodiments, the subject has not received prior treatment with an anti-CD2 antibody or an antigen-binding fragment thereof and/or a CTLA-4 co-stimulation blockade. In some embodiments, the subject is resistant to a treatment for an immune associated disorder or disease. In some embodiments, the subject is being treated or has been treated with a treatment for an immune associated disorder or disease that is not an anti-CD2 antibody or an antigen-binding fragment thereof and/or a CTLA-4 co-stimulation blockade.

In some embodiments, a subject diagnosed with an immune associated disease or disorder, is predisposed or likely to develop an immune associated disease or disorder, or who is experiencing at least one symptom associated with an immune associated disease or disorder can be suitable for treatment with a method provided herein. In some embodiments, the subject was diagnosed with at least one, at least two, at least three, or more than at least three immune associated disease or disorder. Non-limiting examples of immune associated diseases or disorders that can be treated or prevented with a method of the disclosure is provided herein.

Subjects who have undergone or will undergo an organ and/or tissue transplant can be suitable for treatment with a method provided herein. The methods described herein can be used for a subject who has undergone or will undergo any organ and/or tissue transplant (e.g., lung, heart, kidney, liver, stomach, intestines, pancreas, skin, or spleen). Individuals whose organ has been damaged by means including injury, disease, or birth defect may meet the criteria to receive an organ (e.g., liver or kidney) transplant and may be treated in accordance with the methods described herein. A recipient treated in accordance with the methods described herein may have required an organ transplant for any reason. Generally, a patient suffering from end-stage organ disease whose life expectancy is predicted to be extended by an organ transplant beyond the life expectancy without the organ transplant may be considered for an organ transplant.

In specific embodiments, a recipient treated in accordance with the methods described herein has received an organ transplant necessitated by a genetic disease. In specific embodiments, the organ transplant is a living donor organ transplant. In specific embodiments, the organ transplant is a deceased donor organ transplant. In some embodiments, the organ transplant may be an ABO compatible transplant. In some embodiments, the organ transplant may be an ABO incompatible transplant. In some embodiments, a recipient treated in accordance with the methods described herein can have a Model for End-Stage Liver Disease (MELD) score of less than 30, less than 20, or less than 10. In some embodiments, a recipient treated in accordance with the methods described herein can be seropositive for Epstein-Barr Virus (EBV). In some embodiments, the recipient has undergone a splenectomy prior to receiving the transplant. In some embodiments, the recipient has not undergone a splenectomy prior to receiving the transplant. In some embodiments, a subject is in need or has received a liver transplant. Examples of indications of a liver transplant are described, for example, in the EASL Clinical Practice Guidelines:

Liver transplantation (J Hepatol. 2016 February; 64(2):433-485. doi: 10.1016/j.jhep.2015.10.006).

5.3.2 Doses and Regimens for Patients (e.g., Patients with Inflammatory Immune Disorders)

In certain embodiments, the method of treating a human subject who has a chronic or acute inflammatory disorder of the immune system comprises administering to the subject the CD2-binding molecule (or anti-CD2 antibody or antigen-binding fragment thereof) described herein or the pharmaceutical composition comprising the CD2-binding molecule (or anti-CD2 antibody or antigen-binding fragment thereof) described herein as a component of long-term treatment regimens. In certain embodiments, the method of treating a human subject who has an immune related disorder or disease comprises administering to the subject the CD2-binding molecule (or anti-CD2 antibody or antigen-binding fragment thereof) described herein or the pharmaceutical composition comprising the CD2-binding molecule (or anti-CD2 antibody or antigen-binding fragment thereof) described herein. In certain embodiments, the method includes preventing an immune related disorder or disease in a subject. In certain embodiments, a CD2-binding molecule (or anti-CD2 antibody or antigen-binding fragment thereof) described herein can be administered to a subject in need thereof or to a patient with a chronic or acute inflammatory immune disorder at an amount of 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, 5000 mg, between 1000 mg and 1600 mg, between 1500 mg and 2100 mg, between 2000 mg and 2600 mg, between 2500 mg and 3100 mg, between 3000 mg and 3600 mg, between 3500 mg and 4100 mg, between 4000 mg and 4600 mg, or between 4500 mg and 5000 mg. In a specific embodiment, a CD2-binding molecule (or anti-CD2 antibody or antigen-binding fragment thereof) described herein can be administered to a subject in need thereof or to a patient with a chronic or acute inflammatory immune disorder at an amount of 2400 mg.

In certain embodiments, a CD2-binding molecule (or anti-CD2 antibody or antigen-binding fragment thereof) described herein can be administered to a subject in need or to a patient with a chronic or acute inflammatory immune disorder at a dose amount of 0.01 mg/kg/dose, 0.02 mg/kg/dose, 0.03 mg/kg/dose, 0.04 mg/kg/dose, 0.05 mg/kg/dose, 0.1 mg/kg/dose, 0.15 mg/kg/dose, 0.2 mg/kg/dose, 0.25 mg/kg/dose, 0.3 mg/kg/dose, 0.35 mg/kg/dose, 0.4 mg/kg/dose, 0.45 mg/kg/dose, 0.5 mg/kg/dose, 0.55 mg/kg/dose, 0.6 mg/kg/dose, 0.65 mg/kg/dose, 0.7 mg/kg/dose, 0.75 mg/kg/dose, 0.8 mg/kg/dose, 0.85 mg/kg/dose, 0.9 mg/kg/dose, 0.95 mg/kg/dose, 1.0 mg/kg/dose, 2.0 mg/kg/dose, 3.0 mg/kg/dose, 4.0 mg/kg/dose, 5.0 mg/kg/dose, 6.0 mg/kg/dose, 7.0 mg/kg/dose, 8.0 mg/kg/dose, 9.0 mg/kg/dose, 10 mg/kg/dose, 11 mg/kg/dose, 12 mg/kg/dose, 13 mg/kg/dose, 14 mg/kg/dose, 15 mg/kg/dose, 16 mg/kg/dose, 17 mg/kg/dose, 18 mg/kg/dose, 19 mg/kg/dose, 20 mg/kg/dose, 21 mg/kg/dose, 22 mg/kg/dose, 23 mg/kg/dose, 24 mg/kg/dose, 25 mg/kg/dose, 26 mg/kg/dose, 27 mg/kg/dose, 28 mg/kg/dose, 29 mg/kg/dose, 30 mg/kg/dose, 31 mg/kg/dose, 32 mg/kg/dose, 33 mg/kg/dose, 34 mg/kg/dose, 35 mg/kg/dose, 36 mg/kg/dose, 37 mg/kg/dose, 38 mg/kg/dose, 39 mg/kg/dose, 40 mg/kg/dose, 41 mg/kg/dose, 42 mg/kg/dose, 43 mg/kg/dose, 44 mg/kg/dose, 45 mg/kg/dose, 46 mg/kg/dose, 47 mg/kg/dose, 48 mg/kg/dose, 49 mg/kg/dose, 50 mg/kg/dose. In certain embodiments, a CD2-binding molecule (or anti-CD2 antibody or antigen-binding fragment thereof) described herein can be administered to a subject in need or to a patient with a chronic or acute inflammatory immune disorder at dose ranges of 0.1-0.3 mg/kg/dose, 0.2-0.4 mg/kg/dose, 0.3-0.5 mg/kg/dose, 0.4-0.6 mg/kg/dose, 0.45-0.65 mg/kg/dose, 0.5-0.7 mg/kg, 0.55-0.75 mg/kg/dose, 0.6-0.8 mg/kg/dose, 0.65-0.85 mg/kg/dose, 0.7-0.9 mg/kg/dose, 0.8-1.0 mg/kg/dose, between 1.0 mg/kg/dose and 6.0 mg/kg/dose, between 5.0 mg/kg/dose and 10 mg/kg/dose, between 9.0 mg/kg/dose and 15 mg/kg/dose, between 14 mg/kg/dose and 20 mg/kg/dose, between 19 mg/kg/dose and 25 mg/kg/dose, between 24 mg/kg/dose and 30 mg/kg/dose, between 29 mg/kg/dose and 35 mg/kg/dose, between 34 mg/kg/dose and 40 mg/kg/dose, between 39 mg/kg/dose and 45 mg/kg/dose, or between 44 mg/kg/dose and 50 mg/kg/dose. In a specific embodiment, a CD2-binding molecule (or anti-CD2 antibody or antigen-binding fragment thereof) described herein can be administered to a subject in need or to a patient with a chronic or acute inflammatory immune disorder at a dose amount of 0.1 mg/kg/dose. In a specific embodiment, a CD2-binding molecule (or anti-CD2 antibody or antigen-binding fragment thereof) described herein can be administered to a subject in need or to a patient with a chronic or acute inflammatory immune disorder at a dose amount of 0.6 mg/kg/dose.

In certain embodiments, a CD2-binding molecule (or an anti-CD2 antibody or antigen binding fragment thereof) described herein can be administered to a subject in need or to a patient with a chronic or acute inflammatory immune disorder at a dose amount of 2 mg/kg/dose weekly for 6 weeks and then every 4 weeks thereafter; for 5 weeks and then every 4 weeks thereafter; for 4 weeks and then every 4 weeks thereafter; for 3 weeks and then every 4 weeks thereafter; or for 2 weeks and then every 4 weeks thereafter. In a specific embodiment, a CD2-binding molecule (or an anti-CD2 antibody or antigen binding fragment thereof) described herein can be administered to a subject in need or to a patient with a chronic or acute inflammatory immune disorder at a dose amount of 2 mg/kg/dose weekly for 4 weeks and then every 4 weeks thereafter. In certain embodiments, a CD2-binding molecule (or an anti-CD2 antibody or antigen binding fragment thereof) described herein can be administered to a subject in need or to a patient with a chronic or acute inflammatory immune disorder at a dose amount of 2.5 mg/kg/dose weekly for 6 weeks and then every 4 weeks thereafter; for 5 weeks and then every 4 weeks thereafter; for 4 weeks and then every 4 weeks thereafter; for 3 weeks and then every 4 weeks thereafter; or for 2 weeks and then every 4 weeks thereafter. In a specific embodiment, a CD2-binding molecule (or an anti-CD2 antibody or antigen binding fragment thereof) described herein can be administered to a subject in need or to a patient with a chronic or acute inflammatory immune disorder at a dose amount of 2.5 mg/kg/dose weekly for 4 weeks and then every 4 weeks thereafter. In certain embodiments, a CD2-binding molecule (or an anti-CD2 antibody or antigen binding fragment thereof) described herein can be administered to a subject in need or to a patient with a chronic or acute inflammatory immune disorder at a dose amount of 3 mg/kg/dose weekly for 6 weeks and then every 4 weeks thereafter; for 5 weeks and then every 4 weeks thereafter; for 4 weeks and then every 4 weeks thereafter; for 3 weeks and then every 4 weeks thereafter; or for 2 weeks and then every 4 weeks thereafter. In a specific embodiment, a CD2-binding molecule (or an anti-CD2 antibody or antigen binding fragment thereof) described herein can be administered to a subject in need or to a patient with a chronic or acute inflammatory immune disorder at a dose amount of 3 mg/kg/dose weekly for 4 weeks and then every 4 weeks thereafter. In certain embodiments, a CD2-binding molecule (or an anti-CD2 antibody or antigen binding fragment thereof) described herein can be administered to a subject in need or to a patient with a chronic or acute inflammatory immune disorder at a dose amount of 3.5 mg/kg/dose weekly for 6 weeks and then every 4 weeks thereafter; for 5 weeks and then every 4 weeks thereafter; for 4 weeks and then every 4 weeks thereafter; for 3 weeks and then every 4 weeks thereafter; or for 2 weeks and then every 4 weeks thereafter. In a specific embodiment, a CD2-binding molecule (or an anti-CD2 antibody or antigen binding fragment thereof) described herein can be administered to a subject in need or to a patient with a chronic or acute inflammatory immune disorder at a dose amount of 3.5 mg/kg/dose weekly for 4 weeks and then every 4 weeks thereafter. In certain embodiments, a CD2-binding molecule (or an anti-CD2 antibody or antigen binding fragment thereof) described herein can be administered to a subject in need or to a patient with a chronic or acute inflammatory immune disorder at a dose amount of 3.75 mg/kg/dose weekly for 6 weeks and then every 4 weeks thereafter; for 5 weeks and then every 4 weeks thereafter; for 4 weeks and then every 4 weeks thereafter; for 3 weeks and then every 4 weeks thereafter; or for 2 weeks and then every 4 weeks thereafter. In a specific embodiment, a CD2-binding molecule (or an anti-CD2 antibody or antigen binding fragment thereof) described herein can be administered to a subject in need or to a patient with a chronic or acute inflammatory immune disorder at a dose amount of 3.75 mg/kg/dose weekly for 4 weeks and then every 4 weeks thereafter.

In certain embodiments, the CD2-binding molecule (or an anti-CD2 antibody or antigen binding fragment thereof) can be administered to a subject in a convenient manner known in the art including subcutaneously, intravenously, intravascularly, topically, intra-arterially, intra-cranially, intramuscularly, orally, intra-orbitally, by inhalation, transdermally, intra-peritoneally, or through a route of administration which allows for the depletion of T-cells in the recipient. In a specific embodiment, the anti-CD2 antibody or antigen binding fragment thereof, or the CD2-binding molecule is administered intravenously.

In certain embodiments, the CD2-binding molecule (or an anti-CD2 antibody or antigen binding fragment thereof) is a humanized monoclonal antibody. In a specific embodiment, the CD2-binding molecule (or an anti-CD2 antibody or antigen binding fragment thereof) is Siplizumab (MEDI-507). In certain embodiments, the administration of the CD2-binding molecule (or an anti-CD2 antibody or antigen binding fragment thereof) can be modified as described herein. In some embodiments, methylprednisolone is given prior to the administration of the CD2-binding molecule (or an anti-CD2 antibody or antigen binding fragment thereof). In some embodiments, acetaminophen (e.g., 1000 mg) and/or an antihistamine (e.g., 25 mg of an H1-antagonist such as diphenhydramine) is administered prior to the administration of the CD2-binding molecule (or an anti-CD2 antibody or antigen binding fragment thereof).

Without being bound by theory, the CD2-binding molecule (or an anti-CD2 antibody or antigen binding fragment thereof) described herein is administered at a dose sufficient to increase the level of regulatory T cells in the recipient. Specifically, the CD2-binding molecule (or an anti-CD2 antibody or antigen binding fragment thereof) described herein is administered at a dose such that the level of FOXP3+ regulatory T cells in the recipient is increased, e.g., by at least 10%, 20%, 30%, 40%, 50%, 60%, 70%, 80%, 90%, 100%, 125%, 150%, 175%, 200%, or by at least 250% relative to FOXP3+ regulatory T cells without treatment with the CD2-binding molecule (or an anti-CD2 antibody or antigen binding fragment thereof) described herein.

The CD2-binding molecule (or an anti-CD2 antibody or antigen binding fragment thereof) described herein can be administered to a subject in need or to a patient with a chronic or acute inflammatory immune disorder as a component of treatment regimen. In certain embodiments, the CD2-binding molecule (or an anti-CD2 antibody or antigen binding fragment thereof) described herein used in the treatment regimen is the sole component for the treatment regimen. In a specific embodiment, the CD2-binding molecule (or an anti-CD2 antibody or antigen binding fragment thereof) described herein administered in the treatment regimen to a subject in need or to a patient with a chronic or acute inflammatory immune disorder binds to the same epitope as siplizumab.

In certain embodiments, the CD2-binding molecule (or an anti-CD2 antibody or antigen binding fragment thereof) can be administered to a subject in need or to a patient with a chronic or acute inflammatory immune disorder at a dose high enough to induce remission (a loading dose), followed by less frequent dosing such as, but not limited to, once a month, once every two months, or once every three months.

In a specific embodiment, a CD2-binding molecule (or anti-CD2 antibody or antigen-binding fragment thereof) described herein can be administered to a subject in need or to a patient with a chronic or acute inflammatory immune disorder at an interval of weekly. In a specific embodiment, a CD2-binding molecule (or anti-CD2 antibody or antigen-binding fragment thereof) described herein can be administered to a subject in need or to a patient with a chronic or acute inflammatory immune disorder at an interval of bi-weekly. In a specific embodiment, a CD2-binding molecule (or anti-CD2 antibody or antigen-binding fragment thereof) described herein can be administered to a subject in need or to a patient with a chronic or acute inflammatory immune disorder at an interval of daily until induction of disease remission or disease quiescence and then weekly thereafter. In a specific embodiment, a CD2-binding molecule (or anti-CD2 antibody or antigen-binding fragment thereof) described herein can be administered to a subject in need or to a patient with a chronic or acute inflammatory immune disorder at an interval of weekly for 12 weeks followed by administration bi-weekly. In a specific embodiment, a CD2-binding molecule (or anti-CD2 antibody or antigen-binding fragment thereof) described herein can be administered to a subject in need or to a patient with a chronic or acute inflammatory immune disorder at an interval of bi-weekly and then monthly. In a specific embodiment, a CD2-binding molecule (or anti-CD2 antibody or antigen-binding fragment thereof) described herein can be administered to a subject in need or to a patient with a chronic or acute inflammatory immune disorder at an interval of semi-monthly. In a specific embodiment, a CD2-binding molecule (or anti-CD2 antibody or antigen-binding fragment thereof) described herein can be administered to a subject in need or to a patient with a chronic or acute inflammatory immune disorder at an interval of every three months.

In certain embodiments, the CD2-binding molecule (or anti-CD2 antibody or antigen-binding fragment thereof) described herein can be administered to a subject in need or to a patient with a chronic or acute inflammatory immune disorder wherein the patient is being treated for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, 20, 21, 22, 23, 24, or at least 25 years. In certain embodiments, the subject in need or the patient with a chronic or acute inflammatory immune disorder can be treated with the CD2-binding molecule (or anti-CD2 antibody or antigen-binding fragment thereof) described herein or a pharmaceutical composition comprising the CD2-binding molecule (or anti-CD2 antibody or antigen-binding fragment thereof) described herein for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, 20, 21, 22, 23, 24, or at least 25 years.

In certain embodiments, the CD2-binding molecule (or anti-CD2 antibody or antigen-binding fragment thereof) described herein can be formulated for subcutaneous, intravenous, intravascular, topical, intrarticular, intraarterial, intracranial, intramuscular, oral, intraorbital, intravitreal, inhalation, intraperitonial, intraosseous, endotracheal, sublingual, buccal, rectal, intradermal, intrathecal, intramedullary, or transdermal routes of administration. In a specific embodiment, the CD2-binding molecule (or anti-CD2 antibody or antigen-binding fragment thereof) described herein is formulated for intravenous administration to a patient with a chronic or acute inflammatory immune disorder. In a specific embodiment, the CD2-binding molecule (or anti-CD2 antibody or antigen-binding fragment thereof) described herein is formulated for subcutaneous administration to a subject in need or to a patient with a chronic or acute inflammatory immune disorder.

In certain embodiments, the subject in need or the patient with the chronic or acute inflammatory disorder of the immune system can be administered the pharmaceutical composition comprising a therapeutically effective amount of the CD2-binding molecule (or anti-CD2 antibody or antigen-binding fragment thereof) described herein. In certain embodiments, the pharmaceutical composition comprising a therapeutically effective amount of the CD2-binding molecule (or anti-CD2 antibody or antigen-binding fragment thereof) described herein is contained in a kit or system for administration to a subject in need or to a patient with a chronic or acute inflammatory disorder of the immune system. In certain embodiments, the kit will comprise the pharmaceutical composition comprising a therapeutically effective amount of the CD2-binding molecule (or anti-CD2 antibody or antigen-binding fragment thereof) described herein contained in one or more containers. The containers that contain said pharmaceutical composition can be packaged in can include, but are not limited to, bottles, packets, ampoules, tubes, inhalers, bags, vials, and containers. In certain embodiments, the kit comprises instructions for administering the pharmaceutical administration. In certain embodiments, the kit comprises devices that can be used to administer the pharmaceutical composition, including, but not limited to, syringes, needle-less injectors, drip bags, perfusion pumps, pumps, patches and inhalers.

In certain embodiments, an affected organ in a subject or in a patient with a chronic or acute inflammatory disorder can be perfused with the CD2-binding molecule (or anti-CD2 antibody or antigen-binding fragment thereof) as described herein. In a more specific embodiment, an affected organ is perfused with the CD2-binding molecule (or anti-CD2 antibody or antigen-binding fragment thereof) using a perfusion pump. In certain embodiments, the concentration of the CD2-binding molecule (or anti-CD2 antibody or antigen-binding fragment thereof) to be perfused into the affected organ is at least 0.001 mg/liter, at least 0.005 mg/liter, at least 0.01 mg/liter, at least 0.05 mg/liter, at least 0.1 mg/liter, at least 0.5 mg/liter, at least 1.0 mg/liter, at least 5.0 mg/liter, at least 10 mg/liter, or at least 50 mg/liter.

5.3.3 Co-Therapy with Immunosupressants of Patients with Inflammatory Immune Disorders In certain embodiments, the CD2-binding molecule (or anti-CD2 antibody or antigen-binding fragment thereof) described herein is administered concurrently with low doses of immunosuppressants as a component of long term patient therapy. Without being bound by theory, immunosuppressants that can be combined with administration of the CD2-binding molecule (or anti-CD2 antibody or antigen-binding fragment thereof) described herein include, but are not limited to, tacrolimus, cyclosporine, belatacept, anti-CD40 antibodies, anti-OX40L antibodies, anti-CD28 antibodies, anti-CD27 antibodies, anti CD154 antibodies, anti-ICOS antibodies, anti- or agonistic 4-1BB (CD137) antibodies, BCL-2 inhibitors, mycophenolate mofetil, mycophenolic acid derivatives such as Myfortic (enteric coated mycophenolate sodium), sirolimus, everolimus, antiythymocyte globulin, basiliximab, prednisone, cyclophosphamide, fludarabine, and rituximab (Adams et al., *J Immunol,* 2016, 197 (6) 2045-2050; Kinnear et al., *Transplantation.* 2013 Feb. 27; 95(4): 527-535; Zhang and Vignali, *Immunity.* 2016 May 17; 44(5):1034-51). In certain embodiments, the CD2-binding molecule (or anti-CD2 antibody or antigen-binding fragment thereof) described herein may be administered as one part of a dual co-stimulation blockade. In a specific embodiment, the dose of immunosuppressant required to be therapeutically effective is lower when the immunosuppressant is administered concurrently with the CD2-binding molecule (or anti-CD2 antibody or antigen-binding fragment thereof) described herein. In certain embodiments, the CD2-binding molecule (or anti-CD2 antibody or antigen-binding fragment thereof) can be administered concurrently with one immunosuppressant. In other embodiments, the CD2-binding molecule (or anti-CD2 antibody or antigen-binding fragment thereof) can be administered concurrently with more than one immunosuppressant.

Co-therapy of the CD2-binding molecule (or anti-CD2 antibody or antigen-binding fragment thereof) and immunosuppressants can be used to treat patients with chronic or acute inflammatory disorders of the immune system. Such disorders can include, but are not limited to, rheumatoid arthritis, juvenile idiopathic arthritis, psoriatic arthritis, autoimmune liver disease, Kawasaki disease, inflammatory bowel disease, ankylosing spondylitis, psoriasis, ulcerative colitis, sympathetic ophthalmia, age related macular degeneration, non-infectious posterior uveitis, Vogt-Koyanagi-Haranda disease, sarcoidosis, Type-1 diabetes mellitus, Crohn's disease, celiac disease, lupus, Sjögren's syndrome, atopic dermatitis, multiple sclerosis, Graft-Versus-Host Disease (GVHD), and Focal Segmental Glomerulosclerosis.

5.3.4 Organ Transplant Patient Population

Individuals who have one organ, or more than one organ, that has been damaged by means including injury, disease, or birth defect may meet the criteria to receive an organ transplant. Individuals who have been selected to receive an organ transplant may follow these methods described herein with the goal of inducing a state of mixed chimerism in which the recipient and donor hematopoietic cells coexist in the recipient. When the state of mixed chimerism is achieved, it reduces the need for long-term immunosuppressive therapies.

In some embodiments, the recipient can have a highly sensitized immune system. The development of a highly sensitized immune system is caused by previous exposure to foreign tissues and the development of antibodies towards those tissues. Causes of this exposure can include blood transfusions, a previous transplant, or pregnancy. In the sensitized state, the immune system is hyper-vigilant and produces antibodies that will attack the transplanted organ. In certain embodiments, the recipient as described herein can have a sensitized or unsensitized immune system. In such recipients, IdeS can be administered with the rituximab. IdeS, an enzyme that cleaves the heavy chain of the IgG, inhibits antibody dependent cellular cytotoxicity (ADCC) and complement dependent cytotoxicity (CDC). In certain embodiments, IdeS is administered in combination with rituximab. In certain embodiments, other desensitization protocols can be used alone or in combination with rituximab, IdeS, or other desensitization protocols. These can include, but are not limited to, intravenous immunoglobulin, plasmapheresis, immunoadsorption, double filtration, proteasomal inhibitors (e.g. Bortezomib), and complement inhibitors.

5.3.5 Treatment of the Organ Transplant

In certain embodiments, the method can include direct infusion of the CD2-binding molecule (or anti-CD2 antibody or antigen-binding fragment thereof) as described herein into the organ to be transplanted. Organs that can be transplanted utilizing the methods provided herein can be any solid organ. In some embodiments, the organ can be a kidney, heart, intestine, liver, lung, pancreas or other organ that can be transplanted using the methods provided herein. In some embodiments, the organ can be a vascular-composite allograft including hands, feet, other limbs, faces, or other body parts that can be transplanted using the methods provided herein. In some embodiments, the transplanted organ may be whole organ, a part of an organ, or cells derived from an organ.

In certain embodiments, the transplanted organ can be directly injected with the CD2-binding molecule (or anti-CD2 antibody or antigen-binding fragment thereof) described herein. This injection can be administered at one site on the organ to be transplanted or can be administered at multiple sites on the organ to be transplanted. In certain embodiments, the organ to be transplanted can be incubated in a bath containing the CD2-binding molecule (or anti-CD2 antibody or antigen-binding fragment thereof) described herein. This incubation can occur during transport to the surgery or at the surgical location. This incubation will last for a duration of sufficient time to allow uptake of the CD2-binding molecule (or anti-CD2 antibody or antigen-binding fragment thereof) described herein into the organ to be transplanted. This incubation can take place for 15 minutes, 30 minutes, 45 minutes, 1 hour, 1.25 hours, 1.5 hours, 1.75 hours, 2 hours, 2.25 hours, 2.5 hours, 2.75 hours, 3 hours, 3.25 hours, 3.5 hours, 3.75 hours, 4 hours, 4.25 hours, 4.5 hours, 4.75 hours, 5 hours, 5.25 hours, 5.5 hours, 5.75 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 21.5 hours, 22 hours, 22.5 hours, 23 hours, 23.5 hours, or 24 hours. In certain embodiments, the dose of the CD2-binding molecule (or anti-CD2 antibody or antigen-binding fragment thereof) described herein for injection is at least 0.01 mg/kg, at least 0.05 mg/kg, at least 0.1 mg/kg, at least 0.5 mg/kg, at least 1 mg/kg, at least 5 mg/kg, at least 10 mg/kg, or at least 50 mg/kg.

In certain embodiments, the organ to be transplanted is incubated in a bath comprising the CD2-binding molecule (or anti-CD2 antibody or antigen-binding fragment thereof) described herein. In more specific embodiments, the organ is maintained in a bath comprising CD2-binding molecule (or anti-CD2 antibody or antigen-binding fragment thereof) described herein from the time the organ is removed from the donor until implantation in the recipient. In certain embodiments, the concentration of the CD2-binding molecule (or anti-CD2 antibody or antigen-binding fragment thereof) described herein in the organ bath is at least 0.01 mg/liter, at least 0.05 mg/liter, at least 0.1 mg/liter, at least 0.5 mg/liter, at least 1 mg/liter, at least 5 mg/liter, at least 10 mg/liter, or at least 50 mg/liter. In certain embodiments, the CD2-binding molecule (or anti-CD2 antibody or antigen-binding fragment thereof) described herein can be administered to the organ to be transplanted by way of the circulatory system. Specifically, a catheter can be inserted into an adjacent blood vessel and attached to a pump. The CD2-binding molecule (or anti-CD2 antibody or antigen-binding fragment thereof) described herein can be pumped through the blood vessel and delivered to the organ.

In certain embodiments, the organ to be transplanted can be perfused with the CD2-binding molecule (or anti-CD2 antibody or antigen-binding fragment thereof) as described herein. In a more specific embodiment, a transplanted organ is perfused with the CD2-binding molecule (or anti-CD2 antibody or antigen-binding fragment thereof) using a perfusion pump. In certain embodiments, the concentration of the CD2-binding molecule (or anti-CD2 antibody or antigen-binding fragment thereof) to be perfused into the organ is at least 0.001 mg/liter, at least 0.005 mg/liter, at least 0.01 mg/liter, at least 0.05 mg/liter, at least 0.1 mg/liter, at least 0.5 mg/liter, at least 1.0 mg/liter, at least 5.0 mg/liter, at least 10 mg/liter, or at least 50 mg/liter.

5.3.6 Doses and Regimens (e.g., for Organ Transplant Recipients)

In certain embodiments, provided herein is a method of treating or preventing an immune-related disorder or disease in a subject in need thereof by administering a CD2-binding molecule (or anti-CD2 antibody or antigen-binding fragment thereof) described herein or the pharmaceutical composition comprising the CD2-binding molecule (or anti-CD2 antibody or antigen-binding fragment thereof) as described herein alone or in combination with one or more other agents (e.g., CTLA-4 co-stimulation blockade). In certain embodiments, the method of treating a human subject undergoing an organ transplantation procedure comprises administering to the subject the CD2-binding molecule (or anti-CD2 antibody or antigen-binding fragment thereof) described herein or the pharmaceutical composition comprising the CD2-binding molecule (or anti-CD2 antibody or antigen-binding fragment thereof) as described herein as a component of conditioning regimen prior to transplant. In certain embodiments, the CD2-binding molecule (or anti-CD2 antibody or antigen-binding fragment thereof) described herein is administered with the goal of generating tolerance in a transplant recipient as determined, e.g., by assays outlined in the reviews by Massart, A et al. (*Cin Exp Immunol.* 2017; 189(2):138-157) and Newell K A, Turka L A. (*Curr Opin Organ Transplant.* 2015; 20(4):400-405). These assays can include, but are not limited to, antigen-specific assays that determine T cell reactivity and B cell sensitization and assays that identify tolerance biomarkers. In certain embodiments, a method of treatment provided herein comprises administering a CD2-binding molecule (or an anti-CD2 antibody or antigen binding fragment thereof) to a subject prior to the subject being diagnosed with an immune-associated disorder or disease. In certain embodiments, a method of treatment provided herein comprises administering a CD2-binding molecule (or an anti-CD2 antibody or antigen binding fragment thereof) to a subject after the subject is diagnosed with an immune-associated disorder or disease. In certain embodiments, a method of treatment provided herein comprises administering a CD2-binding molecule (or an anti-CD2 antibody or antigen binding fragment thereof) to a transplant recipient prior to transplant. In some embodiments, a CD2-binding molecule (or an anti-CD2 antibody or antigen binding fragment thereof) described herein can be administered to the recipient 1 day prior to transplant, 2 days prior to transplant, 3 days prior to transplant, 4 days prior to transplant, 5 days prior to transplant, 6 days prior to transplant, 7 days prior to transplant, 1 day and 2 days prior to transplant, 2 days and 3 days prior to transplant, 3 days and 4 days prior to transplant, 1 day prior and 2 days and 3 days prior to transplant, or 1 day prior and 2 days prior and 3 days prior and 4 days prior to transplant. In a specific embodiment, a CD2-binding molecule (or an anti-CD2 antibody or antigen binding fragment thereof) described herein can be administered to a recipient 1 day prior and 2 days prior to transplant. In a specific embodiment, a CD2-binding molecule (or an anti-CD2 antibody or antigen binding fragment thereof) described herein can be administered to a recipient 1 day prior and 6 days prior to transplant. In certain embodiments, a test dose of a CD2-binding molecule (or an anti-CD2 antibody or antigen binding fragment thereof) described herein can be administered. In certain embodiments, the administration of the test dose is optional. In particular embodiments, a CD2-binding molecule (or an anti-CD2 antibody or antigen binding fragment thereof) is administered on the day of the transplant surgery. In certain embodiments, the CD2-binding molecule (or an anti-CD2 antibody or antigen binding fragment thereof) can be administered to a subject at a dose high enough to induce remission (a loading dose), followed by less frequent dosing such as, but not limited to, once a month, once every two months, or once every three months.

In some embodiments, a CD2-binding molecule (or an anti-CD2 antibody or antigen binding fragment thereof) described herein can be administered to the recipient daily for 1 week prior to transplant, for 2 weeks prior to transplant, for 3 weeks prior to transplant, or for 4 weeks prior to transplant. In some embodiments, a CD2-binding molecule (or an anti-CD2 antibody or antigen binding fragment thereof) described herein can be administered to the recipient twice a week for 1 week prior to transplant, for 2 weeks prior to transplant, for 3 weeks prior to transplant, or for 4 weeks prior to transplant. In some embodiments, a CD2-binding molecule (or an anti-CD2 antibody or antigen binding fragment thereof) described herein can be administered to the recipient three times a week for 1 week prior to transplant, for 2 weeks prior to transplant, for 3 weeks prior to transplant, or for 4 weeks prior to transplant. In some embodiments, a CD2-binding molecule (or an anti-CD2 antibody or antigen binding fragment thereof) described herein can be administered to the recipient four times a week for 1 week prior to transplant, for 2 weeks prior to transplant, for 3 weeks prior to transplant, or for 4 weeks prior to transplant. In some embodiments, a CD2-binding molecule (or an anti-CD2 antibody or antigen binding fragment thereof) described herein can be administered to the recipient five times a week for 1 week prior to transplant, for 2 weeks prior to transplant, for 3 weeks prior to transplant, or for 4 weeks prior to transplant. In some embodiments, a CD2-binding molecule (or an anti-CD2 antibody or antigen binding fragment thereof) described herein can be administered to the recipient six times a week for 1 week prior to transplant, for 2 weeks prior to transplant, for 3 weeks prior to transplant, or for 4 weeks prior to transplant. In certain embodiments, the CD2-binding molecule (or an anti-CD2 antibody or antigen binding fragment thereof) described herein can be administered on the day of the transplant.

In a specific embodiment, a CD2-binding molecule (or an anti-CD2 antibody or antigen binding fragment thereof) can be administered to a subject at an interval of weekly. In a specific embodiment, a CD2-binding molecule (or an anti-CD2 antibody or antigen binding fragment thereof) can be administered to a subject at an interval of bi-weekly. In a specific embodiment, a CD2-binding molecule (or an anti-CD2 antibody or antigen binding fragment thereof) can be administered to a subject daily until induction of disease remission or disease quiescence and then weekly thereafter. In a specific embodiment, a CD2-binding molecule (or an anti-CD2 antibody or antigen binding fragment thereof) can be administered to a subject at an interval of weekly for 12 weeks followed by administration bi-weekly. In a specific embodiment, a CD2-binding molecule (or an anti-CD2 antibody or antigen binding fragment thereof) can be administered to a subject at an interval of bi-weekly and then monthly. In a specific embodiment, a CD2-binding molecule (or an anti-CD2 antibody or antigen binding fragment thereof) can be administered to a subject at an interval of semi-monthly. In a specific embodiment, a CD2-binding molecule (or an anti-CD2 antibody or antigen binding fragment thereof) can be administered to a subject at an interval of every three months.

In some embodiments, the CD2-binding molecule (or an anti-CD2 antibody or antigen binding fragment thereof) is administered to a subject in an amount of 100 mg, 250 mg, 500 mg, 700 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, 5000 mg, between 1000 mg and 1600 mg, between 1500 mg and 2100 mg, between 2000 mg and 2600 mg, between 2500 mg and 3100 mg, between 3000 mg and 3600 mg, between 3500 mg and 4100 mg, between 4000 mg and 4600 mg, or between 4500 mg and 5000 mg per day that the CD2-binding molecule (or an anti-CD2 antibody or antigen binding fragment thereof) is administered, per dose, per week, biweekly, or per month.

In certain embodiments, a CD2-binding molecule (or an anti-CD2 antibody or antigen binding fragment thereof) described herein can be administered to a subject or to a transplant recipient at a dose amount of about or at least about 0.01 mg/kg/dose, 0.02 mg/kg/dose, 0.03 mg/kg/dose, 0.04 mg/kg/dose, 0.05 mg/kg/dose, 0.1 mg/kg/dose, 0.15 mg/kg/dose, 0.2 mg/kg/dose, 0.25 mg/kg/dose, 0.3 mg/kg/dose, 0.35 mg/kg/dose, 0.4 mg/kg/dose, 0.45 mg/kg/dose, 0.5 mg/kg/dose, 0.55 mg/kg/dose, 0.6 mg/kg/dose, 0.65 mg/kg/dose, 0.7 mg/kg/dose, 0.75 mg/kg/dose, 0.8 mg/kg/dose, 0.85 mg/kg/dose, 0.9 mg/kg/dose, 0.95 mg/kg/dose, 1.0 mg/kg/dose, 2.0 mg/kg/dose, 3.0 mg/kg/dose, 4.0 mg/kg/dose, 5.0 mg/kg/dose, 6.0 mg/kg/dose, 7.0 mg/kg/dose, 8.0 mg/kg/dose, 9.0 mg/kg/dose, 10 mg/kg/dose, 11 mg/kg/dose, 12 mg/kg/dose, 13 mg/kg/dose, 14 mg/kg/dose, 15 mg/kg/dose, 16 mg/kg/dose, 17 mg/kg/dose, 18 mg/kg/dose, 19 mg/kg/dose, 20 mg/kg/dose, 21 mg/kg/dose, 22 mg/kg/dose, 23 mg/kg/dose, 24 mg/kg/dose, 25 mg/kg/dose, 26 mg/kg/dose, 27 mg/kg/dose, 28 mg/kg/dose, 29 mg/kg/dose, 30 mg/kg/dose, 31 mg/kg/dose, 32 mg/kg/dose, 33 mg/kg/dose, 34 mg/kg/dose, 35 mg/kg/dose, 36 mg/kg/dose, 37 mg/kg/dose, 38 mg/kg/dose, 39 mg/kg/dose, 40 mg/kg/dose, 41 mg/kg/dose, 42 mg/kg/dose, 43 mg/kg/dose, 44 mg/kg/dose, 45 mg/kg/dose, 46 mg/kg/dose, 47 mg/kg/dose, 48 mg/kg/dose, 49 mg/kg/dose, or 50 mg/kg/dose. In certain embodiments, a CD2-binding molecule (or an anti-CD2 antibody or antigen binding fragment thereof) described herein can be administered to a subject or to a transplant recipient at dose ranges of between about 0.1 and about 0.3 mg/kg/dose, between about 0.2 and about 0.4 mg/kg/dose, between about 0.3 and about 0.5 mg/kg/dose, between about 0.4 and about 0.6 mg/kg/dose, between about 0.45 and about 0.65 mg/kg/dose, between about 0.5 and about 0.7 mg/kg, between about 0.55 and about 0.75 mg/kg/dose, between about 0.6 and about 0.8 mg/kg/dose, between about 0.65 and about 0.85 mg/kg/dose, between about 0.7 and about 0.9 mg/kg/dose, between about 0.8 and about 1.0 mg/kg/dose, between about 1 and about 1.5 mg/kg/dose, between about 1.5 and about 2 mg/kg/dose, between about 2 and about 2.5 mg/kg/dose, between about 2.5 and about 3 mg/kg/dose, between about 3 and about 3.5 mg/kg/dose, between about 3.5 and about 4 mg/kg/dose, between about 4 and about 4.5 mg/kg/dose, between about 4.5 and about 5 mg/kg/dose, between about 1.0 mg/kg/dose and about 6.0 mg/kg/dose, between about 5.0 mg/kg/dose and about 10 mg/kg/dose, between about 9.0 mg/kg/dose and about 15 mg/kg/dose, between about 14 mg/kg/dose and about 20 mg/kg/dose, between about 19 mg/kg/dose and about 25 mg/kg/dose, between about 24 mg/kg/dose and about 30 mg/kg/dose, between about 29 mg/kg/dose and about 35 mg/kg/dose, between about 34 mg/kg/dose and about 40 mg/kg/dose, between about 39 mg/kg/dose and about 45 mg/kg/dose, or between about 44 mg/kg/dose and about 50 mg/kg/dose. In a specific embodiment, a CD2-binding molecule (or an anti-CD2 antibody or antigen binding fragment thereof) described herein can be administered to a subject or to a transplant recipient at a dose amount of 0.1 mg/kg/dose. In a specific embodiment, a CD2-binding molecule (or an anti-CD2 antibody or antigen binding fragment thereof) described herein can be administered to a subject or to a transplant recipient at a dose amount of 0.6 mg/kg/dose.

In a specific embodiment, a CD2-binding molecule (or anti-CD2 antibody or antigen-binding fragment thereof) described herein can be administered to a subject in need or to a transplant recipient at a dose amount of, or about, 10 mg/kg on the day of transplant followed by a dose of, or about, 10 mg/kg on Day 2, 6, 14, 28, 42, 56 and then every 28 days thereafter. In a specific embodiment, a CD2-binding molecule (or anti-CD2 antibody or antigen-binding fragment thereof) described herein can be administered to aa subject in need or to a transplant recipient at a loading dose amount of, or about, 30 mg/kg on the day of transplant followed by a dose of, or about, 15 mg/kg on Day 5 and a dose of, or about, 7.5 mg/kg thereafter every 14 days. In a specific embodiment, a CD2-binding molecule (or anti-CD2 antibody or antigen-binding fragment thereof) described herein can be administered to a subject in need or to a transplant recipient at a loading dose amount of, of about, 30 mg/kg on the day of transplant followed by a dose of, or about, 15 mg/kg on Day 5 and a dose of, or about, 3.75 mg/kg thereafter every 14 days. In a specific embodiment, a CD2-binding molecule (or anti-CD2 antibody or antigen-binding fragment thereof) described herein can be administered to a subject in need or to a transplant recipient at a loading dose amount of, or about, 30 mg/kg followed by a dose amount of, or about, 5.625 mg/kg thereafter every 14 days.

Without being bound by theory, the CD2-binding molecule (or anti-CD2 antibody or antigen-binding fragment thereof) described herein is administered at a dose sufficient to increase the level of regulatory T cells in the recipient. Specifically, the CD2-binding molecule (or anti-CD2 antibody or antigen-binding fragment thereof) described herein can increase the level of FOXP3+ regulatory T cells in the recipient, e.g., by at least 10%, 20%, 30%, 40%, 50%, 60%, 70%, 80%, 90%, 100%, 125%, 150%, 175%, 200%, or by at least 250% relative to FOXP3+ regulatory T cells without treatment with the CD2-binding molecule (or anti-CD2 antibody or antigen-binding fragment thereof) described herein.

The CD2-binding molecule (or anti-CD2 antibody or antigen-binding fragment thereof) described herein can be administered to a subject in need or to a transplant patients as a constituent of postoperative treatment regimen. In certain embodiments, the CD2-binding molecule (or anti-CD2 antibody or antigen-binding fragment thereof) described herein used in the postoperative regimen is the same as the molecule administered in the conditioning regimen. In certain embodiments, the CD2-binding molecule (or anti-CD2 antibody or antigen-binding fragment thereof) described herein is different than the molecule administered in the conditioning regimen. In a specific embodiment, the CD2-binding molecule (or anti-CD2 antibody or antigen-binding fragment thereof) described herein administered in the postoperative regimen binds to the same epitope as siplizumab.

In certain embodiments, the CD2-binding molecule (or an anti-CD2 antibody or antigen binding fragment thereof) described herein can be administered on the day of the transplant, 1 day after, 2 days after, 3 days after, 4 days after, on the day of and 1 day after, on the day of and 1 day after and 2 days after, on the day of and 1 day after and 2 days after and 3 days after, on the day of and 1 day after and 2 days after and 3 days after and 4 days, on the day of and 1 day after and 2 days after and 3 days after and 4 days after and 5 days after, on the day of and 1 day after and 2 days after and 3 days after and 4 days after and 5 days after and 6 days after, or on the day of and 1 day after and 2 days after and 3 days after and 4 days after and 5 days after and 6 days after and 7 days after the transplant surgery. In certain embodiments, a method of treatment provided herein comprises administering a CD2-binding molecule (or an anti-CD2 antibody or antigen binding fragment thereof) to a subject in need or to a transplant recipient after the transplant. In some embodiments, a CD2-binding molecule (or an anti-CD2 antibody or antigen binding fragment thereof) can be administered to the recipient 1 day after transplant, 2 days after transplant, 3 days after transplant, 4 days after transplant, 5 days after transplant, 6 days after transplant, 7 days after transplant, 8 days after transplant, 9 days after transplant, 10 days after transplant, 11 days after transplant, 12 days after transplant, 13 days after transplant, 14 days after transplant, 15 days after transplant, 16 days after transplant, 17 days after transplant, 18 days after transplant, 19 days after transplant, 20 days after transplant, 21 days after transplant, 22 days after transplant, 23 days after transplant, 24 days after transplant, 25 days after transplant, 26 days after transplant, 27 days after transplant, 28 days after transplant, 29 days after transplant, and/or 30 days after transplant. In specific embodiments, a CD2-binding molecule (or an anti-CD2 antibody or antigen binding fragment thereof) is administered on the day of transplant, 1 day after transplant, 2 days after transplant and/or 4 days after transplant. In certain embodiments, the CD2-binding molecule (or an anti-CD2 antibody or antigen binding fragment thereof) described herein can be administered daily, biweekly, or monthly. In certain embodiments, the CD2-binding molecule (or an anti-CD2 antibody or antigen binding fragment thereof) described herein can be administered by infusion or by subcutaneous administration. In a certain embodiment, the CD2-binding molecule (or an anti-CD2 antibody or antigen binding fragment thereof) described herein can be administered daily for 1 week after transplant surgery, for 2 weeks after transplant surgery, for 3 weeks after transplant surgery, or 4 weeks after transplant surgery. In a specific embodiment, the CD2-binding molecule (or an anti-CD2 antibody or antigen binding fragment thereof) described herein can be administered to a recipient on the day of and 1 day after the transplant. In a specific embodiment, the CD2-binding molecule (or an anti-CD2 antibody or antigen binding fragment thereof) described herein can be administered to a recipient on the day of and 1 day and 7 days after the transplant. In a specific embodiment, the CD2-binding molecule (or an anti-CD2 antibody or antigen binding fragment thereof) described herein can be administered to a recipient on the day of and 1, 8 and 13 days after the transplant.

In certain embodiments, the dose amount of the CD2-binding molecule (or anti-CD2 antibody or antigen-binding fragment thereof) described herein administered to the recipient in the postoperative regimen can be the same as the dose amount administered in the conditioning regimen. In certain embodiments, the dose amount of the CD2-binding molecule (or anti-CD2 antibody or antigen-binding fragment thereof) described herein administered to the recipient in the postoperative regimen can be different than the dose amount administered in the conditioning regimen. In certain embodiments, the CD2-binding molecule (or anti-CD2 antibody or antigen-binding fragment thereof) described herein can be administered to a transplant recipient at a dose amount of 0.01 mg/kg/dose, 0.02 mg/kg/dose, 0.03 mg/kg/dose, 0.04 mg/kg/dose, 0.05 mg/kg/dose, 0.1 mg/kg/dose, 0.15 mg/kg/dose, 0.2 mg/kg/dose, 0.25 mg/kg/dose, 0.3 mg/kg/dose, 0.35 mg/kg/dose, 0.4 mg/kg/dose, 0.45 mg/kg/dose, 0.5 mg/kg/dose, 0.55 mg/kg/dose, 0.6 mg/kg/dose, 0.65 mg/kg/dose, 0.7 mg/kg/dose, 0.75 mg/kg/dose, 0.8 mg/kg/dose, 0.85 mg/kg/dose, 0.9 mg/kg/dose, 0.95 mg/kg/dose, 1.0 mg/kg/dose, 2.0 mg/kg/dose, 3.0 mg/kg/dose, 4.0 mg/kg/dose, 5.0 mg/kg/dose, 6.0 mg/kg/dose, 7.0 mg/kg/dose, 8.0 mg/kg/dose, 9.0 mg/kg/dose, 10 mg/kg/dose, 11 mg/kg/dose, 12 mg/kg/dose, 13 mg/kg/dose, 14 mg/kg/dose, 15 mg/kg/dose, 16 mg/kg/dose, 17 mg/kg/dose, 18 mg/kg/dose, 19 mg/kg/dose, 20 mg/kg/dose, 21 mg/kg/dose, 22 mg/kg/dose, 23 mg/kg/dose, 24 mg/kg/dose, 25 mg/kg/dose, 26 mg/kg/dose, 27 mg/kg/dose, 28 mg/kg/dose, 29 mg/kg/dose, 30 mg/kg/dose, 31 mg/kg/dose, 32 mg/kg/dose, 33 mg/kg/dose, 34 mg/kg/dose, 35 mg/kg/dose, 36 mg/kg/dose, 37 mg/kg/dose, 38 mg/kg/dose, 39 mg/kg/dose, 40 mg/kg/dose, 41 mg/kg/dose, 42 mg/kg/dose, 43 mg/kg/dose, 44 mg/kg/dose, 45 mg/kg/dose, 46 mg/kg/dose, 47 mg/kg/dose, 48 mg/kg/dose, 49 mg/kg/dose, or 50 mg/kg/dose. In certain embodiments, the CD2-binding molecule (or anti-CD2 antibody or antigen-binding fragment thereof) described herein can be administered to a subject in need or to a transplant recipient at dose ranges of between 0.1 and 0.3 mg/kg/dose, between 0.2 and 0.4 mg/kg/dose, between 0.3 and 0.5 mg/kg/dose, between 0.4 and 0.6 mg/kg/dose, between 0.45 and 0.65 mg/kg/dose, between 0.5 and 0.7 mg/kg, between 0.55 and 0.75 mg/kg/dose, between 0.6 and 0.8 mg/kg/dose, between 0.65 and 0.85 mg/kg/dose, between 0.7 and 0.9 mg/kg/dose, between 0.8 and 1.0 mg/kg/dose, between 1.0 mg/kg/dose and 6.0 mg/kg/dose, between 5.0 mg/kg/dose and 10 mg/kg/dose, between 9.0 mg/kg/dose and 15 mg/kg/dose, between 14 mg/kg/dose and 20 mg/kg/dose, between 19 mg/kg/dose and 25 mg/kg/dose, between 24 mg/kg/dose and 30 mg/kg/dose, between 29 mg/kg/dose and 35 mg/kg/dose, between 34 mg/kg/dose and 40 mg/kg/dose, between 39 mg/kg/dose and 45 mg/kg/dose, or between 44 mg/kg/dose and 50 mg/kg/dose. In a specific embodiment, the CD2-binding molecule (or anti-CD2 antibody or antigen-binding fragment thereof) described herein can be administered to a subject in need or to a transplant recipient at a dose amount of 0.6 mg/kg/dose.

In certain embodiments, the CD2-binding molecule (or anti-CD2 antibody or antigen-binding fragment thereof) described herein can be administered to a subject in need or to a patient after transplant surgery wherein the patient is being treated for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, 20, 21, 22, 23, 24, or at least 25 years. In certain embodiments, the patient can be treated with the CD2-binding molecule (or anti-CD2 antibody or antigen-binding fragment thereof) described herein or a pharmaceutical composition comprising the CD2-binding molecule (or anti-CD2 antibody or antigen-binding fragment thereof) described herein for a period of time of at least 1, 2, 3, 4, 5, 6, 7, 8, 9, 10, 11, or 12 months, or at least 1, 2, 3, 4, 5, 6, 7, 8, 9, 10, 11, 12, 13, 14, 15, 16, 17, 18, 19, 20, 21, 22, 23, 24, or at least 25 years.

In certain embodiments, the CD2-binding molecule (or anti-CD2 antibody or antigen-binding fragment thereof) described herein can be formulated for subcutaneous, intravenous, intravascular, topical, intrarticular, intraarterial, intracranial, intramuscular, oral, intraorbital, intravitreal, inhalation, intraperitonial, intraosseous, endotracheal, sublingual, buccal, rectal, intradermal, intrathecal, intramedullary, or transdermal routes of administration. In a specific embodiment, the CD2-binding molecule (or anti-CD2 antibody or antigen-binding fragment thereof) described herein is formulated for intravenous administration to a subject in need or to a transplant surgery patient. In a specific embodiment, the CD2-binding molecule (or anti-CD2 antibody or antigen-binding fragment thereof) described herein is formulated for subcutaneous administration to a subject in need or to a transplant surgery patient.

In certain embodiments, the transplant surgery patient can be administered the pharmaceutical composition comprising a therapeutically effective amount of the CD2-binding molecule (or anti-CD2 antibody or antigen-binding fragment thereof) described herein. In certain embodiments, the pharmaceutical composition comprising a therapeutically effective amount of the CD2-binding molecule (or anti-CD2 antibody or antigen-binding fragment thereof) described herein is contained in a kit or system for administration to a transplant surgery patient. In certain embodiments, the kit will comprise the pharmaceutical composition comprising a therapeutically effective amount of the CD2-binding molecule (or anti-CD2 antibody or antigen-binding fragment thereof) described herein contained in one or more containers. The containers that contain said pharmaceutical composition can be packaged in can include, but are not limited to, bottles, packets, ampoules, tubes, inhalers, bags, vials, and containers. In certain embodiments, the kit comprises instructions for administering the pharmaceutical administration. In certain embodiments, the kit comprises devices that can be used to administer the pharmaceutical composition, including, but not limited to, syringes, needle-less injectors, drip bags, pumps, perfusion pumps. patches, and inhalers.

5.3.7 Co-Therapy with Immunosupressants of Organ Transplant Recipients

In certain embodiments, the CD2-binding molecule (or anti-CD2 antibody or antigen-binding fragment thereof) described herein is administered concurrently with low doses of immunosuppressants as a component of long term patient therapy after organ transplantation surgery. Without being bound by theory, immunosuppressants that can be combined with administration of the CD2-binding molecule (or anti-CD2 antibody or antigen-binding fragment thereof) described herein include, but are not limited to, tacrolimus, cyclosporine, belatacept, anti-CD40 antibodies, anti-OX40L antibodies, anti-CD28 antibodies, anti-CD27 antibodies, anti CD154 antibodies, anti-ICOS antibodies, anti- or agonistic 4-1BB (CD137) antibodies, BCL-2 inhibitors, mycophenolate mofetil, mycophenolic acid derivatives such as Myfortic (enteric coated mycophenolate sodium), sirolimus, everolimus, antiythymocyte globulin, basiliximab, prednisone, cyclophosphamide, fludarabine, and rituximab (Adams et al., *J Immunol,* 2016, 197 (6) 2045-2050; Kinnear et al., *Transplantation.* 2013 Feb. 27; 95(4): 527-535; Zhang and Vignali, *Immunity.* 2016 May 17; 44(5):1034-51). In certain embodiments, the CD2-binding molecule (or anti-CD2 antibody or antigen-binding fragment thereof) described herein may be administered as one part of a dual co-stimulation blockade. In a specific embodiment, the dose of immunosuppressant required to be therapeutically effective as part of a post-transplant therapy regimen is lower when the immunosuppressant is administered concurrently with the CD2-binding molecule (or anti-CD2 antibody or antigen-binding fragment thereof) described herein.

In certain embodiments, the CD2-binding molecule (or anti-CD2 antibody or antigen-binding fragment thereof) described herein can be administered concurrently with one immunosuppressant as part of a post-transplant therapy regimen. In other embodiments, the CD2-binding molecule (or anti-CD2 antibody or antigen-binding fragment thereof) described herein can be administered concurrently with more than one immunosuppressant as part of a post-transplant therapy regimen.

5.3.8 CTLA-4 Co-Stimulation Blockade

In some embodiments, described herein are methods of treating or preventing an immune related disorder or disease in a subject by administering to the subject a CD2-binding molecule (or an anti-CD2 antibody or antigen binding fragment thereof) and a CTLA-4 co-stimulation blockade. Specifically, provided herein are methods of treating or preventing an immune related disorder or disease using a combination of a CD2-binding molecule (or an anti-CD2 antibody or antigen binding fragment thereof) and a CTLA-4 co-stimulation blockade that results in a synergistic effect as compared to using the anti-CD2 antibody or an antigen-binding fragment thereof or the CTLA-4 co-stimulation blockade alone or without the other. In some embodiments, the method of treating or preventing an immune related disorder or disease further comprises administering another agent (e.g., immunosuppressive agent). In certain embodiments, administration of both the CD2-binding molecule (or an anti-CD2 antibody or antigen binding fragment thereof) and the CTLA-4 co-stimulation blockade results in a greater reduction of alloimmune response in the subject as compared to when only one of the anti-CD2 antibody or the CTLA-4 co-stimulation blockade is administered to the subject. In certain embodiments, administration of both the CD2-binding molecule (or an anti-CD2 antibody or antigen binding fragment thereof) and the CTLA-4 co-stimulation blockade results in a greater decrease in the level of CD2 as compared to when only one of the CD2-binding molecule (or an anti-CD2 antibody or antigen binding fragment thereof) or the CTLA-4 co-stimulation blockade is administered to the subject. In certain embodiments, administration of both the CD2-binding molecule (or an anti-CD2 antibody or antigen binding fragment thereof) and the CTLA-4 co-stimulation blockade to the subject results in a lower number of cells in a biological sample from the subject as compared to the number of cells in a biological sample from the subject obtained after only one of the CD2-binding molecule (or an anti-CD2 antibody or antigen binding fragment thereof) or the CTLA-4 co-stimulation blockade is administered to the subject.

In certain embodiments, the methods described herein include administering an anti-CD2 antibody or an antigen-binding fragment thereof in combination with a CTLA-4 co-stimulation blockade to a subject. In some embodiments, a CTLA-4 co-stimulation blockade is a CTLA4-Ig that targets CD80 and/or CD86. In some embodiments, a CTLA4-Ig co-stimulation blockade is a CTLA4-Ig variant that has enhanced binding to B7-1 and/or B7-2. In some embodiments, a CTLA-4 co-stimulation blockade is a CTLA-4 fusion protein. In some embodiments, a CTLA-4 co-stimulation blockade is CTLA-4 Ig (e.g., abatacept). In some embodiments, a CTLA-4 co-stimulation blockade is an extracellular domain of CTLA-4 fused to Fc. In some embodiments, the extracellular domain of CTLA-4 fused to Fc is belatacept (Nulojix®). In some embodiments, the extracellular domain of CTLA-4 fused to Fc is abatacept (Orencia®). In some embodiments, a CTLA-4 co-stimulation blockade comprises A29Y/L104E variant version of human CTLA4. In some embodiments, a CTLA-4 co-stimulation blockade includes at least one, at least two, at least three, at least four, or more than at least four substitutions in the CTLA4 portion of a CTLA-4 fusion protein to enhance affinity for B7-1 and B7-2. For example, a CTLA-4 co-stimulation blockade includes one or more substitutions including, but not limited to, one or more of A29K, A29N, A29E, A29W, A29F, A29Y, A29H, A29Q, A29R, T30D, T30V, T30A, T30N, T30E, T30H, T30R, E31I, E31M, E31T, E31V, E31D, R33F, R33T, R33M, R33W, R33I, R33Y, R33L, R33E, R33Q, T35E, T35V, T35M, T35D, T35F, T35Y, A49T, A49F, A49Y, A49W, A49D, A49E, T51V, T51L, T51N, T51H, T51Q, T51E, T51S, T51R, T51D, M53E, M53Q, M53Y, M53W, M53F, M53H, T59V, T59L, T59N, T59Y, T59H, T59Q, T59I, L61D, L61E, L61I, L61A, L61F, L61G, L61H, L61K, L61M, L61N, L61P, L61Q, L61R, L61S, L61T, L61V, L61W, L61Y, D63E, S64K, S64R, S64Y, K93D, K93E, K93F, K93H, K93Q, K93R, K93T, K93V, K93W, K93Y, K93N, K93S, E95D, E95Q, E95Y, E95H, E95L, M97F, M97D, M97N, M97I, M97V, Y98F, Y98W, Y102F, Y102W, Y103F, Y103W, Y103H, Y103D, Y103E, Y103N, Y103Q, L104D, L104E, L104V, L104M, L104Y, L104W, L104F, L104H, G105D, G105E, I106E, and I106Y. In some embodiments, a CTLA-4 co-stimulation blockade comprises at least one CTLA4 substitution selected from the group consisting of A29H, A29K, A29Y, T51N, L61E, L61Q, K93Q, K93, L104H, L104E, and Y103Q.

In some embodiments, a CTLA4 co-stimulation blockade comprises a sequence that is identical to SEQ ID NO:22. In some embodiments, a CTLA4 co-stimulation blockade comprises a sequence that is about or at least about 75%, 80%, 85%, 90%, 95%, 96%, 97%, 98%, 99%, or 100% identical to SEQ ID NO:22. In some embodiments, a CTLA4 co-stimulation blockade comprises about, at least about, or at most about 1, 2, 3, 4, 5, 6, 7, 8, 9, 10, 15, 20, 25, 30, 35, or 40 amino acid substitution in SEQ ID NO:22. In some embodiments, a CTLA4 co-stimulation blockade comprises a sequence that is identical to SEQ ID NO:23. In some embodiments, a CTLA4 co-stimulation blockade comprises a sequence that is about or at least about 75%, 80%, 85%, 90%, 95%, 96%, 97%, 98%, 99%, or 100% identical to SEQ ID NO:23. In some embodiments, a CTLA4 co-stimulation blockade comprises about, at least about, or at most about 1, 2, 3, 4, 5, 6, 7, 8, 9, 10, 15, 20, 25, 30, 35, or 40 amino acid substitution in SEQ ID NO:23. In some embodiments, the amino acid substitution is a conservative amino acid substitution.

In certain embodiments, a method of treatment provided herein comprises administering an CTLA-4 co-stimulation blockade to a subject prior to the subject being diagnosed with an immune-associated disorder or disease. In certain embodiments, a method of treatment provided herein comprises administering an CTLA-4 co-stimulation blockade to a subject after the subject is diagnosed with an immune-associated disorder or disease. In certain embodiments, a method of treatment provided herein comprises administering an CTLA-4 co-stimulation blockade to a transplant recipient prior to transplant. In some embodiments, an CTLA-4 co-stimulation blockade can be administered to the recipient 1 day prior to transplant, 2 days prior to transplant, 3 days prior to transplant, 4 days prior to transplant, 1 day and 2 days prior to transplant, 2 days and 3 days prior to transplant, 3 days and 4 days prior to transplant, 1 day prior and 2 days and 3 days prior to transplant, or 1 day prior and 2 days prior and 3 days prior and 4 days prior to transplant. In a specific embodiment, the CTLA-4 co-stimulation blockade can be administered to a recipient 1 day prior and 2 days prior to transplant. In particular embodiments, an CTLA-4 co-stimulation blockade is administered on the day of the transplant surgery.

In certain embodiments, a method of treatment provided herein comprises administering an CTLA-4 co-stimulation blockade to a transplant recipient after the transplant. In some embodiments, an CTLA-4 co-stimulation blockade can be administered to the recipient 1 day after transplant, 2 days after transplant, 3 days after transplant, 4 days after transplant, 5 days after transplant, 6 days after transplant, 7 days after transplant, 8 days after transplant, 9 days after transplant, 10 days after transplant, 11 days after transplant, 12 days after transplant, 13 days after transplant, 14 days after transplant, 15 days after transplant, 16 days after transplant, 17 days after transplant, 18 days after transplant, 19 days after transplant, 20 days after transplant, 21 days after transplant, 22 days after transplant, 23 days after transplant, 24 days after transplant, 25 days after transplant, 26 days after transplant, 27 days after transplant, 28 days after transplant, 29 days after transplant, and/or 30 days after transplant. In specific embodiments, an CTLA-4 co-stimulation blockade is administered on the day of transplant, 1 day after transplant, 2 days after transplant and/or 4 days after transplant.

In certain embodiments, a test dose of the CTLA-4 co-stimulation blockade can be administered. In certain embodiments, the administration of the test dose is optional. In certain embodiments, the CTLA-4 co-stimulation blockade can be administered to a subject at a dose high enough to induce remission (a loading dose), followed by less frequent dosing such as, but not limited to, once a month, once every two months, or once every three months. In some embodiments, the CTLA-4 co-stimulation blockade is administered to a subject in a convenient manner known in the art including subcutaneously, intravenously, intravascularly, topically, intra-arterially, intra-cranially, intramuscularly, orally, intra-orbitally, by inhalation, transdermally, or intra-peritoneally. In some embodiments, the CTLA-4 co-stimulation blockade is administered intravenously. In some embodiments, the CTLA-4 co-stimulation blockade is administered intravenously as a 30-minute intravenous infusion. In some embodiments, the CTLA-4 co-stimulation blockade is administered at about 2 and 4 weeks after the first infusion and/or every 4 weeks thereafter. In some embodiments, the CTLA-4 co-stimulation blockade is administered by subcutaneous injection once weekly. In some embodiments, the CTLA-4 co-stimulation blockade is initiated with or without an intravenous loading dose. In some embodiments, the CTLA-4 co-stimulation blockade is initiated with a single intravenous infusion, followed by a first subcutaneous (e.g., 125 mg) injection administered within a day of the intravenous infusion. In some embodiments, the CTLA-4 co-stimulation blockade is administered at a dose of about 500 mg (e.g., to a subject who is less than 60 kg), 750 mg (e.g., to a subject who is 60 to 100 kg), or 1000 mg (e.g., to a subject who is more than 100 kg). In some embodiments, the CTLA-4 co-stimulation blockade is provided in a vial (e.g., in a 250 mg vial). In some embodiments, the CTLA-4 co-stimulation blockade is provided as a lyophilized powder. In some embodiments, after reconstitution of the CTLA-4 co-stimulation blockade, each milliliter contains 25 mg (250 mg/10 mL) of the CTLA-4 co-stimulation blockade. In some embodiments, the CTLA-4 co-stimulation blockade is provided as a 125 mg/mL single-dose prefilled glass syringe.

In some embodiments, the CTLA4 co-stimulation blockade is administered in an amount of about, at least about, or at most about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, or more than 1000 mg per day, per dose, per week, or per month.

In some embodiments, a CTLA4 co-stimulation blockade dosages range from 0.0001 to 100 mg/kg of body weight or greater, for example 0.1, 1, 10, or 50 mg/kg of body weight. In some embodiments, dosages range from 1 to 10 mg/kg. In some embodiments, only a single dose of the CTLA4 co-stimulation blockade is administered to a subject. In some embodiments, multiple doses of the CTLA4 co-stimulation blockade are administered to a subject. In some embodiments, the elapsed time between administrations is less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In some embodiments, a CTLA-4 co-stimulation blockade is administered to a subject in a range from about 1 ng/kg body weight to about 100 mg/kg body weight whether by one or more administrations. In some embodiments, a CTLA-4 co-stimulation blockade is administered in the range of from about 1 ng/kg body weight to about 10 mg/kg body weight, about 1 ng/kg body weight to about 1 mg/kg body weight, about 1 ng/kg body weight to about 100 µg/kg body weight, about 1 ng/kg body weight to about 10 µg/kg body weight, about 1 ng/kg body weight to about 1 µg/kg body weight, about 1 ng/kg body weight to about 100 ng/kg body weight, about 1 ng/kg body weight to about 10 ng/kg body weight, about 10 ng/kg body weight to about 100 mg/kg body weight, about 10 ng/kg body weight to about 10 mg/kg body weight, about 10 ng/kg body weight to about 1 mg/kg body weight, about 10 ng/kg body weight to about 100 µg/kg body weight, about 10 ng/kg body weight to about 10 µg/kg body weight, about 10 ng/kg body weight to about 1 µg/kg body weight, 10 ng/kg body weight to about 100 ng/kg body weight, about 100 ng/kg body weight to about 100 mg/kg body weight, about 100 ng/kg body weight to about 10 mg/kg body weight, about 100 ng/kg body weight to about 1 mg/kg body weight, about 100 ng/kg body weight to about 100 µg/kg body weight, about 100 ng/kg body weight to about 10 µg/kg body weight, about 100 ng/kg body weight to about 1 µg/kg body weight, about 1 µg/kg body weight to about 100 mg/kg body weight, about 1 µg/kg body weight to about 10 mg/kg body weight, about 1 µg/kg body weight to about 1 mg/kg body weight, about 1 µg/kg body weight to about 100 µg/kg body weight, about 1 µg/kg body weight to about 10 µg/kg body weight, about 10 µg/kg body weight to about 100 mg/kg body weight, about 10 µg/kg body weight to about 10 mg/kg body weight, about 10 µg/kg body weight to about 1 mg/kg body weight, about 10 µg/kg body weight to about 100 µg/kg body weight, about 100 µg/kg body weight to about 100 mg/kg body weight, about 100 µg/kg body weight to about 10 mg/kg body weight, about 100 µg/kg body weight to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight per day, per dose, per week, or per month that the CTLA4 co-stimulation blockade is administered.

In some embodiments, a CTLA4 co-stimulation blockade is administered in an amount between 0.1 to 20.0 mg/kg weight of the patient/day (e.g., between 0.5 to 10.0 mg/kg/day). In some embodiments, a CTLA-4 co-stimulation blockade agent is administered to a subject in an amount of about 0.1 to 100 mg/kg weight of the subject, about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, about 95 to 100 mg/kg weight of a subject, about 2 to 10 mg/kg weight of a subject, about 0.1 to 4 mg/kg weight of a subject, about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject, about 3.5 to 4.0 mg/kg weight of a subject, about 4.0 to 4.5 mg/kg weight of a subject, about 4.5 to 5.0 mg/kg weight of a subject, about 5.0 to 5.5 mg/kg weight of a subject, about 5.5 to 6.0 mg/kg weight of a subject, about 6.0 to 6.5 mg/kg weight of a subject, about 6.5 to 7.0 mg/kg weight of a subject, about 7.0 to 7.5 mg/kg weight of a subject, about 7.5 to 8.0 mg/kg weight of a subject, about 8.0 to 8.5 mg/kg weight of a subject, about 8.5 to 9.0 mg/kg weight of a subject, about 9.0 to 9.5 mg/kg weight of a subject, about 9.5 to 10.0 mg/kg weight of a subject, about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject, about 18 to 20 mg/kg weight of a subject, about 0.5 mg/kg weight of the subject, 2 mg/kg weight of the subject, 10 mg/kg weight of the subject, about 0.5 mg/kg to 100 weight of the subject, about 0.5 to 10 mg/kg weight of a subject, about 0.1 to 20 mg/kg weight of a subject, about 500 mg for a subject weighing less than 60 kg, 750 mg for a subject weighing between 60-100 kg or 1000 mg for a subject weighing more than 100 kg.

In some embodiments, a CTLA4 co-stimulation blockade (e.g., belatacept and/or abatacept) is administered in combination therapy with an anti-CD2 antibody or antigen-binding fragment thereof in an amount of about, at least about, or at most about 10 mg/kg, 15 mg/kg, 20 mg/kg, 25 mg/kg, or 30 mg/kg (or any integer amount in between) per day, per CTLA4 co-stimulation blockade administration, per week, or per month

5.3.9 Immunosuppressive Therapy

In some embodiments, the methods provided herein includes administering an anti-CD2 antibody or an antigen fragment thereof, a CTLA-4 co-stimulation blockade and another active agent. In some embodiments, the another active agent is administered before, during, or after the anti-CD2 antibody or an antigen-binding fragment thereof and/or the CTLA-4 co-stimulation blockade is administered to the subject. In some embodiments, the another active agent is administered before, during, or after the anti-CD2 antibody or an antigen-binding fragment thereof is administered to the subject. In some embodiments, the another active agent is administered before, during, or after the CTLA-4 co-stimulation blockade is administered to the subject. In some embodiments, the another active agent includes one or more of methotrexate, nonsteroidal anti-inflammatory drugs (NSAIDs), an agent for alleviating pain, corticosteroids, TNF blocking agents, azathioprine, chloroquine, gold, hydroxychloroquine, leflunomide, sulfasalazine, and/or anakinra. Examples of NSAID include, but are not limited to aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxib, rofecoxib, valdecoxib, parecoxib, lumiracoxib, etoricoxib, nimesulide, licofenac, and niflumic acid. In some embodiments, the another active agent is an immunosuppressive therapy. The immunosuppressive therapy may be any FDA-approved treatment for treating or preventing an immune related disorder or disease in a subject (e.g., indicated to reduce transplant rejection). Non-limiting examples of immunosuppressive therapy include calcineurin inhibitors (e.g., tacrolimus or cyclosporine), antiproliferative agents (e.g., anti-metabolites such a mycophenolate, 6-mercaptopurine or its prodrug azathioprine), cyclophosphamide, inhibitors of mammalian target of rapamycin (mTOR) (e.g., sirolimus, rapamycin), steroids (e.g., prednisone), cell cycle inhibitors (azathioprine or mycophenolate mofetil), lymphocyte-depleting agents (e.g., anti-thymocyte globulin or antibodies such as alemtuzumab or basiliximab) and co-stimulation blockers. See, e.g., Chung et al (2020), Ann Transl Med. March; 8(6): 409; van der Mark et al. (2020), Eur Respir Rev; 29: 190132 and Benvenuto et al. (2018), J Thorac Dis 10:3141-3155.

Immunosuppressive therapy can be administered as induction therapy (perioperative, or immediately after surgery) as a maintenance dose or for an acute immune related disease (e.g., acute rejection). Induction therapy commonly includes basiliximab, anti-thymocyte globulin or alemtuzumab. Immunosuppressive therapy may also be administered as maintenance therapy which is often required to continue for the life of the subject. Maintenance immunosuppressive therapy commonly includes a calcineurin inhibitor (tacrolimus or cyclosporine), an antiproliferative agent (mycophenolate or azathioprine), and corticosteroids. Immunosuppressive therapy for acute rejections commonly includes thymoglobulin or mycophenolate. See, e.g., Chung et al. (2020), Ann Transl Med. March; 8: 409 and Benvenuto et al., (2018) J Thorac Dis 10:3141-3155

Non-limiting examples of immunosuppressants include, (1) antimetabolites, such as purine synthesis inhibitors (such as inosine monophosphate dehydrogenase (IMPDH) inhibitors, e.g., azathioprine, mycophenolate, and mycophenolate mofetil), pyrimidine synthesis inhibitors (e.g., leflunomide and teriflunomide), and antifolates (e.g., methotrexate); (2) calcineurin inhibitors, such as tacrolimus, cyclosporine A, pimecrolimus, and voclosporin; (3) TNF-alpha inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus, and biolimus A9; (6) corticosteroids, such as prednisone; and (7) antibodies to any one of a number of cellular or serum targets (including anti-lymphocyte globulin and anti-thymocyte globulin).

Non-limiting exemplary cellular targets and their respective inhibitor compounds include, but are not limited to, complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CDI 1a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., belimumab); CTLA-4 (e.g., ipilimumab, tremelimumab); CAT (e.g., bertilimumab, lerdelimumab, metelimumab); integrin (e.g., natalizumab); IL-6 receptor (e.g., tocilizumab); LFA-1 (e.g., odulimomab); and IL-2 receptor/CD25 (e.g., basiliximab, daclizumab, inolimomab).

In some embodiments, an immunosuppressive therapy is a nonspecific cytotoxic immunosuppressive drug known as Disease Modifying Anti-Rheumatic Drugs (DMARDs), such as methotrexate, infliximab, cyclophosphamide, azathioprine, cyclosporin A, sulfasalazine, hydroxychloroquine, leflunomide, etanercept, and tumor necrosis factor-alpha (TNFα) or other cytokine blockers or antagonists. In some embodiments, the amount of an immunosuppressive therapy (e.g., DMARDS) administered to a subject is about or at least about 1 to about 5000 mg/day, about 1 to 10 mg/day, about 10 to 50 mg/day, about 50 to 100 mg/day, about 100 to 150 mg/day, about 150 to 200 mg/day, about 200 to 250 mg/day, about 250 to 300 mg/day, about 300 to 350 mg/day, about 350 to 400 mg/day, about 400 to 450 mg/day, about 450 to 500 mg/day, about 500 to 550 mg/day, about 550 to 600 mg/day, about 600 to 650 mg/day, about 650 to 700 mg/day, about 700 to 750 mg/day, about 750 to 800 mg/day, about 800 to 850 mg/day, about 850 to 900 mg/day, about 900 to 950 mg/day, about 950 to 1000 mg/day, about 1000 to 1100 mg/day, about 1100 to 1200 mg/day, about 1200 to 1300 mg/day, about 1300 to 1400 mg/day, about 1400 to 1500 mg/day, about 1500 to 1600 mg/day, about 1600 to 1700 mg/day, about 1700 to 1800 mg/day, about 1800 to 1900 mg/day, about 1900 to 2000 mg/day, about 2000 to 2500 mg/day, about 2500 to 3000 mg/day, about 3000 to 3500 mg/day, about 3500 to 4000 mg/day, about 4000 to 4500 mg/day, or about 4500 to 5000 mg/day on the days that the immunosuppressive therapy is administered to a subject.

In some embodiments, the amount of an immunosuppressive therapy (e.g., DMARDS) administered to a subject is about 0.1 to 40 mg per week, about 5 to 30 mg per week, about 0.1 to 5 mg per week, about 5 to 10 mg per week, about 10 to 15 mg per week, about 15 to 20 mg per week, about 20 to 25 mg per week, about 25 to 30 mg per week, about 30 to 35 mg per week, about 35 to 40 mg per week, about 10 to 30 mg per week, about 10 to 100 mg per week, about 50 mg per week, about 0.1 to 50 mg/kg body weight per week.

5.3.10 Cyclophosphamide

Cyclophosphamide, as used herein, is a compound administered to the recipient to suppress the immune system. In some embodiments, cyclophosphamide (2-[bis(2-chloroethyl)amino]tetrahydro-2H-1,3,2-oxazaphosphorine 2-oxide monohydrate) is administered to induce tolerance towards the transplanted organ (e.g., liver or kidney) and brand names of cyclophosphamide include Cytoxan®, Neosar®, and Endoxan®.

In certain embodiments, a regimen provided herein comprises administering cyclophosphamide to a transplant recipient prior to transplant. In certain embodiments, a regimen provided herein comprises administering cyclophosphamide to treat or prevent an immune related disorder or disease. In some embodiments, the cyclophosphamide can be administered to the recipient three days after transplant, four days after transplant, five days after transplant, six days after transplant, three days and four days after transplant, five days and six days after transplant, three days and four days and five days after transplant, or four days and five days and six days after transplant. In a specific embodiment, cyclophosphamide can be administered to a recipient four days and five days after transplant. In specific embodiments, the cyclophosphamide is first administered to a recipient three days, four days, five days, six days, or seven days after the transplant.

In particular embodiments, a recipient treated in accordance with a method described herein has a MELD score of 30 or higher and the method comprises first administering cyclophosphamide to the recipient 1-2 days after the transplant, 2-4 days after the transplant, 4-6 days after the transplant, 6-8 days after the transplant, 8-10 days after the transplant, 10-12 days after the transplant, 12-14 days after the transplant, 14-16 days after the transplant, 16-18 days after the transplant, 18-20 days after the transplant, 20-22 days after the transplant, 22-24 days after the transplant, 24-26 days after the transplant, 26-28 days after the transplant, 28-30 days after the transplant or more than 30 days after the transplant.

In particular embodiments, a recipient treated in accordance with a method described herein has a MELD score of 30 or less and the method comprises first administering cyclophosphamide to the recipient 1 day after the transplant, 2 days after the transplant, 3 days after the transplant, 4 days after the transplant, 5 days after the transplant, 6 days after the transplant, 7 days after the transplant, 8 days after the transplant, 9 days after the transplant, 10 days after the transplant, 11 days after the transplant, 12 days after the transplant, 13 days after the transplant, 14 days after the transplant, or more than 14 days after the transplant.

In certain embodiments, the cyclophosphamide can be administered to a transplant recipient or can be administered to treat or prevent an immune related disorder or disease in a subject at a dose amount of 20 mg/kg/dose, 25 mg/kg/dose, 30 mg/kg/dose, 35 mg/kg/dose, 40 mg/kg/dose, 45 mg/kg/dose, 50 mg/kg/dose, 55 mg/kg/dose, 56 mg/kg/dose, 57 mg/kg/dose, 58 mg/kg/dose, 59 mg/kg/dose, 60 mg/kg/dose, 61 mg/kg/dose, 62 mg/kg/dose, 63 mg/kg/dose, 64 mg/kg/dose, 65 mg/kg/dose, 70 mg/kg/dose, 75 mg/kg/dose, 80 mg/kg/dose, 85 mg/kg/dose, or 90 mg/kg/dose. In certain embodiments, the cyclophosphamide can be administered at dose ranges of 20-30 mg/kg/dose, 25-35 mg/kg/dose, 30-40 mg/kg/dose, 35-45 mg/kg/dose, 40-50 mg/kg/dose, 45-55 mg/kg/dose, 50-60 mg/kg, 55-65 mg/kg/dose, 60-70 mg/kg/dose, 65-75 mg/kg/dose, 70-80 mg/kg/dose, 75-85 mg/kg/dose, or 80-90 mg/kg/dose. In a specific embodiment, the cyclophosphamide can be administered at a dose amount of 40 mg/kg/dose.

In certain embodiments, the cyclophosphamide can be administered in a convenient manner known in the art including subcutaneously, intravenously, intravascularly, topically, intra-arterially, intracranially, intramuscularly, orally, intraorbitally, by inhalation, transdermally, intraperitoneally, or through a route of administration which allows for the proper action of the cyclophosphamide by the subject. In a specific embodiment, the cyclophosphamide is administration intravenously. In particular embodiments, the cyclophosphamide is administered intravenously over a one hour. In some embodiments, a cyclophosphamide is administered before, during, or after the anti-CD2 antibody or an antigen-binding fragment thereof and/or the CTLA-4 co-stimulation blockade is administered to the subject. In some embodiments, a cyclophosphamide is administered before, during, or after the anti-CD2 antibody or an antigen-binding fragment thereof is administered to the subject. In some embodiments, a cyclophosphamide is administered before, during, or after the CTLA-4 co-stimulation blockade is administered to the subject.

5.3.11 Calcineurin Inhibitors (e.g., Tacrolimus)

In some embodiments, a method of treatment described herein further comprises administering a calcineurin inhibitor to a subject. In specific embodiments, the calcineurin inhibitor is tacrolimus. Tacrolimus, as used herein, is a macrolide antibiotic which may be administered to a subject to suppress the immune system. Tacrolimus has a mode of action similar to CyA (Cyclosporine A, another calcineurin inhibitor), and brand names of tacrolimus include Prograf®, Adport®, Advagraf®, Protopic®, Astagraf XL®, Modigraf®, and Envarsus XR®. A calcineurin inhibitor (e.g., tacrolimus) can be administered to a subject to treat or prevent an immune associated disease or disorder or can be included in the postoperative treatment regimen to suppress the immune system and inhibit the development of Graft versus Host disease in the recipient. In some embodiments, administration of a calcineurin inhibitor include a constant course followed by a tapering course of the calcineurin inhibitor (e.g., tacrolimus) administration to the subject.

In certain embodiments, a regimen provided herein comprises administering cyclophosphamide to treat or prevent an immune related disorder or disease. In certain embodiments, the regimen provided herein comprises administering a calcineurin inhibitor (e.g., tacrolimus) to a transplant recipient. In certain embodiments, a calcineurin inhibitor (e.g., tacrolimus) can be first administered 1 day before the transplant, 2 days before the transplant, 3 days before the transplant, 1 day and 2 days before the transplant, 1 day and 3 days before transplant, or 1 day and 2 days and 3 days before the transplant. In a specific embodiment, a calcineurin inhibitor (e.g., tacrolimus) can be first administered to a recipient 1 day before the transplant. In specific embodiments, a calcineurin inhibitor (e.g., tacrolimus) is administered as soon as possible in the peri-transplant period (i.e., around the time of the transplant surgery). In specific embodiments, a calcineurin inhibitor (e.g., tacrolimus) is administered no later than 24 hours after reperfusion of an organ (e.g., liver) transplant. In certain embodiments, the postoperative treatment regimen provided herein comprises administering a calcineurin inhibitor (e.g., tacrolimus) to a transplant recipient. In certain embodiments, a calcineurin inhibitor (e.g., tacrolimus) can be administered on the day of the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, 30 days after, 1 month after, 2 months after, 3 months after, 4 months after, 5 months after, 6 months after, 7 months after, 8 months after, 9 months after, 10 months after, 11 months after, 12 months after, 13 months after, 14 months after, 15 months after, 16 months after, 17 months after, or 18 months after the transplant surgery.

In certain embodiments, a single dose amount of tacrolimus can be administered. In certain embodiments, multiple dose amounts of a calcineurin inhibitor (e.g., tacrolimus) can be administered. In certain embodiments, a constant dose of a calcineurin inhibitor (e.g., tacrolimus) can be administered. In certain embodiments, a tapering course of the calcineurin inhibitor (e.g., tacrolimus) can be administered. In certain embodiments, a constant dose of the calcineurin inhibitor (e.g., tacrolimus) followed by a tapering course of the calcineurin inhibitor (e.g., tacrolimus) can be administered.

In specific embodiments, a calcineurin inhibitor (e.g., tacrolimus) may be administered at a frequency of once a day. In certain embodiments, tacrolimus can be administered at a frequency of twice a day. In certain embodiments, tacrolimus can be administered at a frequency of twice a day (e.g., beginning on the day of the transplant). In certain embodiments, a calcineurin inhibitor (e.g., tacrolimus) can be administered twice a day at a dose amount of 0.1 mg/kg/dose, 0.2 mg/kg/dose, 0.3 mg/kg/dose, 0.4 mg/kg/dose, 0.5 mg/kg/dose, 0.6 mg/kg/dose, 0.7 mg/kg/dose, 0.8 mg/kg/dose, 0.9 mg/kg/dose, 1 mg/kg/dose, 0.1-0.5 mg/kg/dose, 0.5-1 mg/kg/dose, 0.2-0.6 mg/kg/dose, 0.3-0.7 mg/kg/dose, 0.4-0.8 mg/kg/dose, or 0.1-1 mg/kg/dose. In a specific embodiment, the calcineurin inhibitor is tacrolimus and is administered orally twice a day at a dose amount of at least 0.5 mg/kg/dose.

In certain embodiments, a calcineurin inhibitor (e.g., tacrolimus) can be administered to a subject at a sufficient dose amount to obtain the target trough blood levels of 1-5 ng/ml, 5-10 ng/ml, 10-15 ng/ml, 1-11 ng/ml, 2-12 ng/ml, 3-13 ng/ml, 4-14 ng/ml, 5-15 ng/ml, 6-16 ng/ml, 7-17 ng/ml, 8-18 ng/ml, 9-19 ng/ml, 10-20 ng/ml, or 15-20 ng/ml. In a specific embodiment, the target trough blood levels can be 10-15 ng/ml. In specific embodiments, the calcineurin inhibitor is tacrolimus and is administered to a subject at a dose sufficient to maintain serum trough concentrations in the range of 4-11 ng/mL.

In certain embodiments, a calcineurin inhibitor (e.g., tacrolimus) can be administered to a subject in a convenient manner known in the art including subcutaneously, intravenously, intravascularly, topically, intra-arterially, intra-cranially, intramuscularly, orally, intra-orbitally, by inhalation, transdermally, or intra-peritoneally, or through a route of administration which allows for the proper action of the calcineurin inhibitor (e.g., tacrolimus) by the recipient. In a specific embodiment, the calcineurin inhibitor (e.g., tacrolimus) can be administered orally. In a specific embodiment, the a calcineurin inhibitor (e.g., tacrolimus) can be administered intravenously.

In specific embodiments, a subject is weaned off of the calcineurin inhibitor (e.g., tacrolimus) at 3 months, 4 months, 5 months, 6 months, 7 months, 8 months, 9 months, 10 months, 11 months, 12 months, 1-2 months, 2-3 months, 3-4 months, 4-5 months, 5-6 months, 6-7 months, 7-8 months, 8-9 months, 9-10 months, 10-11 months, 11-12 months, 12-13 months, 13-14 months, 14-15 months, 15-16 months, 16-17 months, 17-18 months, 18-19 months, 19-20 months, 20-21 months, 21-22 months, 22-23 months, or 23-24 months after the subject receives an organ transplant, after the subject is diagnosed with an immune-associate disease or disorder, or after the subject is treated for an immune-associate disease or disorder according to the methods described herein. In specific embodiments, weaning is initiated at six months after the subject receives an organ transplant, after the subject is diagnosed with an immune-associate disease or disorder, or after the subject is treated for an immune-associate disease or disorder according to the methods described herein. In specific embodiments, weaning is only initiated if a biopsy taken from the recipient at six months is free from rejection as determined by the 2016 Banff Criteria (as described in Demetris et al., Am J Transplant. 2016 October; 16(10):2816-2835) and/or the recipient maintains stable graft function.

In specific embodiments, the dose of the calcineurin inhibitor (e.g., tacrolimus) is reduced every 2, 3, 4, 5, or 6 months after weaning begins.

In particular embodiments, a weaning protocol comprises one or more steps of reducing the frequency of administration, for example, reducing the frequency of administration from twice daily to once daily, from once daily to every other day, from once daily to three times a week, from three times a week to twice a week, from twice a week to once w week, from once a week to every other week. In specific embodiments, a weaning protocol comprises a step of reducing the daily dose of the calcineurin inhibitor (e.g., tacrolimus), e.g., reducing an initial daily dose by 10-20%, 20-30%, 30-40%, 40-50%, 50-60%, 60-70%, 70-80%, 80-90%, or more than 90%. In particular embodiments, a weaning protocol comprises a step of decreasing the daily dose of the calcineurin inhibitor (e.g., tacrolimus) by about 25%.

In particular embodiments, administration of a calcineurin inhibitor (e.g., tacrolimus) is stopped about 12-15 months, 15-18 months, 18-21 months, or 21-24 months after the subject receives an organ transplant, after the subject is diagnosed with an immune-associate disease or disorder, or after the subject is treated for an immune-associate disease or disorder according to the methods described herein. In a specific embodiment, administration of a calcineurin inhibitor (e.g., tacrolimus) is stopped 18 months after the subject receives an organ transplant, after the subject is diagnosed with an immune-associate disease or disorder, or after the subject is treated for an immune-associate disease or disorder according to the methods described herein. In specific embodiments, administration of a calcineurin inhibitor (e.g., tacrolimus) is only stopped if a biopsy taken from the recipient at 18 months is free from rejection as determined by the 2016 Banff Criteria as described in Demetris et al., Am J Transplant. 2016 October; 16(10):2816-2835.

An exemplary weaning protocol comprises steps of (i) reducing an initial, twice-daily dose of tacrolimus to once a day at three quarters of the daily dose over three months (e.g., from month 6 to month 9 after transplant); (ii) further reducing the dose to three times per week over three months (e.g., from month 9 to month 12 after transplant); (iii) further reducing the dose to twice a week over three months (e.g., from month 12 to month 15 after transplant); (iv) further reducing the dose to once a week over three months (e.g., from month 15 to month 18 after transplant); and (v) stopping tacrolimus administrations at 18 months after the subject receives an organ transplant, after the subject is diagnosed with an immune-associate disease or disorder, or after the subject is treated for an immune-associate disease or disorder according to the methods described herein.

In certain embodiments, substitute compounds can be used in the place of the calcineurin inhibitor. These compounds can include sirolimus and everolimus. In certain embodiments, the calcineurin inhibitor can be cyclosporine (Gengraf®, Neoral®, and Santimmune®) and can be used of in place of the tacrolimus. In some embodiments, a calcineurin inhibitor is administered before, during, or after the anti-CD2 antibody or an antigen-binding fragment thereof and/or the CTLA-4 co-stimulation blockade is administered to the subject. In some embodiments, a calcineurin inhibitor is administered before, during, or after the anti-CD2 antibody or an antigen-binding fragment thereof is administered to the subject. In some embodiments, a calcineurin inhibitor is administered before, during, or after the CTLA-4 co-stimulation blockade is administered to the subject.

5.3.12 Steroids

A steroid, as used herein, is a compound administered to a subject to treat or prevent an immune associated immune disorder or disease. In some embodiments, a steroid is administered to a recipient of an organ (e.g., liver or kidney) transplant to suppress the immune system. Prednisone is a corticosteroid, chemical name 17,21-dihydroxypregna-1,4- dienne-3,11,20-trione ($C_{21}H_{26}O_5$). Brand names of prednisone include Deltasone®, Sterapred®, Rayos®, Prednicot®, and Meticorten®.

In certain embodiments, a method of treatment provided herein comprises administering corticosteroids to a subject to treat or prevent an immune associated immune disorder or disease or to a transplant recipient. In certain embodiments, corticosteroids can be administered on the day of the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, or 30 days after the transplant surgery.

In certain embodiments, a corticosteroid can be administered on the day of the transplant surgery through 5 days after, on the day of the transplant surgery through 10 days after, on the day of the transplant surgery through 15 days after, on the day of the transplant surgery through 20 days after, on the day of the transplant surgery through 25 days after, or on the day of the transplant surgery through 30 days after the transplant surgery. In specific embodiments, a corticosteroid is administered on the day of the transplant surgery and on days 2-7 after transplant surgery. In particular embodiments, the dose of corticosteroid administered to the patient is reduced from the day of the transplant to one month after transplant.

In certain embodiments, a single dose of the corticosteroid can be administered. In certain embodiments, multiple doses of the corticosteroid can be administered. In certain embodiments, a constant dose of corticosteroids can be administered. In certain embodiments, a pulse of corticosteroids can be administered. In certain embodiments, a tapering course of corticosteroids can be administered. In certain embodiments, a constant dose of corticosteroids followed by a tapering course of corticosteroids can be administered. In certain embodiments, a constant dose of corticosteroids, with pulses of corticosteroids, and a tapering course of corticosteroids can be administered.

In certain embodiments, the corticosteroid can be administered to a subject at a dose amount of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, or 3.0 mg/kg. In a specific embodiment, the steroid can be administered to a subject at a dose amount of 2 mg/kg.

In certain embodiments, the corticosteroid can be administered to a subject at a pulsed dose amount of 100 mg/dose, 200 mg/dose, 300 mg/dose, 400 mg/dose, 500 mg/dose, 600 mg/dose, 700 mg/dose, 800 mg/dose, 900 mg/dose, or 1000 mg/dose. In a specific embodiment, the corticosteroid can be administered at pulsed dose amount of 500 mg/dose. In certain embodiments, a pulse of the corticosteroid can be administered on the day of the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, the day of and 1 day and 2 days after, 3 days and 4 days and 5 days after, 6 days and 7 days and 8 days after, 9 days and 10 days and 11 days after, 10 days and 11 days and 12 days after, 11 days and 12 days and 13 days after, or 13 days and 14 days and 15 days after the transplant. In a specific embodiment, a pulse of the corticosteroid is administered the day of the transplant. In a specific embodiment, a pulse of corticosteroid is administered 10 days and 11 days and 12 days after the transplant.

In certain embodiments, the steroid can be administered to a subject at a constant dose. The duration of time a constant dose is administered can be 1 day, 2 days, 3 days, 4 days, 5 days, 6 days, 7 days, 8 days, 9 days, or 10 days. In certain embodiments, the corticosteroids administered to a subject can be tapered to discontinuation. In certain embodiments, this tapering course can take place over 5 days, 6 days, 7 days, 8 days, 9 days, 10 days, 11 days, 12 days, 13 days, 14 days 15 days, 16 days, 17 days, 18 days, 19 days, 20 days, 21 days, 22 days, 23 days, 24 days 25 days, 26 days, 27 days, 28 days, 29 days, or 30 days. In a specific embodiment, the tapering course can take place over 10 days. In a specific embodiment, the tapering course can take place over 20 days.

In certain embodiments, for the tapering course, the corticosteroids administered to a subject can be reduced by 0.01 mg/kg per day, 0.02 mg/kg per day, 0.03 mg/kg per day, 0.04 mg/kg per day, 0.05 mg/kg per day, 0.06 mg/kg per day, 0.07 mg/kg per day, 0.08 mg/kg per day, 0.09 mg/kg per day, 0.1 mg/kg per day, 0.2 mg/kg per day, 0.3 mg/kg per day, 0.4 mg/kg per day, 0.5 mg/kg per day, 0.6 mg/kg per day, 0.7 mg/kg per day, 0.8 mg/kg per day, 0.9 mg/kg per day, 1.0 mg/kg per day, 1.1 mg/kg per day, 1.2 mg/kg per day, 1.3 mg/kg per day, 1.4 mg/kg per day, 1.5 mg/kg per day, 1.6 mg/kg per day, 1.7 mg/kg per day, 1.8 mg/kg per day, 1.9 mg/kg per day, or 2.0 mg/kg per day.

An exemplary steroid dosing regimen comprises administering the following doses to a subject: (i) 1000 mg methylprednisolone intravenously on the day of transplant surgery; (ii) 250 mg oral steroid on day 2 after transplant surgery, (iii) 125 mg oral steroid on day 3 after transplant surgery; (iv) 75 mg oral steroid on day 4 after transplant surgery; (v) 60 mg oral steroid on each of days 5-7 after the transplant surgery; and (vi) 20 mg oral steroid daily from day 7 to one month after transplant surgery.

In certain embodiments, the corticosteroid can be administered to a subject in a convenient manner known in the art including subcutaneously, intravenously, intravascularly, topically, intra-arterially, intra-cranially, intramuscularly, orally, intra-orbitally, by inhalation, transdermally, or intraperitoneally, or through a route of administration which allows for the proper action of the corticosteroid by the recipient. In a specific embodiment, the corticosteroid can be administered orally. In a specific embodiment, the corticosteroid can be administered intravenously.

Examples of steroids that may be used in a method described herein include Deltison®, Prednisolone EQL Pharma, and Prednisolon Alternova.

In a specific embodiment, the corticosteroid is prednisone. In a specific embodiment, the pulsed corticosteroid is methylprednisone. In certain embodiments, the administration of corticosteroids can be modified as described herein. In some embodiments, a steroid is administered before, during, or after the anti-CD2 antibody or an antigen-binding fragment thereof and/or the CTLA-4 co-stimulation blockade is administered to the subject. In some embodiments, a steroid is administered before, during, or after the anti-CD2 antibody or an antigen-binding fragment thereof is administered to the subject. In some embodiments, a steroid is administered before, during, or after the CTLA-4 co-stimulation blockade is administered to the subject.

5.3.13 Cyclosporine

Cyclosporine (CyA) can be included to treat or prevent an immune associated immune disorder or disease in a subject.

Cyclosporine (CyA) can be included in the postoperative treatment regimen to suppress the immune system and inhibit the development of Graft versus Host disease in the recipient. The treatment regimen can include a constant course followed by a tapering course of CyA administration to the subject. In certain embodiments, cyclosporine can be used in place of a calcineurin inhibitor (e.g., tacrolimus) in a method provided herein. In some embodiments, cyclosporine may be used in a subject who experienced adverse events with a calcineurin inhibitor. In specific embodiments, cyclosporine may be used in a subject who experienced tacrolimus-related adverse events.

In certain embodiments, the postoperative treatment regimen provided herein comprises administering CyA to a transplant recipient. In certain embodiments, CyA can be administered on the day of the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, 30 days after, 1 month after, 2 months after, 3 months after, 4 months after, 5 months after, 6 months after, 7 months after, 8 months after, 9 months after, 10 months after, 11 months after, 12 months after, 13 months after, 14 months after, 15 months after, 16 months after, 17 months after, or 18 months after the transplant surgery.

In certain embodiments, a single dose amount of CyA can be administered. In certain embodiments, multiple dose amounts of the CyA can be administered. In certain embodiments, a constant dose of CyA can be administered. In certain embodiments, a tapering course of CyA can be administered. In certain embodiments, a constant dose of CyA followed by a tapering course of CyA can be administered.

In certain embodiments, CyA can be administered to a subject at a dose amount of 2 mg/kg/day, 2.5 mg/kg/day, 3 mg/kg/day, 3.5 mg/kg/day, 4 mg/kg/day, 4.5 mg/kg/day, 5 mg/kg/day, 5.5 mg/kg/day, 6 mg/kg/day, 6.5 mg/kg/day, 7 mg/kg/day, 7.5 mg/kg/day, 8 mg/kg/day, 8.5 mg/kg/day, 9 mg/kg/day, 9.5 mg/kg/day, 10 mg/kg/day, 10.5 mg/kg/day, 11 mg/kg/day, 11.5 mg/kg/day, 12 mg/kg/day, 12.5 mg/kg/day, 13 mg/kg/day, 13.5 mg/kg/day, 14 mg/kg/day, 14.5 mg/kg/day, 15 mg/kg/day, 15.5 mg/kg/day, 16 mg/kg/day, 16.5 mg/kg/day, 17 mg/kg/day, 17.5 mg/kg/day, 18 mg/kg/day, 2-6 mg/kg/day, 3-7 mg/kg/day, 4-8 mg/kg/day, 5-9 mg/kg/day, 6-10 mg/kg/day, 7-11 mg/kg/day, 8-12 mg/kg/day, 9-13 mg/kg/day, 10-14 mg/kg/day, 11-15 mg/kg/day, 12-16 mg/kg/day, 13-17 mg/kg/day, or 14-18 mg/kg/day. In a specific embodiment, CyA can be administered to a subject at a dose amount of 8 mg/kg/day. In a specific embodiment, CyA can be administered to a subject at a dose amount of 9 mg/kg/day. In a specific embodiment, CyA can be administered to a subject at a dose amount of 10 mg/kg/day. In a specific embodiment, CyA can be administered to a subject at a dose amount of 11 mg/kg/day. In a specific embodiment, CyA can be administered to a subject at a dose amount of 12 mg/kg/day. In a specific embodiment, CyA can be administered to a subject at a dose range of 8-12 mg/kg/day.

In certain embodiments, CyA can be administered to a subject at a sufficient dose amount to obtain the target trough blood levels of 100-200 ng/ml, 125-225 ng/ml, 150-250 ng/ml, 175-275 ng/ml, 200-300 ng/ml, 225-325 ng/ml, 250-350 ng/ml, 275-375 ng/ml, 300-400 ng/ml, 325-425 ng/ml, 350-450 ng/ml, 375-475 ng/ml, or 400-500 ng/ml. In a specific embodiment, the target trough blood levels can be 250-350 ng/ml.

In certain embodiments, CyA can be administered to a subject at a constant dose. The duration of time a constant dose is administered can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days (e.g., after the transplant). In certain embodiments, CyA can be tapered to discontinuation. In certain embodiments, this tapering course can take place over 1 month, 2 months, 3 months, 4 months, 5 months, 6 months, 7 months, 8 months, 9 months, 10 months, 11 months, 12 months, 13 months, 14 months, 15 months, 16 months, 17 months, or 18 months after a subject is diagnosed with an immune associated disease or disorder, after a subject starts treatment with an anti-CD2 antibody or an antigen-binding fragment thereof and a CTLA-4 co-stimulation blockade, or after an organ or tissue transplant.

In certain embodiments, CyA can be administered to a subject in a convenient manner known in the art including subcutaneously, intravenously, intravascularly, topically, intra-arterially, intra-cranially, intramuscularly, orally, intra-orbitally, by inhalation, transdermally, or intra-peritoneally, or through a route of administration which allows for the proper action of the CyA by the subject. In a specific embodiment, CyA can be administered orally. In a specific embodiment, the CyA can be administered intravenously.

In certain embodiments, substitute compounds can be used in the place of CyA. These compounds can include tacrolimus (Prograf®, Adport®, Advagraf®, Envarsus®, Modigraf®, Astagraf®), sirolimus, and everolimus. In some embodiments, a cyclosporine is administered before, during, or after the anti-CD2 antibody or an antigen-binding fragment thereof and/or the CTLA-4 co-stimulation blockade is administered to the subject. In some embodiments, a cyclosporine is administered before, during, or after the anti-CD2 antibody or an antigen-binding fragment thereof is administered to the subject. In some embodiments, a cyclosporine is administered before, during, or after the CTLA-4 co-stimulation blockade is administered to the subject.

Antimetabolite (e.g. Mycophenolate) Therapy

In some aspects, a method of treatment provided herein comprises administering standard-of-care-antimetabolite therapy to a subject. In some embodiments, the standard-of-care antimetabolite therapy is mycophenolate. Mycophenolate, as used herein, can be included the methods of treatment provided herein to suppress the immune system and inhibit the development of Graft versus Host disease in the subject. Brand names of mycophenolate can include CellCept®, Mycophenolate Mofetil Accord, Mycophenolate Mofetil Sandoz, Myfenax, Myfortic, Mycophenolate Mofetil Actavis, Mycophenolic Acid Accord, Mycophenolate Mofetil 2care4, Mycophenolate Mofetil EQL, Mycophenolate Mofetil Orifarm, and Myfortic® mycophenolic acid. The treatment regimen can include a constant course followed by a tapering course of mycophenolate administration to the subject.

In certain embodiments, a postoperative treatment regimen provided herein comprises administering standard-of-care antimetabolite (e.g. mycophenolate) therapy to a transplant recipient. In specific embodiments, standard-of-care antimetabolite (e.g. mycophenolate) therapy is first administered to a recipient within 24 hours of reperfusion of the transplanted liver. In certain embodiments, standard-of-care antimetabolite (e.g. mycophenolate) therapy can be administered on the day of the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, 30 days after, 1 month after, 2 months after, 3 months after, 4 months after, 5 months after, 6 months after, 7 months after, 8 months after, 9 months after, 10 months after, 11 months after, 12 months after, 13 months after, 14 months after, 15 months after, 16 months after, 17 months after, or 18 months after the transplant surgery.

In certain embodiments, a single dose amount of standard-of-care antimetabolite (e.g. mycophenolate) therapy can be administered. In certain embodiments, multiple dose amounts of standard-of-care antimetabolite (e.g. mycophenolate) therapy can be administered. In certain embodiments, a constant dose of standard-of-care antimetabolite (e.g. mycophenolate) therapy can be administered. In certain embodiments, a tapering course of standard-of-care antimetabolite (e.g. mycophenolate) therapy can be administered. In certain embodiments, a constant dose of standard-of-care antimetabolite (e.g. mycophenolate) therapy followed by a tapering course of standard-of-care antimetabolite (e.g. mycophenolate) therapy can be administered. In certain embodiments, standard-of-care antimetabolite (e.g. mycophenolate) therapy is administered twice a day.

In certain embodiments, standard-of-care antimetabolite (e.g. mycophenolate) therapy can be administered to a subject at a total daily dose of 100 mg/dose, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 100-1000 mg, 200-1200 mg, 300-1300 mg, 400-1400 mg, 500-1500 mg, 600-1600 mg, 700-1700 mg, 800-1800 mg, 900-1900 mg, 1000-2000 mg, 1100-2100 mg, 1200-2200 mg, 1300-2300 mg, 1400-2400 mg, or 1500-2500 mg. A total daily dose may be administered in 1, 2, 3, 4 or more doses per day. In a specific embodiment, standard-of-care antimetabolite (e.g. mycophenolate) therapy is administered to a subject at a dose range of 500-1500 mg/day twice per day. In specific embodiments, standard-of-care antimetabolite (e.g. mycophenolate) therapy is administered to a subject at a dose range of 250-750 mg per dose twice a day. In particular embodiments, myfortic is administered to a subject at a total daily dose of about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In specific embodiments, myfortic is administered to a subject at a total daily dose of about 1440 mg.

In certain embodiments, standard-of-care antimetabolite (e.g. mycophenolate) therapy can be administered to a subject at a constant dose. The duration of time a constant dose is administered can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days after a subject is diagnosed with an immune associated disease or disorder, after a subject starts treatment with an anti-CD2 antibody or an antigen-binding fragment thereof and a CTLA-4 co-stimulation blockade, or after an organ or tissue transplant. In certain embodiments, standard-of-care anti-metabolite (e.g. mycophenolate) therapy is administered to a subject and can be tapered to discontinuation. In certain embodiments, this tapering course can take place over 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, or 6 months after a subject is diagnosed with an immune associated disease or disorder, after a subject starts treatment with an anti-CD2 antibody or an antigen-binding fragment thereof and a CTLA-4 co-stimulation blockade, or after an organ or tissue transplant.

In certain embodiments, standard-of-care antimetabolite (e.g. mycophenolate) therapy can be administered to a subject in a convenient manner known in the art including subcutaneously, intravenously, intravascularly, topically, intra-arterially, intra-cranially, intramuscularly, orally, intra-orbitally, by inhalation, transdermally, or intra-peritoneally, or through a route of administration which allows for the proper action of the standard-of-care antimetabolite (e.g. mycophenolate) therapy by the subject. In a specific embodiment, standard-of-care antimetabolite (e.g. myco-phenolate) therapy can be administered orally. In a specific embodiment, the standard-of-care antimetabolite (e.g. mycophenolate) therapy can be administered intravenously. In certain embodiments, the administration of standard-of-care antimetabolite (e.g. mycophenolate) therapy can be modified as described herein.

In some embodiments, a antimetabolite is administered before, during, or after the anti-CD2 antibody or an antigen-binding fragment thereof and/or the CTLA-4 co-stimulation blockade is administered to the subject. In some embodiments, a antimetabolite is administered before, during, or after the anti-CD2 antibody or an antigen-binding fragment thereof is administered to the subject. In some embodiments, a antimetabolite is administered before, during, or after the CTLA-4 co-stimulation blockade is administered to the subject.

5.3.14 mTOR Inhibitor

In certain embodiments, the methods described herein further include administering an mTOR inhibitor to a subject. Without being bound by theory, the mTOR inhibitor can be administered to a subject to inhibit T-cell and B-cell activation to treat or prevent an immune related disorder or disease in a subject, e.g., to prevent transplant rejection. In certain embodiments, an mTOR inhibitor can be used in combination with a calcineurin inhibitor (e.g., tacrolimus) or can be used instead of the calcineurin inhibitor (e.g., tacro-limus). In specific embodiments, the mTOR inhibitor described in the methods presented herein can be rapamycin or everolimus. In some embodiments, an mTOR inhibitor may be used in place of a calcineurin inhibitor (e.g., tacro-limus) in a method provided herein. In some embodiments, an mTOR inhibitor may be used in a subject who experience adverse events with a calcineurin inhibitor. In specific embodiments, an mTOR inhibitor may be used in a subject who experienced tacrolimus-related adverse events.

In certain embodiments, the postoperative regimen provided herein comprises administering rapamycin to a transplant recipient after the transplant. In certain embodiments, rapamycin is administered daily. In certain embodiments, administration of rapamycin can be initiated immediately after the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, or 30 days after a subject is diagnosed with an immune associated disease or disorder, after a subject starts treatment with an anti-CD2 antibody or an antigen-binding fragment thereof and a CTLA-4 co-stimulation blockade, or after an organ or tissue transplant. In certain embodiments, rapamycin is administered for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, or at least 12 months. In certain embodiments, rapamycin is administered in 1, 2, 3, 4, or 5 daily doses.

In certain embodiments, the first dose of rapamycin is a loading dose and can be higher than the subsequent daily doses. In certain embodiments, the first dose can be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 1-4 mg/kg, 2-6 mg/kg, 4-8 mg/kg, 6-10 mg/kg, or 8-12 mg/kg. In certain embodiments, the daily dose can be 0.5 mg/kg, 1 mg/kg, 1.5 mg/kg, 2 mg/kg, 2.5 mg/kg, 3 mg/kg, 3.5 mg/kg, 4 mg/kg, 1-3 mg/kg, or 1.5-2.5 mg/kg. In a specific embodiment, the rapamycin is administered at an initial dose of 6 mg/kg and followed by a daily dose of 2 mg/kg. In a specific embodiment, rapamycin is administered orally.

In certain embodiments, rapamycin can be administered to a subject at a sufficient dose amount to obtain the target whole blood levels of 1-5 ng/ml, 2-10 ng/ml, 4-12 ng/ml, 6-14 ng/ml, 8-16 ng/ml, 10-18 ng/ml, 12-20 ng/ml, 14-22 ng/ml, or 16-24 ng/ml. In a specific embodiment, the target whole blood levels can be 4-12 ng/ml.

In certain embodiments, rapamycin can be administered to a subject in a convenient manner known in the art including subcutaneously, intravenously, intravascularly, topically, intra-arterially, intra-cranially, intramuscularly, orally, intra-orbitally, by inhalation, transdermally, intra-peritoneally, or through a route of administration which allows for the appropriate action of rapamycin to occur in the subject. In a specific embodiment, the rapamycin is administered orally.

In certain embodiments, the mTOR inhibitor can be everolimus. In certain embodiments, everolimus is administered twice daily. In certain embodiments, administration of everolimus can be initiated immediately after the transplant, 1 day after, 2 days after, 3 days after, 4 days after, 5 days after, 6 days after, 7 days after, 8 days after, 9 days after, 10 days after, 11 days after, 12 days after, 13 days after, 14 days after, 15 days after, 16 days after, 17 days after, 18 days after, 19 days after, 20 days after, 21 days after, 22 days after, 23 days after, 24 days after, 25 days after, 26 days after, 27 days after, 28 days after, 29 days after, or 30 days after a subject is diagnosed with an immune associated disease or disorder, after a subject starts treatment with an anti-CD2 antibody or an antigen-binding fragment thereof and a CTLA-4 co-stimulation blockade, or after an organ or tissue transplant. In certain embodiments, everolimus is administered for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, or at least 12 months.

In certain embodiments, the dose range of everolimus administered can be 0.25 mg/kg/dose, 0.5 mg/kg/dose, 0.75 mg/kg/dose, 1.0 mg/kg/dose, 1.25 mg/kg/dose, 1.5 mg/kg/dose, 1.75 mg/kg/dose, 2.0 mg/kg/dose, 0.25-0.5 mg/kg/dose, 0.5-0.75 mg/kg/dose, 0.75-1.0 mg/kg/dose, 1.0-1.25 mg/kg/dose, 1.25-1.50 mg/kg/dose, 1.50-1.75 mg/kg/dose, or 1.75-2.0 mg/kg/dose. In a specific embodiment, the everolimus is administered twice daily at a dose range of 0.75-1.0 mg/kg/dose. In a specific embodiment, everolimus is administered orally.

In certain embodiments, everolimus can be administered to a subject at a sufficient dose amount to obtain the target whole blood levels of 0.1-5 ng/ml, 1-6 ng/ml, 2-7 ng/ml, 3-8 ng/ml, 4-9 ng/ml, 5-10 ng/ml, 6-11 ng/ml, 7-12 ng/ml, or 8-13 ng/ml. In a specific embodiment, the target whole blood levels can be 3-8 ng/ml.

In certain embodiments, the mTOR inhibitor can be temsirolimus, everolimus, sirolimus (rapamycin), ridaforolimus, non-rapamycin analog mTOR inhibiting compounds including, but not limited to, LY294002, wortmannin, quercetin, myricentin, staurosporine, or ATP competitive inhibitors. In some embodiments, a mTOR inhibitor is administered before, during, or after the anti-CD2 antibody or an antigen-binding fragment thereof and/or the CTLA-4 co-stimulation blockade is administered to the subject. In some embodiments, a mTOR inhibitor is administered before, during, or after the anti-CD2 antibody or an antigen-binding fragment thereof is administered to the subject. In some embodiments, a mTOR inhibitor is administered before, during, or after the CTLA-4 co-stimulation blockade is administered to the subject.

5.4 Pharmaceutical Compositions

Provided herein are pharmaceutical compositions comprising a pharmaceutically effective amount of a CD2-binding molecule as described herein. Also provided herein are pharmaceutical compositions comprising a pharmaceutically effective amount of an anti-CD2 antibody or antigen-binding fragment thereof and/or the CTLA-4 co-stimulation blockade as described herein. In certain embodiments, pharmaceutical compositions described herein can be formulated for subcutaneous, intravenous, intravascular, topical, intrarticular, intraarterial, intracranial, intramuscular, oral, intraorbital, inhalation, intraperitonial, intraosseous, endotracheal, sublingual, buccal, rectal, intradermal, intrathecal, intramedullary, or transdermal routes of administration. In a specific embodiment, the composition comprising the CD2-binding molecule described herein are formulated for intravenous administration. In a specific embodiment, the composition comprising the CD2-binding molecule described herein are formulated for subcutaneous administration. In a specific embodiment, the composition comprising the anti-CD2 antibody or antigen-binding fragment thereof and/or the CTLA-4 co-stimulation blockade described herein are formulated for intravenous administration. In a specific embodiment, the composition comprising the anti-CD2 antibody or antigen-binding fragment thereof and/or the CTLA-4 co-stimulation blockade described herein are formulated for subcutaneous administration.

In certain embodiments, the composition formulated for intravenous or subcutaneous administration can be a solution, suspension, or an emulsion. In certain embodiments, the CD2-binding molecule described herein can be formulated for intravenous or subcutaneous administration by combining the CD2-binding molecule described herein with a pharmaceutically appropriate vehicle. In certain embodiments, the anti-CD2 antibody or antigen-binding fragment thereof and/or the CTLA-4 co-stimulation blockade described herein can be formulated for intravenous or subcutaneous administration by combining the anti-CD2 antibody or antigen-binding fragment thereof and/or the CTLA-4 co-stimulation blockade described herein with a pharmaceutically appropriate vehicle. In certain embodiments, vehicles used can be, but are not limited to, water, saline, Ringer's solution, dextrose solution, glycerol, ethanol, 1-10% human serum albumin, 5% dextrose in water, N-methylpyrrolidone, dimethyl sulfoxide, N,N-dimethylacetamide, propylene glycol, polyethylene glycol 400, diethylene glycol monoethyl ether, TWEEN 80, TWEEN 20, polyoxyl-35 castor oil, polyoxyl 40 hydrogenated castor oil, caprylocaproyl macrogol-8-glycerides, soybean oil, polyxoyethyllated oleic glycerides, and medium chain mono- and diglycerides. In certain embodiments, liposomes and non-aqueous vehicles such as fixed oils can also be used to administer the CD2-binding molecule described herein. In certain embodiments, liposomes and non-aqueous vehicles such as fixed oils can also be used to administer the anti-CD2 antibody or antigen-binding fragment thereof and/or the CTLA-4 co-stimulation blockade described herein.

In certain embodiments, the vehicle can contain additives that maintain isotonicity (e.g., sodium chloride, mannitol). In certain embodiments the vehicle can contain additives to maintain chemical stability. These additives can include, but are not limited to, buffers (e.g. maleic acid, tartaric acid, lactic acid, citric acid, acetic acid, sodium bicarbonate, and sodium phosphate), and preservatives (e.g. detergents, oxidizing agents, and ionic buffers.) The resulting pharmaceutical formulation is sterilized by known or suitable techniques.

In certain embodiments, the intravenous administration of the composition comprising the CD2-binding molecule described herein can be administered as a bolus injection, a slow intravenous injection, or a continuous intravenous infusion. In certain embodiments, the subcutaneous administration of the composition comprising the CD2-binding molecule described herein can be administered as a bolus injection. In certain embodiments, the intravenous administration of the composition comprising the anti-CD2 antibody or antigen-binding fragment thereof and/or the CTLA-4 co-stimulation blockade described herein can be administered as a bolus injection, a slow intravenous injection, or a continuous intravenous infusion. In certain embodiments, the subcutaneous administration of the composition comprising the anti-CD2 antibody or antigen-binding fragment thereof and/or the CTLA-4 co-stimulation blockade described herein can be administered as a bolus injection

5.5 Kits

Provided herein is a kit comprising a pharmaceutical composition described herein, contained in one or more containers. Provided herein is a kit containing an anti-CD2 antibody or an antigen-binding fragment thereof and/or a CTLA-4 co-stimulation blockade, or a composition thereof, and optionally another active agent as described herein. In some embodiments, a kit comprises a pharmaceutical composition described herein, contained in one or more containers. In some embodiments, a kit includes at least one anti-CD2 antibody or an antigen-binding fragment thereof or a composition thereof of the disclosure. In some embodiments, a kit includes one or more anti-CD2 antibody or an antigen-binding fragment thereof of the disclosure or a composition thereof in the same or a different container. In some embodiments, a kit includes at least one CTLA-4 co-stimulation blockade of the disclosure. In some embodiments, a kit includes one or more CTLA-4 co-stimulation blockade of the disclosure or a composition thereof in the same or a different container. In some embodiments, a kit includes at least one anti-CD2 antibody or an antigen-binding fragment thereof and at least one CTLA-4 co-stimulation blockade in the same or a different container. In some embodiments, a kit contains a library of anti-CD2 antibody or an antigen-binding fragment thereof and/or a library of CTLA-4 co-stimulation blockade. In some embodiments, a kit includes another active agent or another immunosuppressive agent. In some embodiments, a kit includes a control and/or a reference antibody. In some embodiments, a kit may further include reagents and/or instructions for creating and/or synthesizing compounds and/or compositions described herein. In some embodiments, a kit may also include one or more buffers. In some embodiments, a kit includes another agent (e.g., another active agent) or a third agent (e.g., agents from Section 5.3) in the same or a different container. In some embodiments, a container with an anti-CD2 antibody or an antigen-binding fragment thereof and/or CTLA-4 co-stimulation blockade is provided for a single dose administration or multiple dose administrations. In some embodiments, an anti-CD2 antibody or an antigen-binding fragment thereof and/or CTLA-4 co-stimulation blockade is present in a container in a kit in an amount sufficient for multiple dosages, usages, or administration. In some embodiments, a kit includes other components necessary for administration of an anti-CD2 antibody or an antigen-binding fragment thereof and/or CTLA-4 co-stimulation blockade (e.g., a kit includes a syringe, a catheter, a cannula, a pump, or any injection device). In certain embodiments, the kit comprises devices that can be used to administer the pharmaceutical composition described herein, including, but not limited to, syringes, needle-less injectors, drip bags, perfusion pumps, pumps, patches, and inhalers. In some embodiments, a kit includes a pharmaceutically acceptable carrier, diluent, excipient, and/or buffer, in the same or separate container as the container holding one or more of an anti-CD2 antibody or an antigen-binding fragment thereof and/or CTLA-4 co-stimulation blockade.

Components of a kit can be in separate containers or can be combined in a single container. In some embodiments, kit components may be packaged either in aqueous media, in powder form, in crystal form, or in lyophilized form. The containers that the pharmaceutical composition can be packaged in can include, but are not limited to, bottles, packets, ampoules, tubes, inhalers, bags, vials, and containers. The container means of the kits can include at least one of a vial, test tube, flask, bottle, needle-less injectors, drip bags, perfusion pumps, pumps, patches, an inhaler, ampoules, syringe or other container means, into which a component may be placed. In some embodiments, a component is suitably aliquoted. Where there is more than one kit component, a reagent and the corresponding label can be packaged together. In some embodiments, a kit contains second, third or other additional containers into which additional components may be separately placed. In some embodiments, a kit includes a second container means for containing sterile, pharmaceutically acceptable buffers and/or other diluents. In some embodiments, various combinations of components are included in one or more vial. In some embodiments, a kit includes a means for containing antibody and/or compounds and/or compositions of the disclosure in close confinement for commercial sale. Such containers may include injection or blow-molded plastic containers into which desired vials are retained.

In some embodiments, kit components are provided in one and/or more liquid solutions. In some embodiments, a liquid solution is an aqueous solution or a sterile aqueous solution. In some embodiments, kit components are provided as dried powder(s). When reagents and/or components are provided as dry powders, such powders may be reconstituted by the addition of suitable volumes of a solvent. In some embodiments, the solvents are provided in another container means. In some embodiments, labeling dyes are provided as dried powders. In some embodiments, labeling dyes are provided in an amount of about, at least about, or at most about 10, 20, 30, 40, 50, 60, 70, 80, 90, 100, 120, 120, 130, 140, 150, 160, 170, 180, 190, 200, 300, 400, 500, 600, 700, 800, 900, 1000 micrograms. In some embodiments, dye can be resuspended in any suitable solvent, such as DMSO.

In some embodiments, a kit include instructions for using the components of the kit. In some embodiments, a kit contains instructions related to dosage, administration, applications, storage conditions, a list of diseases that can be treated or prevented by using one or more of the kit components, and/or use of the components. In some embodiments, instructions are recorded on a suitable recording medium. For example, instructions can be printed on a substrate, such as a paper, a tag (e.g., adhesive tag), or plastic. In some embodiments, instructions are present in a kit as a package insert or on a label attached to a container or components of a kit. In some embodiments, instructions are provided as electronic storage data file present on a suitable computer readable storage medium, e.g. CD-ROM, diskette, USB storage device, or flash drive. In some embodiments, instructions are not present in a kit but are present in a remote source, e.g. via the internet.

5.6 Outcome Assessments

Exemplary methods of assessing the outcome of a method described herein are described in Section below.

In certain embodiments, the efficacy of a method of treatment described herein can be assessed by determining cell proliferation, T cell activation, CD2 levels in a biological sample, and/or alloimmune response. In certain embodiments, the efficacy of a method of treatment described herein can be assessed by any suitable assay or method known to a skilled artisan, e.g., by using an in vitro human T cell proliferation assay or a mixed lymphocyte reaction (MLR) assay.

In certain embodiments, the efficacy of a method of treatment described herein can be assessed by determining the survival of the transplanted graft (e.g., liver or kidney). In certain embodiments, a biopsy of the transplanted graft (e.g., liver or kidney) can be performed to examine the health of the transplanted organ (e.g., liver or kidney) and determine induction of tolerance or evidence of graft rejection. Tissue biopsies can be examined using routine light microscopy, immunofluorescence, and electron microscopy.

In certain embodiments, the efficacy of a method of treatment described herein can be determined by detecting treated biopsy-proven acute rejection (tBPAR) in a recipient. In specific embodiments, no tBPAR is detected in a recipient at 10 months, 12 months, 15 months, 18 months, 20 months, 25 months, 30 months, 35 months, 40 months, 45 months, 50 months, 55 months, or 60 months post-transplant.

In certain embodiments, assessments of the outcome of the transplant surgery can include the monitoring of the function of the transplanted organ (e.g., liver or kidney) in the recipient. For example, the efficacy of a method of treatment described herein may be assessed by measuring organ function at 1 month, 2 months, 3 months, 4 months, 5 months, 6 months, 7.5 months, 9 months, 10.5 months, 12 months, 13.5 months, 15 months, 16.5 months, 18 months, 19.5 months, 21 months, 22.5 months, 24 months, 27 months, 30 months, 36 months, 42 months, 48 months, or, 54 months post-transplant, or at 1-5 months, 5-10 months, 10-15 months, 15-20 months, 20-25 months, 25-30 months, 30-35 months, 35-40 months, 40-45 months, 45-50 months, 50-55 months, or 55-60 months post-transplant. Liver function may be determined, for example, by conducting liver function tests, such as measurements of alanine transaminase (ALT), aspartate transaminase (AST), alkaline phosphatase (ALP), gamma-glutamyl transferase (GGT), serum bilirubin, prothrombin time (PT), the international normalized ratio (INR) and/or albumin. In particular embodiments, a method of treatment described herein results in a recipient having normal organ function (as determined by organ function tests) for at least 10 months, at least 15 months, at least 20 months, at least 25 months, at least 30 months, at least 35 months, at least 40 months, at least 45 months, at least 50 months, at least 55 months, or at least 60 months post-transplant. In particular embodiments, a method of treatment described herein results in a recipient having better organ function (as determined by organ function tests) for at least 10 months, at least 15 months, at least 20 months, at least 25 months, at least 30 months, at least 35 months, at least 40 months, at least 45 months, at least 50 months, at least 55 months, or at least 60 months post-transplant as compared to a patient undergoing standard of care post-organ transplant therapy.

In specific embodiments, a method of treatment described herein results in a recipient having ALT values of 5-60 U/L, 7-55 U/L, 10-55 U/L, 15-50 U/L, 20-40 U/L or 25-35 U/L for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having AST values of 5-50 U/L, 8-48 U/L, 10-45 U/L, 15-40 U/L, or 20-30 U/L for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having ALP values of 30-150 U/L, 40-129 U/L, 50-120 U/L, 60-110 U/L, 70-100 U/L, or 80-90 U/L for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having GGT values of 5-70 U/L, 8-61 U/L, 10-50 U/L, 15-45 U/L, 20-40 U/L, or 25-35 U/L for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having serum bilirubin values of 0.05-2 mg/dL, 0.1-1.5 mg/dL, 0.1-1.2 mg/dL, 0.5-1 mg/dL or 0.7-1 mg/dL for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having a PT of 7-15 seconds, 8-14 seconds, 9-13 seconds, 9.4-12.5 seconds, or 10-12 seconds for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having albumin values of 2-6 g/dL, 2.5-5.5 g/dL, 3-5 g/Dl, 3.5-5 g/dL, or 4-4.5 g/dL for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having an INR 1-3, 1.5-2.5, 1.5-2 or below 1.1 for at least 10 months, at least 15 months, at least 20 months, at least 25 months, at least 30 months, at least 35 months, at least 40 months, at least 45 months, at least 50 months, at least 55 months, or at least 60 months post-transplant.

For example, the efficacy of a method of treatment described herein may be assessed by measuring renal function at 10 months, 15 months, 20 months, 25 months, 30 months, 35 months, 40 months, 45 months, 50 months, 55 months, or 60 months post-transplant. Renal function may be determined, for example, by measuring serum creatinine and/or glomerular filtration rate. In particular embodiments, a method described herein can result in a recipient having normal kidney function (as determined by serum creatinine and/or glomerular filtration rate (GFR)). In particular embodiments, a method described herein can result in a recipient having better kidney function (as determined by serum creatinine and/or glomerular filtration rate) as compared to a patient undergoing standard of care post-liver transplant therapy.

In specific embodiments, a method of treatment described herein results in a recipient having serum creatinine values of 0.5-1.5 mg/mL, 0.6-1.4 mg/mL, 0.7-1.3 mg/mL, 0.8-1.2 mg/mL, or 0.9-1.1 mg/mL for at least 10 months, at least 15 months, at least 20 months, at least 25 months, at least 30 months, at least 35 months, at least 40 months, at least 45 months, at least 50 months, at least 55 months, or at least 60 months post-transplant.

In specific embodiments, a method of treatment described herein results in a recipient having a GFR of 40-90, 45-85, 50-80, 55-75, 60-70, or above 90 for at least 10 months, at least 15 months, at least 20 months, at least 25 months, at least 30 months, at least 35 months, at least 40 months, at least 45 months, at least 50 months, at least 55 months, or at least 60 months post-transplant.

In certain embodiments, other assessments of the outcome of the transplant surgery can include the monitoring of the incidence of infection, the incidence of opportunistic infection, the onset of any treatment-related adverse events, and the patient's post-transplant quality of life. In certain embodiments, the efficacy of a method of treatment described herein may be determined by the recipient's requirement for immunosuppressive therapy. In particular embodiments, a method of treatment described herein results in no requirement for immunosuppressive therapy within 10 months, 15 months, 20 months, 25 months, 30 months, 35 months, 40 months, 45 months, 50 months, 55 months, or 60 months post-transplant.

In certain embodiments, functional assays can be used to detect biomarkers which are predictive of transplant rejection including the presence of circulating donor-specific antibodies (DSA) in the serum of the recipient which can be determined by ELISA. In certain embodiments, flow cytometric analyses on circulating lymphocytes can be performed to determine status of immune system reconstitution of the recipient. In certain embodiments, mixed lymphocyte reaction (MLR) of the recipient's peripheral blood mononuclear cells can be performed to assess the response of the recipient's cells to the donor cells and if the response changes after transplant surgery.

In certain embodiments, functional assays can be used to determine if induction of tolerance to the transplanted organ (e.g., liver or kidney) was achieved. These assays can include flow cytometric analysis to determine FoxP3+ T cells: CD4+ T cells ratio as an indicator for the presence of regulatory T-cells.

5.7 Equivalents and Incorporation by Reference

The present invention is not to be limited in scope by the specific embodiments described herein. it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference in their entireties.

6. EXAMPLES

6.1 Methods

6.1.1 Reporter Assays for FcγR I, II and III Affinity

To determine Fcγ receptor (FcγR) affinity, 6× serial dilutions of RT-CD2 and RH-CD2 were incubated with reporter cells stably transfected with human FcγRI, FcγRIIA-H or FcγRIIIA-V and a luciferase reporter gene (Promega). Luciferase reporter gene expression was triggered if reporter cells bound to the Fc-fragment of a target-bound IgG antibody with their respective FcγR. The reporter cells were from a human Jurkat CD2$^+$ acute T cell leukemia cell line. Since the antibodies have affinity for the reporter cells they can act as a target and reporter in the assay. Siplizumab, CD2-binding molecule 1, siplizumab Fc fragment or Fab fragment was added at several concentrations from 0.0001-10 µg/mL. Siplizumab Fab or Fc fragments were obtained using FragIT kit (Genovis) according to the manufacturer's instructions, they were added as whole IgG equivalents. After 23 hours of incubation at 37° C. and 5% $CO_2$, Bio-Glo Luciferase assay reagent (Promega) was added and luminescence measured after 10-15 min of incubation at room temperature and shielded from light using a Synergy HTX Multi-mode plate reader (BioTek). Luminescence values were normalized to the luminescence signal obtained with the highest concentration of the positive control. Each run contained triplicate serial dilutions of each antibody.

6.1.2 Flow Cytometry-Based Complement Activation Assay

For assessment of complement-dependent cytolysis (CDC), Ficoll density-gradient centrifugation isolated PBMCs were incubated with 10× serial dilutions of siplizumab or CD2-binding molecule in 10% Ultra low-IgG FBS (Gibco) in PBS at room temperature with shaking. Subsequently, an equal volume of reconstituted rabbit complement (InnoTrain) was added followed by incubation at room temperature with shaking for 60 minutes. PBMCs were washed in PBS and stained with 7-AAD (Life Technologies), anti-CD56 BV421 (BD, Clone NCAM16.2), anti-CD89 PE (Miltenyi, Clone REA234), anti-CD3 APC and anti-CD19 APC-H7 (BD; Clone SJ25C1). Samples were incubated on ice and shielded from light until sample acquisition using a FACSVerse flow cytometer (BD Biosciences). FlowJo software (FlowJo LLC, Ashland) and GraphPad Prism 8 (GraphPad Software) were used for sample processing and data analysis.

6.1.3 Mixed Lymphocyte Reaction (MLR)

Peripheral blood mononuclear cells (PBMC) were isolated via Ficoll® Paque Plus (GE Healthcare) density gradient centrifugation from buffy coats. Buffy coats were obtained from healthy donors via Uppsala University Hospital blood bank and PBMC isolation was carried out within 24 hours of blood collection.

PBMC from two donors were mixed in PBS at a concentration of $1.5*10^7$ cells per mL and stained with violet proliferation dye 450 (VPD450; BD Biosciences) according to the manufacturer's instructions. Subsequently, stained PBMC were washed and resuspended in 10% heat-inactivated fetal bovine serum (FBS) in RPMI-1640 (ATCC modification; Gibco) supplemented with 50 IU/mL Streptomycin and Penicillin, respectively. Resuspended PBMC were dispensed into round-bottomed 96-well tissue culture and pure medium (Untreated controls), siplizumab, CD2-binding molecule 1, or siplizumab Fab fragment (0.01-50 µg/mL) diluted in cell culture medium was added to a final concentration of $2*10^6$ cells per mL (Final volume 200 µL; quadruplicates of each condition). PBMC cultures were then incubated at 37° C. 5% $O_2$ 95% $CO_2$ for up to 7 days. For NK cell experiments a concentration of 10 µg/mL was used. For activation, proliferation and immune regulation concentrations of 0.01, 0.1, 1, 10 and, 50 µg/mL were used.

6.1.4 Analysis of NK Cells

Samples intended for analysis of NK cell activation were stained with anti-CD16 FITC (Clone 3G8), anti-CD56 PE (Miltenyi; Clone REA196), anti-CD3 PerCP-Cy5.5 (Clone SP34-2), anti-CD69 APC (Clone FN50) and anti-CD14 APC-H7 (Clone MφP-9).

Samples were stained shielded from light at 4° C. for 30 minutes. All antibodies were purchased from BD Biosciences if not indicated otherwise. After staining, the samples were acquired using a FACSVerse flow cytometer (BD Biosciences) with a three laser setup (405 nm, 488 nm, 640 nm). Samples were phenotyped via flow cytometry at baseline (day 0) as well as days 1, 2, 4 and. Cell proliferation was assessed using VPD450 (VPD450'9: Non-proliferated; VPD450$_{low}$: Proliferated). NK cells were identified as CD3– CD14– CD56+ and/or CD16+ lymphocytes. Post-acquisition editing and data analysis was conducted using FlowJo® software (FlowJo LLC, Ashland).

6.1.5 Analysis of Activation, Proliferation and Immune Regulation

PBMC isolation and two-way MLR setup were performed as detailed above. Harvesting and was conducted after 7 days. Cells were surface stained with anti-CD4 FITC, anti-CD127 PerCP-Cy5.5 and anti-CD25 PE and then fixed and permeabilized using FoxP3 staining kit, according to the manufacturer's instructions, (BD Biosciences) for staining with anti-FoxP3 Alexa 647 (clone 236A/E7). Cell proliferation was assessed using VDP450 (VDP450$^{high}$: Non-proliferated; VPD450$_{low}$: Proliferated). Regulatory T cells (Tregs) were identified as CD4+, CD127$_{low}$, CD25$^{high}$ and FoxP3+. Activated cells were identified as CD4+ and CD25$^{high}$. Post-acquisition editing and data analysis was conducted using FlowJo® software (FlowJo LLC, Ashland).

6.1.6 Generation of Fc-Silent Anti-CD2 Antibodies

Siplizumab (humanized anti-CD2 IgGlu) is an investigational drug and was provided by the manufacturer (ITB-Med, Stockholm, Sweden). CD2-binding molecule 1 (a deglycosylated CD2-binding molecule) was produced using GlycINATOR® (EndoS2; Genovis #A0-GL1-020) according to the manufacturer's instructions (Genovis AB, Lund, Sweden).

Fc-silent (FcS) anti-CD2 mAbs were generated via introduction of amino acid substitutions into the sequence of siplizumab or standard IgG2/IgG4 frameworks. All Fc-silent antibodies had identical light chains and complementarity-determining regions and were produced by Wuxi Biologics Limited (Wuxi, China). Genetic sequences for each antibody were cloned into plasmids followed by transient transfection and production in Chinese hamster ovary (CHO-K1) cells. Anti-CD2 mAbs were purified using protein A and IEX/SEC columns to at least 95% purity and endotoxin levels below 1 EU/mg. Fc-silent Siplizumab (CD2-binding molecule 2; FcS anti-CD2 IgG1) was generated by introducing the commonly known LALA-PG mutations to equivalent sites in Siplizumab (Arduin et al. 2017, Lo et al. 2017). FcS anti-CD2 IgG2 (CD2-binding molecule 3) was generated by introducing the following mutations at equivalent sites in a standard IgG2 framework: V234A, G237A, P238S, H268A, V309L, A330S, P331S (Wang et al. 2018). FcS anti-CD2 IgG4 (CD2-binding molecule 4) was generated by introducing the following mutations at equivalent sites in a standard IgG4 framework: S228P, L235E, P329G (Silva et al. 2015, Schlothauer et al. 2016).

6.1.7 Surface Plasmon Resonance (SPR) CD2 Binding

Interaction experiments were performed using a Biacore T200 instrument (Cytiva Life Sciences/Biacore, Uppsala, Sweden). IgG was immobilized to a surface density of 200-1300 RU using standard amine coupling and CM5 biosensor chips (Cytiva Life Sciences/Biacore, Uppsala, Sweden) with a 10 mM HEPES buffer at pH 7.4, with 150 mM NaCl, 0.5 mM EDTA, 0.05% Tween20 running buffer. Each antibody was immobilized at least twice.

All interaction experiments were performed at 25° C. Recombinant truncated human CD2 (Sino Biological, Beijing, China) was diluted in two-fold dilution series with the highest concentration being 5 nM and injected for 180 seconds over immobilized IgG. After 15 minutes of dissociation, the sensor chip was regenerated by 30 seconds injection of 10 mM glycine pH 1.7. Sensorgrams from reference surfaces and blank injections were subtracted from the raw data prior to data analysis. A two-state (induced fit) interaction model was fitted to the data using T200 evaluation software v3.0 (Cytiva Life Sciences/Biacore, Uppsala, Sweden) to determine kinetic rate constants and affinities.

6.1.8 SPR FcγR Binding

Recombinant truncated human CD2 (Sino Biological, Beijing, China) was covalently immobilized by amine coupling to CM5 biosensor chips (Cytiva Life Sciences/Biacore, Uppsala, Sweden). IgG was captured to amine coupled CD2. All experiments were performed using a Biacore T200™ instrument (Cytiva Life Sciences/Biacore, Uppsala, Sweden) at 25° C. The characterization of compound interactions were conducted in a 10 mM HEPES buffer at pH 7.4, with 150 mM NaCl, 0.5 mM EDTA, 0.05% Tween20. Fcγ receptors (R&D systems, Minneapolis USA) were injected for 120 seconds in multi-cycle or single-cycle experiments in concentration series up to 0.5 μM over CD2-captured IgGs. The R131 isoform of FcγRIIA and V176 isoform of FcγRIIIA were used for all experiments. CD2 surfaces were regenerated by a 120 seconds injection of 50 mM NaOH. Sensorgrams were double-referenced (reference surface, blanks) prior to global analysis using a 1:1 interaction model or a heterogeneous binding model. For weaker interactions with fast dissociation the affinity was determined by steady state analysis using a sum of a Langmuir isotherm and a linear term (compensating for non-specific interaction). Kinetic parameters were determined as average values based on 2-3 replicate experimental series.

6.1.9 Cell-Based FcγR Signaling Assay

Jurkat reporter cell lines (Promega Corp., Madison, Wisconsin USA) transfected with FcγRI, FcγRIIA or FcγRIIIA, respectively, were incubated with serial dilutions of each antibody agent for 23 hours. Binding of a target-bound antibody through the respective FcγR induced expression of luciferase in reporter cells. Luciferase expression was detected after 23 hours of incubation at 37° C. 5% CO2 via addition of luciferase assay substrate (Promega Corp., Madison, Wisconsin USA) and luminescence measurement using a Synergy HTX multiplate reader (BioTek, Winooski, Vermont USA).

6.1.10 Isolation of Peripheral Blood Mononuclear Cells

Peripheral blood mononuclear cells (PBMC) were isolated via Ficoll® Paque Plus (Cytiva Life Sciences, Uppsala, Sweden) density gradient centrifugation from buffy coats. Buffy coats were obtained from healthy donors via Uppsala University Hospital blood bank (Uppsala, Sweden) as well as Karolinska University Hospital blood bank (Stockholm, Sweden) and PBMC isolation was carried out within 24 hours of blood collection.

6.1.11 CD2 Expression Analysis

Resting PBMC were stained and analyzed for target antigen expression. Subsequently, PBMC in autologous culture were activated via CD28/CD3 beads (Miltenyi, Bergisch Gladbach, Germany; bead to cell ratio 5:1) for 48 hours and cultured in 10% heat-inactivated fetal bovine serum (FBS; Gibco, Thermo Fisher Scientific Inc., Waltham, USA) in RPMI-1640 ATCC Mod. supplemented with 50 U/mL Streptomycin and Penicillin (Gibco, Thermo Fisher Scientific Inc., Waltham, USA) and target antigen expression was investigated.

PBMC were washed twice in saline solution. Samples were incubated with Fc-receptor binding inhibitor (Invitrogen; Thermo Fisher Scientific Inc., Waltham, USA) and then washed twice in FBS stain buffer (BD BioSciences, San Diego, USA) followed by incubation with 10 µg/mL siplizumab for 20 minutes. Unbound antibody was removed before staining with secondary anti-human IgG Fc BV421 (Biolegend, San Diego, USA; Clone HP6017). Unbound secondary antibody was removed before surface staining for T cell subpopulations, regulatory T cells or B and NK cells. All antibodies listed below were purchased from BD Biosciences (San Diego, USA) if not indicated otherwise.

Samples to be used for analysis of T cell subpopulation distribution were stained with anti-CD3 PerCP (Clone SK7), anti-CD4 FITC (Clone SK3) and anti-CD8 PE (Clone SK1), with anti-CCR7 Alexa647 (Clone 3D12) and anti-CD45RA APC-H7 (Clone HI100) (Naïve T cells: CCR7+CD45RA+; Central memory T cells: CCR7+CD45RA−; Effector memory T cells: CCR7− CD45RA−; Terminally-differentiated effector memory T cells (Temra): CCR7− CD45RA+). Samples that analyzed Tregs were stained anti-CD4 FITC (Clone RPA-T4), anti-CD25 PE (Clone M-A251), anti-CD45RA APC-H7 (Clone HI100), anti-CD127 PerCP-Cy5.5 (Clone HIL-7R-M21) and anti-FoxP3 Alexa647 (Clone 259D/C7). They were permeabilized using BD Human FoxP3 Buffer Set (BD BioSciences, San Diego, USA) according to the vendor's protocol. Tregs were identified as CD4+CD127− CD25+ FoxP3+.

NK/B cell panel consisted of anti-CD16 FITC (Clone 3G8), anti-CD56 PE (Miltenyi, Bergisch Gladbach, Germany; Clone REA196), anti-CD3 APC (Clone SK7) anti-CD14 APC-H7 (Clone M5E2) and anti-CD20 PerCP (Clone SJ25C1). Samples were stained in the dark at 4° C. and were acquired using a FACSVerse flow cytometer (BD Biosciences, San Diego, USA). Post-acquisition editing and data analysis was conducted using FlowJo® 10.5.3 software (FlowJo LLC, Ashland, USA).

6.1.12 FcγR Expression Analysis

NK cells were isolated via negative magnetic bead selection using NK cell isolation kit (Miltenyi, Bergisch Gladbach, Germany) according to the manufacturer's instructions. A fraction of NK cells were washed twice in saline solution and stained with anti-CD56 BV421 (Clone NACM16.2), anti-CD3 VioGreen (Miltenyi, Bergisch Gladbach, Germany; Clone REA613), anti-CD16 FITC (Miltenyi, Bergisch Gladbach, Germany; Clone REA423), anti-CD32 PE (Miltenyi, Bergisch Gladbach, Germany; Clone REA997) and anti-CD64 APC (Miltenyi, Bergisch Gladbach, Germany; Clone REA978). Samples were stained in the dark at 4° C. and were acquired using a FACSCelesta flow cytometer (BD Biosciences, San Diego, USA). Post-acquisition editing and data analysis was conducted using FlowJo® 10.6.2 software (FlowJo LLC, Ashland, USA). NK cells were defined as CD3− CD56+ and/or CD16+ lymphocytes.

6.1.13 Autologous Lymphocyte Culture (ALC) and Mixed Lymphocyte Reaction (MLR)

For analysis of NK cell activation over time in the presence of siplizumab and CD2-binding molecule 1 (a deglycosylated CD2-binding molecule), equal amounts of PBMC from each donor were stained with violet proliferation dye 450 (BD Biosciences, San Diego, USA; VPD450) for another experiment. Cells were resuspended in 10% heat-inactivated FBS (Gibco, Thermo Fisher Scientific Inc., Waltham, USA) in RPMI-1640 ATCC Mod. supplemented with 50 U/mL Streptomycin and Penicillin (Gibco, Thermo Fisher Scientific Inc., Waltham, USA), respectively. Resuspended PBMC were dispensed into round-bottom 96-well cell culture plates and pure medium (no antibody controls) or one of the respective antibody agents diluted in cell culture medium (10 µg/mL) was added to a final concentration of $2\times10^6$ cells per mL (final volume 200 µL). ALCs and MLRs were then incubated at 37° C. 5% $CO_2$ for one, two, four and seven days, respectively. On each day, cells were washed twice in saline solution and incubated with Fc-receptor binding inhibitor (Invitrogen; Thermo Fisher Scientific Inc., Waltham, USA) followed by staining with anti-CD16 FITC (Clone 3G8), anti-CD56 PE (Miltenyi, Bergisch Gladbach, Germany; Clone REA196), anti-CD3 PerCP-Cy5.5 (Clone SP34-2), anti-CD69 APC (Clone FN50) and anti-CD14 APC-H7 (Clone MφP-9). NK cells were identified as $CD3^-$ $CD14^-$ $CD56^+$ and/or $CD16^+$ lymphocytes. All flow cytometry antibodies were purchased from BD Biosciences (San Diego, USA) if not indicated otherwise. Samples were stained in the dark at 4° C. and were acquired using a FACSVerse flow cytometer (BD Biosciences, San Diego, USA). Post-acquisition editing and data analysis was conducted using FlowJo® 10.5.3 software (FlowJo LLC, Ashland, USA).

For analysis of NK cell activation after seven days in the presence of different anti-CD2 variants, equal amounts of PBMC from each donor were stained with VPD450 for another experiment. Cells were resuspended in 10% heat-inactivated FBS (Gibco, Thermo Fisher Scientific Inc., Waltham, USA) in AIM-V medium supplemented with 50 µg/mL streptomycin sulfate and 10 µg/mL gentamicin sulfate (Gibco, Thermo Fisher Scientific Inc., Waltham), respectively. Resuspended PBMC were dispensed into round-bottom 96-well cell culture plates and pure medium (No antibody controls) or one of the respective antibody agents diluted in cell culture medium (10-0.0001 µg/mL) was added to a final concentration of $2\times10^6$ cells per mL (final volume 200 µL). MLRs were then incubated at 37° C. 5% $CO_2$ for seven days, respectively. Fresh culture medium (100 µL) was added to each well on day five. On day 7, cells were washed twice in saline solution and incubated with Fc-receptor binding inhibitor (Invitrogen; Thermo Fisher Scientific Inc., Waltham, USA) followed by staining with anti-CD3 VioGreen (Miltenyi, Bergisch Gladbach, Germany; Clone REA613), anti-CD45RA BV650 (Clone HI100), anti-CD69 BV786 (Clone FN50), anti-CD8 BB550 (Clone RPA-T8), anti-CD56 PE (Miltenyi, Bergisch Gladbach, Germany; Clone REA196), anti-CD2 PE-CF594 (Clone RPA-2.10; Note: This clone binds a different CD2 epitope than siplizumab), anti-CCR7 APC (BioLegend, San Diego, USA; Clone G043H7) and anti-CD4 APC-Vio770 (Miltenyi, Bergisch Gladbach, Germany; Clone REA623). NK cells were identified as $CD3^-$ $CD56^+$ lymphocytes. Remaining colors were used for another experiment. All flow cytometry antibodies were purchased from BD Biosciences (San Diego, USA) if not indicated otherwise. Samples were stained in the dark at 4° C. and were acquired using a FACSCelesta flow cytometer (BD Biosciences, San Diego, USA). Post-acquisition editing and data analysis was conducted using FlowJo® 10.6.2 software (FlowJo LLC, Ashland, USA).

6.1.14 NK Fratricide

NK cells were isolated from PBMC via negative MACS selection using NK cell isolation kit (Miltenyi, Bergisch Gladbach, Germany). NK cells were resuspended in 10% heat-inactivated FBS (Gibco, Thermo Fisher Scientific Inc., Waltham, USA) in AIM-V medium supplemented with 50 µg/mL streptomycin sulfate and 10 µg/mL gentamicin sulfate (Gibco, Thermo Fisher Scientific Inc., Waltham) as well as 500 IU/mL human IL-2 (Miltenyi, Bergisch Gladbach, Germany) and, depending on yield, dispensed into round-bottom 96-well cell culture plates at a final density between $1.25 \times 10^6$ and $2.0 \times 10^6$ NK cells per mL. Further, pure medium (No antibody controls) or one of the respective antibody agents diluted in cell culture medium (final concentration 10-0.001 µg/mL) was added followed by overnight incubation at 37° C. 5% CO2. Subsequently, NK cells were washed in saline solution followed by incubation with Fc-receptor binding inhibitor (Invitrogen; Thermo Fisher Scientific Inc., Waltham, USA) and staining with anti-CD3 VioGreen (Miltenyi, Bergisch Gladbach, Germany; Clone REA613), anti-CD107a BV786 (BioLegend, San Diego, USA; Clone H4A3), anti-CD16 FITC (Miltenyi, Bergisch Gladbach, Germany; Clone REA423), anti-CD56 PE (Miltenyi, Bergisch Gladbach, Germany; Clone REA196), 7-AAD (Invitrogen; Thermo Fisher Scientific Inc., Waltham, USA) and anti-CD69 APC (Miltenyi, Bergisch Gladbach, Germany; Clone REA824). NK cells were identified as CD3− CD56+ and/or CD16+ lymphocytes. Samples were stained in the dark at 4° C. and were acquired using a FACSCelesta flow cytometer (BD Biosciences, San Diego, USA). Post-acquisition editing and data analysis was conducted using FlowJo® 10.6.2 software (FlowJo LLC, Ashland, USA).

6.1.15 Natural Cytotoxicity Assay

NK cells were isolated from PBMC via negative MACS selection using NK cell isolation kit (Miltenyi, Bergisch Gladbach, Germany). For runs with short pre-incubation, NK cells were resuspended in 10% heat-inactivated FBS (Gibco, Thermo Fisher Scientific Inc., Waltham, USA) in AIM-V medium supplemented with 50 µg/mL streptomycin sulfate and 10 µg/mL gentamicin sulfate (Gibco, Thermo Fisher Scientific Inc., Waltham) and dispensed into round-bottom 96-well cell culture plates followed by resting at 37° C. 5% $CO_2$ overnight. Following, pure medium (no antibody controls) or one of the respective antibody agents diluted in cell culture medium (final concentration 10-0.001 µg/mL) were added followed by 30 minutes incubation at 37° C. 5% $CO_2$ before addition of HLA class I-negative target cells (SPI-801, DSMZ Cat. ACC 86; NK cell to target cell ratio between 1:1 and 1:2 depending on yield of MACS isolation). Addition of target cells was followed by incubation at 37° C.

5% $CO_2$ for 2 hours and subsequent flow cytometry staining as described in NK fratricide section.

For runs with pre-incubation of NK cells with antibody, NK cells were resuspended in in 10% heat-inactivated FBS (Gibco, Thermo Fisher Scientific Inc., Waltham, USA) in AIM-V medium supplemented with 50 µg/mL streptomycin sulfate and 10 µg/mL gentamicin sulfate (Gibco, Thermo Fisher Scientific Inc., Waltham) as well as 500 IU/mL human IL-2 (Miltenyi, Bergisch Gladbach, Germany). Further, pure medium (No antibody controls) or one of the respective antibody agents diluted in cell culture medium (final concentration 10-0.001 µg/mL) were added followed by incubation at 37° C. 5% $CO_2$ for two days. On day two, HLA class I-negative target cells were added (SPI-801; NK cell to target cell ratio between 1:1 and 1:2 depending on yield of MACS isolation) followed by incubation at 37° C. 5% $CO_2$ for 2 hours and subsequent flow cytometry staining as described in NK fratricide section.

6.1.16 Rituximab-Induced ADCC Assay

NK cells were isolated from PBMC via negative MACS selection using NK cell isolation kit (Miltenyi, Bergisch Gladbach, Germany). resuspended in 10% heat-inactivated FBS (Gibco, Thermo Fisher Scientific Inc., Waltham, USA) in AIM-V medium supplemented with 50 µg/mL streptomycin sulfate and 10 µg/mL gentamicin sulfate (Gibco, Thermo Fisher Scientific Inc., Waltham) and dispensed into round-bottom 96-well cell culture plates. Further, pure medium (No antibody controls) or one of the respective anti-CD2 antibody agents diluted in cell culture medium (final concentration 10 µg/mL) were added followed by overnight incubation at 37° C. 5% CO2. The next day Daudi target cells (DSMZ Cat. ACC 78; CD20+; NK to Daudi ratio 4:1) and Rituximab (final concentration 0.0001-1 µg/mL) were added followed by 2 hours of incubation at 37° C. 5% CO2. Subsequently, cells were washed in saline solution and incubated with Fc-receptor binding inhibitor (Invitrogen; Thermo Fisher Scientific Inc., Waltham, USA) followed by staining with anti-CD56 BV421 (BD Biosciences, San Diego, USA; Clone NCAM16.2), anti-CD3 VioGreen (Miltenyi, Bergisch Gladbach, Germany; Clone REA613), anti-CD107a BV786 (BioLegend, San Diego, USA; Clone H4A3), anti-CD16 FITC (Miltenyi, Bergisch Gladbach, Germany; Clone REA423), anti-CD2 PE-CF594 (BD Biosciences, San Diego, USA; Clone RPA-2.10), anti-CD69 APC (Miltenyi, Bergisch Gladbach, Germany; Clone REA824) and anti-CD19 APC-H7 (BD Biosciences, San Diego, USA; Clone SJ25C1). NK cells were identified as CD3− CD56+ and/or CD16+ lymphocytes. Samples were stained in the dark at 4° C. and were acquired using a FACSCelesta flow cytometer (BD Biosciences, San Diego, USA). Post-acquisition editing and data analysis was conducted using FlowJo® 10.6.2 software (FlowJo LLC, Ashland, USA).

6.1.17 Graphs and Statistical Analysis

Visualization of results and statistical analysis of underlying data were carried out using GraphPad Prism 8 software (GraphPad Software, San Diego). Data were analyzed using repeated-measure one-way ANOVA followed by Dunnett's multiple comparison test or two-way ANOVA followed by Dunnett's multiple comparison test unless specified otherwise. Untreated controls served as the comparator if not specified otherwise.

Figure 1:
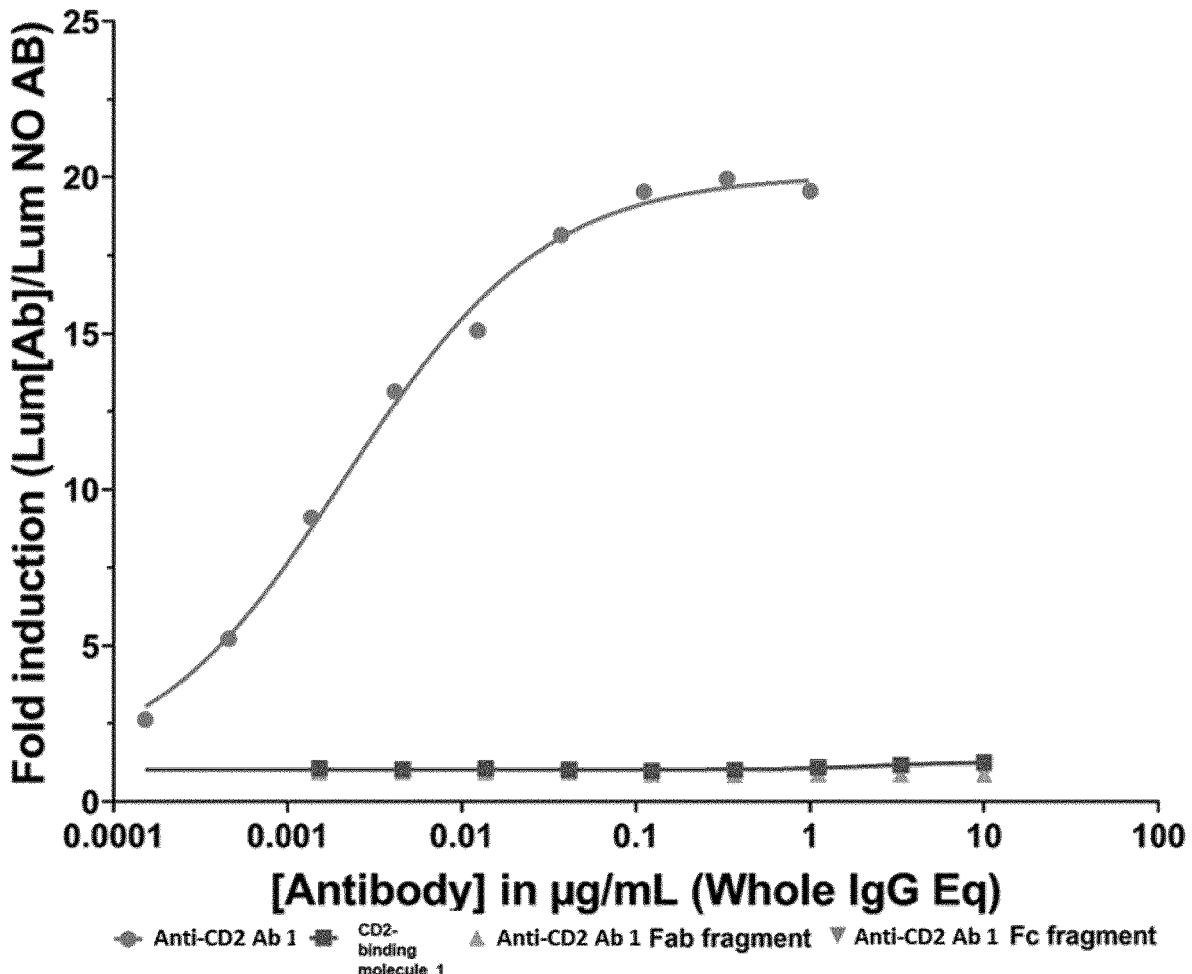

6.2 Example 1: Effect of CD2-Binding Molecule 1 on ADCC and Immunomodulatory Activity The Fc γ receptor (FcγR) IIIA is an important mediator of ADCC activity. The affinity of siplizumab and siplizumab fragments for the FcγRIIIA was compared with the FcγRIIIA receptor affinity of the CD2-binding molecule 1. As shown in FIG. 1, siplizumab has a high affinity for FcγRIIIA as measured by a fold increase in the luciferase reporter gene expression. Conversely, the siplizumab Fab fragment, Fc fragment, and CD2-binding molecule 1 do not exhibit any affinity for the FcγRIIIA (FIG. 1). Because cells expressing FcγRIIIA are the main mediators of ADCC, without FcγRIIIA-binding and signaling, CD2-expressing cells bound by the CD2-binding molecule 1 will not be depleted via ADCC.

Figure 2A:
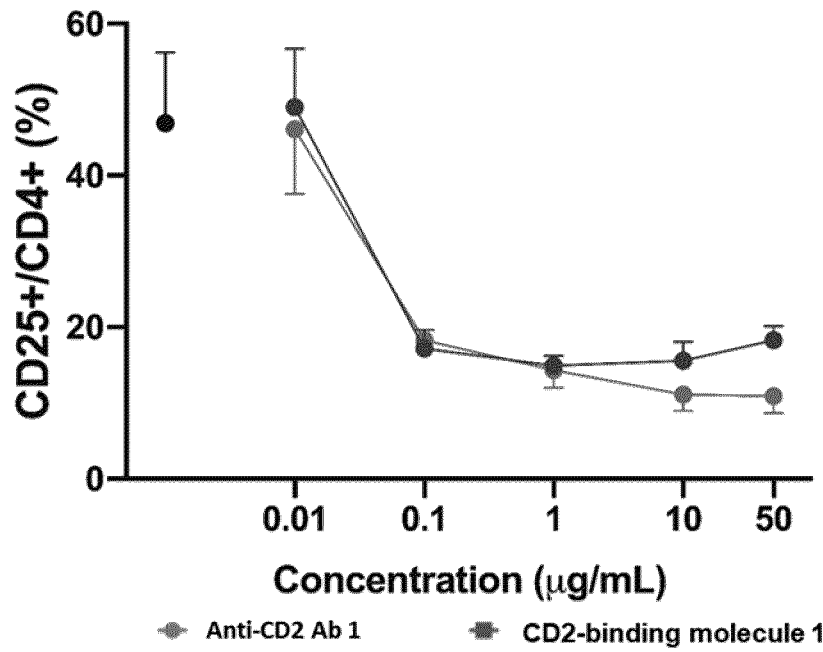
FIGS. 2A-2B shows the comparable ability of CD2-binding molecule 1 (a deglycosylated CD2-binding molecule) and anti-CD2 Ab1 (e.g., siplizumab) to inhibit the activation (FIG. 2A) and proliferation (FIG. 2B) of CD4+/CD25+ T cells.
Figure 2B:
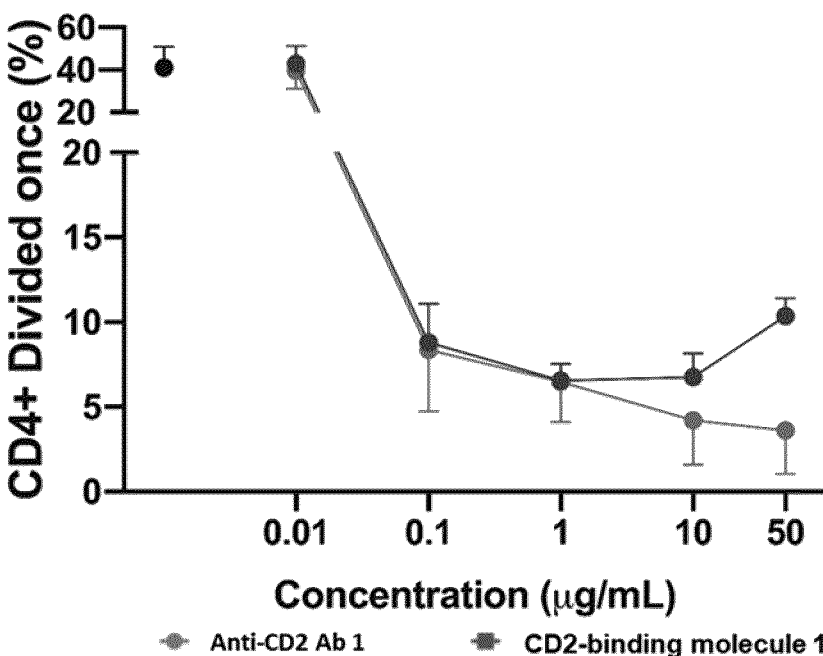
Figure 3:
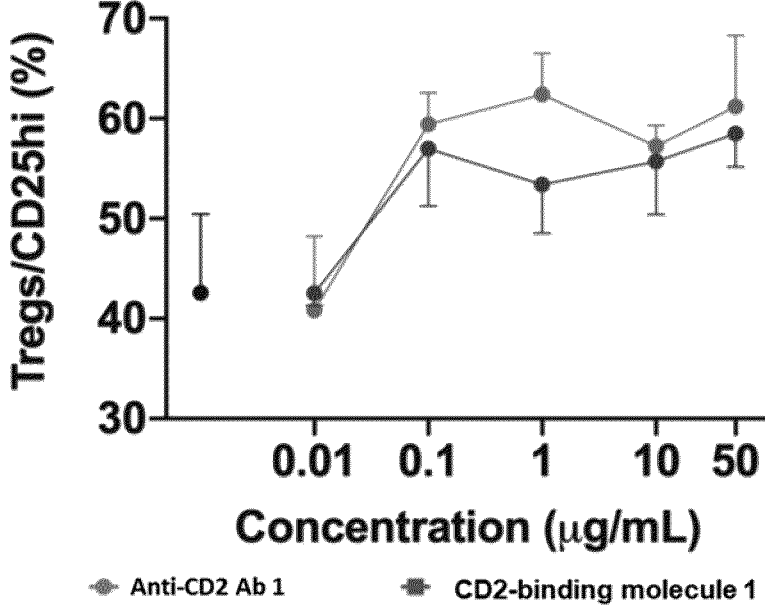
FIG. 3 shows the comparable ability of CD2-binding molecule 1 (a deglycosylated CD2-binding molecule) and anti-CD2 Ab1 (e.g., siplizumab) to induce cells important in immune system regulation. The ability to regulate the immune response as measured by the increasing percentage of T regulatory (Tregs) cells upon interaction with CD2-binding molecule 1 or anti-CD2 Ab1 (e.g., siplizumab).

While the ability of CD2-binding molecule 1 to bind FcγRIIIA, and therefore mediate ADCC, was inhibited, the ability of the CD2-binding molecule 1 to modulate immune activity is maintained. FIG. 2 shows that CD2-binding molecule 1 exhibits comparable inhibition of activation (FIG. 2A) and proliferation (FIG. 2B) of CD4+/CD25+ T cells as siplizumab. As an additional measure of immune modulatory activity, the CD2-binding molecule 1 shows a comparable ability to induce expression of T regulatory cells (Tregs) as siplizumab (FIG. 3).

6.3 Example 2: Effect of CD2-Binding Molecule 1 on NK Cells

Figure 4A:
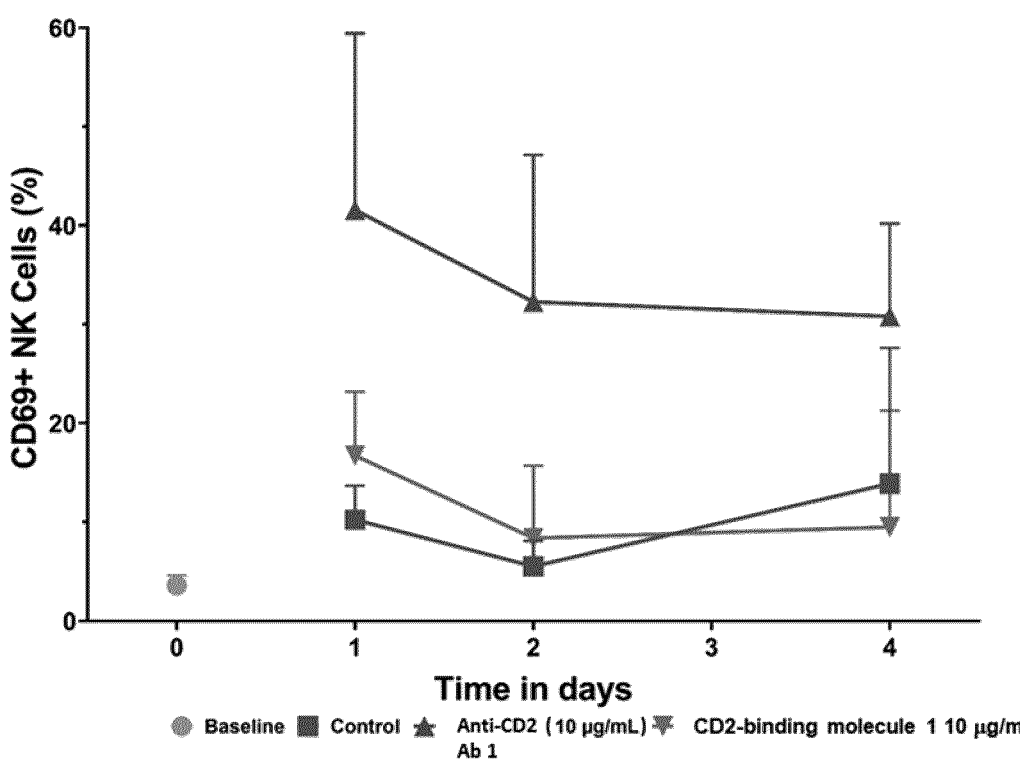
FIGS. 4A-4B shows the ability of CD2-binding molecule 1 (a deglycosylated CD2-binding molecule) to inhibit NK cell activation (Induction of CD69 expression on NK cells) as compared to anti-CD2 Ab1 (e.g., siplizumab) in both an autologous (FIG. 4A) or allogenic (FIG. 4B) mixed lymphocyte reaction (MLR).
Figure 4B:
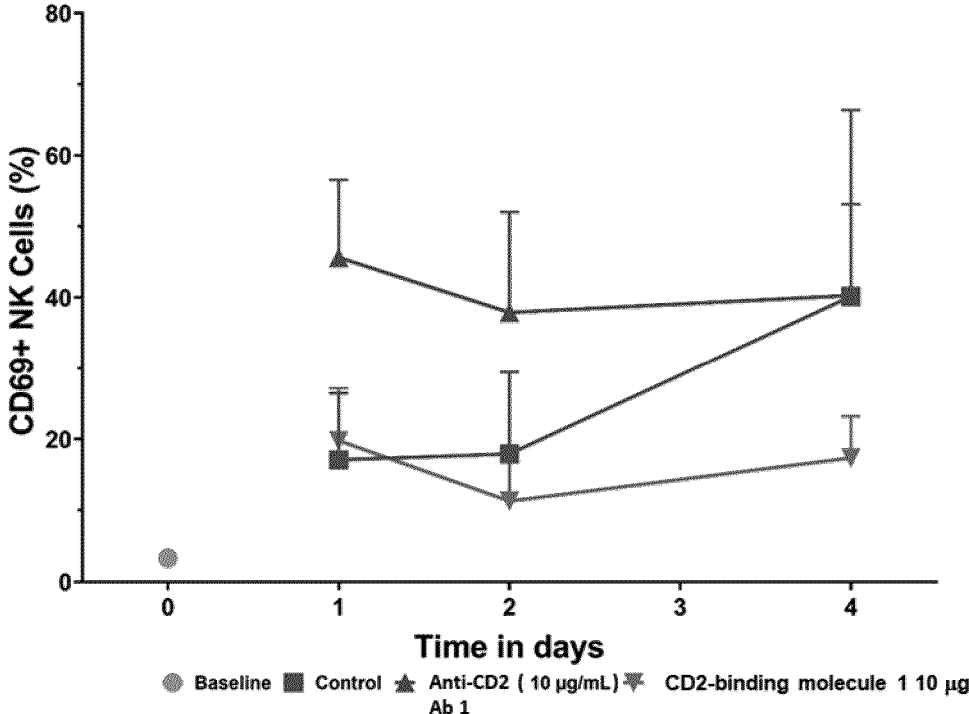

The effect of the CD2-binding molecule 1 on NK cells was examined. NK cells are a major effector of the innate immune system and bind to immune-complexed IgG by way of its FcγRIIIA. While the CD2-binding molecule 1 had no affinity for the FcγRIIIA (as seen from FIG. 1), the CD2-binding molecule 1 still exhibited an effect on the NK cells. FIG. 4 illustrates that CD2-binding molecule 1 exhibited an inhibitory effect on the expression of CD69+ NK cells as compared to siplizumab in both an autologous (FIG. 4A) or allogenic (FIG. 4B) mixed lymphocyte reaction (MLR).

6.4 Example 3: Effect of CD2-Binding Molecule 1 on ADCP

In vivo, cells expressing FcγRIIA are the main mediators of antibody-dependent cell phagocytosis (ADCP). The effect of CD2-binding molecule 1 on CD2-expressing cells was examined to determine the affinity of CD2-binding molecule 1 to FcγRIIA. FIG. 5 shows the lack of FcγRIIA signaling induced by the CD2-binding molecule 1 as compared to siplizumab. Without FcγRIIA-binding and signaling, CD2-expressing cells bound by CD2-binding molecule 1 will likely not be depleted via ADCP.

The siplizumab Fab fragment was examined for immunomodulatory activity as measured by the ability to inhibit the activation of CD69+ T cells. While the Fab fragment did not inhibit activation of CD69+ T cells compared to control, both the siplizumab and the CD2-binding molecule 1 showed ability to inhibit activation (FIG. 6). Although the CD2-binding molecule 1 appeared to inhibit the CD69+ T cell activation to a lesser extent than siplizumab, importantly the CD2-binding molecule 1 retained significant immunomodulatory activity as compared to the Fab fragment. Taken together, these data show that the ADCC activity of the CD2-binding molecule 1 is eliminated while the immune regulatory activity is maintained.

6.5 Example 4: Effect of Modifications of the Constant Region of the CD2-Binding Molecule CD2-binding molecules will be constructed using various combinations of antibody subclass scaffold and Fc modification. The resulting CD2-binding molecules will be tested for ADCC activity and immunomodulatory effects.

6.5.1 IgG1 Subclass CD2-Binding Molecules

A CD2-binding molecule will be constructed of the IgG1 scaffold, a VH variable region that is 100% identical to the VH variable region of siplizumab, a VL variable region that is 100% identical to the VL variable region of siplizumab, and a constant region that is 100% identical to the constant region of siplizumab except with a point mutation at N297. The mutation at N297 can include, but is not limited to N297G, N297Q, and N297A. The N297 point mutation will result in the lack of glycosylation and silencing of the Fc. The ADCC activity of this CD2-binding molecule will be determined in vitro by quantification of luciferase produced as a result of NFAT pathway activation. The binding of the Fc region of the CD2-binding molecule to the FcγRIIIA stably expressed on Jurkat cells will signal an NFAT activation response that drives expression of luciferase. The luciferase activity in the effector cell will be quantified with luminescence readout. The immunomodulatory activity of this CD2-binding molecule will be determined in vitro by quantifying the ability of the CD2-molecule to activate cell subsets important in the regulation of the immune response, including CD69+ T cells, CD69+ NK cells, and Tregs. Cell activation and proliferation will be determined using a mixed lymphocyte reaction (MLR) assay.

A CD2-binding molecule will be constructed of the IgG1 scaffold, a VH variable region that is 100% identical to the VH variable region of siplizumab, a VL variable region that is 100% identical to the VL variable region of siplizumab, and a native constant region obtained from a different antibody. The ADCC activity of this CD2-binding molecule will be determined in vitro as described above. The immunomodulatory activity of this CD2-binding molecule will be determined in vitro as described above.

A CD2-binding molecule will be constructed of the IgG1 scaffold, a VH variable region that is 100% identical to the VH variable region of siplizumab, a VL variable region that is 100% identical to the VL variable region of siplizumab, and a native constant region obtained from a different antibody wherein the switched constant region has a point mutation at N297. The mutation at N297 can include, but is not limited to N297G, N297Q, and N297A. The N297 point mutation will result in the lack of glycosylation and silencing of the Fc. The ADCC activity of this CD2-binding molecule will be determined in vitro as described above. The immunomodulatory activity of this CD2-binding molecule will be determined in vitro as described above.

6.5.2 IgG2 Subclass CD2-Binding Molecules

IgG2 CD2-binding molecules will be produced and evaluated for ADCC activity and immunomodulatory effects as compared to IgG1 CD2-binding molecules.

A CD2-binding molecule will be constructed of the IgG2 scaffold, a VH variable region that is 100% identical to the VH variable region of siplizumab, a VL variable region that is 100% identical to the VL variable region of siplizumab, and a native constant region obtained from a different antibody. The ADCC activity of this CD2-binding molecule will be determined in vitro as described above. The immunomodulatory activity of this CD2-binding molecule will be determined in vitro as described above.

A CD2-binding molecule will be constructed of the IgG2 scaffold, a VH variable region that is 100% identical to the VH variable region of siplizumab, a VL variable region that is 100% identical to the VL variable region of siplizumab, and a native constant region obtained from a different antibody wherein the switched constant region has a point mutation at N297. The mutation at N297 can include, but is not limited to N297G, N297Q, and N297A. The N297 point mutation will result in the lack of glycosylation and silencing of the Fc. The ADCC activity of this CD2-binding molecule will be determined in vitro as described above. The immunomodulatory activity of this CD2-binding molecule will be determined in vitro as described above.

6.5.3 IgG4 Subclass CD2-Binding Molecules

IgG4 CD2-binding molecules will be produced and evaluated for ADCC activity and immunomodulatory effects as compared to IgG1 CD2-binding molecules.

A CD2-binding molecule will be constructed of the IgG4 scaffold, a VH variable region that is 100% identical to the VH variable region of siplizumab, a VL variable region that is 100% identical to the VL variable region of siplizumab, and a native constant region obtained from a different antibody. The ADCC activity of this CD2-binding molecule will be determined in vitro as described above. The immunomodulatory activity of this CD2-binding molecule will be determined in vitro as described above.

A CD2-binding molecule will be constructed of the IgG4 scaffold, a VH variable region that is 100% identical to the VH variable region of siplizumab, a VL variable region that is 100% identical to the VL variable region of siplizumab, and a native constant region obtained from a different antibody wherein the switched constant region has a point mutation at N297. The mutation at N297 can include, but is not limited to N297G, N297Q, and N297A. The N297 point mutation will result in the lack of glycosylation and silencing of the Fc. The ADCC activity of this CD2-binding molecule will be determined in vitro as described above. The immunomodulatory activity of this CD2-binding molecule will be determined in vitro as described above.

6.6 Example 5: Siplizumab Induces NK Cell Fratricide Through Antibody-Dependent Cell-Mediated Cytotoxicity

6.6.1 Introduction

The glycoprotein CD2 (also known as LFA2) is expressed on T and NK cells where it serves as an adhesion and activation receptor (Binder et. al. 2020a). In humans, the main binding partner of CD2 is lymphocyte associated antigen 3 (LFA3; also known as CD58) which is broadly expressed, especially on antigen-presenting cells (APCs). Siplizumab is a monoclonal anti-CD2 IgG1 antibody that is currently undergoing clinical trials in the field of transplantation (ClinicalTrials.gov Identifier: NCT04311632). Previous evidence showed Siplizumab-induced in vivo NK cell depletion in primates (Sellberg et al. 2020) and human patients (O'Mahony et al. 2007).

NK cells express activating and inhibitory receptors. The balance of signaling through both sets of receptors is integrated and determines whether mature NK cells remain in a resting state or become activated (Watzl 2014). Thus, NK cell activation can be elicited by a reduction of inhibitory signaling, an increase in activation signaling, or a combination of both. Among activating NK cell receptors, CD16 is one whose signaling can induce NK cell activation in isolation. Most remaining activating NK cell receptors require activation in conjunction to elicit NK cell activation. CD16a is a low affinity Fc γ receptor (FcγR) and is also known as FcγRIIIA. NK cell binding to target-bound IgG antibodies via CD16a promotes antibody-dependent cell-mediated cytotoxicity (ADCC). Other activating NK cell receptors include NKG2D, certain killer cell immunoglobulin-like receptors (KIRs) and NKp46 which bind to tumor antigens, foreign HLA and viral proteins, respectively. Most prominent among inhibitory NK cell receptors are KIRs which recognize self-HLA (Paul and Lal 2017). Antibody-independent target cell killing by NK cells is commonly termed natural or spontaneous NK cell cytotoxicity.

A critical event preceding NK cell cytotoxicity is stable target cell conjugation via cell-cell adhesion molecules (Orange et. al. 2003). Once stable target cell conjugation has occurred and the NK cell immunological synapse (NKIS) has been formed, actin cytoskeleton rearrangement proceeds to facilitate transport of lytic vesicles to the NKIS and subsequent release to achieve target cell killing. Examples of adhesion molecules involved in NK-target cell conjugation and NKIS formation are LFA-1 (Paul and Lal 2017) and CD2 (Orange et. al. 2003) binding to ICAM-1 and LFA3 on the target cell, respectively. Even in natural NK cell cytotoxicity CD16 is enriched in the NKIS through interaction with CD2. Abrogation of this interaction between CD2 and CD16 markedly decreases natural NK cell cytotoxicity but does not affect NK-mediated ADCC (Grier et. al. 2012). CD2 has two Ig domains, one membrane distal domain and one membrane proximal domain. Similar to what has been observed during T cell-antigen presenting cell (APC) conjugation, CD2 accumulates in the immunological synapse that NK cells form upon target cell conjugation.

Here, the effects of siplizumab on NK cell activation in mixed lymphocyte reaction (MLR) and in pure NK cell culture were characterized and the effect of CD2 blockade on natural cytotoxicity and ADCC were investigated.

6.6.2 CD2 and Fc Mamma Receptor Binding

Anti-CD2 antibody binding to CD2 and FcγR binding was characterized via surface plasmon resonance (SPR). As shown in Table 6, all tested antibodies displayed a similar CD2 binding affinity with an affinity constant (KD) of circa 0.9-1.5 nM. Siplizumab binds FcγRI, FcγRIIA and FcγRIIIA. In contrast, CD2-binding molecule 1 (a deglycosylated CD2-binding molecule) binds FcγRI but not FcγRIIA and FcγRIIIA. All three Fc-silent anti-CD2 antibodies (CD2-binding molecule 2, 3, and 4) did not display detectable FcγR affinity.

TABLE 6

| KD[a] in nM | Siplizumab | CD2-binding molecule 1 [b] | CD2-binding molecule 2 [c] | CD2-binding molecule 3 [c] | CD2-binding molecule 4 [c] |
|---|---|---|---|---|---|
| Affinity of different anti-CD2 antibodies for CD2 and Fc gamma receptor (FcγR) I, IIA and IIIA | | | | | |
| CD2 | 1.2 | 1.2 | 1.5 | 0.9 | 1.4 |
| Fc gamma RI | 0.2 | 1.13 | >2000 | >2000 | >2000 |
| Fc gamma RIIA | 579 | >5000 | >5000 | >5000 | >5000 |
| Fc gamma RIIIA | 131 | >2000 | >5000 | >5000 | >5000 |

KD of siplizumab, CD2-binding molecule 1, CD2-binding molecule 2, CD2-binding molecule 3, and CD2-binding molecule 4 for CD2, FcγRI, FcγRIIA, and FcγRIIIA was measured via surface plasmon resonance.
[a]KD, Affinity constant;
[b] deglycosylated CD2 binding molecule;
[c] Fc-silent To confirm that FcγR-binding results in FcγR-induced signaling, each antibody was tested in a cell-based FcγR signaling assay (Tables 7-9). As shown in FIG. 9, consistent with SPR results siplizumab induced signaling through FcγRI, FcγRIIA and FcγRIIIA. In contrast, CD2-binding molecule 1 (a deglycosylated CD2-binding molecule) only induced signaling through FcγRI. None of the Fc-silenced anti-CD2 variants induced FcγR-mediated signaling.

6.6.3 CD2 and FcγR Expression on NK Cells

CD2 expression on NK cells was measured via flow cytometry. As shown in FIG. 10A, NK cells tend to have a lower CD2 expression than T cells. While CD56$^{bright}$ NK cells express CD2 at comparable levels as the average T cell, CD56$^{dim}$ and CD56$^{reg}$ CD16$^+$ NK cells express CD2 at significantly lower levels (p=0.0074 and p=0.0111, respectively; Repeated-measure one-way ANOVA followed by Dunnett's multiple comparison test; (Table 10). Nevertheless, NK cells show notable CD2 expression when compared to CD2$^-$ cell types, e.g. B cells.

Additionally, CD2 expression on T and NK cells was measured before and after activation of PBMC with anti-CD3 and anti-CD28 antibody-conjugated microbeads (Table 11). As displayed in FIG. 10B, CD2 expression is significantly elevated after activation on T cells (p=0.0034), CD56$^{dim}$ NK cells (p=0.0024), CD56$^{bright}$ cells (p=0.017) and CD56$^-$ CD16$^+$ NK cells (p=0.0029; two-tailed paired t-test).

Figure 11:
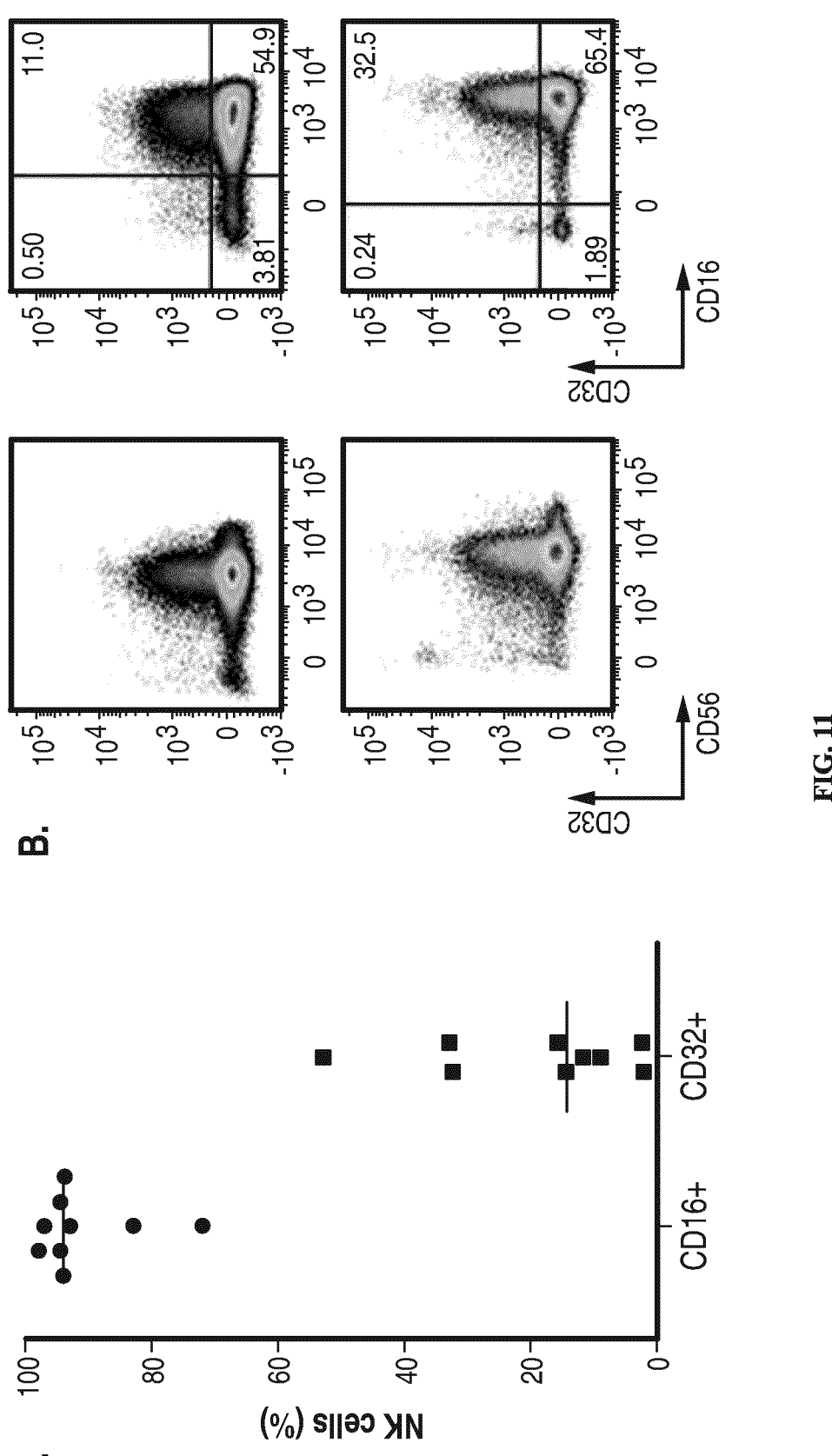

As shown in FIG. 11, almost all NK cells (91.0%) expressed FcγRIIIA (CD16) while FcγRII expression was heterogeneous (19.2%, CD32). NK cells did not express FcγRI (data not shown).

Figure 12:
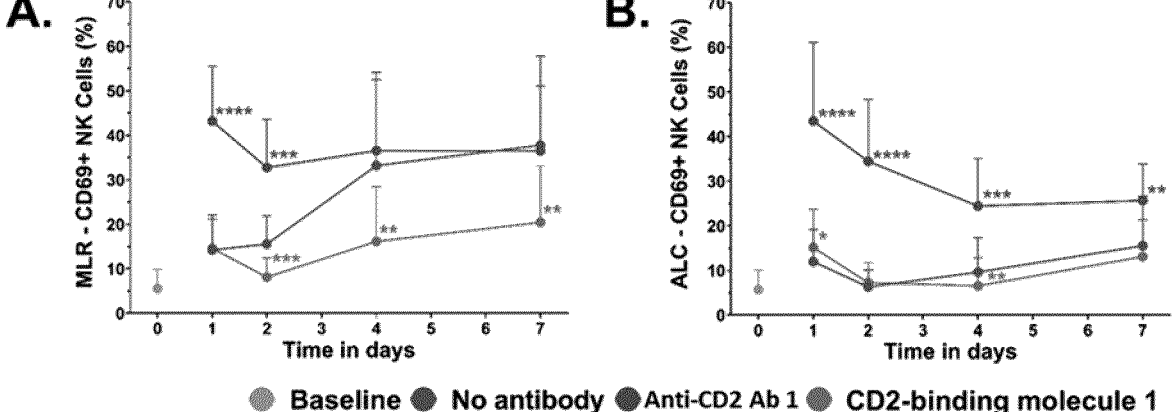

6.6.4 Effect of CD2 Blockade on Antibody-Mediated and Natural NK Cell Activation in Autologous and Mixed Lymphocyte Culture To investigate the effect of siplizumab on NK cell activation, autologous lymphocyte culture (ALC) and MLR were performed with a saturating dose of siplizumab. As shown in FIG. 12, siplizumab significantly increased the percentage of CD69+ NK cells (% CD69$^+$ NK cells) after one (p<0.0001) and two (p=0.0001) days of MLR as well as after one (p<0.0001), two (p<0.0001), four (p=0.0006) and seven days (p=0.0082) of ALC (Tables 12 and 13). On days four and seven of MLR an increase in % CD69$^+$ NK cells in untreated controls (no antibody) was observed. This likely derived from NK cells reacting against allogeneic HLA and/or absence of self-HLA on PBMC from the other donor. As shown in FIG. 12, CD2-binding molecule 1 (a deglycosylated CD2-binding molecule) significantly reduced % CD69+NK cells after four (p=0.0012) and seven (p=0.0035) days (Repeated-measure two-way ANOVA followed by Dunnett's multiple comparison test). Addition of CD2-binding molecule 1 (a deglycosylated CD2-binding molecule) did not meaningfully change the percentage of CD69$^+$ NK cells in ALC.

To further characterize the inhibition of NK cell activation in MLR by CD2 blockade, dose titrations from 0.0001 to 10 μg/mL were performed and CD69 expression on NK cells was analyzed after seven days of MLR. MLRs were incubated with siplizumab, CD2-binding molecule 1 (a deglycosylated CD2-binding molecule), CD2-binding molecule 2, CD2-binding molecule 3, or CD2-binding molecule 4. As displayed in FIG. 13A, doses of siplizumab induced a significant increase in % CD69$^+$ NK cells at 0.1 μg/mL (p=0.0003), 1 μg/mL (p=0.0018) and 10 μg/mL (p=0.0256) relative to untreated controls (No antibody). In contrast, CD2-binding molecule 1 (a deglycosylated CD2-binding molecule) induced a significant decrease of % CD69$^+$ NK cells at 1 μg/mL (p=0.0012) and 10 μg/mL (p=0.006). CD2-binding molecule 2, 3, and 4 significantly reduced % CD69$^+$ NK cells at 0.1 μg/mL (p=0.0178, p=0.0122, p=0.0234, respectively), 1 μg/mL (p=0.0311, p=0.0039, p=0.0388, respectively) and 10 μg/mL (p=0.0008, p=0.0027, p=0.0023, respectively) (Repeated-measure one-way ANOVA followed by Dunnett's multiple comparison test; Table 14).

Additionally, median CD2 fluorescence intensity (CD2 MFI) on NK cells was measured to assess if Siplizumab or CD2 binding molecule 2, 3, or 4 (FcS anti-CD2 mAbs) affect CD2 expression (FIG. 13B-C). Siplizumab induced a significant decrease of CD2 MFI on NK cells at 0.001-10 μg/mL (p≤0.0354) relative to untreated controls. Varying degrees of significant CD2 downregulation were observed with CD2-binding molecule 1 (a deglycosylated CD2-binding molecule) (p≤0.0064), CD2-binding molecule 2 (p≤0.0050), CD2-binding molecule 3 (p≤0.0091) and CD2-binding molecule 4 (p≤0.0142) at 0.01-10 μg/mL (Repeated-measure one-way ANOVA followed by Dunnett's multiple comparison test; Table 15).

6.6.5 NK Fratricide

Figure 14:
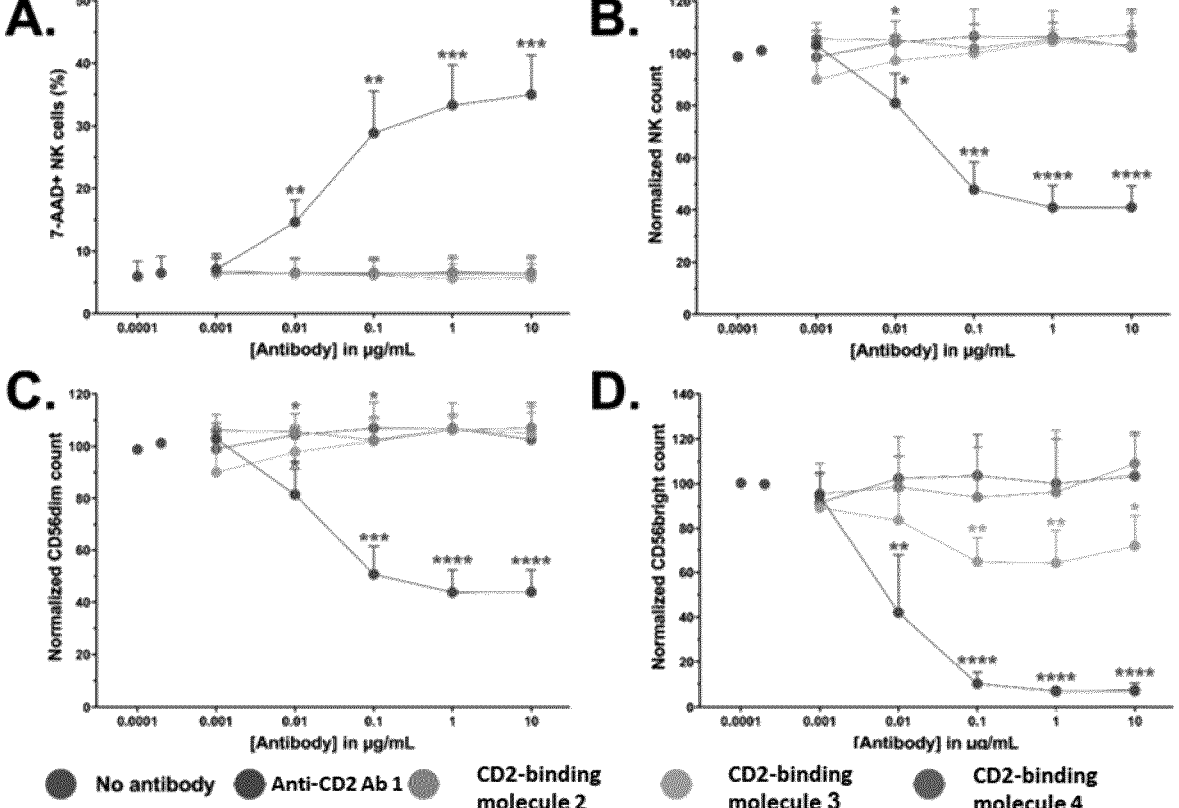

To test whether Siplizumab can induce NK cell fratricide, purified NK cells were cultured in the presence of increasing doses of Siplizumab or Fc-silent anti-CD2 mAbs. As shown in FIG. 14, Siplizumab significantly increased NK cell lysis in purified NK cell culture at 0.01-10 μg/mL (p≤0.0018) relative to untreated controls. Furthermore, Siplizumab induced a significant dose-dependent depletion of total NK cells (p≤0.0301), CD56$^{dim}$ NK cells (p≤0.0191) and CD56$^{bright}$ NK cells (p≤0.0093) at 0.01-10 µg/mL when compared to untreated controls. In contrast, CD2-binding molecule 2, 3, and 4 did not induce dose-dependent NK cell lysis or depletion in pure NK culture, except CD2 binding molecule 3 (FcS anti-CD2 IgG2) which induced a mild but statistically significant depletion of CD56$^{bright}$ NK cells at 0.1-10 µg/mL (p≤0.0132; Repeated-measure one-way ANOVA followed by Dunnett's multiple comparison test; Tables 16-19).

Figure 15:
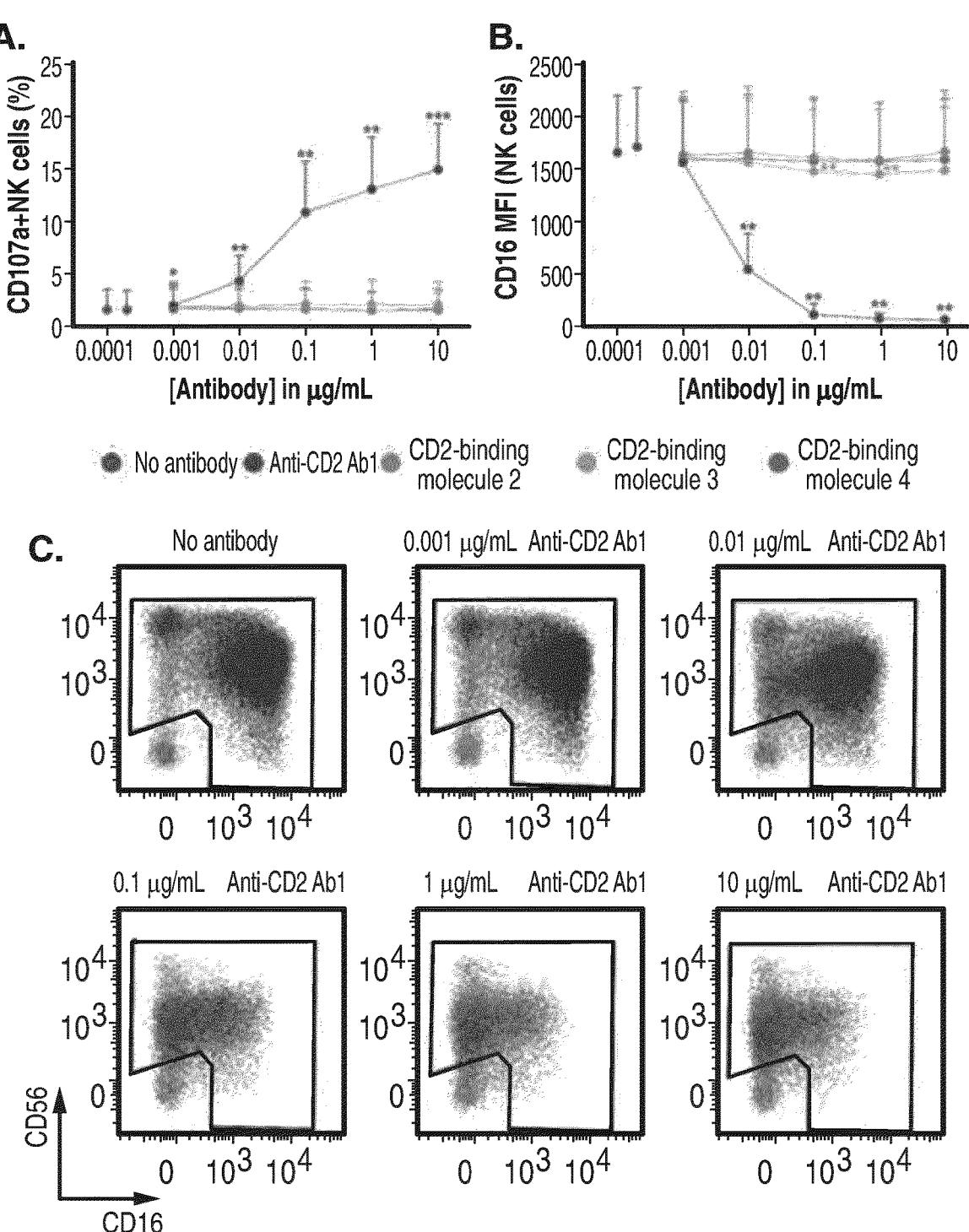

Additionally, FIG. 15 shows that Siplizumab induced a significant dose-dependent increase in NK cell degranulation (p≤0.0114; CD107a$^+$ NK cells) and a strong decrease of CD16 expression on NK cells (p≤0.0022), indicative of ADCC. None of CD2 binding molecule 2, 3, or 4 (FcS anti-CD2 mAb) induced degranulation and only CD2-binding molecule 3 induced a minor but statistically significant decrease in CD16 MFI at 0.1-1 µg/mL (p≤0.0269; Repeated-measure one-way ANOVA followed by Dunnett's multiple comparison test; Tables 20 and 21).

6.6.6 Natural NK Cytotoxicity

Figure 16:
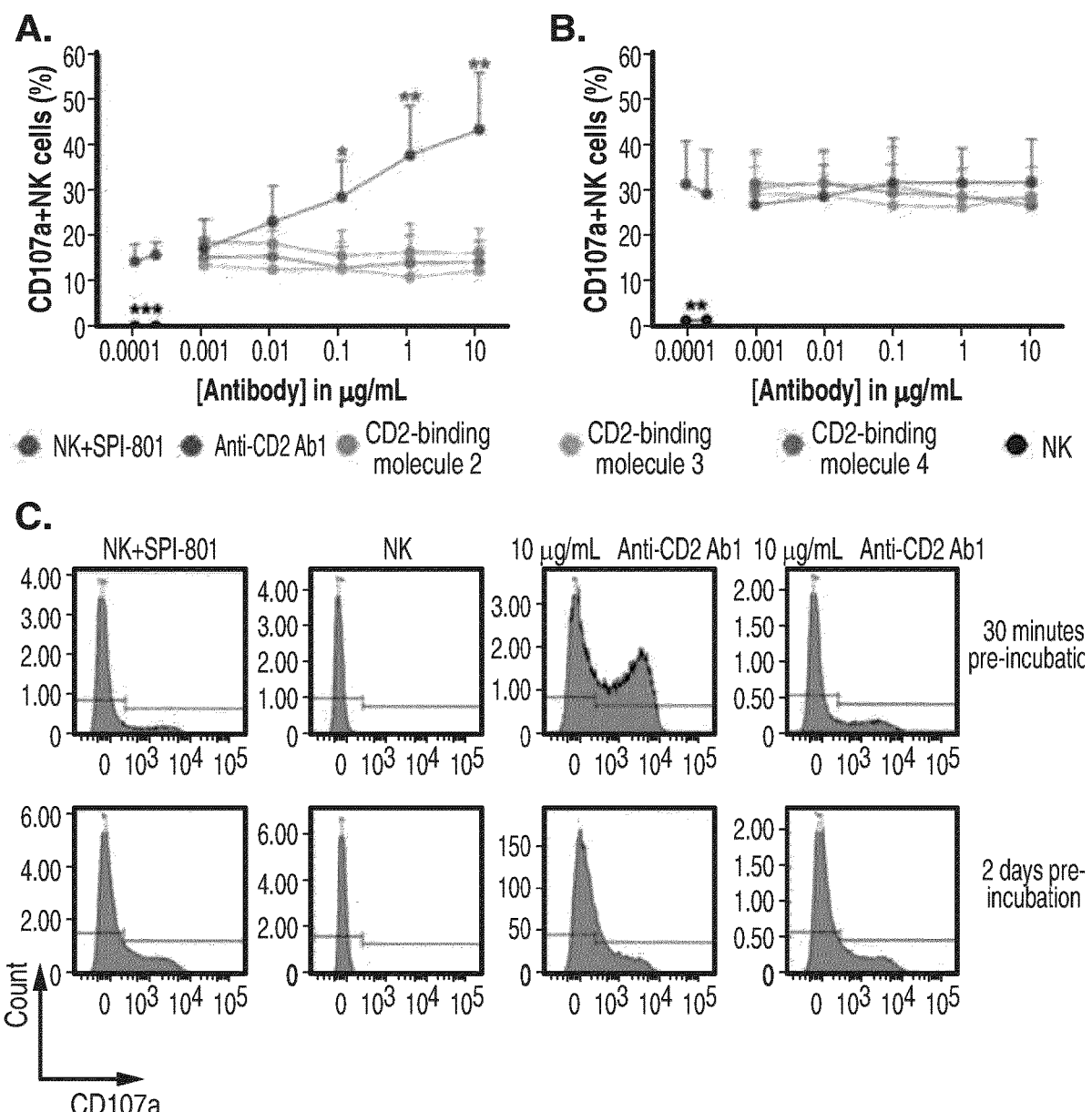

To test the effect of CD2 blockade on natural cytotoxicity, purified NK cells were incubated with titrated doses of Siplizumab or CD2-binding molecule 2, 3, or 4 in the presence of SPI-801 target cells (HLA). As shown in FIG. 16, CD2 blockade with CD2-binding molecule 2, 3, or 4 did not significantly inhibit NK cell degranulation in response to SPI-801 target cells, irrespective of whether pre-incubation of NK cells with CD2 binding molecule 2, 3, or 4 (FcS anti-CD2 mAb) lasted 30 minutes or 2 days prior to target cell addition. After 30 minutes of pre-incubation, Siplizumab significantly increased NK cell degranulation at 0.1-10 µg/mL (p≤0.0482) but not after 2 days of pre-incubation (Repeated-measure one-way ANOVA followed by Dunnett's multiple comparison test; Tables 22 and 23). CD2 blockade did not induce any change in SPI-801 count (data not shown).

6.6.7 Antibody-Dependent Cytotoxicity

To test whether CD2 blockade influences ADCC, purified NK cells were pre-incubated with Siplizumab or CD2-binding molecule 2, 3, or 4 before addition of titrated doses of Rituximab and CD20$^+$ target cells (Daudi). As shown in FIGS. 17A and 17B, CD2 blockade with CD2-binding molecule 2, 3, or 4 did not significantly affect NK cell degranulation or target cell killing in response to increasing doses of Rituximab (Tables 24 and 25). As displayed in FIG. 17C, Rituximab induced a significant increase of CD2 expression on NK cells at 0.01-1 µg/mL (p≤0.0248; Repeated-measure one-way ANOVA followed by Dunnett's multiple comparison test; Table 26). While anti-CD2 mAbs induced different degrees of CD2 downregulation in this setting, this did not seem to affect ADCC.

TABLE 7

Cell-based FcγRI signaling assay. Mean normalized luminescence ± SD (N = 3).

| [ANTIBODY] in nM | Siplizumab | | CD2-binding molecule 1 | | CD2-binding molecule 2 | | CD2-binding molecule 3 | | CD2-binding molecule 4 | |
|---|---|---|---|---|---|---|---|---|---|---|
| 6.67 | 100.0 | 0.0 | 125.6 | 2.7 | 5.7 | 0.4 | 3.8 | 0.7 | 3.2 | 0.4 |
| 1.11 | 103.1 | 6.0 | 123.0 | 11.0 | 5.8 | 0.9 | 3.5 | 0.5 | 3.0 | 0.4 |
| 0.19 | 106.0 | 11.9 | 127.3 | 8.5 | 6.0 | 0.5 | 3.2 | 0.3 | 2.9 | 0.2 |
| 0.031 | 101.7 | 13.6 | 107.8 | 6.9 | 3.4 | 0.4 | 2.9 | 0.7 | 2.8 | 0.2 |
| 0.0051 | 26.7 | 3.9 | 41.9 | 2.6 | 2.5 | 0.3 | 2.6 | 0.1 | 2.6 | 0.5 |
| 0.00086 | 5.1 | 0.4 | 8.5 | 1.2 | 2.5 | 0.3 | 2.5 | 0.5 | 2.9 | 0.4 |
| 0.000143 | 2.4 | 0.7 | 2.5 | 0.4 | 2.4 | 0.6 | 2.4 | 0.4 | 2.6 | 0.5 |
| 0.000024 | 2.4 | 0.5 | 2.6 | 0.6 | 2.7 | 0.4 | 2.4 | 0.3 | 2.8 | 0.5 |

TABLE 8

Cell-based FcγRIIA signaling assay. Mean normalized luminescence ± SD (N = 3).

| [ANTIBODY] in nM | Siplizumab | | CD2-binding molecule 1 | | CD2-binding molecule 2 | | CD2-binding molecule 3 | | CD2-binding molecule 4 | |
|---|---|---|---|---|---|---|---|---|---|---|
| 666.7 | 100.0 | 0.0 | | | | | | | | |
| 111.1 | 107.8 | 17.5 | | | | | | | | |
| 18.52 | 70.1 | 3.7 | | | | | | | | |
| 3.09 | 45.3 | 1.2 | | | | | | | | |
| 0.51 | 40.7 | 4.0 | | | | | | | | |
| 0.086 | 11.0 | 1.4 | | | | | | | | |
| 0.014 | 3.2 | 0.6 | | | | | | | | |
| 0.002 | 3.0 | 0.3 | | | | | | | | |
| 66.7 | | | 4.4 | 0.9 | 3.1 | 0.6 | 6.6 | 2.0 | 3.8 | 0.9 |
| 11.1 | | | 3.2 | 0.4 | 3.4 | 0.8 | 5.7 | 0.4 | 3.1 | 0.6 |
| 1.85 | | | 3.2 | 0.4 | 3.1 | 0.7 | 4.4 | 0.4 | 3.7 | 1.4 |
| 0.31 | | | 2.9 | 0.7 | 3.0 | 0.6 | 4.4 | 0.5 | 3.5 | 0.2 |
| 0.051 | | | 3.4 | 0.6 | 2.8 | 0.6 | 3.6 | 0.4 | 3.3 | 1.2 |
| 0.009 | | | 2.6 | 0.4 | 2.7 | 0.7 | 2.9 | 0.4 | 2.4 | 0.2 |
| 0.001 | | | 3.0 | 0.4 | 3.0 | 1.1 | 3.2 | 0.1 | 2.3 | 0.5 |
| 0.00024 | | | 2.6 | 0.4 | 2.5 | 0.5 | 3.0 | 0.5 | 3.4 | 0.4 |

TABLE 9

| Cell-based FcγRIIIA signaling assay. Mean normalized luminescence ± SD (N = 3). | | | | | | | | | | |
|---|---|---|---|---|---|---|---|---|---|---|
| [ANTIBODY) in uM | Sislizumab | | CD1-binding molecule 1 | | CD2-binding molecule 2 | | CD2-binding molecule a | | CD2-binding molecule 4 | |
| 6.67 | 100.0 | 0.0 | 7.3 | 0.6 | 6.8 | 0.7 | 3.8 | 0.5 | 6.8 | 0.3 |
| 1.11 | 100.0 | 13.8 | 8.4 | 1.9 | 7.0 | 0.2 | 3.2 | 0.1 | 7.3 | 1.1 |
| 0.19 | 89.0 | 7.1 | 7.0 | 0.2 | 7.3 | 0.9 | 2.8 | 0.2 | 6.7 | 1.1 |
| 0.031 | 74.8 | 4.4 | 6.5 | 0.9 | 6.4 | 0.8 | 4.1 | 0.4 | 6.2 | 0.4 |
| 0.0051 | 44.5 | 3.9 | 6.5 | 0.7 | 6.3 | 0.5 | 5.4 | 0.2 | 6.4 | 0.9 |
| 0.00086 | 13.4 | 3.0 | 6.0 | 0.9 | 6.8 | 1.4 | 6.2 | 0.3 | 6.3 | 0.1 |
| 0.000143 | 6.6 | 0.9 | 7.5 | 2.0 | 6.7 | 0.5 | 6.5 | 0.6 | 6.1 | 1.4 |
| 0.000024 | 6.1 | 0.4 | 5.9 | 1.0 | 6.6 | 1.5 | 6.1 | 6.5 | 6.4 | 0.5 |

TABLE 10

CD2 expression. Average CD2 median fluorescent intensity ± SEM (N = 5). ). Repeated-measure one-way ANOVA results followed by Dunnett's multiple comparison test (*p < 0.05, **p < 0.01).

| | AVERAGE MFI | SEM |
|---|---|---|
| T CELLS | 651.9 | 56.3 |
| CD4 TN | 442.6 | 7.6 |
| CD4 TCM | 644.7 | 48.9 |
| CD4 TEM | 791.8 | 102.4 |
| CD4 TMERA | 468.9 | 36.6 |
| CD8 TN | 655.7 | 28.3 |
| CD8 TCM | 852.5 | 147.9 |
| CD8 TEM | 1165.1 | 92.7 |
| CD8 TEMRA | 740.4 | 117.7 |
| RTREG | 442.1 | 43.2 |
| NSTREG | 621.1 | 38.7 |
| ATREG | 777.5 | 97.0 |
| B CELLS | 2.7** | 21.2 |
| $CD56^{BRIGHT}$ | 713.3 | 120.6 |
| $CD56^{DIM}$ | 150.5** | 33.1 |
| $CD56^{NEG} CD16^+$ | 145.1* | 46.0 |

TABLE 11

CD2 expression on resting and activated PBMC. Two-tailed paired t-test results (*p < 0.05, **p < 0.01). Data shown as average median fluorescence intensity ± SEM.

| | T cells | | B cells | | $CD56^{bright}$ | | $CD56^{dim}$ | | $CD56^{neg} CD16^+$ | |
|---|---|---|---|---|---|---|---|---|---|---|
| RESTING | 657.3 | 102.0 | 2.7 | 47.4 | 713.3 | 269.6 | 150.5 | 74.0 | 145.1 | 102.8 |
| ACTVATED | 11226.6** | 3749.1 | 0.0 | 196.4 | 3465.0* | 1674.6 | 990.8** | 256.1 | 990.8** | 256.1 |

TABLE 12

CD69+ NK cells in mixed lymphocyte reaction over time. Mean percentage of CD69+ NK cells ± SD (N = 12). Repeated-measure two-way ANOVA results followed by Dunnett's multiple comparison test (*p < 0.05, p < 0.01, *p < 0.001, ****p < 0.0001).

| Time in days | No antibody | | Siplizumab | | CD2-binding molecule 1 | |
|---|---|---|---|---|---|---|
| 0 | 5.6 | 4.4 | | | | |
| 1 | 14.2 | 7.9 | 43.2**** | 12.4 | 14.6 | 6.6 |
| 2 | 15.5 | 6.4 | 32.7*** | 10.8 | 8.1*** | 4.3 |
| 4 | 33.2 | 19.4 | 36.5 | 17.7 | 16.1** | 12.3 |
| 7 | 37.8 | 20.0 | 36.5 | 14.6 | 20.4** | 12.7 |

TABLE 13

CD69+ NK cells in autologous lymphocyte culture over time. Mean percentage of CD69+ NK cells ± SD (N = 12). Repeated-measure two-way ANOVA results followed by Dunnett's multiple comparison test (*p < 0.05, p < 0.01, * p < 0.001, ****p < 0.0001).

| Time in days | No antibody | | Siplizumab | | CD2-binding molecule 1 | |
|---|---|---|---|---|---|---|
| 0 | 5.7 | 4.4 | | | | |
| 1 | 12.0 | 7.2 | 43.5**** | 17.7 | 15.1* | 8.6 |
| 2 | 6.3 | 3.8 | 34.5**** | 13.9 | 7.3 | 4.5 |
| 4 | 9.6 | 7.7 | 24.4*** | 10.7 | 6.5** | 6.3 |
| 7 | 15.5 | 11.1 | 25.7** | 8.2 | 13.1 | 8.2 |

TABLE 14

CD69+ NK cells after seven days of mixed lymphocyte reaction incubated with increasing doses of anti-CD2 antibody. Mean percentage of CD69+ NK cells ± SD (N = 9). Repeated-measure one-way ANOVA results followed by Dunnett's multiple comparison test (*p < 0.05, p < 0.01, *p < 0.001.

| [Antibody] in µg/ml | Siglizumab | | CD2-binding molecule 1 | | CD2-binding molecule 2 | | CD2-binding molecule 3 | | CD2-binding molecule 4 | |
|---|---|---|---|---|---|---|---|---|---|---|
| 0 | 28.6 | 15.1 | | | | | | | | |
| 0.0001 | 29.6 | 13.8 | 31.3 | 14.3 | 34.9 | 16.3 | 33.1 | 14.8 | 31.3 | 15.9 |
| 0.001 | 28.3 | 14.9 | 28.6 | 13.2 | 34.2 | 15.5 | 29.9 | 13.7 | 31.3 | 14.3 |
| 0.01 | 41.0 | 23.1 | 23.2 | 10.9 | 27.2 | 14.3 | 29.4 | 13.7 | 28.4 | 14.6 |
| 0.1 | 49.7*** | 17.7 | 23.2 | 11.3 | 19.8* | 10.9 | 11.9* | 4.2 | 19.9* | 10.7 |
| 1 | 42.9** | 18.5 | 18.1** | 12.0 | 18.7* | 8.1 | 8.7** | 4.3 | 18.6* | 9.9 |
| 10 | 42.1* | 19.7 | 14.4** | 8.0 | 14.3*** | 8.7 | 8.1** | 4.9 | 14.1** | 9.5 |

TABLE 15

CD2 expression on NK cells after seven days of mixed lymphocyte reaction incubated with increasing doses of anti-CD2 antibody. Median CD2 fluorescence intensity on NK cells ± SEM (N = 9). Repeated-measure one-way ANOVA results followed by Dunnett's multiple comparison test (*p < 0.05, p < 0.01, *p < 0.001. ****p < 0.0001).

| [Antibody] in ng/ml | Siplizumab | | CD2-binding molecule-1 | | CD2-binding molecule 2 | | CD2-binding molecule 3 | | CD2-binding molecule 4 | |
|---|---|---|---|---|---|---|---|---|---|---|
| 0 | 3091.0 | 358.0 | | | | | | | | |
| 0.0001 | 2912.0 | 397.8 | 2910.0* | 371.7 | 3190.3 | 300.9 | 1143.6 | 396.7 | 3013.1 | 279.8 |
| 0.001 | 2783.6* | 347.8 | 3033.1 | 414.1 | 3146.7 | 406.9 | 3075.2 | 381.7 | 2876.9 | 322.7 |
| 0.01 | 1968.2** | 370.2 | 2393.1** | 306.5 | 2378.8** | 256.8 | 2447.1** | 283.2 | 2418.6* | 210.1 |
| 0.1 | 159.8*** | 20.5 | 909.3*** | 135.0 | 1577.1*** | 206.4 | 816.0*** | 110.6 | 1245.3*** | 130.0 |
| 1 | 124.8*** | 17.2 | 856.3*** | 146.5 | 1494.9*** | 177.5 | 284.1*** | 22.4 | 1059.8*** | 122.7 |
| 10 | 156.2*** | 28.8 | 1073.4**** | 228.8 | 1466.1*** | 175.0 | 288.1*** | 26.8 | 950.8*** | 114.8 |

TABLE 16

NK cell lysis after incubation of purified NK cells with increasing doses of anti-CD2 antibody. Mean percentage of 7-AAD+ NK cells ± SD (N = 6). Repeated-measure one-way ANOVA results followed by Dunnett's multiple comparison test (*p < 0.05, p < 0.01, *p < 0.001).

| [Antibody] in ng/ml | Siplizamab | | CD2-binding molecule 2 | | CD2-binding molecule 3 | | CD2-binding molecule 4 | |
|---|---|---|---|---|---|---|---|---|
| 0 | 6.0 | 2.4 | | | | | | |
| 0.001 | 7.1 | 2.5 | 6.7 | 2.4 | 6.4 | 2.3 | 6.5 | 2.4 |
| 0.01 | 14.6** | 3.5 | 6.6 | 2.4 | 6.4 | 2.5 | 6.3 | 2.4 |
| 0.1 | 28.8** | 6.7 | 6.6 | 2.5 | 6.1 | 2.3 | 6.3 | 2.4 |
| 1 | 33.3*** | 6.4 | 6.7 | 2.6 | 5.6 | 2.3 | 6.4 | 2.4 |
| 10 | 35.0*** | 8.3 | 6.6 | 2.7 | 5.8 | 2.2 | 6.3 | 2.5 |

TABLE 17

Normalized NK cell count after incubation of purified NK cells with increasing doses of anti-CD2 antibody. Mean normalized NK cell count ± SD (N = 6). Repeated-measure one-way ANOVA results followed by Dunnett's multiple comparison test (p < 0.05, p < 0.01, *p < 0.001, ****p < 0.0001).

| [Antibody] in ng/ml | Siplizumab | | CD2-binding molecule 2 | | CD2-binding molecule 3 | | CD2-binding molecule 4 | |
|---|---|---|---|---|---|---|---|---|
| 0 | 100.0 | 0.0 | | | | | | |
| 0.001 | 103.1 | 3.0 | 105.7 | 6.1 | 90.0 | 14.3 | 98.7 | 10.1 |
| 0.01 | 81.0* | 11.3 | 105.3 | 7.3 | 97.3 | 10.1 | 104.3* | 2.3 |
| 0.1 | 47.8*** | 10.6 | 102.0 | 15.1 | 100.1 | 6.8 | 106.6 | 4.6 |
| 1 | 41.0**** | 8.4 | 105.5 | 10.9 | 104.7 | 4.6 | 106.3 | 5.6 |
| 10 | 41.1**** | 8.2 | 107.4 | 8.2 | 103.2 | 7.3 | 102.6 | 14.3 |

TABLE 18

Normalized CD56$^{dim}$ NK cell count after incubation of purified NK cells with increasing doses of anti-CD2 antibody. Mean normalized CD56dim NK cell count ± SD (N = 6). Repeated-measure one-way ANOVA results followed by Dunnett's multiple comparison test (*p < 0.05, p < 0.01, *p < 0.001, ****p < 0.0001).

| [Antibody] in ng/ml | Siplizamab | | CD2-binding molecule 2 | | CD2-binding molecule 3 | | CD2-binding molecule 4 | |
|---|---|---|---|---|---|---|---|---|
| 0 | 100.0 | 0.0 | | | | | | |
| 0.001 | 102.8 | 2.8 | 106.1 | 6.1 | 90.1 | 14.2 | 99.0 | 9.8 |
| 0.01 | 81.5* | 9.8 | 105.7 | 6.9 | 97.8 | 10.5 | 104.4* | 2.8 |
| 0.1 | 50.7*** | 10.7 | 102.4 | 14.5 | 101.9 | 8.2 | 106.9* | 4.4 |
| 1 | 43.8**** | 8.6 | 106.3 | 10.3 | 106.3 | 4.8 | 106.9 | 5.3 |
| 10 | 44.0**** | 8.4 | 107.2 | 8.1 | 104.9 | 8.0 | 102.5 | 14.1 |

TABLE 19

Normalized CD56bright NK cell count after incubation of purified NK cells with increasing doses of anti-CD2 antibody. Mean normalized CD56bright NK cell count ± SD (N = 6). Repeated-measure one-way ANOVA results followed by Dunnett's multiple comparison test (*p < 0.05, p < 0.01, *p < 0.001, ****p < 0.0001).

| [Antibody] in µg/ml | Siplizumab | | CD2-Binding molecule 2 | | CD2-binding molecule 3 | | CD2-binding molecule 4 | |
|---|---|---|---|---|---|---|---|---|
| 0 | 100.0 | 0.0 | | | | | | |
| 0.001 | 94.6 | 10.2 | 95.4 | 13.7 | 89.2 | 14.5 | 91.4 | 13.4 |
| 0.01 | 42.0** | 25.8 | 98.5 | 22.3 | 83.6 | 13.5 | 102.4 | 9.8 |
| 0.1 | 10.2**** | 5.1 | 93.9 | 22.2 | 64.7** | 11.0 | 103.6 | 18.3 |
| 1 | 7.0**** | 2.3 | 96.1 | 27.8 | 64.2** | 14.8 | 100.1 | 19.9 |
| 10 | 7.3**** | 3.3 | 108.9 | 12.6 | 71.9* | 13.6 | 103.3 | 19.7 |

TABLE 20

CD107a expression on NK cells after incubation of purified NK cells with increasing doses of anti-CD2 antibody. Mean percentage of CD107a+ NK cells ± SD (N = 6). Repeated-measure one-way ANOVA results followed by Dunnett's multiple comparison test (*p < 0.05, p < 0.01, *p < 0.001).

| (Antibody] in µg/ml | Siplizumab | | CD2-binding molecule 2 | | CD2-binding molecule 3 | | CD2-binding molecule 4 | |
|---|---|---|---|---|---|---|---|---|
| 0 | 1.6 | 1.9 | | | | | | |
| 0.001 | 2.0* | 1.9 | 1.9 | 2.4 | 1.9 | 2.2 | 1.7 | 2.0 |
| 0.01 | 4.3** | 2.4 | 1.7 | 2.1 | 2.0 | 2.2 | 1.7 | 1.9 |
| 0.1 | 10.9** | 4.8 | 1.7 | 2.0 | 2.1 | 2.2 | 1.7 | 1.9 |
| 1 | 13.0** | 4.9 | 1.6 | 1.7 | 2.1 | 2.4 | 1.5 | 1.8 |
| 10 | 14.8*** | 4.4 | 1.5 | 1.7 | 2.0 | 2.2 | 1.7 | 1.9 |

TABLE 21

CD16 expression on NK cells after incubation of purified NK cells with increasing doses of anti-CD2 antibody. Median CD16 fluorescence intensity on NK cells ± SEM (N = 6). Repeated-measure one-way ANOVA results followed by Dunnett's multiple comparison test (*p < 0.05, p < 0.01, *p < 0.001, ****p < 0.0001).

| [Antibody] in µg/ml | Siplizumab | | CD2-binding molecule 2 | | CD2-binding molecule 3 | | CD2-binding molecule 4 | |
|---|---|---|---|---|---|---|---|---|
| 0 | 1673.8 | 223.0 | | | | | | |
| 0.001 | 1577.5 | 242.0 | 1645.5 | 250.0 | 1624.0 | 220.4 | 1598.7 | 246.1 |
| 0.01 | 553.7** | 140.5 | 1671.2 | 259.9 | 1577.8 | 245.5 | 1612.3 | 249.9 |
| 0.1 | 118.9** | 43.1 | 1624.7 | 240.7 | 1491.0* | 242.2 | 1589.5 | 242.1 |
| 1 | 80.3** | 21.5 | 1599.2 | 227.6 | 1464.2* | 253.1 | 1589.2 | 230.9 |
| 10 | 69.3** | 15.1 | 1677.5 | 242.7 | 1502.8 | 248.8 | 1602.5 | 239.0 |

TABLE 22

CD107a expression on NK cells after incubation of purified NK cells with increasing doses of anti-CD2 antibody and SPI-801 target cells. Mean percentage of CD107a+ NK cells ± SD (N = 6). Pre-incubation of NK cells with anti-CD2 mAbs for 30 minutes before target cell addition. Repeated-measure one-way ANOVA results followed by Dunnett's multiple comparison test (*p < 0.05, p < 0.01, *p < 0.001).

| [Antibody] in µg/ml | Siplizumab | | FeS anti-CD2 IgG1 | | FeS anti-CD2 IgG2 | | FcS anti-CD2 IgG4 | | NK only | |
|---|---|---|---|---|---|---|---|---|---|---|
| 0 | 14.7*** | 3.8 | | | | | | | 0.4*** | 0.2 |
| 0.001 | 17.6 | 6.1 | 19.1 | 4.8 | 13.9 | 4.5 | 15.7 | 4.2 | | |
| 0.01 | 23.3 | 7.9 | 18.6 | 5.8 | 13.0 | 4.4 | 15.8 | 5.7 | | |
| 0.1 | 28.8* | 8.0 | 16.0 | 5.5 | 13.1 | 5.9 | 13.4 | 4.5 | | |
| 1 | 37.9** | 10.9 | 16.8 | 6.2 | 11.3 | 4.2 | 14.4 | 6.0 | | |
| 10 | 43.5** | 12.6 | 16.6 | 5.3 | 12.6 | 5.3 | 34.5 | 4.7 | | |

TABLE 23

CD107a expression on NK cells after incubation of purified NK cells with increasing doses of anti-CD2 antibody and SPI-801 target cells. Mean percentage of CD107a+ NK cells ± SD (N = 6). Pre-incubation of NK cells with anti-CD2 mAbs for 48 hours before target cell addition. Repeated-measure one-way ANOVA results followed by Dunnett's multiple comparison test (*p < 0.05, p < 0.01, *p < 0.001).

| (Antibody) in µg/ml | Siplizumab | | CD2-binding molecule 2 | | CD2-binding molecule 3 | | CD2-binding molecule 4 | | NK only | |
|---|---|---|---|---|---|---|---|---|---|---|
| 0 | 14.7*** | 3.8 | | | | | | | 0.4*** | 0.2 |
| 0.001 | 17.6 | 6.1 | 19.1 | 4.2 | 13.9 | 4.5 | 15.7 | 4.2 | | |
| 0.01 | 23.3 | 7.9 | 18.6 | 5.8 | 13.0 | 4.4 | 15.8 | 5.7 | | |
| 0.1 | 28.8* | 8.0 | 16.0 | 5.5 | 13.1 | 5.9 | 13.4 | 4.5 | | |
| 1 | 37.9** | 10.9 | 16.8 | 6.2 | 11.3 | 4.2 | 14.4 | 6.0 | | |
| 10 | 43.5** | 12.6 | 16.6 | 5.3 | 12.6 | 5.3 | 14.5 | 4.7 | | |

TABLE 24

CD107a expression on NK cells after incubation of purified NK cells with increasing doses of Rituximab and CD20+ target cells. Mean percentage of CD107a+ NK cells ± SD (N = 6). Repeated-measure one-way ANOVA results followed by Dunnett's multiple comparison test ((*)p < 0.1, *p < 0.05, p < 0.01, *p < 0.001).

| [Rituximab] in µg/ml | No anti-CD2 | | Siplizamab | | CD2-binding molecule 2 | | CD2-binding molecule 3 | | CD2-binding molecule 4 | |
|---|---|---|---|---|---|---|---|---|---|---|
| 0 | 2.2 | 2.5 | | | | | | | | |
| 0.0001 | 2.4 | 2.4 | 5.1(*) | 4.3 | 2.2 | 2.1 | 1.7 | 1.7 | 2.3 | 2.7 |
| 0.001 | 2.7 | 2.0 | 5.3* | 4.3 | 2.6 | 2.2 | 1.9 | 1.8 | 2.6 | 2.2 |
| 0.01 | 5.8(*) | 2.8 | 5.4* | 4.3 | 5.5* | 3.0 | 4.7 | 3.0 | 5.3 | 3.4 |
| 0.1 | 13.7* | 7.1 | 7.0* | 4.2 | 13.4* | 7.0 | 12.8(*) | 8.0 | 13.3(*) | 8.8 |
| 1 | 18.8(*) | 10.9 | 8.7** | 3.7 | 17.9* | 9.8 | 15.4* | 8.5 | 15.7* | 8.4 |

TABLE 25

Normalized target cell count after incubation of purified NK cells with increasing doses of Rituximab and CD20+ target cells. Mean normalized target cell count ± SD (N = 6). Repeated-measure one-way ANOVA results followed by Dunnett's multiple comparison test ($^{(*)}$p < 0.1, *p < 0.05, p < 0.01, *p < 0.001, ****p < 0.0001).

| [Rituximab] in µg/ml | No anti-CD2 | | Siplizamab | | CD2-binding molecule 2 | | CD2-binding molecule 3 | | CD2-binding molecule 4 | |
|---|---|---|---|---|---|---|---|---|---|---|
| 0 | 100 | 0 | | | | | | | | |
| 0.0001 | 91.9 | 16.2 | 155.3 | 49.8 | 113.9 | 16.7 | 137.1 | 30.8 | 106.0 | 21.1 |
| 0.001 | 82.4 | 22.8 | 145.3 | 47.9 | 99.0 | 31.4 | 114.9 | 32.1 | 85.5 | 26.5 |
| 0.01 | 47.5** | 15.2 | 132.9 | 35.9 | 53.2* | 21.6 | 67.0$^{(*)}$ | 24.6 | 59.9* | 24.0 |
| 0.1 | 29.6**** | 10.3 | 94.7 | 20.7 | 29.0*** | 13.3 | 28.2**** | 9.5 | 30.3*** | 13.1 |
| 1 | 21.0**** | 8.0 | 64.1* | 22.1 | 22.1**** | 10.6 | 22.8**** | 8.4 | 26.0**** | 10.8 |

TABLE 26

CD2 expression on NK cells after incubation of purified NK cells with increasing doses of Rituximab and CD20+ target cells. Median CD2 fluorescence intensity on NK cells ± SEM (N = 6). Repeated-measure one-way ANOVA results followed by Dunnett's multiple comparison test (*p < 0.05, p < 0.01, *p < 0.001).

| [Rituximab] in µg/ml | No anti-CD2 | | Siplizamab | | CD2-binding molecule 2 | | CD2-binding molecule 3 | | CD2-binding molecule 4 | |
|---|---|---|---|---|---|---|---|---|---|---|
| 0 | 3299.7 | 451.4 | | | | | | | | |
| 0.0001 | 3346.0 | 456.6 | 1050.0** | 246.2 | 2469.3** | 333.1 | 679.2** | 71.8 | 1136.7** | 151.0 |
| 0.001 | 3452.2 | 456.6 | 1082.0** | 245.9 | 2610.5* | 334.7 | 706.5** | 69.3 | 1249.7** | 162.1 |
| 0.01 | 3780.0* | 491.8 | 1098.8** | 250.9 | 3037.2 | 394.4 | 792.5** | 84.4 | 1632.5** | 252.6 |
| 0.1 | 4155.3* | 587.9 | 1206.5** | 282.0 | 3647.2 | 470.9 | 898.2** | 105.4 | 2369.7* | 317.1 |
| 1 | 4303.0* | 601.5 | 1287.3** | 303.4 | 3898.5* | 495.1 | 889.3** | 109.2 | 2660.2* | 343 6 |

6.7 Example 6: Combination Therapy of an Anti-CD2 Antibody or an Antigen Binding Fragment Thereof and a CTLA-4 Co-Stimulation Blockade This example describes the effect of a combination therapy of an anti-CD2 antibody or an antigen binding fragment thereof and a CTLA-4 co-stimulation blockade in cell proliferation, CD2 response, and CD28 response.

6.7.1 Methods

Allogenic lymphocyte reaction (MLR): PBMC from two donors were mixed in PBS at a concentration of $1.5\text{-}2.0 \times 10^7$ cells per mL and stained with violet proliferation dye 450 (VPD450; BD Biosciences, San Diego, USA) following the manufacturer's instructions. This experiment used two-way allogeneic MLR (i.e. PBMC from neither donor were inactivated via irradiation/chemical treatment). Thus, PBMC from both donors functioned as responders and stimulators.

VPD450-stained PBMC were washed and resuspended in 10% heat-inactivated FBS (Gibco, Thermo Fisher Scientific Inc., Waltham, USA) in AIM V medium (Gibco, Thermo Fisher Scientific Inc., Waltham, USA). The resuspended PBMC were dispensed into round-bottom 96-well cell culture plates (for flow cytometry) and pure medium (no antibody controls) or medium supplemented with anti-CD2 antibody 1 (e.g., siplizumab) and/or abatacept or belatacept was added to a final concentration of $2 \times 10^6$ cells per mL (final volume 200 µL). MLRs were incubated at 37° C., 5% $CO_2$ for seven and/or 10 days. On day six, 100 µL fresh culture medium (no additional antibody; final volume=300 µL) was added to each well. On day eight, 100 µL medium was aspirated from each well without disturbing the cell pellet and replaced with 100 µL fresh culture medium.

Antibody concentrations used for anti-CD2 antibody 1 titrations were between 1 µg/mL and 50.8 µg/mL (10-step 3-fold serial dilution in culture medium). Anti-CD2 antibody 1 titrations with added CTLA4-Ig were supplemented with 100 µg/mL abatacept or belatacept throughout all serial dilution steps. Fusion protein concentrations used for abatacept/belatacept titrations were between 100 µg/mL and 0.1 µg/mL (10-step 10-fold serial dilution in culture medium). Abatacept/belatacept titrations with added anti-CD2 antibody 1 were supplemented with 1 µg/mL anti-CD2 antibody 1 throughout all serial dilution steps.

Flow cytometry: after seven days of MLR, samples were blocked with Fc-receptor binding inhibitor (Invitrogen; Thermo Fisher Scientific Inc., Waltham, USA) and then stained with anti-CD3 VioGreen (Clone REA613; Miltenyi, Bergisch Gladbach, Germany), anti-CD45RA BV650 (Clone HI100; BD Biosciences, San Diego USA), anti-CD2 BV786 (Clone RPA-2.10; BD Biosciences, San Diego USA), anti-CD8 BB550 (Clone RPA-T8; BD Biosciences, San Diego USA), anti-CD56 PE (Clone REA196; Miltenyi, Bergisch Gladbach, Germany), anti-HLA-DR PerCP-Cy5.5 (Clone G46-6; BD Biosciences, San Diego USA), anti-CCR7 APC (Clone G43H7; BD Biosciences, San Diego USA) and anti-CD4 APC-Vio770 (Clone REA623; Miltenyi, Bergisch Gladbach, Germany). T cells were gated as $CD3^+ CD56^-$. After 10 days of MLR, samples were blocked with Fc-receptor binding inhibitor (Invitrogen; Thermo Fisher Scientific Inc., Waltham, USA) and then stained with anti-CD45RA BV650 (Clone HI100; BD Biosciences, San Diego USA), anti-CD3 BV786 (Clone SK7; BD Biosciences, San Diego USA), anti-CD8 BB550 (Clone RPA-T8; BD Biosciences, San Diego USA), anti-FoxP3 PE (Clone 236A/E7; BD Biosciences, San Diego USA), anti-CD127 PerCP-Cy5.5 (Clone HIL-7R-M21 [BD Biosciences, San Diego USA] or A019D5 [Biolegend, Sunnyvale USA]), anti-CCR7 APC (Clone G43H7; BD Biosciences, San Diego USA), anti-CD25 Alexa Fluor 700 (Clone M-A251; BD Biosciences, San Diego USA) and anti-CD4 APC-Vio770 (Clone REA623; Miltenyi, Bergisch Gladbach, Germany). T cells were gated as $CD3^+$. Cell proliferation was assessed using VPD450 (VPD450high: Non-proliferated; VPD450low: Proliferated). Samples were stained in the dark at 4° C. and washed twice in saline solution followed by acquisition using a BD Celesta flow cytometer (BD Biosciences, San Diego USA). Intracellular FoxP3 staining was carried out using eBioscience FoxP3/transcription factor staining buffer set (Invitrogen; Thermo Fisher Scientific Inc., Waltham, USA) according to the manufacturer's instructions. Tregs were identified as $CD4^+$ $CD127^-$ $CD25^+$ $FoxP3^+$.

Graphs and statistical analysis: visualization of results and statistical analysis of underlying data were carried out using GraphPad Prism 8 software (GraphPad Software, San Diego, USA) (refer to Tables 27-35). Data were analyzed using one-way ANOVA followed by Dunnett's multiple comparison test with no antibody controls serving as the comparison data set.

6.7.2 Results

Figure 10:
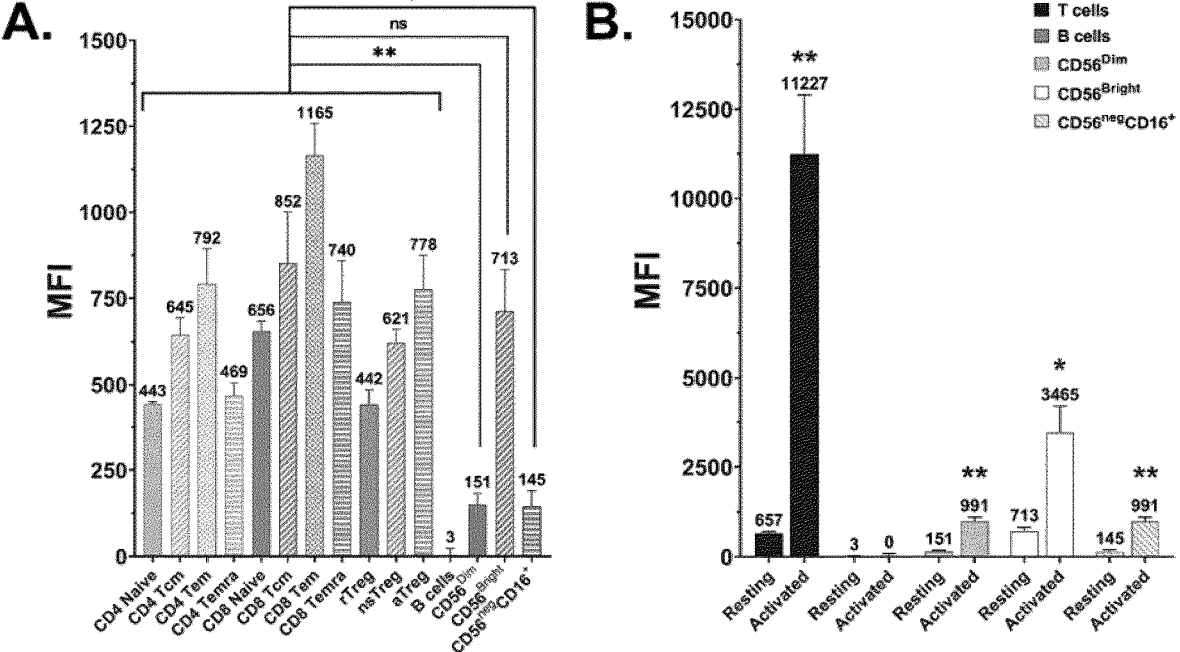

T cell proliferation: T cell proliferation was assessed via flow cytometry after seven and 10 days of MLR to assess the inhibitory effects of combining anti-CD2 antibody 1 (e.g., siplizumab) with abatacept or belatacept (n=6; Tables 27-30). As shown in FIG. 18A, 10-100 µg/mL abatacept (or in some cases alefacept) ($p \leq 0.0303$), 1-100 µg/mL belatacept ($p \leq 0.0156$) and 0.012-1 µg/mL anti-CD2 antibody 1 ($p \leq 0.0105$) induced significant reduction in CD4 T cell proliferation after seven days of MLR relative to untreated controls. Further, 100 µg/mL abatacept (or in some cases alefacept) ($p \leq 0.0028$), 1-100 µg/mL belatacept ($p \leq 0.0411$), and 0.11-1 µg/mL anti-CD2 antibody 1 ($p \leq 0.0071$) induced significant reduction in CD4 T cell proliferation after ten days of MLR (FIG. 18C). Additionally, a significant and near complete inhibition of CD4 T cell proliferation was mediated by combination of anti-CD2 antibody 1 with 100 µg/mL abatacept ($p \leq 0.0183$) or 100 µg/mL belatacept ($p \leq 0.0061$) (FIGS. 18A and 18C). Combination therapy with abatacept or belatacept decreased the half maximum inhibitory concentration (IC50) for the suppressive effect of anti-CD2 antibody 1 on day seven of MLR from 0.0068 µg/mL (monotherapy) to 0.0015 µg/mL and 0.0011 µg/mL, respectively. Following ten days of MLR, IC50 of anti-CD2 antibody 1 monotherapy was 0.0235 µg/mL and 0.0035 µg/mL or 0.0025 µg/mL for combination with 100 µg/mL abatacept or 100 µg/mL belatacept, respectively. A similar pattern was observed for inhibition of CD8 T cell proliferation (FIGS. 18B and 18D). After seven days of MLR, inhibition of CD8 T cell proliferation by anti-CD2 antibody 1 monotherapy had an IC50 of 0.0105 µg/mL whereas combination therapy with abatacept or belatacept lowered the IC50 of anti-CD2 antibody 1 to 0.0012 µg/mL for both the combination of anti-CD2 antibody 1 with abatacept and of anti-CD2 antibody 1 with belatacept. Following 10 days of MLR, anti-CD2 antibody 1 monotherapy had an IC50 of 0.024 µg/mL which was lowered to 0.0017 µg/mL when combined with abatacept or belatacept. Similar results were observed in a separate experiment (with the same conditions) as shown in FIGS. 18E-18H.

TABLE 27

| CD4 T cell proliferation after 7 days of allogeneic mixed lymphocyte reaction | | | | | | | | | | |
|---|---|---|---|---|---|---|---|---|---|---|
| [ANTIBODY/ FUSION PROTEIN] µg/mL | ABATACEPT | | BELATACEPT | | ANTI-CD2 ANTIBODY 1 | | ANTI-CD2 ANTIBODY 1 + 100 µg/mL ABATACEPT | | ANTI-CD2 ANTIBODY 1 + 100 µg/mL BELATACEPT | |
| 0 | 80.8 | 2.0 (SD) | | | | | | | | |
| 100 | 43.0* | 15.8 (SD) | 40.6** | 13.5 (SD) | | | | | | |
| 10 | 44.5* | 12.9 (SD) | 51.9* | 10.3 (SD) | | | | | | |
| 1 | 47.6 | 20.1 (SD) | 46.2** | 10.1 (SD) | | | | | | |
| 0.1 | 56.7 | 15.1 (SD) | 53.9 | 15.7 (SD) | | | | | | |
| 0.01 | 73.6 | 7.3 (SD) | 70.4 | 9.9 (SD) | | | | | | |
| 0.001 | 81.9 | 3.8 (SD) | 75.9 | 7.5 (SD) | | | | | | |
| 0.0001 | 83.5 | 4.4 (SD) | 80.0 | 7.6 (SD) | | | | | | |
| 0.00001 | 79.4 | 8.5 (SD) | 84.5 | 3.2 (SD) | | | | | | |
| 0.000001 | 83.2 | 2.7 (SD) | 83.2 | 3.0 (SD) | | | | | | |
| 0.0000001 | 82.5 | 3.6 (SD) | 79.2 | 8.2 (SD) | | | | | | |
| 1 | | | | | 6.3**** | 3.8 (SD) | 1.6**** | 1.6 (SD) | 0.9**** | 0.3 (SD) |
| 0.333333 | | | | | 7.1**** | 4.3 (SD) | 1.3**** | 0.9 (SD) | 2.9**** | 4.7 (SD) |
| 0.111111 | | | | | 8.3**** | 5.6 (SD) | 1.6**** | 1.2 (SD) | 1.1**** | 0.9 (SD) |
| 0.037037 | | | | | 9.0**** | 8.0 (SD) | 2.2**** | 2.5 (SD) | 2.2**** | 1.9 (SD) |
| 0.012346 | | | | | 20.9* | 20.2 (SD) | 2.8**** | 3.1 (SD) | 2.9**** | 3.8 (SD) |

TABLE 27-continued

CD4 T cell proliferation after 7 days of allogeneic mixed lymphocyte reaction

| [ANTIBODY/ FUSION PROTEIN] µg/mL | ABATACEPT | BELATACEPT | ANTI-CD2 ANTIBODY 1 | | ANTI-CD2 ANTIBODY 1 + 100 µg/mL ABATACEPT | | ANTI-CD2 ANTIBODY 1 + 100 µg/mL BELATACEPT | |
|---|---|---|---|---|---|---|---|---|
| 0.004115 | | | 61.6 | 21.6 (SD) | 9.0*** | 9.8 (SD) | 9.7**** | 8.0 (SD |
| 0.001372 | | | 82.3 | 8.1 (SD) | 24.8** | 17.8 (SD) | 24.4** | 11.2 (SD) |
| 0.000457 | | | 84.6 | 3.9 (SD) | 36.7** | 14.0 (SD) | 40.5** | 13.3 (SD) |
| 0.000152 | | | 73.2 | 14.4 (SD) | 41.8* | 16.0 (SD) | 49.2** | 9.6 (SD) |
| 0.0000508 | | | 83.7 | 7.1 (SD) | 40.0** | 13.2 (SD) | 48.1** | 8.4 (SD) |

Data displayed as mean percentage of proliferated CD4 T cells + standard deviation (SD) (N = 6 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001).
Standard deviation is shown as SD.

TABLE 28

CD4 T cell proliferation after 10 days of allogeneic mixed lymphocyte reaction

| [ANTIBODY/ FUSION PROTEIN] µg/mL | ABATACEPT | | BELATACEPT | | ANTI-CD2 ANTIBODY 1 | | ANTI-CD2 ANTIBODY 1 + 100 µg/mL ABATACEPT | | ANTI-CD2 ANTIBODY 1 + 100 µg/mL BELATACEPT | |
|---|---|---|---|---|---|---|---|---|---|---|
| 0 | 85.9 | 5.9 (SD) | | | | | | | | |
| 100 | 64.2** | 9.2 (SD) | 65.3* | 14.6 (SD | | | | | | |
| 10 | 69.9 | 13.8 (SD | 64.8* | 14.4 (SD) | | | | | | |
| 1 | 65.3 | 19.9 (SD | 62.1* | 11.3 (SD | | | | | | |
| 0.1 | 76.1 | 9.2 (SD) | 69.4 | 14.0 (SD | | | | | | |
| 0.01 | 80.5 | 8.8 (SD) | 76.0 | 10.6 (SD | | | | | | |
| 0.001 | 86.3 | 5.6 (SD | 83.8 | 8.6 (SD | | | | | | |
| 0.0001 | 87.5 | 5.1 (SD) | 86.1 | 5.6 (SD) | | | | | | |
| 0.00001 | 84.7 | 7.4 (SD) | 84.5 | 7.7 (SD) | | | | | | |
| 0.000001 | 86.0 | 7.3 (SD) | 84.8 | 5.8 (SD | | | | | | |
| 0.0000001 | 84.8 | 5.4 (SD) | 88.1 | 4.4 (SD) | | | | | | |
| 1 | | | | | 21.4** | 20.7 (SD) | 1.8**** | 1.8 (SD) | 1.9**** | 1.2 (SD) |
| 0.333333 | | | | | 27.7** | 17.8 (SD) | 2.3**** | 1.9 (SD) | 1.9**** | 1.3 (SD) |
| 0.111111 | | | | | 24.8*** | 12.2 (SD) | 2.5**** | 1.7 (SD) | 3.6**** | 3.4 (SD) |
| 0.037037 | | | | | 43.2 | 24.8 (SD) | 4.6**** | 7.7 (SD) | 2.5**** | 1.8 (SD) |
| 0.012346 | | | | | 68.1 | 27.2 (SD) | 10.4*** | 14.4 (SD) | 8.5**** | 11.2 (SD) |
| 0.004115 | | | | | 79.5 | 11.0 (SD) | 30.1** | 21.5 (SD) | 26.5* | 24.7 (SD) |
| 0.001372 | | | | | 82.9 | 8.4 (SD) | 47.4* | 19.0 (SD) | 42.4** | 16.6 (SD) |
| 0.000457 | | | | | 86.6 | 7.7 (SD) | 62.6 | 15.4 (SD) | 54.9 | 20.4 (SD) |
| 0.000152 | | | | | 84.1 | 7.5 (SD) | 62.9 | 15.2 (SD) | 62.2* | 13.0 (SD) |
| 0.0000508 | | | | | 87.8 | 4.8 (SD) | 58.2* | 13.0 (SD) | 61.6* | 16.3 (SD) |

Data displayed as mean percentage of proliferated CD4 T cells ± standard deviation (SD) (N = 6 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001).

115 116

TABLE 29

CD8 T cell proliferation after 7 days of allogeneic mixed lymphocyte reaction

| [ANTIBODY/ FUSION PROTEIN] µg/mL | ABATACEPT | (SD) | BELATACEPT | (SD) | ANTI-CD2 ANTIBODY 1 | (SD) | ANTI-CD2 ANTIBODY 1 + 100 µg/mL ABATACEPT | (SD) | ANTI-CD2 ANTIBODY 1 + 100 µg/mL BELATACEPT | (SD) |
|---|---|---|---|---|---|---|---|---|---|---|
| 0 | 85.0 | 6.1 | | | | | | | | |
| 100 | 60.5 | 21.2 | 40.8** | 18.5 | | | | | | |
| 10 | 57.4 | 20.4 | 53.9 | 23.9 | | | | | | |
| 1 | 60.0 | 20.2 | 61.4* | 11.2 | | | | | | |
| 0.1 | 65.1 | 17.7 | 60.0 | 22.5 | | | | | | |
| 0.01 | 85.1 | 8.5 | 82.4 | 9.5 | | | | | | |
| 0.001 | 86.0 | 9.6 | 84.4 | 4.4 | | | | | | |
| 0.0001 | 85.4 | 8.1 | 88.6 | 6.4 | | | | | | |
| 0.00001 | 83.7 | 7.9 | 87.9 | 8.5 | | | | | | |
| 0.000001 | 85.6 | 10.3 | 87.6 | 7.5 | | | | | | |
| 0.0000001 | 86.6 | 7.9 | 87.3 | 6.9 | | | | | | |
| 1 | | | | | 9.4**** | 8.0 | 2.2**** | 1.9 | 2.2**** | 2.1 |
| 0.333333 | | | | | 7.9**** | 9.2 | 2.8**** | 2.5 | 2.3**** | 2.1 |
| 0.111111 | | | | | 9.8*** | 11.4 | 2.5**** | 2.5 | 2.1**** | 2.0 |
| 0.037037 | | | | | 13.1*** | 12.8 | 3.7**** | 4.0 | 1.9**** | 2.0 |
| 0.012346 | | | | | 39.6 | 33.6 | 4.1**** | 4.5 | 8.6**** | 7.9 |
| 0.004115 | | | | | 76.1 | 22.8 | 10.3*** | 11.9 | 6.5**** | 5.7 |
| 0.001372 | | | | | 89.1 | 7.6 | 24.5** | 22.3 | 25.7** | 16.5 |
| 0.000457 | | | | | 87.9 | 5.9 | 45.3* | 19.3 | 35.6* | 22.3 |
| 0.000152 | | | | | 84.8 | 10.9 | 42.7* | 19.2 | 48.5* | 21.5 |
| 0.0000508 | | | | | 85.8 | 9.4 | 50.9* | 18.7 | 42.6* | 24.3 |

Data displayed as mean percentage of proliferated CD8 T cells ± standard deviation (SD) (N = 6 donor pairs). Data were analyzed using one-way ANOVA followed by Dunnett's multiple comparison test with untreated controls (no antibody) serving as the comparison data set ($*p < 0.05$, $p < 0.01$, $*p < 0.001$, $****p < 0.0001$).

TABLE 30

CD8 T cell proliferation after 10 days of allogeneic mixed lymphocyte reaction

| [ANTIBODY/ FUSION PROTEIN] µg/mL | ABATACEPT | (SD) | BELATACEPT | (SD) | ANTI-CD2 ANTIBODY 1 | ANTI-CD2 ANTIBODY 1 + 100 µg/mL ABATACEPT | ANTI-CD2 ANTIBODY 1 + 100 µg/mL BELATACEPT |
|---|---|---|---|---|---|---|---|
| 0 | 94.6 | 3.1 | | | | | |
| 100 | 73.7 | 17.7 | 79.8 | 10.6 | | | |
| 10 | 83.4 | 9.5 | 78.1 | 12.9 | | | |
| 1 | 87.7 | 6.6 | 73.9 | 17.4 | | | |
| 0.1 | 89.6 | 6.7 | 81.1 | 11.6 | | | |
| 0.01 | 93.0 | 2.9 | 90.6 | 6.3 | | | |

TABLE 30-continued

| CD8 T cell proliferation after 10 days of allogeneic mixed lymphocyte reaction | | | | | | | | |
|---|---|---|---|---|---|---|---|---|
| [ANTIBODY/ FUSION PROTEIN] μg/mL | ABATACEPT | | BELATACEPT | | ANTI-CD2 ANTIBODY 1 | ANTI-CD2 ANTIBODY 1 + 100 μg/mL ABATACEPT | | ANTI-CD2 ANTIBODY 1 + 100 μg/mL BELATACEPT |
| 0.001 | 94.7 | 2.7 (SD) | 94.2 | 3.1 (SD) | | | | |
| 0.0001 | 94.9 | 4.2 (SD) | 94.8 | 1.9 (SD) | | | | |
| 0.00001 | 95.1 | 2.2 (SD) | 94.8 | 2.4 (SD) | | | | |
| 0.000001 | 95.2 | 1.6 (SD) | 94.2 | 3.4 (SD) | | | | |
| 0.0000001 | 94.4 | 2.8 (SD) | 94.5 | 2.4 (SD) | | | | |
| 1 | | | | | 15.0*** 13.1 (SD) | 5.2**** | 7.5 (SD) | 2.8**** 3.0 (SD) |
| 0.333333 | | | | | 15.2*** 14.0 (SD) | 3.4**** | 4.5 (SD) | 2.3**** 1.8 (SD) |
| 0.111111 | | | | | 21.8* 27.0 (SD) | 2.1**** | 1.5 (SD) | 5.4**** 9.0 (SD) |
| 0.037037 | | | | | 32.0* 29.9 (SD) | 4.3**** | 4.3 (SD) | 2.5**** 2.3 (SD) |
| 0.012346 | | | | | 76.3 26.6 (SD) | 7.4**** | 10.3 (SD) | 4.2**** 4.1 (SD) |
| 0.004115 | | | | | 92.8 4.0 (SD) | 27.4* | 34.3 (SD) | 23.3* 30.7 (SD) |
| 0.001372 | | | | | 93.0 6.3 (SD) | 44.4 | 32.4 (SD) | 44.2 30.0 (SD) |
| 0.000457 | | | | | 94.4 2.7 (SD) | 62.5 | 24.4 (SD) | 63.0 25.5 (SD) |
| 0.000152 | | | | | 93.3 3.0 (SD) | 77.6 | 14.3 (SD) | 72.8 13.4 (SD) |
| 0.0000508 | | | | | 93.7 4.2 (SD) | 73.1 | 17.7 (SD) | 70.9 18.5 (SD) |

Data displayed as mean percentage of proliferated CD8 T cells ± standard deviation (SD) (N = 6 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001)

Different concentrations of abatacept and belatacept were tested to determine the concentrations of abatacept and belatacept required to reach maximum efficacy in combination with anti-CD2 antibody 1 (FIGS. 19A-19H and FIG. 20). As such, concentrations of abatacept or belatacept were titrated while keeping the concentration of the anti-CD2 antibody 1 fixed (n=9 for FIGS. 19A-19D and n=3 for FIGS. 19E-19H; Tables 31-34). The mean T cell (CD4 and CD8) proliferation after cells were incubated for seven days or 10 days with a control, anti-CD2 antibody 1, belatacept, abatacept, a combination of anti-CD2 antibody 1 and belatacept, or a combination of anti-CD2 antibody 1 and abatacept are shown in FIGS. 19A-19H. Varying amounts of belatacept and abatacept were tested (between ~1-100 μg/mL). A synergistic effect was observed when varying amounts of belatacept (1-100 pig/mL) was used in combination with anti-CD2 antibody 1 and when varying amounts of abatacept (10-100 pig/mL) was used in combination with anti-CD2 antibody 1.

TABLE 31

| CD4 T cell proliferation after 7 days of allogeneic mixed lymphocyte reaction | | | | | | | | | |
|---|---|---|---|---|---|---|---|---|---|
| [ANTIBODY/ FUSION PROTEIN] μg/mL | ABATACEPT | | BELATACEPT | | ANTI-CD2 ANTIBODY 1 | ABATACEPT + 1 μg/mL ANTI-CD2 ANTIBODY 1 | | BELATACEPT + 1 μg/mL ANTI-CD2 ANTIBODY 1 | |
| 0 | 65.2 | 13.4 (SD) | | | | | | | |
| 100 | 23.1*** | 13.3 (SD) | 22.1*** | 14.5 (SD) | | 1.4**** | 1.0 (SD) | 1.5**** | 0.9 (SD) |
| 10 | 26.5*** | 15.7 (SD) | 21.0*** | 14.0 (SD) | | 1.9**** | 1.0 (SD) | 2.2**** | 2.2 (SD) |
| 1 | 31.4**** | 15.8 (SD) | 23.8*** | 8.5 (SD) | | 4.1**** | 3.1 (SD) | 1.5**** | 0.8 (SD) |
| 0.1 | 36.1**** | 17.8 (SD) | 32.0*** | 11.0 (SD) | | 5.8**** | 3.3 (SD) | 2.8**** | 1.6 (SD) |
| 0.01 | 60.3 | 18.8 (SD) | 43.3* | 21.9 (SD) | | 6.7**** | 5.0 (SD) | 6.3**** | 4.2 (SD) |
| 0.001 | 67.1 | 12.6 (SD) | 56.4 | 20.1 (SD) | | 9.9**** | 7.6 (SD) | 7.9**** | 6.8 (SD |

TABLE 31-continued

| CD4 T cell proliferation after 7 days of allogeneic mixed lymphocyte reaction | | | | | | | | | | |
|---|---|---|---|---|---|---|---|---|---|---|
| [ANTIBODY/ FUSION PROTEIN] μg/mL | ABATACEPT | | BELATACEPT | | ANTI-CD2 ANTIBODY 1 | | ABATACEPT + 1 μg/mL ANTI-CD2 ANTIBODY 1 | | BELATACEPT + 1 μg/mL ANTI-CD2 ANTIBODY 1 | |
| 0.0001 | 64.0 | 19.1 (SD) | 64.8 | 17.8 (SD) | | | 7.4**** | 3.4 (SD) | 8.0**** | 5.2 (SD) |
| 0.00001 | 61.6 | 16.6 (SD) | 66.7 | 14.0 (SD) | | | 8.1**** | 5.9 (SD) | 10.6**** | 6.9 (SD) |
| 0.000001 | 64.3 | 17.4 (SD | 61.8 | 16.3 (SD | | | 9.0**** | 6.9 (SD) | 8.2**** | 5.3 (SD) |
| 0.0000001 | 58.4 | 18.0 (SD | 60.4 | 19.2 (SD | | | 7.2**** | 4.7 (SD) | 8.8**** | 4.7 (SD |
| 1 | | | | | 10.8**** | 8.0 (SD) | | | | |
| 0.333333 | | | | | 10.7**** | 7.6 (SD) | | | | |
| 0.111111 | | | | | 11.7**** | 9.2 (SD) | | | | |
| 0.037037 | | | | | 15.3*** | 13.8 (SD) | | | | |
| 0.012346 | | | | | 35.9** | 13.5 (SD) | | | | |
| 0.004115 | | | | | 62.7 | 16.0 (SD) | | | | |
| 0.001372 | | | | | 68.5 | 10.9 (SD) | | | | |
| 0.000457 | | | | | 65.0 | 17.4 (SD | | | | |
| 0.000152 | | | | | 65.1 | 19.0 (SD) | | | | |
| 0.0000508 | | | | | 65.9 | 16.9 (SD) | | | | |

Data displayed as mean percentage of proliferated CD4 T cells ± standard deviation (SD) (N = 9 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001).

TABLE 32

| CD4 T cell proliferation after 10 days of allogeneic mixed lymphocyte reaction | | | | | | | | | | |
|---|---|---|---|---|---|---|---|---|---|---|
| [ANTIBODY/ FUSION PROTEIN] μg/mL | ABATACEPT | | BELATACEPT | | ANTI-CD2 ANTIBODY 1 | | ABATACEPT + 1 μg/mL ANTI-CD2 ANTIBODY 1 | | BELATACEPT + 1 μg/mL ANTI-CD2 ANTIBODY 1 | |
| 0 | 74.1 | 13.6 (SD) | | | | | | | | |
| 100 | 37.6**** | 17.7 (SD) | 41.1*** | 17.1 (SD) | | | 2.8**** | 2.1 (SD) | 2.9**** | 2.4 (SD) |
| 10 | 45.2*** | 12.6 (SD) | 41.1*** | 16.4 (SD) | | | 4.3**** | 3.6 (SD) | 2.3**** | 1.7 (SD) |
| 1 | 54.4** | 14.1 (SD) | 42.9*** | 18.1 (SD) | | | 10.6**** | 8.0 (SD) | 3.0**** | 2.9 (SD |
| 0.1 | 55.3* | 15.7 (SD) | 48.7*** | 11.4 (SD) | | | 21.0*** | 19.1 (SD) | 9.7**** | 11.9 (SD |
| 0.01 | 67.5 | 16.5 (SD) | 62.0 | 11.7 (SD) | | | 25.2** | 19.3 (SD) | 18.0*** | 14.5 (SD) |
| 0.001 | 76.2 | 11.4 (SD) | 71.0 | 13.0 (SD) | | | 28.0*** | 15.6 (SD) | 26.0** | 19.6 SD) |
| 0.0001 | 73.3 | 14.3 (SD) | 75.0 | 9.3 (SD) | | | 30.9** | 16.6 (SD) | 28.7*** | 18.4 (SD) |
| 0.00001 | 74.3 | 14.3 (SD) | 73.5 | 12.3 (SD) | | | 29.3** | 19.3 (SD) | 24.5*** | 12.8 (SD) |
| 0.000001 | 72.1 | 13.2 (SD) | 69.5 | 19.3 (SD) | | | 28.4** | 16.0 (SD) | 29.6*** | 14.7 (SD) |
| 0.0000001 | 70.8 | 19.3 (SD) | 72.1 | 18.0 (SD) | | | 27.4** | 15.6 (SD) | 25.5*** | 16.0 (SD) |
| 1 | | | | | 28.0** | 17.9 (SD) | | | | |
| 0.333333 | | | | | 34.6** | 19.4 (SD) | | | | |
| 0.111111 | | | | | 42.6* | 18.3 (SD) | | | | |

TABLE 32-continued

| CD4 T cell proliferation after 10 days of allogeneic mixed lymphocyte reaction | | | | | |
| --- | --- | --- | --- | --- | --- |
| [ANTIBODY/ FUSION PROTEIN] µg/mL | ABATACEPT | BELATACEPT | ANTI-CD2 ANTIBODY 1 | | ABATACEPT + 1 µg/mL ANTI-CD2 ANTIBODY 1 | BELATACEPT + 1 µg/mL ANTI-CD2 ANTIBODY 1 |
| 0.037037 | | | 55.9 | 21.3 (SD) | | |
| 0.012346 | | | 70.9 | 17.0 (SD) | | |
| 0.004115 | | | 73.8 | 10.3 (SD) | | |
| 0.001372 | | | 78.4 | 8.5 (SD) | | |
| 0.000457 | | | 73.1 | 13.4 (SD) | | |
| 0.000152 | | | 70.9 | 16.4 (SD) | | |
| 0.0000508 | | | 76.9 | 13.2 (SD) | | |

Data displayed as mean percentage of proliferated CD4 T cells ± standard deviation (SD) (N = 9 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001)

TABLE 33

| CD8 T cell proliferation after 7 days of allogeneic mixed lymphocyte reaction | | | | | |
| --- | --- | --- | --- | --- | --- |
| [ANTIBODY/ FUSION PROTEIN] µg/mL | ABATACEPT | BELATACEPT | ANTI-CD2 ANTIBODY 1 | ABATACEPT + 1 µg/mL ANTI-CD2 ANTIBODY 1 | BELATACEPT + 1 µg/mL ANTI-CD2 ANTIBODY 1 |
| 0 | 80.5 11.9 (SD) | | | | |
| 100 | 35.3** 24.6 (SD) | 27.8*** 17.3 (SD) | | 1.1**** 1.0 (SD) | 1.6**** 1.3 (SD) |
| 10 | 31.0*** 17.0 (SD) | 33.3** 24.8 (SD) | | 1.3**** 0.8 (SD) | 1.6**** 1.3 (SD) |
| 1 | 46.9** 17.9 (SD) | 41.6** 23.5 (SD) | | 2.3**** 1.4 (SD) | 1.4**** 0.9 (SD) |
| 0.1 | 51.2* 15.6 (SD) | 41.3** 22.0 (SD) | | 3.9**** 2.6 (SD) | 2.8**** 2.2 (SD) |
| 0.01 | 74.4 13.4 (SD) | 60.3 19.9 (SD) | | 7.9**** 4.9 (SD) | 5.1**** 2.6 (SD) |
| 0.001 | 80.7 11.5 (SD) | 74.9 15.7 (SD) | | 7.8**** 4.6 (SD) | 6.9**** 4.9 (SD) |
| 0.0001 | 78.0 13.3 (SD) | 77.2 15.7 (SD) | | 8.0**** 4.5 (SD) | 8.1**** 6.7 (SD) |
| 0.00001 | 78.2 15.7 (SD) | 79.5 13.8 (SD) | | 7.1**** 4.7 (SD) | 8.9**** 4.5 (SD) |
| 0.000001 | 77.9 15.7 (SD) | 77.9 17.0 (SD) | | 7.2**** 5.3 (SD) | 7.8**** 4.9 (SD) |
| 0.0000001 | 77.4 10.6 (SD) | 78.3 12.0 (SD) | | 7.8**** 5.3 (SD) | 12.4**** 10.2 (SD) |
| 1 | | | 7.9**** 4.7 (SD) | | |
| 0.333333 | | | 9.5**** 5.7 (SD) | | |
| 0.111111 | | | 11.4**** 5.6 (SD) | | |
| 0.037037 | | | 15.0**** 8.2 (SD) | | |
| 0.012346 | | | 49.1* 24.3 (SD) | | |
| 0.004115 | | | 68.4 26.1 (SD) | | |
| 0.001372 | | | 70.3 21.7 (SD) | | |
| 0.000457 | | | 74.9 18.5 (SD) | | |

TABLE 33-continued

CD8 T cell proliferation after 7 days of allogeneic mixed lymphocyte reaction

| [ANTIBODY/ FUSION PROTEIN] µg/mL | ABATACEPT | BELATACEPT | ANTI-CD2 ANTIBODY 1 | | ABATACEPT + 1 µg/mL ANTI-CD2 ANTIBODY 1 | BELATACEPT + 1 µg/mL ANTI-CD2 ANTIBODY 1 |
|---|---|---|---|---|---|---|
| 0.000152 | | | 80.6 | 13.5 (SD) | | |
| 0.0000508 | | | 79.6 | 11.4 (SD) | | |

Data displayed as mean percentage of proliferated CD8 T cells ± standard deviation (SD) (N = 9 donor pairs). Data were analyzed using one-way ANOVA followed by Dunnett's multiple comparison test with untreated controls (no antibody) serving as the comparison data set (*$p < 0.05$, $p < 0.01$, *$p < 0.001$, ****$p < 0.0001$)

TABLE 34

CD8 T cell proliferation after 10 days of allogeneic mixed lymphocyte reaction

| [ANTIBODY/ FUSION PROTEIN] µg/mL | ABATACEPT | | BELATACEPT | | ANTI-CD2 ANTIBODY 1 | | ABATACEPT + 1 µg/mL ANTI-CD2 ANTIBODY 1 | | BELATACEPT + 1 µg/mL ANTI-CD2 ANTIBODY 1 | |
|---|---|---|---|---|---|---|---|---|---|---|
| 0 | 88.9 | 8.7 (SD) | | | | | | | | |
| 100 | 56.3* | 24.5 (SD) | 50.7** | 23.3 (SD) | | | 1.5**** | 1.6 (SD) | 1.5**** | 1.5 (SD) |
| 10 | 67.7* | 20.8 (SD) | 55.7** | 21.1 (SD) | | | 2.4**** | 1.8 (SD) | 1.2**** | 1.1 (SD) |
| 1 | 68.0* | 20.1 (SD) | 57.1** | 22.4 (SD) | | | 6.2**** | 6.5 (SD) | 1.6**** | 1.2 (SD) |
| 0.1 | 74.2* | 16.0 (SD) | 58.3* | 23.2 (SD) | | | 12.0**** | 9.9 (SD) | 4.5**** | 5.8 (SD) |
| 0.01 | 86.5 | 12.8 (SD) | 80.2* | 12.7 (SD) | | | 12.2**** | 9.1 (SD | 8.0**** | 6.1 (SD |
| 0.001 | 88.8 | 7.4 (SD) | 85.9 | 12.3 (SD) | | | 13.5**** | 11.7 (SD | 11.5**** | 8.0 (SD |
| 0.0001 | 87.0 | 9.9 (SD) | 87.7 | 10.5 (SD) | | | 17.8**** | 15.1 (SD) | 11.9**** | 5.6 (SD) |
| 0.00001 | 88.5 | 10.1 (SD) | 88.9 | 7.5 (SD) | | | 14.0**** | 13.5 (SD) | 13.6**** | 6.6 (SD) |
| 0.000001 | 86.2 | 12.9 (SD) | 88.4 | 7.4 (SD) | | | 15.1**** | 10.2 (SD | 15.0**** | 9.3 SD |
| 0.0000001 | 87.3 | 10.8 (SD) | 88.5 | 9.3 (SD) | | | 13.3**** | 12.7 (SD) | 11.9**** | 8.3 (SD) |
| 1 | | | | | 16.1**** | 11.8 (SD) | | | | |
| 0.333333 | | | | | 17.6**** | 14.4 (SD) | | | | |
| 0.111111 | | | | | 25.3*** | 19.6 (SD) | | | | |
| 0.037037 | | | | | 42.0* | 27.4 (SD) | | | | |
| 0.012346 | | | | | 77.7 | 19.6 (SD) | | | | |
| 0.004115 | | | | | 81.6 | 18.6 (SD) | | | | |
| 0.001372 | | | | | 85.2 | 12.7 (SD) | | | | |
| 0.000457 | | | | | 85.7 | 10.5 (SD | | | | |
| 0.000152 | | | | | 86.9 | 10.8 (SD) | | | | |
| 0.0000508 | | | | | 87.4 | 11.6 (SD) | | | | |

Data displayed as mean percentage of proliferated CD8 T cells ± standard deviation (SD) (N = 9 donor pairs). Data were analyzed using one-way ANOVA followed by Dunnett's multiple comparison test with untreated controls (no antibody) serving as the comparison data set (*$p < 0.05$, $p < 0.01$, *$p < 0.001$, ****$p < 0.0001$)

Regulatory T cell (Treg) enrichment: combination therapy of anti-CD2 antibody 1 (e.g., siplizumab) and abatacept or belatacept were evaluated for their effect of Treg enrichment increased to where maximum inhibition of T cell proliferation was reached (10-100 µg/mL abatacept or 1-100 µg/mL belatacept).

TABLE 35

| [ANTIBODY/FUSION PROTEIN] µg/mL | ABATACEPT | | BELATACEPT | | ANTI-CD2 ANTIBODY 1 | | ABATACEPT + 1 µg/mL ANTI-CD2 ANTIBODY 1 | | BELATACEPT + 1 µg/mL ANTI-CD2 ANTIBODY 1 | |
|---|---|---|---|---|---|---|---|---|---|---|
| | | | | | | | | | | |
| 0 | 5.4 | 6.2 (SD) | | | | | | | | |
| 100 | 8.7 | 9.4 (SD) | 8.3 | 12.9 (SD) | | | 5.2 | 4.5 (SD) | 3.4 | 3.1 (SD) |
| 10 | 11.2 | 11.7 (SD) | 11.2 | 15.3 (SD) | | | 9.0 | 7.1 (SD) | 6.5 | 5.7 (SD) |
| 1 | 9.7 | 9.2 (SD) | 10.2 | 10.7 (SD) | | | 20.2** | 8.6 (SD) | 6.9 | 6.2 (SD) |
| 0.1 | 11.1 | 10.0 (SD) | 15.5 | 15.1 (SD) | | | 20.0** | 7.2 (SD) | 17.2 | 9.1 (SD) |
| 0.01 | 7.2 | 6.5 (SD) | 9.1 | 8.4 (SD) | | | 24.3** | 8.2 (SD) | 23.2* | 13.8 (SD) |
| 0.001 | 5.5 | 5.7 (SD) | 7.0 | 8.0 (SD) | | | 27.0** | 14.2 (SD) | 23.8* | 12.1 (SD) |
| 0.0001 | 5.0 | 5.6 (SD) | 5.4 | 6.4 (SD) | | | 27.7*** | 11.3 (SD) | 22.3* | 8.0 (SD) |
| 0.00001 | 5.5 | 5.9 (SD) | 6.1 | 7.0 (SD) | | | 29.2* | 16.0 (SD) | 25.8** | 7.6 (SD) |
| 0.000001 | 6.2 | 6.4 (SD) | 5.4 | 5.0 (SD) | | | 30.6*** | 9.1 (SD) | 28.0** | 11.5 (SD) |
| 0.0000001 | 5.3 | 5.8 (SD) | 5.2 | 5.9 (SD) | | | 27.1** | 14.2 (SD) | 23.0** | 10.8 (SD) |
| 1 | | | | | 27.3** | 12.0 (SD) | | | | |
| 0.333333 | | | | | 22.0* | 11.7 (SD) | | | | |
| 0.111111 | | | | | 20.9* | 12.4 (SD) | | | | |
| 0.037037 | | | | | 18.1* | 12.1 (SD) | | | | |
| 0.012346 | | | | | 12.1 | 12.4 (SD) | | | | |
| 0.004115 | | | | | 7.2 | 9.5 (SD) | | | | |
| 0.001372 | | | | | 6.7 | 9.2 (SD) | | | | |
| 0.000457 | | | | | 5.3 | 6.6 (SD) | | | | |
| 0.000152 | | | | | 5.6 | 7.2 (SD) | | | | |
| 0.0000508 | | | | | 5.0 | 5.4 (SD) | | | | |

Data displayed as mean percentage of Tregs among proliferated (VPD450low) CD4 T cells ± standard deviation (SD) (N = 9 donor pairs). Data were analyzed using one-way ANOVA followed by Dunnett's multiple comparison test with untreated controls (no antibody) serving as the comparison data set (*p < 0.05, p < 0.01, *p < 0.001, ****p < 0.0001).

in MLRs (FIG. 21). In this experiment, MLRs were supplemented with increasing concentrations of abatacept ($1 \times 10^{-7}$ to 100 µg/mL), belatacept ($1 \times 10^{-7}$ to 100 µg/mL) and anti-CD2 antibody 1 ($5.08 \times 10^{-5}$ to 1 µg/mL). Further, additional titration series of abatacept or belatacept ($1 \times 10^{-7}$ to 100 Ig/mL) were supplemented with 1 µg/mL anti-CD2 antibody 1 throughout the entire titration series. Following 10 days of MLR, percentages of Tregs among proliferated CD34 T cells were measured via flow cytometry (n=9) (Table 35). It was observed that anti-CD2 antibody 1 induced significant enrichment of Tregs among proliferated CD34 T cells at 0.037-1 µg/mL (p≤0.0338) (FIG. 21). In contrast, combination of anti-CD2 antibody 1 with increasing doses of abatacept or belatacept induced a dose-dependent decrease in percentage of Tregs among proliferated CD34 T cells. It was noted that significant Treg enrichment was lost once the concentration of abatacept or belatacept This experiment also showed that incubating T cells with a combination of anti-CD2 antibody 1 and belatacept or a combination of anti-CD2 antibody 1 and abatacept resulted in lower levels of CD2 as compared to T cells incubated with belatacept or abatacept alone (FIGS. 22A-22B). As shown in FIGS. 22A-22B, T cells proliferating in the presence of abatacept o belatacept displayed relatively high CD2 expression (average CD2 MFI+SD after 7 days of MLR (n=3)). Further, incubating T cells with a combination of anti-CD2 antibody 1 and belatacept or a combination of anti-CD2 antibody 1 and abatacept resulted in a lower number of cells as compared to T cells incubated with belatacept or abatacept alone (FIGS. 23A-23D). It was observed that treatment with a combination of anti-CD2 antibody 1 and belatacept or a combination of anti-CD2 antibody 1 and abatacept reduced the number of proliferated T cells to almost zero (refer to FIGS. 23A-23D showing mean VPD450high/low T cell count+SD after 7 or 10 days of MLR (n=6)). It was also observed that there were more replicate wells on day 10 (did not compare absolute cell counts between days) (FIGS. 23A-23D). Further, incubating T cells with a combination of anti-CD2 antibody 1 and belatacept or a combination of anti-CD2 antibody 1 and abatacept resulted in lower levels of CD2 and CD28 as compared to T cells incubated with belatacept or abatacept alone (refer to FIGS. 24A-24D showing average CD2/CD28 median FI+SD on T cells after 7 days of MLR (n=6)). FIGS. 24A-24D show that anti-CD2 antibody 1 downregulated CD2. FIGS. 24A-24D showed that VPD450low T cells in samples with high [CTLA4-Ig] display relatively high CD2 MFI, and that CD28 MFI on VPD450high T cell in samples with high [anti-CD2 antibody 1] stays at ~baseline.

Flow cytometry graphs using Violet Proliferation Dye 450 (VPD450) low T cells after cells were incubated with a control, anti-CD2 antibody 1, belatacept, abatacept, a combination of anti-CD2 antibody 1 and belatacept, or a combination of anti-CD2 antibody 1 and abatacept are shown in FIGS. 25A-25F. Flow cytometry graphs using Violet Proliferation Dye 450 (VPD450) high T cells after cells were incubated with a control, anti-CD2 antibody 1, belatacept, abatacept, a combination of anti-CD2 antibody 1 and belatacept, or a combination of anti-CD2 antibody 1 and abatacept are shown in FIGS. 26A-26G.

Experiments with a combination of Fc-silent anti-CD2 (IgG4) and belatacept or abatacept were also performed (refer to FIGS. 27A-27D). It was observed that Fc-silent anti-CD2 improves inhibition of CD8 T cell proliferation. FIGS. 27A-27D show mean CD4/CD8 T cell proliferation after seven or 10 days of MLR+SD (N=6).

Conclusion: this example showed that combination therapy using anti-CD2 antibody 1 and CTLA4-Ig (abatacept or belatacept) has additive effects in inhibition of T cell proliferation. In contrast, combination of anti-CD2 antibody 1 and CTLA4-Ig at concentrations inducing maximum inhibition of proliferation ablated Treg enrichment seen with anti-CD2 antibody 1 monotherapy. Weaning transplant patients off immunosuppressive medication post-transplantation using a belatacept-based protocol has been reported to result in a high frequency of acute cellular allograft rejection. This may partly stem from alloreactive CD28− T cells not being affected by belatacept. This example showed that combining anti-CD2 antibody 1 and a CTLA-4 co-stimulation blockade (e.g., belatacept) can be more effective in preventing an anti-allograft immunity while weaning patients off immunosuppression. Clinical trials in patients that may benefit from combination therapy with anti-CD2 antibody 1 and a CTLA-4 co-stimulation blockade (e.g., abatacept or belatacept) can further show a synergistic effect of the combination therapy. Organ transplant recipients can be treated with anti-CD2 antibody 1 and a CTLA-4 co-stimulation blockade (e.g., belatacept) with the aim of weaning traditional immunosuppression and thus avoiding associated side effects. Additionally, patients suffering from autoimmune disease like new-onset type 1 diabetes or rheumatic arthritis can benefit from anti-CD2 antibody 1 and CTLA4-Ig combination therapy. This example shows that dual costimulation blockade targeting both CD2/CD58 and CD28/B7 costimulatory pathways can aid in more efficiently suppressing autoimmunity than targeting either pathway alone.

6.8 Example 7: Combination Therapy of an Fc Silent Anti-CD2 Antibody or an Antigen Binding Fragment Thereof and a CTLA-4 Co-Stimulation Blockade This example describes the effect of a combination therapy of an Fc silent anti-CD2 antibody or an antigen binding fragment thereof and a CTLA-4 co-stimulation blockade in cell proliferation and activation. The Fc silent anti-CD2 antibodies used in this example are: Fc silent anti-CD2 Ab-1 (e.g., siplizumab expressed in CHO cells); Fc silent anti-CD2 Ab-2 (e.g., siplizumab with two mutations (L234A/L235A)); Fc silent anti-CD2 Ab-3 (e.g., siplizumab with the same two mutations as Fc silent anti-CD2 Ab-2 and also containing an additional mutation (P329G/L234A/L235A)); Fc silent anti-CD2 Ab-4 (e.g., siplizumab CDRs in IgG2 heavy chain); Fc silent anti-CD2 Ab-5 (e.g., siplizumab CDRs in IgG2 heavy chain and seven mutations (V234A/G237A/P238S/H268A/V309L/A330S/P331S)); Fc silent anti-CD2 Ab-6 (e.g., siplizumab CDRs in IgG4 heavy chain and one mutation (S228P)); Fc silent anti-CD2 Ab-7 (e.g., siplizumab CDRs in IgG4 heavy chain and three mutations (P329G/S228P/L235E)). All of the Fc silent anti-CD2 antibodies used in this example have the same light chain. Fc-silent anti-CD2 Ab1 (e.g., siplizumab; Fc silent anti-CD2 Ab-1 IgG1) was generated by introducing the commonly known LALA-PG mutations to equivalent sites in siplizumab (Arduin E, Arora S, Bamert P R, Kuiper T, Popp S, Geisse S, et al. Highly reduced binding to high and low affinity mouse Fc gamma receptors by L234A/L235A and N297A Fc mutations engineered into mouse IgG2a. Mol Immunol (2015) 63:456-63. doi: 10.1016/j.molimm.2014.09.017; Lo D J, Weaver T A, Stempora L, Mehta A K, Ford M L, Larsen C P, et al. Selective targeting of human alloresponsive CD8 effector memory T cells based on CD2 expression. Am J Transplant Off J Am Soc Transplant Am Soc Transpl Surg (2011) 11:22. doi: 10.1111/j.1600-6143.2010.03317.x). Fc silent anti-CD2 Ab-5 was generated by introducing the following mutations at equivalent sites in a standard IgG2 framework: V234A, G237A P238S, H268A, V309L, A330S, P331S (Wang X, Mathieu M, Brezski R J. IgG Fc engineering to modulate antibody effector functions. Protein Cell (2018) 9:63-73. doi: 10.1007/s13238-017-0473-8). Fc silent anti-CD2 Ab-7 was generated by introducing the following mutations at equivalent sites in a standard IgG4 framework: S228P, L235E, P329G (Silva J-P, Vetterlein O, Jose J, Peters S, Kirby H. The S228P mutation prevents in vivo and in vitro IgG4 Fab-arm exchange as demonstrated using a combination of novel quantitative immunoassays and physiological matrix preparation. J Biol Chem (2015) 290:5462-9. doi: 10.1074/jbc.M114.600973; Schlothauer T, Herter S, Koller C F, Grau-Richards S, Steinhart V, Spick C, et al. Novel human IgG1 and IgG4 Fc-engineered antibodies with completely abolished immune effector functions. Protein Eng Des Sel (2016) 29:457-66. doi: 10.1093/protein/gzw040).

Cell-based FcγR binding assay: In brief, different concentrations of antibodies (anti-CD2 antibody (or siplizumab); Fc silent anti-CD2 Ab-1; Fc silent anti-CD2 Ab-2; Fc silent anti-CD2 Ab-3; Fc silent anti-CD2 Ab-4; Fc silent anti-CD2 Ab-5; Fc silent anti-CD2 Ab-6; and Fc silent anti-CD2 Ab-7) were tested for their ability to bind to FcγRI, FcγRIIA, and FcγRIIIA (refer to FIG. 28). The highest concentration for the FcγRI and the FcγRIIIA binding assays was 1 μg/mL/6.67 nM and for the FcγRIIA binding assay was 100 μg/mL/667 nM (refer to FIG. 28 and Table 36).

TABLE 36

| Cell-based FcγR binding assay | | | |
|---|---|---|---|
| | FcγR-binding and -signaling | | |
| Antibody agent | FcγRI | FcγRIIA | FcγRIIIA |
| anti-CD2 antibody | 0.0326 | 5.3100 | 0.0520 |
| Fc-silent anti-CD2 Ab-1 | 0.0306 | 0.1415 | 0.0108 |
| Fc-silent anti-CD2 Ab-2 | 0.0042 | 0.3102 | 0.0862 |
| Fc-silent anti-CD2 Ab-3 | N/A | N/A | N/A |
| Fc-silent anti-CD2 Ab-4 | 0.0589 | 0.2505 | 0.1426 |
| Fc-silent anti-CD2 Ab-5 | N/A | N/A | N/A |
| Fc-silent anti-CD2 Ab-6 | 0.0245 | 0.3496 | 0.3236 |
| Fc-silent anti-CD2 Ab-7 | N/A | N/A | N/A |

Allogeneic mixed lymphocyte reaction (MLR): In brief, peripheral blood mononuclear cells (PBMC) from two donors were mixed in PBS at a concentration of $1.5\text{-}2.0\times10^7$ cells per mL and stained with violet proliferation dye 450 (VPD450; BD Biosciences, San Diego, USA) following manufacturer's protocol. This example used two-way allogeneic MLR, i.e. PBMC from neither donor were inactivated via irradiation/chemical treatment. Thus, PBMC from both donors functioned as responders and stimulators.

VPD450-stained PBMC were washed and resuspended in 10% heat-inactivated FBS (Gibco, Thermo Fisher Scientific Inc., Waltham, USA) in AIM V medium (Gibco, Thermo Fisher Scientific Inc., Waltham, USA). Resuspended PBMC were dispensed into round-bottom 96-well cell culture plates (for flow cytometry) and pure medium (no antibody control) or medium supplemented with Fc-silent anti-CD2 antibody (Fc silent anti-CD2 Ab-5 or Fc silent anti-CD2 Ab-7 and/or abatacept or belatacept was added to a final concentration of $2\times10^6$ cells per mL (final volume 200 µL). MLRs were incubated at 37° C., 5% CO2 for seven and 10 days, respectively. On day six, 100 µL fresh culture medium (no additional antibody) was added to each well. On day eight, 100 µL medium was aspirated from each well without disturbing the cell pellet and replaced with 100 µL fresh culture medium.

For the first round of experiments, antibody concentrations used for Fc silent anti-CD2 Ab-5 or Fc silent anti-CD2 Ab-7 titrations were between 67.2 nM and 0.67 nM (10-fold serial dilution). Fc silent anti-CD2 Ab-5 or Fc silent anti-CD2 Ab-7 titrations with added CTLA4-Ig were supplemented with 433.4 nM belatacept throughout all serial dilution steps. Concentrations used for belatacept monotherapy titrations were between 433.4 nM and 0.0043 nM (10-fold serial dilution) (refer to FIGS. 29A, 29B, 30A, 30B, 31A, and 31B).

For the second round of experiments, antibody concentrations used for Fc silent anti-CD2 Ab-7 titrations were between 10 µg/mL and 50.8 µg/mL (3-fold serial dilution). Fc silent anti-CD2 Ab-7 titrations with added CTLA4-Ig were supplemented with 100 µg/mL abatacept or belatacept throughout all serial dilution steps. Fusion protein concentrations used for abatacept/belatacept titrations were between 100 µg/mL and 0.1 µg/mL (10-fold serial dilution) (refer to FIGS. 32A-32B).

Flow cytometry: After seven days of MLR, samples were blocked with Fc-receptor binding inhibitor (Invitrogen; Thermo Fisher Scientific Inc., Waltham, USA) and then stained with anti-CD3 VioGreen (Clone REA613; Miltenyi, Bergisch Gladbach, Germany), anti-CD45RA BV650 (Clone HI100; BD Biosciences, San Diego USA), anti-CD2 BV786 (Clone RPA-2.10; BD Biosciences, San Diego USA), anti-CD8 BB550 (Clone RPA-T8; BD Biosciences, San Diego USA), anti-CD56 PE (Clone REA196; Miltenyi, Bergisch Gladbach, Germany), anti-HLA-DR PerCP-Cy5.5 (Clone G46-6; BD Biosciences, San Diego USA), anti-CCR7 APC (Clone G43H7; BD Biosciences, San Diego USA) and anti-CD4 APC-Vio770 (Clone REA623; Miltenyi, Bergisch Gladbach, Germany) (refer to FIG. 32A). T cells were gated as CD3+CD56-. After 10 days of MLR, samples were blocked with Fc-receptor binding inhibitor (Invitrogen; Thermo Fisher Scientific Inc., Waltham, USA) and then stained with anti-CD45RA BV650 (Clone HI100; BD Biosciences, San Diego USA), anti-CD3 BV786 (Clone SK7; BD Biosciences, San Diego USA), anti-CD8 BB550 (Clone RPA-T8; BD Biosciences, San Diego USA), anti-FoxP3 PE (Clone 236A/E7; BD Biosciences, San Diego USA), anti-CD127 PerCP-Cy5.5 (Clone HIL-7R-M21 (BD Biosciences, San Diego USA); or A019D5 (Biolegend, Sunnyvale USA)), anti-CCR7 APC (Clone G43H7; BD Biosciences, San Diego USA), anti-CD25 Alexa Fluor 700 (Clone M-A251; BD Biosciences, San Diego USA) and anti-CD4 APC-Vio770 (Clone REA623; Miltenyi, Bergisch Gladbach, Germany) (refer to FIG. 32B). T cells were gated as CD3+. Cell proliferation was assessed using VPD450 (VPD450high: Non-proliferated; VPD450low: Proliferated). Samples were stained in the dark at 4° C. and washed twice in saline solution followed by acquisition using a BD Celesta flow cytometer (BD Biosciences, San Diego USA).

Results: To assess the inhibitory effects of combining Fc-silent anti-CD2 antibody and belatacept, T cell proliferation was assessed via flow cytometry after seven and ten days of MLR. As shown in the right-side panels on FIGS. 29A and 29B, the combination of Fc silent anti-CD2 Ab-5 and belatacept induced reduction in CD8 T cell proliferation compared to either monotherapy or untreated control. Moreover, the combination of Fc silent anti-CD2 Ab-5 and belatacept resulted in reduced T cell activation as measure by markers CD69 and HLA-DR (FIG. 31A). In the case of IgG4 Fc-silent anti-CD2 antibody Fc silent anti-CD2 Ab-7 and belatacept, the combination therapy induced reduction in CD8 T cell proliferation (FIGS. 30A and 30B) and T cell activation (FIG. 31B).

Additional investigations with Fc silent anti-CD2 Ab-7 titrations over a broader dilution range (between 10 µg/mL and 50.8 µg/mL) in combination with 100 µg/mL abatacept or belatacept induced reduction in CD8 T cell proliferation compared to either monotherapy or untreated control (right-side panels of FIGS. 32A and 32B).

| SEQUENCES | | |
|---|---|---|
| SEQ ID NO | DESCRIPTION | SEQUENCE |
| 1 | heavy chain variable region | QVQLVQSGAEVQRPGASVKVSCKASGYIFTEYYMYWVRQAPGQG LELVGRIDPEDGSIDYVEKFKKKVTLTADTSSSTAYMELSSLTS DDTAVYYCARGKFNYRFAYWGQGTLVTVSS |

-continued

| SEQUENCES | | |
|---|---|---|
| SEQ ID NO | DESCRIPTION | SEQUENCE |
| 2 | light chain variable region | DVVMTQSPPSLLVTLGQPASISCRSSQSLLHSSGNTYLNWLLQR PGQSPQPLIYLVSKLESGVPDRFSGSGSGTDFTLKISGVEAEDV GVYYCMQFTHYPYTFGQGTKLEIK |
| 3 | heavy chain variable region CDR 1 | EYYMY |
| 4 | heavy chain variable region CDR 2 | RIDPEDGSIDYVEKFKK |
| 5 | heavy chain variable region CDR 3 | GKFNYRFAY |
| 6 | light chain variable region CDR 1 | RSSQSLLHSSGNTYLN |
| 7 | light chain variable region CDR 2 | LVSKLES |
| 8 | light chain variable region CDR 3 | MQFTHYPYT |
| 9 | heavy chain constant region | ASTKGPSVFPLAPSSKSTSGGTAALGCLVKDYFPEPVTVSWNSG ALTSGVHTFPAVLQSSGLYSLSSVVTVPSSSLGTQTYICNVNHK PSNTKVDKRVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPGK |
| 10 | heavy chain constant region | ASTKGPSVFPLAPSSKSTSGGTAALGCLVKDYFPEPVTVSWNSG ALTSGVHTFPAVLQSSGLHSLSSVVTVPSSSLGTQTYICNVNHK PSNTKVDKKVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSRDELTKNQVSLTCLVKGFYPSDIAVEW ESNGQPENNYKTTPPVLDSDGSFFLYSKLTVDKSRWQQGNVFSC SVMHEALHNHYTQKSLSLSPGK |
| 11 | heavy chain constant region | ASTKGPSVFPLAPSSKSTSGGTAALGCLVKDYFPEPVTVSWNSG ALTSGVHTFPAVLQSSGLYSLSSVVTVPSSSLGTQTYICNVNHK PSNTKVDKKVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSRDELTKNQVSLTCLVKGFYPSDIAVEW ESNGQPENNYKTTPPVLDSDGSFFLYSKLTVDKSRWQQGNIFSC SVMHEALHNHYTQKSLSLSPGK |
| 12 | heavy chain constant region | ASTKGPSVFPLAPSSKSTSGGTAALGCLVKDYFPEPVTVSWNSG ALTSGVHTFPAVLQSSGLYSLSSVVTVPSSSLGTQTYICNVNHK PSNTKVDKKVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSRDELTKNQVSLTCLVKGFYPSDIAVEW ESNGQPENNYKTTPPVLDSDGSFFLYSKLTVDKSRWQQGNVFSC SVMHEALHNHYTQKSLSLSPGK |
| 13 | heavy chain constant region | ASTKGPSVFPLAPSSKSTSGGTAALGCLVKDYFPEPVTVSWNSG ALTSGVHTFPAVLQSSGLYSLSSVVTVPSSSLGTQTYICNVNHK PSNTKVDKKVEPKSCDKTHTCPPCPAPELLGGPSVFLFPPKPKD TLMISRTPEVTCVVVDVSHEDPEVKFNWYVDGVEVHNAKTKPRE EQYNSTYRVVSVLTVLHQDWLSGKEYKCKVSNKALPAPIEKTIS KAKGQPREPQVYTLPPSRDELTKNQVSLTCLVKGFYPSDIAVEW ESNGQPENNYKTTPPVLDSDGSFFLYSKLTVDKSRWQQGNVFSC SVMHEALHNHYTQKSLSLSPGK |

-continued

| SEQ ID NO | DESCRIPTION | SEQUENCE |
|---|---|---|
| 14 | light chain constant region | RTVAAPSVFIFPPSDEQLKSGTASVVCLLNNFYPREAKVQWKVD NALQSGNSQESVTEQDSKDSTYSLSSTLTLSKADYEKHKLYACE VTHQGLSSPVTKSFNRGEC |
| 15 | light chain constant region | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |
| 16 | optimized heavy chain sequence | CAAGTGCAGCTGGTGCAGAGCGGAGCTGAGGTGCAGAGACCCGG CGCCAGCGTCAAGGTGAGCTGTAAGGCCAGCGGCTACATCTTCA CAGAATACTACATGTACTGGGTGAGGCAAGCCCCCGGCCAAGGA CTGGAGCTGGTGGGCAGAATCGATCCAGAGGATGGCAGCATCGA CTACGTGGAGAAGTTCAAGAAGAAGGTGACTCTGACAGCCGACA CAAGCAGCAGCACTGCTTACATGGAGCTGAGCTCTCTGACTAGC GATGACACTGCCGTGTACTACTGTGCTAGGGGCAAGTTCAACTA TAGGTTCGCCTACTGGGGCCAAGGCACTCTGGTGACAGTCAGCA GCGCTAGCACCAAGGGCCCATCGGTCTTCCCCCTGGCACCCTCC TCCAAGAGCACCTCTGGGGGCACAGCGGCCCTGGGCTGCCTGGT CAAGGACTACTTCCCCGAACCGGTGACGGTGTCGTGGAACTCAG GCGCCCTGACCAGCGGCGTGCACACCTTCCCGGCCGTCCTACAG TCCTCAGGACTCTACTCCCTCAGCAGCGTGGTGACCGTGCCCTC CAGCAGCTTGGGCACCCAGACCTACATCTGCAACGTGAATCACA AGCCCAGCAACACCAAGGTGGACAAGAAGGTTGAGCCCAAATCT TGTGACAAAACTCACACATGCCCACCGTGCCCAGCACCTGAACT CCTGGGGGGACCGTCAGTCTTCCTCTTCCCCCCAAAACCCAAGG ACACCCTCATGATCTCCCGGACCCCTGAGGTCACATGCGTGGTG GTGGACGTGAGCCACGAAGACCCTGAGGTCAAGTTCAACTGGTA CGTGGACGGCGTGGAGGTGCATAATGCCAAGACAAAGCCGCGGG AGGAGCAGTACAACAGCACGTACCGTGTGGTCAGCGTCCTCACC GTCCTGCACCAGGACTGGCTGAATGGCAAGGAGTACAAGTGCAA GGTCTCCAACAAAGCCCTCCCAGCCCCCATCGAGAAAACCATCT CCAAAGCCAAAGGGCAGCCCCGAGAACCACAGGTGTACACCCTG CCCCCATCCCGGGACGAGCTGACCAAGAACCAGGTCAGCCTGAC CTGCCTGGTCAAAGGCTTCTATCCCAGCGACATCGCCGTGGAGT GGGAGAGCAATGGGCAGCCGGAGAACAACTACAAGACCACGCCT CCCGTGCTGGACTCCGACGGCTCCTTCTTCCTCTACAGCAAGCT CACCGTGGACAAGAGCAGGTGGCAGCAGGGGAACGTCTTCTCAT GCTCCGTGATGCATGAGGCTCTGCACAACCACTACACGCAGAAG AGCCTCTCCCTGTCTCCGGGTAAATGATGA |
| 17 | optimized Light chain sequence | GACGTGGTGATGACTCAGAGCCCTCCTTCTCTGCTGGTGACTCT GGGCCAGCCAGCCAGCATCAGCTGTAGGAGCAGCCAGTCTCTGC TGCACTCCAGCGGCAACACTTATCTGAACTGGCTGCTGCAGAGA CCCGGCCAGAGCCCTCAGCCTCTGATCTACCTCGTGAGCAAGCT GGAGAGCGGCGTGCCAGATAGGTTTAGCGGCAGCGGAAGCGGCA CTGACTTCACTCTGAAGATCAGCGGCGTGGAAGCTGAGGATGTG GGCGTCTACTACTGCATGCAGTTCACACACTACCCATACACTTT CGGCCAAGGCACAAAGCTGGAAATCAAGCGTACGGTGGCTGCAC CATCTGTCTTCATCTTCCCGCCATCTGATGAGCAGTTGAAATCT GGAACTGCCTCTGTTGTGTGCCTGCTGAATAACTTCTATCCCAG AGAGGCCAAAGTACAGTGGAAGGTGGATAACGCCCTCCAATCGG GTAACTCCCAGGAGAGTGTCACAGAGCAGGACAGCAAGGACAGC ACCTACAGCCTCAGCAGCACCCTGACGCTGAGCAAAGCAGACTA CGAGAAACACAAAGTCTACGCCTGCGAAGTCACCCATCAGGGCC TGAGCTCGCCCGTCACAAAGAGCTTCAACAGGGGAGAGTGTTGA TGA |
| 18 | CH2 domain | SVFLFPPKPKDTLMISRTPEVTCVVVDVSAEDPEVQFNWYVDGV EVHNAKTKPREEQFNSTFRVVSVLTVLHQDWLNGKEYKCKVSNK GLPSSIEKTISKTK |
| 19 | CH2 domain | SVFLFPPKPKDTLMISRTPEVTCVVVDVSQEDPEVQFNWYVDGV EVHNAKTKPREEQFNSTYRVVSVLTVLHQDWLNGKEYKCKVSNK GLGSSIEKTISKAK |
| 20 | CH3 domain | GQPREPQVYTLPPSREEMTKNQVSLTCLVKGFYPSDIAVEWESN GQPENNYKTTPPMLDSDGSFFLYSKLTVDKSRWQQGNVFSCSVM HEALHNHYTQKSLSLSPGK |
| 21 | CH3 domain | GQPREPQVYTLPPSQEEMTKNQVSLTCLVKGFYPSDIAVEWESN GQPENNYKTTPPVLDSDGSFFLYSRLTVDKSRWQEGNVFSCSVM HEALHNHYTQKSLSLSLGK |

| SEQ ID NO | DESCRIPTION | SEQUENCE |
|---|---|---|
| 22 | belatacept | MHVAQPAVVLASSRGIASFVCEYASPGKYTEVRVTVLRQADSQV<br>TEVCAATYMMGNELTFLDDSICTGTSSGNQVNLTIQGLRAMDTG<br>LYICKVELMYPPPYYEGIGNGTQIYVIDPEPCPDSDQEPKSSDK<br>THTSPPSPAPELLGGSSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPAPIEKTISKAKGQPREPQVYTLPPS<br>RDELTKNQVSLTCLVKGFYPSDIAVEWESNGQPENNYKTTPPVL<br>DSDGSFFLYSKLTVDKSRWQQGVFSCSVMHEALHNHYTQKSLSL<br>SPGK |
| 23 | abatacept | MGVLLTQRTLLSLVLALLFPSMASMAMHVAQPAVVLASSRGIAS<br>FVCEYASPGKATEVRVTVLRQADSQVTEVCAATYMMGNELTFLD<br>DSICTGTSSGNQVNLTIQGLRAMDTGLYICKVELMYPPPYYLGI<br>GNGTQIYVIDPEPCPDSDQEPKSSDKTHTSPPSPAPELLGGSSV<br>FLFPPKPKDTLMISRTPEVTCVVVDVSHEDPEVKFNWYVDGVEV<br>HNAKTKPREEQYNSTYRVVSVLTVLHQDWLNGKEYKCKVSNKAL<br>PAPIEKTISKAKGQPREPQVYTLPPSRDELTKNQVSLTCLVKGF<br>YPSDIAVEWESNGQPENNYKTTPPVLDSDGSFFLYSKLTVDKSR<br>WQQGNVFS |

The invention claimed is:

1. A method of treating or preventing an immune-related disorder or disease associated with a kidney transplant or a transplant of kidney tissue in a subject in need thereof, the method comprising:
   a) administering more than one dose of an anti-CD2 antibody or an antigen-binding fragment thereof to the subject; and
   b) administering a CTLA-4 co-stimulation blockade to the subject, wherein the CTLA-4 co-stimulation blockade comprises the amino acid sequence of SEQ ID NO: 22:
   wherein a dose of about or at least about 0.6 mg/kg of the anti-CD2 antibody or antigen-binding fragment thereof is administered to the subject on the same day that the kidney or tissue thereof is transplanted into the subject, and wherein another dose of the anti-CD2 antibody or antigen-binding fragment thereof is administered to the subject once within two weeks after the kidney or tissue thereof is transplanted into the subject; and wherein the anti-CD2 antibody or antigen-binding fragment thereof comprises:
   i) a heavy chain variable region CDR1 comprising the amino acid sequence of SEQ ID NO: 3;
   ii) a heavy chain variable region CDR2 comprising the amino acid sequence of SEQ ID NO: 4;
   iii) a heavy chain variable region CDR3 comprising the amino acid sequence of SEQ ID NO: 5;
   iv) a light chain variable region CDR1 comprising the amino acid sequence of SEQ ID NO: 6;
   v) a light chain variable region CDR2 comprising the amino acid sequence of SEQ ID NO: 7; and
   vi) a light chain variable region CDR3 comprising the amino acid sequence of SEQ ID NO: 8.

2. The method of claim 1, wherein the CTLA-4 co-stimulation blockade is belatacept.

3. The method of claim 1, wherein the immune-related disorder or disease is a disease associated with the kidney transplant or transplant of kidney tissue, graft rejection, graft-versus-host-disease, or any combination thereof.

4. The method of claim 1, wherein a dose of the anti-CD2 antibody or antigen-binding fragment thereof is not thera-peutically effective when the CTLA-4 co-stimulation blockade is not administered to the subject.

5. The method of claim 1, wherein a dose of the CTLA-4 co-stimulation blockade is not therapeutically effective when the anti-CD2 antibody or antigen-binding fragment thereof is not administered to the subject.

6. The method of claim 1, wherein the method results in a greater decrease in the level of CD2 in a biological sample obtained from the subject after both the anti-CD2 antibody or antigen-binding fragment thereof and the CTLA-4 co-stimulation blockade are administered to the subject as compared to:
   (a) a decrease in the level of CD2 in a biological sample obtained from the subject prior to at least one of the administering the anti-CD2 antibody or antigen-binding fragment thereof and/or the administering the CTLA-4 co-stimulation blockade to the subject; and/or
   (b) a decrease in the level of CD2 in a biological sample obtained from the subject after the anti-CD2 antibody or antigen-binding fragment thereof or after the CTLA-4 co-stimulation blockade, but not both, is administered to the subject; and
   wherein the greater decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%.

7. The method of claim 1, wherein the anti-CD2 antibody or antigen-binding fragment thereof is administered to the subject on the day of the kidney or the kidney tissue transplantation, on day 1 after the kidney or the kidney tissue transplantation, and/or on day 4 after the kidney or the kidney tissue transplantation.

8. The method of claim 1, wherein the anti-CD2 antibody or antigen-binding fragment thereof is administered intra-venously or subcutaneously to the subject.

9. The method of claim 1, wherein the method further comprises administering an additional agent to the subject.

10. The method of claim 9, wherein the additional agent comprises one or more of a steroid, a calcineurin inhibitor, a cyclosporine, a cyclophosphamide, an antimetabolite therapy, a nonsteroidal anti-inflammatory drugs (NSAID), an agent used for treating rheumatoid arthritis, and/or an mTOR inhibitor.

11. The method of claim 9, wherein the additional agent comprises basiliximab induction, mycophenolate mofetil, corticosteroids, or a combination thereof.

12. The method of claim 1, wherein a first dose of the anti-CD2 antibody or antigen-binding fragment thereof is administered before a first dose of the CTLA-4 co-stimulation blockade.

13. The method of claim 1, wherein a first dose of the anti-CD2 antibody or antigen-binding fragment thereof is administered after a first dose of the CTLA-4 co-stimulation blockade.

14. The method of claim 1, wherein a first dose of the anti-CD2 antibody or antigen-binding fragment thereof is administered concurrently with a first dose of the CTLA-4 co-stimulation blockade.

15. The method of claim 1, wherein the subject is a treatment-naïve subject.

16. The method of claim 1, wherein the subject is resistant to a treatment of the immune-related disorder or disease.

17. The method of claim 1, wherein the administering of the anti-CD2 antibody or antigen-binding fragment thereof and the CTLA-4 co-stimulation blockade is synergistic in comparison to the administering the anti-CD2 antibody or to the administering the CTLA-4 co-stimulation blockade, but not both, to the subject.

18. The method of claim 1, wherein the administering of the anti-CD2 antibody or antigen-binding fragment thereof and the CTLA-4 co-stimulation blockade results in a greater decrease in alloimmune response in the subject in comparison to a decrease in alloimmune response after the administering the anti-CD2 antibody or the administering the CTLA-4 co-stimulation blockade, but not both, to the subject; and wherein the greater decrease is greater by about or at least about 5%, 10%, 15%, 20%, 25%, 30%, 35%, 40%, 45%, 50%, 55%, 60%, 65%, 70%, 75%, 80%, 85%, 90%, 100%, or more than 100%.

19. The method of claim 18, wherein the alloimmune response is determined using an in vitro human T cell proliferation assay or a mixed lymphocyte reaction (MLR) assay.

\* \* \* \* \*

SEQUENCE LISTING

<160> NUMBER OF SEQ ID NOS: 23

<210> SEQ ID NO 1
<211> LENGTH: 118
<212> TYPE: PRT
<213> ORGANISM: Artificial Sequence
<220> FEATURE:
<223> OTHER INFORMATION: heavy chain variable region

<400> SEQUENCE: 1

```
Gln Val Gln Leu Val Gln Ser Gly Ala Glu Val Gln Arg Pro Gly Ala
1               5                   10                  15

Ser Val Lys Val Ser Cys Lys Ala Ser Gly Tyr Ile Phe Thr Glu Tyr
                20                  25                  30

Tyr Met Tyr Trp Val Arg Gln Ala Pro Gly Gln Gly Leu Glu Leu Val
            35                  40                  45

Gly Arg Ile Asp Pro Glu Asp Gly Ser Ile Asp Tyr Val Glu Lys Phe
        50                  55                  60

Lys Lys Lys Val Thr Leu Thr Ala Asp Thr Ser Ser Ser Thr Ala Tyr
65                  70                  75                  80

Met Glu Leu Ser Ser Leu Thr Ser Asp Asp Thr Ala Val Tyr Tyr Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
        115
```

<210> SEQ ID NO 2
<211> LENGTH: 112
<212> TYPE: PRT
<213> ORGANISM: Artificial Sequence
<220> FEATURE:
<223> OTHER INFORMATION: light chain variable region

<400> SEQUENCE: 2

```
Asp Val Val Met Thr Gln Ser Pro Pro Ser Leu Leu Val Thr Leu Gly
1               5                   10                  15
```

Gln Pro Ala Ser Ile Ser Cys Arg Ser Ser Gln Ser Leu Leu His Ser
            20                      25                      30

Ser Gly Asn Thr Tyr Leu Asn Trp Leu Leu Gln Arg Pro Gly Gln Ser
        35                      40                      45

Pro Gln Pro Leu Ile Tyr Leu Val Ser Lys Leu Glu Ser Gly Val Pro
    50                      55                      60

Asp Arg Phe Ser Gly Ser Gly Ser Gly Thr Asp Phe Thr Leu Lys Ile
65                      70                      75                      80

Ser Gly Val Glu Ala Glu Asp Val Gly Val Tyr Tyr Cys Met Gln Phe
                85                      90                      95

Thr His Tyr Pro Tyr Thr Phe Gly Gln Gly Thr Lys Leu Glu Ile Lys
            100                     105                     110

<210> SEQ ID NO 3
<211> LENGTH: 5
<212> TYPE: PRT
<213> ORGANISM: Artificial Sequence
<220> FEATURE:
<223> OTHER INFORMATION: heavy chain variable region CDR 1

<400> SEQUENCE: 3

Glu Tyr Tyr Met Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: heavy chain variable region CDR 2

<400> SEQUENCE: 4

Arg Ile Asp Pro Glu Asp Gly Ser Ile Asp Tyr Val Glu Lys Phe Lys
1               5                   10                  15

Lys

<210> SEQ ID NO 5
<211> LENGTH: 9
<212> TYPE: PRT
<213> ORGANISM: Artificial Sequence
<220> FEATURE:
<223> OTHER INFORMATION: heavy chain variable region CDR 3

<400> SEQUENCE: 5

Gly Lys Phe Asn Tyr Arg Phe Ala Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: light chain variable region CDR 1

<400> SEQUENCE: 6

Arg Ser Ser Gln Ser Leu Leu His Ser Ser Gly Asn Thr Tyr Leu Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: light chain variable region CDR 2

```
<400> SEQUENCE: 7

Leu Val Ser Lys Leu Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: light chain variable region CDR 3

<400> SEQUENCE: 8

Met Gln Phe Thr His Tyr Pro Tyr Thr
1               5

<210> SEQ ID NO 9
<211> LENGTH: 330
<212> TYPE: PRT
<213> ORGANISM: Artificial Sequence
<220> FEATURE:
<223> OTHER INFORMATION: heavy chain constant region

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 330
<212> TYPE: PRT
<213> ORGANISM: Artificial Sequence
<220> FEATURE:
<223> OTHER INFORMATION: heavy chain constant region

<400> SEQUENCE: 10

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu His Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: Artificial Sequence
<220> FEATURE:
<223> OTHER INFORMATION: heavy chain constant region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 12
<211> LENGTH: 330
<212> TYPE: PRT
<213> ORGANISM: Artificial Sequence
<220> FEATURE:
<223> OTHER INFORMATION: heavy chain constant region

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: Artificial Sequence
```

<220> FEATURE:
<223> OTHER INFORMATION: heavy chain constant region

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Ser Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 107
<212> TYPE: PRT
<213> ORGANISM: Artificial Sequence
<220> FEATURE:
<223> OTHER INFORMATION: light chain constant region

<400> SEQUENCE: 14

Arg Thr Val Ala Ala Pro Ser Val Phe Ile Phe Pro Pro Ser Asp Glu

-continued

```
1                 5                10                15

Gln Leu Lys Ser Gly Thr Ala Ser Val Val Cys Leu Leu Asn Asn Phe
            20                25                30

Tyr Pro Arg Glu Ala Lys Val Gln Trp Lys Val Asp Asn Ala Leu Gln
        35                40                45

Ser Gly Asn Ser Gln Glu Ser Val Thr Glu Gln Asp Ser Lys Asp Ser
    50                55                60

Thr Tyr Ser Leu Ser Ser Thr Leu Thr Leu Ser Lys Ala Asp Tyr Glu
65                70                75                80

Lys His Lys Leu Tyr Ala Cys Glu Val Thr His Gln Gly Leu Ser Ser
            85                90                95

Pro Val Thr Lys Ser Phe Asn Arg Gly Glu Cys
            100                105
```

<210> SEQ ID NO 15
<211> LENGTH: 107
<212> TYPE: PRT
<213> ORGANISM: Artificial Sequence
<220> FEATURE:
<223> OTHER INFORMATION: light chain constant region

<400> SEQUENCE: 15

```
Arg Thr Val Ala Ala Pro Ser Val Phe Ile Phe Pro Pro Ser Asp Glu
1                 5                10                15

Gln Leu Lys Ser Gly Thr Ala Ser Val Val Cys Leu Leu Asn Asn Phe
            20                25                30

Tyr Pro Arg Glu Ala Lys Val Gln Trp Lys Val Asp Asn Ala Leu Gln
        35                40                45

Ser Gly Asn Ser Gln Glu Ser Val Thr Glu Gln Asp Ser Lys Asp Ser
    50                55                60

Thr Tyr Ser Leu Ser Ser Thr Leu Thr Leu Ser Lys Ala Asp Tyr Glu
65                70                75                80

Lys His Lys Val Tyr Ala Cys Glu Val Thr His Gln Gly Leu Ser Ser
            85                90                95

Pro Val Thr Lys Ser Phe Asn Arg Gly Glu Cys
            100                105
```

<210> SEQ ID NO 16
<211> LENGTH: 1350
<212> TYPE: DNA
<213> ORGANISM: Artificial Sequence
<220> FEATURE:
<223> OTHER INFORMATION: optimized heavy chain sequence

<400> SEQUENCE: 16

```
caagtgcagc tggtgcagag cggagctgag gtgcagagac ccggcgccag cgtcaaggtg      60
agctgtaagg ccagcggcta catcttcaca gaatactaca tgtactgggt gaggcaagcc     120
cccggccaag gactggagct ggtgggcaga atcgatccag aggatggcag catcgactac     180
gtggagaagt tcaagaagaa ggtgactctg acagccgaca caagcagcag cactgcttac     240
atggagctga gctctctgac tagcgatgac actgccgtgt actactgtgc taggggcaag     300
ttcaactata ggttcgccta ctggggccaa ggcactctgg tgacagtcag cagcgctagc     360
accaagggcc catcggtctt ccccctggca ccctcctcca gagcacctc tggggggcaca     420 gcggccctgg gctgcctggt caaggactac ttccccgaac cggtgacggt gtcgtggaac     480
tcaggcgccc tgaccagcgg cgtgcacacc ttcccggccg tcctacagtc ctcaggactc     540
```

-continued

```
tactccctca gcagcgtggt gaccgtgccc tccagcagct tgggcaccca gacctacatc        600
tgcaacgtga atcacaagcc cagcaacacc aaggtggaca agaaggttga gcccaaatct        660
tgtgacaaaa ctcacacatg cccaccgtgc ccagcacctg aactcctggg gggaccgtca        720
gtcttcctct tccccccaaa acccaaggac accctcatga tctcccggac ccctgaggtc        780
acatgcgtgg tggtggacgt gagccacgaa gaccctgagg tcaagttcaa ctggtacgtg        840
gacggcgtgg aggtgcataa tgccaagaca aagccgcggg aggagcagta caacagcacg        900
taccgtgtgg tcagcgtcct caccgtcctg caccaggact ggctgaatgg caaggagtac        960
aagtgcaagg tctccaacaa agccctccca gcccccatcg agaaaaccat ctccaaagcc       1020
aaagggcagc cccgagaacc acaggtgtac accctgcccc catcccggga cgagctgacc       1080
aagaaccagg tcagcctgac ctgcctggtc aaaggcttct atcccagcga catcgccgtg       1140
gagtgggaga gcaatgggca gccggagaac aactacaaga ccacgcctcc cgtgctggac       1200
tccgacggct ccttcttcct ctacagcaag ctcaccgtgg acaagagcag gtggcagcag       1260
gggaacgtct tctcatgctc cgtgatgcat gaggctctgc acaaccacta cacgcagaag       1320
agcctctccc tgtctccggg taaatgatga                                        1350
```

```
<210> SEQ ID NO 17
<211> LENGTH: 663
<212> TYPE: DNA
<213> ORGANISM: Artificial Sequence
<220> FEATURE:
<223> OTHER INFORMATION: optimized Light chain sequence

<400> SEQUENCE: 17
```

```
gacgtggtga tgactcagag ccctccttct ctgctggtga ctctgggcca gccagccagc         60
atcagctgta ggagcagcca gtctctgctg cactccagcg gcaacactta tctgaactgg        120
ctgctgcaga cacccggcca gagccctcag cctctgatct acctcgtgag caagctggag        180
agcggcgtgc cagataggtt tagcggcagc ggaagcggca ctgacttcac tctgaagatc        240
agcggcgtgg aagctgagga tgtgggcgtc tactactgca tgcagttcac acactaccca        300 tacacttttcg gccaaggcac aaagctggaa atcaagcgta cggtggctgc accatctgtc        360
ttcatcttcc cgccatctga tgagcagttg aaatctggaa ctgcctctgt tgtgtgcctg        420
ctgaataact ctatcccag agaggccaaa gtacagtgga aggtggataa cgccctccaa        480
tcgggtaact cccaggagag tgtcacagag caggacagca aggacagcac ctacagcctc        540
agcagcaccc tgacgctgag caaagcagac tacgagaaac acaaagtcta cgcctgcgaa        600
gtcacccatc agggcctgag ctcgcccgtc acaaagagct tcaacagggg agagtgttga        660
tga                                                                      663
```

```
<210> SEQ ID NO 18
<211> LENGTH: 102
<212> TYPE: PRT
<213> ORGANISM: Artificial Sequence
<220> FEATURE:
<223> OTHER INFORMATION: CH2 domain

<400> SEQUENCE: 18
```

```
Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Ala Glu Asp
            20                  25                  30

Pro Glu Val Gln Phe Asn Trp Tyr Val Asp Gly Val Glu Val His Asn
```

-continued

```
        35              40              45

Ala Lys Thr Lys Pro Arg Glu Glu Gln Phe Asn Ser Thr Phe Arg Val
    50              55              60

Val Ser Val Leu Thr Val Leu His Gln Asp Trp Leu Asn Gly Lys Glu
65              70              75              80

Tyr Lys Cys Lys Val Ser Asn Lys Gly Leu Pro Ser Ser Ile Glu Lys
                85              90              95

Thr Ile Ser Lys Thr Lys
            100

<210> SEQ ID NO 19
<211> LENGTH: 102
<212> TYPE: PRT
<213> ORGANISM: Artificial Sequence
<220> FEATURE:
<223> OTHER INFORMATION: CH2 domain

<400> SEQUENCE: 19

Ser Val Phe Leu Phe Pro Pro Lys Pro Lys Asp Thr Leu Met Ile Ser
1               5               10              15

Arg Thr Pro Glu Val Thr Cys Val Val Val Asp Val Ser Gln Glu Asp
                20              25              30

Pro Glu Val Gln Phe Asn Trp Tyr Val Asp Gly Val Glu Val His Asn
        35              40              45

Ala Lys Thr Lys Pro Arg Glu Glu Gln Phe Asn Ser Thr Tyr Arg Val
    50              55              60

Val Ser Val Leu Thr Val Leu His Gln Asp Trp Leu Asn Gly Lys Glu
65              70              75              80

Tyr Lys Cys Lys Val Ser Asn Lys Gly Leu Gly Ser Ser Ile Glu Lys
                85              90              95

Thr Ile Ser Lys Ala Lys
            100

<210> SEQ ID NO 20
<211> LENGTH: 107
<212> TYPE: PRT
<213> ORGANISM: Artificial Sequence
<220> FEATURE:
<223> OTHER INFORMATION: CH3 domain

<400> SEQUENCE: 20

Gly Gln Pro Arg Glu Pro Gln Val Tyr Thr Leu Pro Pro Ser Arg Glu
1               5               10              15

Glu Met Thr Lys Asn Gln Val Ser Leu Thr Cys Leu Val Lys Gly Phe
                20              25              30

Tyr Pro Ser Asp Ile Ala Val Glu Trp Glu Ser Asn Gly Gln Pro Glu
        35              40              45

Asn Asn Tyr Lys Thr Thr Pro Pro Met Leu Asp Ser Asp Gly Ser Phe
    50              55              60

Phe Leu Tyr Ser Lys Leu Thr Val Asp Lys Ser Arg Trp Gln Gln Gly
65              70              75              80

Asn Val Phe Ser Cys Ser Val Met His Glu Ala Leu His Asn His Tyr
                85              90              95

Thr Gln Lys Ser Leu Ser Leu Ser Pro Gly Lys
            100             105

<210> SEQ ID NO 21
<211> LENGTH: 107
```

```
<212> TYPE: PRT
<213> ORGANISM: Artificial Sequence
<220> FEATURE:
<223> OTHER INFORMATION: CH3 domain

<400> SEQUENCE: 21

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 22
<211> LENGTH: 356
<212> TYPE: PRT
<213> ORGANISM: Artificial Sequence
<220> FEATURE:
<223> OTHER INFORMATION: belatacept

<400> SEQUENCE: 22

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
        210                 215                 220
```

-continued

```
Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
        290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 23
<211> LENGTH: 360
<212> TYPE: PRT
<213> ORGANISM: Artificial Sequence
<220> FEATURE:
<223> OTHER INFORMATION: abatacept

<400> SEQUENCE: 23

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
        50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
        130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
                180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
        210                 215                 220
```

-continued

```
Thr Lys Pro Arg Glu Glu Gln Tyr Asn Ser Thr Tyr Arg Val Val Ser
225             230             235             240

Val Leu Thr Val Leu His Gln Asp Trp Leu Asn Gly Lys Glu Tyr Lys
            245             250             255

Cys Lys Val Ser Asn Lys Ala Leu Pro Ala Pro Ile Glu Lys Thr Ile
            260             265             270

Ser Lys Ala Lys Gly Gln Pro Arg Glu Pro Gln Val Tyr Thr Leu Pro
        275             280             285

Pro Ser Arg Asp Glu Leu Thr Lys Asn Gln Val Ser Leu Thr Cys Leu
    290             295             300

Val Lys Gly Phe Tyr Pro Ser Asp Ile Ala Val Glu Trp Glu Ser Asn
305             310             315             320

Gly Gln Pro Glu Asn Asn Tyr Lys Thr Thr Pro Pro Val Leu Asp Ser
            325             330             335

Asp Gly Ser Phe Phe Leu Tyr Ser Lys Leu Thr Val Asp Lys Ser Arg
            340             345             350

Trp Gln Gln Gly Asn Val Phe Ser
        355             360
```